(12) United States Patent
Harmsen et al.

(10) Patent No.: US 6,699,853 B2
(45) Date of Patent: Mar. 2, 2004

(54) 4-HALOALKYL-3-HETEROCYCLYLPYRIDINES, 4-HALOALKYL-5-HETEROCYCLYL-PYRIMIDINES AND 4-TRIFLUOROMETHYL-3-OXADIAZOLYLPYRIDINES, PROCESSES FOR THEIR PREPARATION, COMPOSITIONS COMPRISING THEM, AND THEIR USE AS PESTICIDES

(75) Inventors: Sven Harmsen, Lübeck (DE); Henricus Maria Martinus Bastiaans, Usingen (DE); Wolfgang Schaper, Diedorf (DE); Jörg Tiebes, Offenbach (DE); Uwe Döller, Rodgau (DE); Daniela Jans, Bad Homburg (DE); Ulrich Sanft, Hofheim (DE); Waltraud Hempel, Liederbach (DE); Maria-Theresia Thönessen, Heidesheim (DE); Thomas Taapken, Frankfurt (DE); Burkhard Rook, Selters (DE); Manfred Kern, Lörzweiler (DE)

(73) Assignee: Hoechst Schering AgrEvo GmbH, Berlin (DE)

( * ) Notice: Subject to any disclaimer, the term of this patent is extended or adjusted under 35 U.S.C. 154(b) by 0 days.

(21) Appl. No.: 10/056,274

(22) Filed: Jan. 24, 2002

(65) Prior Publication Data

US 2003/0162812 A1 Aug. 28, 2003

Related U.S. Application Data

(63) Continuation-in-part of application No. 09/808,194, filed on Mar. 14, 2001, now Pat. No. 6,521,610, which is a division of application No. 09/096,748, filed on Jun. 12, 1998, now Pat. No. 6,239,160, which is a continuation-in-part of application No. 09/461,792, filed on Dec. 15, 1999, now abandoned.

(30) Foreign Application Priority Data

Jun. 16, 1997 (DE) ......... 197 25 450
Dec. 17, 1998 (DE) ......... 198 58 193

(51) Int. Cl.[7] .......... A61K 31/33; A61K 31/44; A61K 31/41; C07D 213/08; C07D 271/06

(52) U.S. Cl. .......... 514/183; 514/356; 514/357; 514/340; 514/364; 546/268.4; 546/269.2; 546/269.1; 546/270.4; 546/315; 546/343; 546/346; 548/131

(58) Field of Search .......... 514/183, 356, 514/357, 340, 364; 546/268.4, 269.4, 269.1, 270.4, 315, 343, 346, 1; 548/131

(56) References Cited

U.S. PATENT DOCUMENTS 5,578,550 A * 11/1996 Buck .......... 504/253

FOREIGN PATENT DOCUMENTS

| DE | 2 127 404 A | 4/1984 |
| DE | 42 39 727 A1 | 6/1994 |
| EP | 0 185 256 B1 | 6/1986 |
| EP | 0 357 241 A1 | 3/1990 |

* cited by examiner

Primary Examiner—Mukund J. Shah
Assistant Examiner—Sudhaker B. Patel
(74) Attorney, Agent, or Firm—Frommer Lawrence & Haug LLP

(57) ABSTRACT

The present invention relates to 4-Haloalkyl-3-heterocyclylpyridines, 4-haloalkyl-5-heterocyclyl-pyrimidines and 4-trifluoromethyl-3-oxadiazolylpyridines, Processes for Their Preparation, Compositions Comprising Them, and Their Use as Pesticides More particularly, the present invention relates to 4-trifluoromethyl-3-oxadiazolylpyridines of the formula (I'), to processes for their preparation, to compositions comprising them and to the use of these compounds for controlling animal pests, in particular insects, spider mites, ectoparasites and helminths:

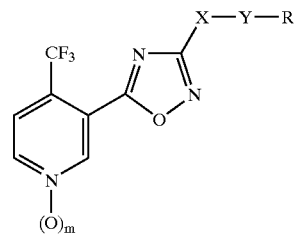

wherein X, Y are as defined in the description.

12 Claims, No Drawings

4-HALOALKYL-3-HETEROCYCLYLPYRIDINES, 4-HALOALKYL-5-HETEROCYCLYL-PYRIMIDINES AND 4-TRIFLUOROMETHYL-3-OXADIAZOLYLPYRIDINES, PROCESSES FOR THEIR PREPARATION, COMPOSITIONS COMPRISING THEM, AND THEIR USE AS PESTICIDES

CROSS-REFERENCE TO RELATED APPLICATIONS

This application is a continuation-in-part of U.S. application Ser. No. 09/808,194, filed on Mar. 14, 2001, now U.S. Pat. No. 6,521,610, which is a divisional application of U.S. application Ser. No. 09/096,748, filed on Jun. 12, 1998, now U.S. Pat. No. 6,239,160, and claims the benefit of priority to DE 19725450, filed on Jun. 16, 1997. This application is also a continuation-in-part of U.S. application Ser. No. 09/461,792, filed on Dec. 15, 1999, now abandoned, and claims benefit of priority to DE 19858193.9, filed on Dec. 17, 1998.

FIELD OF THE INVENTION

The present invention relates to 4-haloalkyl-3-heterocyclylpyridines and 4-haloalkyl-5-heterocyclylpyrimidines, to processes for their preparation, to compositions comprising them and to the use of novel and known 4-haloalkyl-3-heterocyclylpyridines and 4-haloalkyl-5-heterocyclylpyrimidines for controlling animal pests, in particular insects, spider mites, ectoparasites and helminths. More particularly, the invention relates to 4-trifluoromethyl-3-oxadiazolylpyridines, to processes for their preparation, to compositions comprising them and to their use for controlling animal pests, in particular insects, spider mites, ectoparasites and helminths.

BACKGROUND OF THE INVENTION

It is already known that appropriately substituted pyridines or pyrimidines have acaricidal and insecticidal activity. Thus, WO 95/07891 describes pyridines which carry a cycloalkyl radical in position 4 which is linked via a hetero atom and a group of various substituents in position 3. WO 93/19050 discloses 4-cycloalkylamino- and 4-cycloalkoxypyrimidines which carry in position 5 inter alia alkyl, alkoxy or haloalkoxy groups. However, the desired activity against the harmful organisms is not always sufficient. Additionally, these compounds often have undesirable toxicologic properties toward mammals and aquatic living beings.

Pyridyl-1,2,4-thiadiazoles having fungicidal properties are described in DE-A 42 39 727. The compounds disclosed therein carry the thiadiazole ring in position 2, 3 or 4 of the unsubstituted pyridine.

WO-A-98/57969, which is not prepublished, proposes 4-haloalkylpyridines and -pyrimidines for use as pesticides.

EP-A 0 371 925 discloses some 1,3,4-oxadiazolyl- and 1,3,4-thiadiazolyl-pyrimidines having nematicidal and fungicidal properties. In the biologically effective compounds disclosed in this publication, the pyrimidine carries the oxadiazolyl or thiadiazolyl ring either a) in position 5 and is optionally substituted by a thiomethyl group in position 2, or b) in position 2 and is optionally substituted in position 4 and 6, in each case by a methyl group.

Aryltriazole derivatives for use as pesticides are known from EP-A 0 185 256. In addition to the phenyltriazoles, which are particularly preferred, three haloalkyl-3-pyridyltriazoles are disclosed:

3-(2-chlorophenyl)-1-methyl-5-(4-trifluoromethyl-3-pyridyl)-1H-1,2,4-triazole 3-(2,6-difluorophenyl)-1-methyl-5-(4-trifluoromethyl-3-pyridyl)-1H-1,2,4-triazole and 3-(2-chloro-4-fluorophenyl)-1-methyl-5-(4-trifluoromethyl-3-pyridyl)-1H-1,2,4-triazole, their desired activity at low application rates, however, is not always satisfactory, especially when controlling insects and spider mites.

Some commercially available 4-haloalkyl-3-heterocyclylpyridines are known from the Maybridge Catalogue 1996/1997, Maybridge Chemical CO. LTD., Trevillett Tintagel, GB:

3-(3,5-dichlorophenyl)-5-(4-trifluoromethyl-3-pyridyl)-1,2,4-oxadiazole 5-(4-trifluoromethyl-3-pyridyl)-3-phenyl-1,2,4-oxadiazole 3-(4-trifluoromethyl-3-pyridyl)-5-phenyl-1,2,4-oxadiazole 5-(2-chlorophenyl)-3-(4-trifluoromethyl-3-pyridyl)-1,2,4-oxadiazole 5-(3-chlorophenyl)-3-(4-trifluoromethyl-3-pyridyl)-1,2,4-oxadiazole 5-(4-chlorophenyl)-3-(4-trifluoromethyl-3-pyridyl)-1,2,4-oxadiazole 5-(2-fluorophenyl)-3-(4-trifluoromethyl-3-pyridyl)-1,2,4-oxadiazole 5-(4-fluorophenyl)-3-(4-trifluoromethyl-3-pyridyl)-1,2,4-oxadiazole 5-(2,4-dichlorophenyl)-3-(4-trifluoromethyl-3-pyridyl)-1,2,4-oxadiazole 5-(3,4-dichlorophenyl)-3-(4-trifluoromethyl-3-pyridyl)-1,2,4-oxadiazole 5-(3,5-dichlorophenyl)-3-(4-trifluoromethyl-3-pyridyl)-1,2,4-oxadiazole 5-(2,6-dichloro-4-pyridyl)-3-(4-trifluoromethyl-3-pyridyl)-1,2,4-oxadiazole 5-(3,5-bistrifluoromethylphenyl)-3-(4-trifluoromethyl-3-pyridyl)-1,2,4-oxadiazole 2-(2-chlorophenyl)-5-(4-trifluoromethyl-3-pyridyl)-1,3,4-oxadiazole 2-(3-chlorophenyl)-5-(4-trifluoromethyl-3-pyridyl)-1,3,4-oxadiazole 2-(4-chlorophenyl)-5-(4-trifluoromethyl-3-pyridyl)-1,3,4-oxadiazole 2-(2-trifluoromethoxyphenyl)-5-(4-trifluoromethyl-3-pyridyl)-1,3,4-oxadiazole 2-(4-trifluoromethoxyphenyl)-5-(4-trifluoromethyl-3-pyridyl)-1,3,4-oxadiazole 2-(4-trifluoromethyl-3-pyridyl)-5-phenyl-1,3,4-oxadiazole 2-(4-trifluoromethyl-3-pyridyl)-4-methylthiazolecarbohydrazide ethyl 2-(4-trifluoromethyl-3-pyridyl)-4-methylthiazolecarboxylate N-(4-chlorophenyl)carbonyl-N'-[2-(4-trifluoromethyl-3-pyridyl)-4-methyl-5-thiazolyl]carbonylhydrazine 2-(4-trifluoromethyl-3-pyridyl)-4-thiazolecarbohydrazide 4-(4-chlorophenyl)-2-(4-trifluoromethyl-3-pyridyl)thiazole 4-(4-cyanophenyl)-2-(4-trifluoromethyl-3-pyridyl)
thiazole N-(4-trifluoromethylphenyl)carbonyl-N'-[2-(4-trifluoromethyl-3-pyridyl)-4-thiazolyl]
carbonylhydrazine 2-(2-(4-trifluoromethyl-3-pyridyl)thiazolyl)-5-chloro-3-methylbenzo[b]thiophene 2-(4-chlorophenylmethylthio)-5-(4-trifluoromethyl-3-pyridyl)-1-methyl-1H-1,3,4-triazole 2-(4-chlorophenylcarbonylmethylthio)-5-(4-trifluoromethyl-3-pyridyl)-1-methyl-1H-1,3,4-triazole and 2-ethoxycarbonylmethylthio-5-(4-trifluoromethyl-3-pyridyl)-1-methyl-1H-1,3,4-triazole.

However, a biological activity toward harmful organisms has hitherto not been disclosed.

SUMMARY OF THE INVENTION

It is an object of the present invention to provide compounds having good insecticidal and acaricidal properties and simultaneously low toxicity toward mammals and aquatic living beings.

DETAILED DESCRIPTION OF THE INVENTION

It has now been found that compounds of the formula I, optionally as salts, have a wider activity spectrum against animal pests and simultaneously more favorable toxicologic properties toward mammals and aquatic living beings than the prior art compounds.

(I)

In the formula (I):
Y is halo-$C_1$–$C_6$-alkyl;
X is CH or N;
m is 0 or 1;
Q is a 5-membered heterocyclic group in which

| | | | |
|---|---|---|---|
| a) $X^1$ = W, | $X^2$ = $NR^a$, | $X^3$ = $CR^bR^1$ | or |
| b) $X^1$ = $NR^a$, | $X^2$ = $CR^bR^1$, | $X^3$ = W | or |
| c) $X^1$ = V, | $X^2$ = $CR^aR^1$, | $X^3$ = $NR^b$ | or |
| d) $X^1$ = V, | $X^2$ = $CR^aR^2$, | $X^3$ = $CR^bR^3$ | or |
| e) $X^1$ = V, | $X^2$ = $CR^4R^5$, | $X^3$ = $CR^6R^7$ | or |
| f) $X^1$ = $NR^a$, | $X^2$ = $CR^bR^1$, | $X^3$ = $NR^8$; | |

$R^a$ and $R^b$ together are a bond
V is oxygen, sulfur or $NR^9$;
W is oxygen or sulfur;

$R^1$ is hydrogen,
($C_1$–$C_{20}$)-alkyl, ($C_2$–$C_{20}$)-alkenyl, ($C_2$–$C_{20}$)-alkynyl, ($C_3$–$C_8$)-cycloalkyl,
($C_4$–$C_8$)-cycloalkenyl, ($C_6$–$C_8$)-cycloalkynyl,
where the six last-mentioned radicals are optionally substituted by one or more radicals from the group halogen, cyano, nitro, hydroxyl, —C(=W)$R^{10}$, —C(=NO$R^{10}$)$R^{10}$, —C(=NN$R^{10}_2$)$R^{10}$, —C(=W)O$R^{10}$, —C(=W)N$R^{10}_2$, —OC(=W)$R^{10}$, —OC(=W)O$R^{10}$, —N$R^{10}$C(=W)$R^{10}$, —N[C(=W)$R^{10}$]$_2$, —N$R^{10}$C(=W)O$R^{10}$, —C(=W)N$R^{10}$—N$R^{10}_2$, —C(=W)N$R^{10}$—N$R^{10}$[C(=W)$R^{10}$], —N$R^{10}$—C(=W)N$R^{10}_2$, —N$R^{10}$—N$R^{10}$C(=W)$R^{10}$, —N$R^{10}$—N[C(=W)$R^{10}$]$_2$, —N[(C=W)$R^{10}$]—N$R^{10}_2$, —N$R^{10}$—N$R^{10}$[(C=W)$R^{10}$], —N$R^{10}$—N$R^{10}$[(C=W)W$R^{10}$], —N$R^{10}$—$R^{10}$[(C=W)N$R^{10}_2$], —N$R^{10}$(C=N$R^{10}$)$R^{10}$, —N$R^{10}$(C=N$R^{10}$)N$R^{10}_2$, —O—N$R^{10}_2$, —O—N$R^{10}$(C=W)$R^{10}$, —SO$_2$N$R^{10}_2$, —N$R^{10}$SO$_2R^{10}$, —SO$_2$O$R^{10}$, —OSO$_2R^{10}$, —O$R^{10}$, —N$R^{10}_2$, —S$R^{10}$, —SiR$^{10}_3$, —SeR$^{10}$, —P$R^{10}_2$, —P(=W)$R^{10}_2$, —SOR$^{10}$, —SO$_2R^{10}$, —PW$_2R^{10}_2$, —PW$_3R^{10}_2$,
aryl and heterocyclyl,
the two last-mentioned radicals optionally being substituted by one or more radicals from the group ($C_1$–$C_6$)-alkyl, ($C_2$–$C_6$)-alkenyl, ($C_2$–$C_6$)-alkynyl, ($C_3$–$C_8$)-cycloalkyl, ($C_4$–$C_8$)-cycloalkenyl, ($C_6$–$C_8$)-cycloalkynyl, ($C_1$–$C_6$)-haloalkyl, ($C_2$–$C_6$)-haloalkenyl, ($C_2$–$C_6$)-haloalkynyl, halogen, —O$R^{10}$, —N$R^{10}_2$, —S$R^{10}$, —SiR$^{10}_3$, —C(=W)$R^{10}$, —C(=W)O$R^{10}$, —C(=W)N$R^{10}_2$, —SOR$^{10}$, —SO$_2R^{10}$, nitro, cyano and hydroxyl,
aryl,
which is optionally substituted by one or more radicals from the group
($C_1$–$C_6$)-alkyl, ($C_2$–$C_6$)-alkenyl, ($C_2$–$C_6$)-alkynyl, ($C_3$–$C_8$)-cycloalkyl, ($C_4$–$C_8$)-cycloalkenyl and ($C_6$–$C_8$)-cycloalkynyl,
where these six abovementioned radicals are optionally substituted by one or more radicals from the group
halogen, cyano, nitro, —C(=W)$R^{10}$, —C(=W)O$R^{10}$, —C(=W)N$R^{10}_2$, —O$R^{10}$, —N$R^{10}_2$, —S$R^{10}$, —SOR$^{10}$ and —SO$_2R^{10}$,
halogen, cyano, nitro, —C(=W)$R^{10}$, —C(=NO$R^{10}$)$R^{10}$, —C(=NN$R^{10}_2$)$R^{10}$, —C(=W)O$R^{10}$, —C(=W)N$R^{10}_2$, —OC(=W)$R^{10}$, —OC(=W)O$R^{10}$, —N$R^{10}$C(=W)$R^{10}$, —N[C(=W)$R^{10}$]$_2$, —N$R^{10}$C(=W)O$R^{10}$, —O$R^{10}$, —N$R^{10}_2$, —S$R^{10}$, —SiR$^{10}_3$, —P$R^{10}_2$, —SOR$^{10}$, —SO$_2R^{10}$, —PW$_2R^{10}_2$ and —PW$_3R^{10}_2$,
heterocyclyl,
which is optionally substituted by one or more radicals from the group
($C_1$–$C_6$)-alkyl, ($C_2$–$C_6$)-alkenyl, ($C_2$–$C_6$)-alkynyl, ($C_3$–$C_8$)-cycloalkyl, ($C_4$–$C_8$)-cycloalkenyl and ($C_6$–$C_8$)-cycloalkynyl,
where the six abovementioned radicals are optionally substituted by one or more radicals from the group
cyano, nitro, halogen, —C(=W)$R^{10}$, —C(=W)O$R^{10}$, —C(=W)N$R^{10}_2$, —N$R^{10}$C(=W)$R^{10}$, —N[C(=W)$R^{10}$]$_2$, —OC(=W)$R^{10}$, —OC(=W)O$R^{10}$, —O$R^{10}$, —N$R^{10}_2$, —S$R^{10}$, —SOR$^{10}$ and —SO$_2R^{10}$;

halogen, cyano, nitro, —C(=W)R$^{10}$, —C(=W)OR$^{10}$, —C(=W)NR$^{10}$$_2$, —OC(=W)R$^{10}$, —OR$^{10}$, —NR$^{10}$$_2$, —SR$^{10}$, —SOR$^{10}$ and —SO$_2$R$^{10}$;

—OR$^{10}$, —NR$^{10}$$_2$, —SR$^{10}$, —SOR$^{10}$, —SO$_2$R$^{10}$, —C(=W)R$^{10}$, —C(=NOR$^{10}$)R$^{10}$, —C(=NNR$^{10}$$_2$)R$^{10}$, —C(=W)OR$^{10}$, —C(=W)NR$^{10}$$_2$, —OC(=W)R$^{10}$, —OC(=W)OR$^{10}$, —NR$^{10}$C(=W)R$^{10}$, —N[C(=W)R$^{10}$]$_2$, —NR$^{10}$C(=W)OR$^{10}$, —C(=W)NR$^{10}$—NR$^{10}$$_2$, —C(=W)NR$^{10}$—NR$^{10}$[C(=W)R$^{10}$], —NR$^{10}$—C(=W)NR$^{10}$$_2$, —NR$^{10}$—NR$^{10}$C(=W)R$^{10}$, —NR$^{10}$—NC(=W)R$^{10}$$_2$, —N(C=W)R$^{10}$—NR$^{10}$$_2$, —NR$^{10}$—NR$^{10}$[(C=W)R$^{10}$], —NR$^{10}$—NR$^{10}$[(C=W)WR$^{10}$], —NR$^{10}$—NR$^{10}$[(C=W)NR$^{10}$$_2$], —NR$^{10}$(C=NR$^{10}$)R$^{10}$, —NR$^{10}$(C=NR$^{10}$)NR$^{10}$$_2$, —O—NR$^{10}$$_2$, —O—NR$^{10}$(C=W)R$^{10}$, —SO$_2$NR$^{10}$$_2$, —NR$^{10}$SO$_2$R$^{10}$, —SO$_2$OR$^{10}$, —OSO$_2$R$^{10}$, —SC(=W)R$^{10}$, —SC(=W)OR$^{10}$, —SC(=W)R$^{10}$, —PR$^{10}$$_2$, —PW$_2$R$^{10}$$_2$, —PW$_3$R$^{10}$$_2$, SiR$^{10}$$_3$ or halogen;

R$^2$ and R$^3$ independently of one another have the definitions given in R$^1$;

R$^2$ and R$^3$ together form a 5- to 7-membered ring which may be partially or fully unsaturated and may be interrupted by one or more atoms from the group nitrogen, oxygen and sulfur, the oxygen atoms not being directly adjacent to one another, and the ring optionally being substituted by one or more, but at most 5, radicals R$^1$;

R$^4$ and R$^6$ independently of one another have the definitions given in R$^1$;

R$^4$ and R$^6$ together form a 4- to 7-membered ring which may be partially or fully unsaturated and may be interrupted by one or more atoms from the group nitrogen, oxygen and sulfur, the oxygen atoms not being directly adjacent to one another, and the ring optionally being substituted by one or more, but at most 5, radicals R$^1$;

R$^5$ and R$^7$ independently of one another are hydrogen, (C$_1$–C$_{20}$)-alkyl, (C$_2$–C$_{20}$)-alkenyl, (C$_2$–C$_{20}$)-alkynyl, (C$_3$–C$_8$)-cycloalkyl, (C$_4$–C$_8$)-cycloalkenyl, (C$_6$–C$_8$)-cycloalkynyl,
  where the six last-mentioned radicals are optionally substituted by one or more radicals from the group
    halogen, cyano, nitro, hydroxyl, —C(=W)R$^{10}$, —C(=NOR$^{10}$)R$^{10}$, —C(=NNR$^{10}$$_2$)R$^{10}$, —C(=W)OR$^{10}$, —C(=W)NR$^{10}$$_2$, —OC(=W)R$^{10}$, —OC(=W)OR$^{10}$, —NR$^{10}$C(=W)R$^{10}$, —N[C(=W)R$^{10}$]$_2$, —NR$^{10}$C(=W)OR$^{10}$, —C(=W)NR$^{10}$—NR$^{10}$$_2$, —C(=W)NR$^{10}$—NR$^{10}$[C(=W)R$^{10}$], —NR$^{10}$—C(=W)NR$^{10}$$_2$, —NR$^{10}$—NR$^{10}$C(=W)R$^{10}$, —NR$^{10}$—N[C(=W)R$^{10}$]$_2$, —N[(C=W)R$^{10}$]—NR$^{10}$$_2$, —NR$^{10}$—NR$^{10}$[(C=W)R$^{10}$], —NR$^{10}$—NR$^{10}$[(C=W)WR$^{10}$], —NR$^{10}$—NR$^{10}$[(C=W)NR$^{10}$$_2$], —NR$^{10}$(C=NR$^{10}$)R$^{10}$, —NR$^{10}$(C=NR$^{10}$)NR$^{10}$$_2$, —O—NR$^{10}$$_2$, —O—NR$^{10}$(C=W)R$^{10}$$_2$, —OR$^{10}$, —NR$^{10}$$_2$, —SR$^{10}$, —SiR$^{10}$$_3$, —SeR$^{10}$, —PR$^{10}$$_2$, —P(=W)R$^{10}$$_2$, —SOR$^{10}$, —SO$_2$R$^{10}$, —PW$_2$R$^{10}$$_2$, —PW$_3$R$^{10}$$_2$, aryl and heterocyclyl,
of which the two mentioned last are optionally substituted by one or more radicals from the group
  (C$_1$–C$_6$)-alkyl, (C$_2$–C$_6$)-alkenyl, (C$_2$–C$_6$)-alkynyl, (C$_3$–C$_8$)-cycloalkyl, (C$_4$–C$_8$)-cycloalkenyl, (C$_6$–C$_8$)-cycloalkynyl, (C$_1$–C$_6$)-haloalkyl, (C$_2$–C$_6$)-haloalkenyl, (C$_2$–C$_6$)-haloalkynyl, halogen, —OR$^{10}$, —NR$^{10}$$_2$, —SR$^{10}$, —SiR$^{10}$$_3$, —C(=W)R$^{10}$, —C(=W)OR$^{10}$, —C(=W)NR$^{10}$$_2$, —SOR$^{10}$, —SO$_2$R$^{10}$, nitro, cyano and hydroxyl, aryl,
which is optionally substituted by one or more radicals from the group
  (C$_1$–C$_6$)-alkyl, (C$_2$–C$_6$)-alkenyl, (C$_2$–C$_6$)-alkynyl, (C$_3$–C$_8$)-cycloalkyl, (C$_4$–C$_8$)-cycloalkenyl and (C$_6$–C$_8$)-cycloalkynyl,
  where these six abovementioned radicals are optionally substituted by one or more radicals from the group
    halogen, cyano, nitro, —C(=W)R$^{10}$, —C(=W)OR$^{10}$, —C(=W)NR$^{10}$$_2$, —OR$^{10}$, —NR$^{10}$$_2$, —SR$^{10}$, —SOR$^{10}$ and —SO$_2$R$^{10}$;
    halogen, cyano, nitro, —C(=W)R$^{10}$, —C(=NOR$^{10}$)R$^{10}$, —C(=NNR$^{10}$$_2$)R$^{10}$, —C(=W)OR$^{10}$, —C(=W)NR$^{10}$$_2$, —OC(=W)R$^{10}$, —OC(=W)OR$^{10}$, —NR$^{10}$C(=W)R$^{10}$, —N[C(=W)R$^{10}$]$_2$, —NR$^{10}$C(=W)OR$^{10}$, —OR$^{10}$, —NR$^{10}$$_2$, —SR$^{10}$, —SiR$^{10}$$_3$, —PR$^{10}$$_2$, —SOR$^{10}$, —SO$_2$R$^{10}$, —PW$_2$R$^{10}$$_2$ and —PW$_3$R$^{10}$$_2$;

pyridyl,
which is optionally substituted by one or more radicals from the group
  (C$_1$–C$_6$)-alkyl, (C$_2$–C$_6$)-alkenyl, (C$_2$–C$_6$)-alkynyl, (C$_3$–C$_8$)-cycloalkyl, (C$_4$–C$_8$)-cycloalkenyl and (C$_6$–C$_8$)-cycloalkynyl,
  where the six abovementioned radicals are optionally substituted by one or more radicals from the group
    cyano, nitro, halogen, —C(=W)R$^{10}$, —C(=W)OR$^{10}$, —C(=W)NR$^{10}$$_2$, —OR$^{10}$, —NR$^{10}$$_2$, —SR$^{10}$, —SOR$^{10}$ and —SO$_2$R$^{10}$,
    halogen, cyano, nitro, —C(=W)R$^{10}$, —C(=W)OR$^{10}$, —C(=W)NR$^{10}$$_2$, —OC(=W)R$^{10}$, —OR$^{10}$, —NR$^{10}$$_2$, —SR$^{10}$, —SOR$^{10}$ and —SO$_2$R$^{10}$;
    —C(=W)R$^{10}$, —C(=NOR$^{10}$)R$^{10}$, —C(=NNR$^{10}$$_2$)R$^{10}$, —C(=W)OR$^{10}$, —C(=W)NR$^{10}$$_2$ or halogen;

R$^4$ and R$^5$ together form a 4- to 7-membered ring which may be partially unsaturated and may be interrupted by one or more atoms from the group nitrogen, oxygen and sulfur, oxygen atoms not being directly adjacent to one another, and the ring optionally being substituted by one or more, but at most 5, radicals R$^1$;

R$^4$ and R$^5$ together form one of the groups =O, =S or =N—R$^9$;

R$^6$ and R$^7$ together form a 5- to 7-membered ring which may be partially unsaturated and may be interrupted by one or more atoms from the group nitrogen, oxygen and sulfur, oxygen atoms not being directly adjacent to one another, and the ring optionally being substituted by one or more, but at most 5, radicals R$^1$;

R$^6$ and R$^7$ together form one of the groups =O, =S or =N—R$^9$;

R$^8$ is hydrogen,
  (C$_1$–C$_6$)-alkyl, (C$_2$–C$_6$)-alkenyl, (C$_2$–C$_6$)-alkynyl, (C$_3$–C$_8$)-cycloalkyl, (C$_4$–C$_8$)-cycloalkenyl, (C$_3$–C$_8$)-cycloalkyl-(C$_1$–C$_4$)-alkyl, (C$_4$–C$_8$)-cycloalkenyl-(C$_1$–C$_4$)-alkyl, (C$_3$–C$_8$)-cycloalkyl-(C$_2$–C$_4$)-alkenyl, (C$_4$–C$_8$)-cycloalkenyl-(C$_1$–C$_4$)- alkenyl, $(C_1-C_6)$-alkyl-$(C_3-C_8)$-cycloalkyl, $(C_2-C_6)$-alkenyl-$(C_3-C_8)$-cycloalkyl, $(C_2-C_6)$-alkynyl-$(C_3-C_8)$-cycloalkyl, $(C_1-C_6)$-alkyl-$(C_4-C_8)$-cycloalkenyl, $(C_2-C_6)$-alkenyl-$(C_4-C_8)$-cycloalkenyl, where the fourteen last-mentioned radicals are optionally substituted by one or more radicals from the group halogen, cyano, nitro, hydroxyl, thio, amino, formyl, $(C_1-C_6)$-alkoxy, $(C_2-C_6)$-alkenyloxy, $(C_2-C_6)$-alkynyloxy, $(C_1-C_6)$-haloalkyloxy, $(C_2-C_6)$-haloalkenyloxy, $(C_2-C_6)$-haloalkynyloxy, $(C_3-C_8)$-cycloalkoxy, $(C_4-C_8)$-cycloalkenyloxy, $(C_3-C_8)$-halocycloalkoxy, $(C_4-C_8)$-halocycloalkenyloxy, $(C_3-C_8)$-cycloalkyl-$(C_1-C_4)$-alkoxy, $(C_4-C_8)$-cycloalkenyl-$(C_1-C_4)$-alkoxy, $(C_3-C_8)$-cycloalkyl-$(C_2-C_4)$-alkenyloxy, $(C_4-C_8)$-cycloalkenyl-$(C_1-C_4)$-alkenyloxy, $(C_1-C_6)$-alkyl-$(C_3-C_8)$-cycloalkoxy, $(C_2-C_6)$-alkenyl-$(C_3-C_8)$-cycloalkoxy, $(C_2-C_6)$-alkynyl-$(C_3-C_8)$-cycloalkoxy, $(C_1-C_6)$-alkyl-$(C_4-C_8)$-cycloalkenyloxy, $(C_2-C_6)$-alkenyl-$(C_4-C_8)$-cycloalkenyloxy, $(C_1-C_4)$-alkoxy-$(C_1-C_6)$-alkoxy, $(C_1-C_4)$-alkoxy-$(C_2-C_6)$-alkenyloxy, carbamoyl, $(C_1-C_6)$-mono- or dialkylcarbamoyl, $(C_1-C_6)$-mono- or dihaloalkylcarbamoyl, $(C_3-C_8)$-mono- or dicycloalkylcarbamoyl, $(C_1-C_6)$-alkoxycarbonyl, $(C_3-C_8)$-cycloalkoxycarbonyl, $(C_1-C_6)$-alkanoyloxy, $(C_3-C_8)$-cycloalkanoyloxy, $(C_1-C_6)$-haloalkoxycarbonyl, $(C_1-C_6)$-haloalkanoyloxy, $(C_1-C_6)$-alkaneamido, $(C_1-C_6)$-haloalkaneamido, $(C_2-C_6)$-alkeneamido, $(C_3-C_8)$-cycloalkaneamido, $(C_3-C_8)$-cycloalkyl-$(C_1-C_4)$-alkaneamido, $(C_1-C_6)$-alkylthio, $(C_2-C_6)$-alkenylthio, $(C_2-C_6)$-alkynylthio, $(C_1-C_6)$-haloalkylthio, $(C_2-C_6)$-haloalkenylthio, $(C_2-C_6)$-haloalkynylthio, $(C_3-C_8)$-cycloalkylthio, $(C_4-C_8)$-cycloalkenylthio, $(C_3-C_8)$-halocycloalkylthio, $(C_4-C_8)$-halocycloalkenylthio, $(C_3-C_8)$-cycloalkyl-$(C_1-C_4)$-alkylthio, $(C_4-C_8)$-cycloalkenyl-$(C_1-C_4)$-alkylthio, $(C_3-C_8)$-cycloalkyl-$(C_2-C_4)$-alkenylthio, $(C_4-C_8)$-cycloalkenyl-$(C_1-C_4)$-alkenylthio, $(C_1-C_6)$-alkyl-$(C_3-C_8)$-cycloalkylthio, $(C_2-C_6)$-alkenyl-$(C_3-C_8)$-cycloalkylthio, $(C_2-C_6)$-alkynyl-$(C_3-C_8)$-cycloalkylthio, $(C_1-C_6)$-alkyl-$(C_4-C_8)$-cycloalkenylthio, $(C_2-C_6)$-alkenyl-$(C_4-C_8)$-cycloalkenylthio, $(C_1-C_6)$-alkylsulfinyl, $(C_2-C_6)$-alkenylsulfinyl, $(C_2-C_6)$-alkynylsulfinyl, $(C_1-C_6)$-haloalkylsulfinyl, $(C_2-C_6)$-haloalkenylsulfinyl, $(C_2-C_6)$-haloalkynylsulfinyl, $(C_3-C_8)$-cycloalkylsulfinyl, $(C_4-C_8)$-cycloalkenylsulfinyl, $(C_3-C_8)$-halocycloalksulfinyl, $(C_4-C_8)$-halocycloalkenylsulfinyl, $(C_3-C_8)$-cycloalkyl-$(C_1-C_4)$-alkylsulfinyl, $(C_4-C_8)$-cycloalkenyl-$(C_1-C_4)$-alkylsulfinyl, $(C_3-C_8)$-cycloalkyl-$(C_2-C_4)$-alkenylsulfinyl, $(C_4-C_8)$-cycloalkenyl-$(C_1-C_4)$-alkenylsulfinyl, $(C_1-C_6)$-alkyl-$(C_3-C_8)$-cycloalkylsulfinyl, $(C_2-C_6)$-alkenyl-$(C_3-C_8)$-cycloalkylsulfinyl, $(C_2-C_6)$-alkynyl-$(C_3-C_8)$-cycloalkylsulfinyl, $(C_1-C_6)$-alkyl-$(C_4-C_8)$-cycloalkenylsulfinyl, $(C_2-C_6)$-alkenyl-$(C_4-C_8)$-cycloalkenylsulfinyl, $(C_1-C_6)$-alkylsulfonyl, $(C_2-C_6)$-alkenylsulfonyl, $(C_2-C_6)$-alkynylsulfonyl, $(C_1-C_6)$-haloalkylsulfonyl, $(C_2-C_6)$-haloalkenylsulfonyl, $(C_2-C_6)$-haloalkynylsulfonyl, $(C_3-C_8)$-cycloalkylsulfonyl, $(C_4-C_8)$-cycloalkenylsulfonyl, $(C_3-C_8)$-halocycloalkylsulfonyl, $(C_4-C_8)$-halocycloalkenylsulfonyl, $(C_3-C_8)$-cycloalkyl-$(C_1-C_4)$-alkylsulfonyl, $(C_4-C_8)$-cycloalkenyl-$(C_1-C_4)$-alkylsulfonyl, $(C_3-C_8)$-cycloalkyl-$(C_2-C_4)$-alkenylsulfonyl, $(C_4-C_8)$-cycloalkenyl-$(C_1-C_4)$-alkenylsulfonyl, $(C_1-C_6)$-alkyl-$(C_3-C_8)$-cycloalkylsulfonyl, $(C_2-C_6)$-alkenyl-$(C_3-C_8)$-cycloalkylsulfonyl, $(C_2-C_6)$-alkynyl-$(C_3-C_8)$-cycloalkylsulfonyl, $(C_1-C_6)$-alkyl-$(C_4-C_8)$-cycloalkenylsulfonyl, $(C_2-C_6)$-alkenyl-$(C_4-C_8)$-cycloalkenylsulfonyl, $(C_1-C_6)$-alkylamino, $(C_2-C_6)$-alkenylamino, $(C_2-C_6)$-alkynylamino, $(C_1-C_6)$-haloalkylamino, $(C_2-C_6)$-haloalkenylamino, $(C_2-C_6)$-haloalkynylamino, $(C_3-C_8)$-cycloalkylamino, $(C_4-C_8)$-cycloalkenylamino, $(C_3-C_8)$-halocycloalkamino, $(C_4-C_8)$-halocycloalkenylamino, $(C_3-C_8)$-cycloalkyl-$(C_1-C_4)$-alkylamino, $(C_4-C_8)$-cycloalkenyl-$(C_1-C_4)$-alkylamino, $(C_3-C_8)$-cycloalkyl-$(C_2-C_4)$-alkenylamino, $(C_4-C_8)$-cycloalkenyl-$(C_1-C_4)$-alkenylamino, $(C_1-C_6)$-alkyl-$(C_3-C_8)$-cycloalkylamino, $(C_2-C_6)$-alkenyl-$(C_3-C_8)$-cycloalkylamino, $(C_2-C_6)$-alkynyl-$(C_3-C_8)$-cycloalkylamino, $(C_1-C_6)$-alkyl-$(C_4-C_8)$-cycloalkenylamino, $(C_2-C_6)$-alkenyl-$(C_4-C_8)$-cycloalkenylamino, $(C_1-C_6)$-trialkylsilyl, aryl, aryloxy, arylthio, arylamino, arylcarbamoyl, aroyl, aroyloxy, aryloxycarbonyl, aryl-$(C_1-C_4)$-alkoxy, aryl-$(C_2-C_4)$-alkenyloxy, aryl-$(C_1-C_4)$-alkylthio, aryl-$(C_2-C_4)$-alkenylthio, aryl-$(C_1-C_4)$-alkylamino, aryl-$(C_2-C_4)$-alkenylamino, aryl-$(C_1-C_6)$-dialkylsilyl, diaryl-$(C_1-C_6)$-alkylsilyl, triarylsilyl and 5- or 6-membered heterocyclyl, of which the nineteen last-mentioned radicals are optionally substituted in their cyclic moiety by one or more substituents from the group halogen, cyano, nitro, amino, hydroxyl, thio, $(C_1-C_4)$-alkyl, $(C_1-C_4)$-haloalkyl, $(C_1-C_4)$-alkoxy, $(C_1-C_4)$-haloalkoxy, $(C_1-C_4)$-alkylthio, $(C_1-C_4)$-haloalkylthio, $(C_1-C_4)$-alkylamino, $(C_1-C_4)$-haloalkylamino, formyl and $(C_1-C_4)$-alkanoyl;

aryl, which is optionally substituted by one or more radicals from the group halogen, cyano, nitro, hydroxyl, thio, amino, formyl, $(C_1-C_6)$-alkoxy, $(C_2-C_6)$-alkenyloxy, $(C_2-C_6)$-alkynyloxy, $(C_1-C_6)$-haloalkyloxy, $(C_2-C_6)$-haloalkenyloxy, $(C_2-C_6)$-haloalkynyloxy, $(C_3-C_8)$-cycloalkoxy, $(C_4-C_8)$-cycloalkenyloxy, $(C_3-C_8)$-halocycloalkoxy, $(C_4-C_8)$-halocycloalkenyloxy, carbamoyl, $(C_1-C_6)$-mono- or dialkylcarbamoyl, $(C_1-C_6)$-alkoxycarbonyl, $(C_1-C_6)$-alkanoyloxy, $(C_1-C_6)$-mono- or dihaloalkylcarbamoyl, $(C_1-C_6)$-haloalkoxycarbonyl, $(C_1-C_6)$-haloalkanoyloxy, $(C_1-C_6)$-alkaneamido, $(C_1-C_6)$-haloalkaneamido, $(C_2-C_6)$-alkeneamido, $(C_1-C_6)$-alkylthio, $(C_2-C_6)$-alkenylthio, $(C_2-C_6)$-alkynylthio, $(C_1-C_6)$-haloalkylthio, $(C_2-C_6)$-haloalkenylthio, $(C_2-C_6)$-haloalkynylthio, $(C_3-C_8)$-cycloalkylthio, $(C_4-C_8)$-cycloalkenylthio, $(C_3-C_8)$-halocycloalkthio, $(C_3-C_8)$-halocycloalkenylthio, ($C_1$–$C_6$)-alkylsulfinyl, ($C_2$–$C_6$)-alkenylsulfinyl, ($C_2$–$C_6$)-alkynylsulfinyl, ($C_1$–$C_6$)-haloalkylsulfinyl, ($C_2$–$C_6$)-haloalkenylsulfinyl, ($C_2$–$C_6$)-haloalkynylsulfinyl, ($C_3$–$C_8$)-cycloalkylsulfinyl, ($C_4$–$C_8$)-cycloalkenylsulfinyl, ($C_3$–$C_8$)-halocycloalksulfinyl, ($C_4$–$C_8$)-halocycloalkenylsulfinyl, ($C_1$–$C_6$)-alkylsulfonyl, ($C_2$–$C_6$)-alkenylsulfonyl, ($C_2$–$C_6$)-alkynylsulfonyl, ($C_1$–$C_6$)-haloalkylsulfonyl, ($C_2$–$C_6$)-haloalkenylsulfonyl, ($C_2$–$C_6$)-haloalkynylsulfonyl, ($C_3$–$C_8$)-cycloalkylsulfonyl, ($C_4$–$C_8$)-cycloalkenylsulfonyl, ($C_3$–$C_8$)-halocycloalksulfonyl, ($C_4$–$C_8$)-halocycloalkenylsulfonyl, ($C_1$–$C_6$)-alkylamino, ($C_2$–$C_6$)-alkenylamino, ($C_2$–$C_6$)-alkynylamino, ($C_1$–$C_6$)-haloalkylamino, ($C_2$–$C_6$)-haloalkenylamino, ($C_2$–$C_6$)-haloalkynylamino, ($C_3$–$C_8$)-cycloalkylamino, ($C_4$–$C_8$)-cycloalkenylamino, ($C_3$–$C_8$)-halocycloalkamino and ($C_4$–$C_8$)-halocycloalkenylamino,
—C(=W)$R^{11}$, O$R^{11}$ or N$R^{11}_2$;

$R^9$ is ($C_1$–$C_6$)-alkyl, ($C_2$–$C_6$)-alkenyl, ($C_2$–$C_6$)-alkynyl, ($C_3$–$C_8$)-cycloalkyl, ($C_4$–$C_8$)-cycloalkenyl, ($C_3$–$C_8$)-cycloalkyl-($C_1$–$C_4$)-alkyl, ($C_4$–$C_8$)-cycloalkenyl-($C_1$–$C_4$)-alkyl, ($C_3$–$C_8$)-cycloalkyl-($C_2$–$C_4$)-alkenyl, ($C_4$–$C_8$)-cycloalkenyl-($C_1$–$C_4$)-alkenyl,
where the nine last-mentioned radicals are optionally substituted by one or more radicals from the group halogen, cyano, ($C_1$–$C_6$)-alkoxy, ($C_2$–$C_6$)-alkenyloxy, ($C_2$–$C_6$) alkynyloxy and ($C_1$–$C_6$)-haloalkyloxy;

$R^{10}$ is hydrogen,
($C_1$–$C_6$)-alkyl, ($C_2$–$C_6$)-alkenyl, ($C_2$–$C_6$)-alkynyl, ($C_3$–$C_8$)-cycloalkyl, ($C_4$–$C_8$)-cycloalkenyl, ($C_3$–$C_8$)-cycloalkyl-($C_1$–$C_4$)-alkyl, ($C_4$–$C_8$)-cycloalkenyl-($C_1$–$C_4$)-alkyl, ($C_3$–$C_8$)-cycloalkyl-($C_2$–$C_4$)-alkenyl, ($C_4$–$C_8$)-cycloalkenyl-($C_1$–$C_4$)-alkenyl, ($C_1$–$C_6$)-alkyl-($C_3$–$C_8$)-cycloalkyl, ($C_2$–$C_6$)-alkenyl-($C_3$–$C_8$)-cycloalkyl, ($C_2$–$C_6$)-alkynyl-($C_3$–$C_8$)-cycloalkyl, ($C_1$–$C_6$)-alkyl-($C_4$–$C_8$)-cycloalkenyl, ($C_2$–$C_6$)-alkenyl-($C_4$–$C_8$)-cycloalkenyl,
where the fourteen last-mentioned radicals are optionally substituted by one or more radicals from the group
halogen, cyano, nitro, hydroxyl, thio, amino, formyl, ($C_1$–$C_6$)-alkoxy, ($C_2$–$C_6$)-alkenyloxy, ($C_2$–$C_6$)-alkynyloxy, ($C_1$–$C_6$)-haloalkyloxy, ($C_2$–$C_6$)-haloalkenyloxy, ($C_2$–$C_6$)-haloalkynyloxy, ($C_3$–$C_8$)-cycloalkoxy, ($C_4$–$C_8$)-cycloalkenyloxy, ($C_3$–$C_8$)-halocycloalkoxy, ($C_4$–$C_8$)-halocycloalkenyloxy, ($C_3$–$C_8$)-cycloalkyl-($C_1$–$C_4$)-alkoxy, ($C_4$–$C_8$)-cycloalkenyl-($C_1$–$C_4$)-alkoxy, ($C_3$–$C_8$)-cycloalkyl-($C_2$–$C_4$)-alkenyloxy, ($C_4$–$C_8$)-cycloalkenyl-($C_1$–$C_4$)-alkenyloxy, ($C_1$–$C_6$)-alkyl-($C_3$–$C_8$)-cycloalkoxy, ($C_2$–$C_6$)-alkenyl-($C_3$–$C_8$)-cycloalkoxy, ($C_2$–$C_6$)-alkynyl-($C_3$–$C_8$)-cycloalkoxy, ($C_1$–$C_6$)-alkyl-($C_4$–$C_8$)-cycloalkenyloxy, ($C_2$–$C_6$)-alkenyl-($C_4$–$C_8$)-cycloalkenyloxy, ($C_1$–$C_4$)-alkoxy-($C_1$–$C_6$)-alkoxy, ($C_1$–$C_4$)-alkoxy-($C_2$–$C_6$)-alkenyloxy, carbamoyl,
($C_1$–$C_6$)-mono- or dialkylcarbamoyl, ($C_1$–$C_6$)-mono- or dihaloalkylcarbamoyl, ($C_3$–$C_8$)-mono- or dicycloalkylcarbamoyl, ($C_1$–$C_6$)-alkoxycarbonyl, ($C_3$–$C_8$)-cycloalkoxycarbonyl, ($C_1$–$C_6$)-alkanoyloxy, ($C_3$–$C_8$)-cycloalkanoyloxy, ($C_1$–$C_6$)-haloalkoxycarbonyl, ($C_1$–$C_6$)-haloalkanoyloxy, ($C_1$–$C_6$)-alkaneamido, ($C_1$–$C_6$)-haloalkaneamido, ($C_2$–$C_6$)-alkeneamido, ($C_3$–$C_8$)-cycloalkaneamido, ($C_3$–$C_8$)-cycloalkyl-($C_1$–$C_4$)-alkaneamido, ($C_1$–$C_6$)-alkylthio, ($C_2$–$C_6$)-alkenylthio, ($C_2$–$C_6$)-alkynylthio, ($C_1$–$C_6$)-haloalkylthio, ($C_2$–$C_6$)-haloalkenylthio, ($C_2$–$C_6$)-haloalkynylthio, ($C_3$–$C_8$)-cycloalkylthio, ($C_4$–$C_8$)-cycloalkenylthio, ($C_3$–$C_8$)-halocycloalkthio, ($C_4$–$C_8$)-halocycloalkenylthio, ($C_3$–$C_8$)-cycloalkyl-($C_1$–$C_4$)-alkylthio, ($C_4$–$C_8$)-cycloalkenyl-($C_1$–$C_4$)-alkylthio, ($C_3$–$C_8$)-cycloalkyl-($C_2$–$C_4$)-alkenylthio, ($C_4$–$C_8$)-cycloalkenyl-($C_1$–$C_4$)-alkenylthio, ($C_1$–$C_6$)-alkyl-($C_3$–$C_8$)-cycloalkylthio, ($C_2$–$C_6$)-alkenyl-($C_3$–$C_8$)-cycloalkylthio, ($C_2$–$C_6$)-alkynyl-($C_3$–$C_8$)-cycloalkylthio, ($C_1$–$C_6$)-alkyl-($C_4$–$C_8$)-cycloalkenylthio, ($C_2$–$C_6$)-alkenyl-($C_4$–$C_8$)-cycloalkenylthio, ($C_1$–$C_6$)-alkylsulfinyl, ($C_2$–$C_6$)-alkenylsulfinyl, ($C_2$–$C_6$)-alkynylsulfinyl, ($C_1$–$C_6$)-haloalkylsulfinyl, ($C_2$–$C_6$)-haloalkenylsulfinyl, ($C_2$–$C_6$)-haloalkynylsulfinyl, ($C_3$–$C_8$)-cycloalkylsulfinyl, ($C_4$–$C_8$)-cycloalkenylsulfinyl, ($C_3$–$C_8$)-halocycloalksulfinyl, ($C_4$–$C_8$)-halocycloalkenylsulfinyl, ($C_3$–$C_8$)-cycloalkyl-($C_1$–$C_4$)-alkylsulfinyl, ($C_4$–$C_8$)-cycloalkenyl-($C_1$–$C_4$)-alkylsulfinyl, ($C_3$–$C_8$)-cycloalkyl-($C_2$–$C_4$)-alkenylsulfinyl, ($C_4$–$C_8$)-cycloalkenyl-($C_1$–$C_4$)-alkenylsulfinyl, ($C_1$–$C_6$)-alkyl-($C_3$–$C_8$)-cycloalkylsulfinyl, ($C_2$–$C_6$)-alkenyl-($C_3$–$C_8$)-cycloalkylsulfinyl, ($C_2$–$C_6$)-alkynyl-($C_3$–$C_8$)-cycloalkylsulfinyl, ($C_1$–$C_6$)-alkyl-($C_4$–$C_8$)-cycloalkenylsulfinyl, ($C_2$–$C_6$)-alkenyl-($C_4$–$C_8$)-cycloalkenylsulfinyl, ($C_1$–$C_6$)-alkylsulfonyl, ($C_2$–$C_6$)-alkenylsulfonyl, ($C_2$–$C_6$)-alkynylsulfonyl, ($C_1$–$C_6$)-haloalkylsulfonyl, ($C_2$–$C_6$)-haloalkenylsulfonyl, ($C_2$–$C_6$)-haloalkynylsulfonyl, ($C_3$–$C_8$)-cycloalkylsulfonyl, ($C_4$–$C_8$)-cycloalkenylsulfonyl, ($C_3$–$C_8$)-halocycloalksulfonyl, ($C_4$–$C_8$)-halocycloalkenylsulfonyl, ($C_3$–$C_8$)-cycloalkyl-($C_1$–$C_4$)-alkylsulfonyl, ($C_4$–$C_8$)-cycloalkenyl-($C_1$–$C_4$)-alkylsulfonyl, ($C_3$–$C_8$)-cycloalkyl-($C_2$–$C_4$)-alkenylsulfonyl, ($C_4$–$C_8$)-cycloalkenyl-($C_1$–$C_4$)-alkenylsulfonyl, ($C_1$–$C_6$)-alkyl-($C_3$–$C_8$)-cycloalkylsulfonyl, ($C_2$–$C_6$)-alkenyl-($C_3$–$C_8$)-cycloalkylsulfonyl, ($C_2$–$C_6$)-alkynyl-($C_3$–$C_8$)-cycloalkylsulfonyl, ($C_1$–$C_6$)-alkyl-($C_4$–$C_8$)-cycloalkenylsulfonyl, ($C_2$–$C_6$)-alkenyl-($C_4$–$C_8$)-cycloalkenylsulfonyl, ($C_1$–$C_6$)-alkylamino, ($C_2$–$C_6$)-alkenylamino, ($C_2$–$C_6$)-alkynylamino, ($C_1$–$C_6$)-haloalkylamino, ($C_2$–$C_6$)-haloalkenylamino, ($C_2$–$C_6$)-haloalkynylamino, ($C_3$–$C_8$)-cycloalkylamino, ($C_4$–$C_8$)-cycloalkenylamino, ($C_3$–$C_8$)-halocycloalkamino, ($C_4$–$C_8$)-halocycloalkenylamino, ($C_3$–$C_8$)-cycloalkyl-($C_1$–$C_4$)-alkylamino, ($C_4$–$C_8$)-cycloalkenyl-($C_1$–$C_4$)-alkylamino, ($C_3$–$C_8$)-cycloalkyl-($C_2$–$C_4$)-alkenylamino, ($C_4$–$C_8$)-cycloalkenyl-($C_1$–$C_4$)-alkenylamino, ($C_1$–$C_6$)-alkyl-($C_3$–$C_8$)-cycloalkylamino, ($C_2$–$C_6$)-alkynyl-($C_3$–$C_8$)-cycloalkylamino, ($C_1$–$C_6$)-alkyl-($C_4$–$C_8$)-cycloalkenylamino, ($C_2$–$C_6$)-alkenyl-($C_4$–$C_8$)-cycloalkenylamino, ($C_1$–$C_6$)-trialkylsilyl, aryl, aryloxy, arylthio, arylamino, aryl-($C_1$–$C_4$)-alkoxy, aryl-($C_2$–$C_4$)-alkenyloxy, aryl-$(C_1$–$C_4)$-alkylthio, aryl-$(C_2$–$C_4)$-alkenylthio, aryl-$(C_1$–$C_4)$-alkylamino, aryl-$(C_2$–$C_4)$-alkenylamino, aryl-$(C_1$–$C_6)$-dialkylsilyl, diaryl-$(C_1$–$C_6)$-alkylsilyl, triarylsilyl and 5- or 6-membered heterocyclyl,
where the cyclic moiety of the fourteen last-mentioned radicals is optionally substituted by one or more radicals from the group
halogen, cyano, nitro, amino, hydroxyl, thio, $(C_1$–$C_4)$-alkyl, $(C_1$–$C_4)$-haloalkyl, $(C_3$–$C_8)$-cycloalkyl, $(C_1$–$C_4)$-alkoxy, $(C_1$–$C_4)$-haloalkoxy, $(C_1$–$C_4)$-alkylthio, $(C_1$–$C_4)$-haloalkylthio, $(C_1$–$C_4)$-alkylamino, $(C_1$–$C_4)$-haloalkylamino, formyl and $(C_1$–$C_4)$-alkanoyl;
aryl, 5- or 6-membered heteroaromatic,
where the two last-mentioned radicals are optionally substituted by one or more radicals from the group
halogen, cyano, nitro, hydroxyl, thio, amino, formyl, $(C_1$–$C_6)$-alkoxy, $(C_2$–$C_6)$-alkenyloxy, $(C_2$–$C_6)$-alkynyloxy, $(C_1$–$C_6)$-haloalkyloxy, $(C_2$–$C_6)$-haloalkenyloxy, $(C_2$–$C_6)$-haloalkynyloxy, $(C_3$–$C_8)$-cycloalkoxy, $(C_4$–$C_8)$-cycloalkenyloxy, $(C_3$–$C_8)$-halocycloalkoxy, $(C_4$–$C_8)$-halocycloalkenyloxy, carbamoyl, $(C_1$–$C_6)$-mono- or dialkylcarbamoyl, $(C_1$–$C_6)$-alkoxycarbonyl, $(C_1$–$C_6)$-alkanoyloxy, $(C_1$–$C_6)$-mono- or dihaloalkylcarbamoyl, $(C_1$–$C_6)$-haloalkoxycarbonyl, $(C_1$–$C_6)$-haloalkanoyloxy, $(C_1$–$C_6)$-alkaneamido, $(C_1$–$C_6)$-haloalkaneamido, $(C_2$–$C_6)$-alkeneamido, $(C_1$–$C_6)$-alkylthio, $(C_2$–$C_6)$-alkenylthio, $(C_2$–$C_6)$-alkynylthio, $(C_1$–$C_6)$-haloalkylthio, $(C_2$–$C_6)$-haloalkenylthio, $(C_2$–$C_6)$-haloalkynylthio, $(C_3$–$C_8)$-cycloalkylthio, $(C_4$–$C_8)$-cycloalkenylthio, $(C_3$–$C_8)$-halocycloalkthio, $(C_4$–$C_8)$-halocycloalkenylthio, $(C_1$–$C_6)$-alkylsulfinyl, $(C_2$–$C_6)$-alkenylsulfinyl, $(C_2$–$C_6)$-alkynylsulfinyl, $(C_1$–$C_6)$-haloalkylsulfnyl, $(C_2$–$C_6)$-haloalkenylsulfinyl, $(C_2$–$C_6)$-haloalkynylsulfinyl, $(C_3$–$C_8)$-cycloalkylsulfinyl, $(C_4$–$C_8)$-cycloalkenylsulfinyl, $(C_3$–$C_8)$-halocycloalksulfinyl, $(C_4$–$C_8)$-halocycloalkenylsulfinyl, $(C_1$–$C_6)$-alkylsulfonyl, $(C_2$–$C_6)$-alkenylsulfonyl, $(C_2$–$C_6)$-alkynylsulfonyl, $(C_1$–$C_6)$-haloalkylsulfonyl, $(C_2$–$C_6)$-haloalkenylsulfonyl, $(C_2$–$C_6)$-haloalkynylsulfonyl, $(C_3$–$C_8)$-cycloalkylsulfonyl, $(C_4$–$C_8)$-cycloalkenylsulfonyl, $(C_3$–$C_8)$-halocycloalksulfonyl, $(C_4$–$C_8)$-halocycloalkenylsulfonyl, $(C_1$–$C_6)$-alkylamino, $(C_2$–$C_6)$-alkenylamino, $(C_2$–$C_6)$-alkynylamino, $(C_1$–$C_6)$-haloalkylamino, $(C_2$–$C_6)$-haloalkenylamino, $(C_2$–$C_6)$-haloalkynylamino, $(C_3$–$C_8)$-cycloalkylamino, $(C_4$–$C_8)$-cycloalkenylamino, $(C_3$–$C_8)$-halocycloalkylamino and $(C_4$–$C_8)$-halocycloalkenylamino;
$R^{11}$ is $(C_1$–$C_{10})$-alkyl, haloalkyl, aryl,
which is optionally substituted by one or more radicals from the group
halogen, cyano, nitro, $(C_1$–$C_4)$-alkoxy, $(C_1$–$C_4)$-alkyl, amino, $(C_1$–$C_4)$-monoalkylamino and $(C_1$–$C_4)$-dialkylamino;
$NR^{10}{}_2$, $OR^{10}$ or $SR^{10}$.

The term "halogen" includes fluorine, chlorine, bromine and iodine.

The term "$(C_1$–$C_4)$-alkyl" is to be understood as a straight-chain or branched hydrocarbon radical having 1, 2, 3 or 4 carbon atoms, such as, for example, the methyl, ethyl, propyl, isopropyl, 1-butyl, 2-butyl, 2-methylpropyl or tert-butyl radical. Correspondingly, alkyl radicals having a greater range of carbon atoms are to be understood as straight-chain or branched saturated hydrocarbon radicals which contain a number of carbon atoms which corresponds to the range stated. Thus, the term "$(C_1$–$C_6)$-alkyl" includes the abovementioned alkyl radicals, and, for example, the pentyl, 2-methylbutyl, 1,1-dimethylpropyl, hexyl radical. The term "$(C_1$–$C_{10})$-alkyl" is to be understood as the abovementioned alkyl radicals, and, for example, the nonyl, 1-decyl or 2-decyl radical and the term "$(C_1$–$C_{20})$-alkyl" is to be understood as the abovementioned alkyl radicals, and, for example, the undecyl, dodecyl, pentadecyl or eicosyl radical.

"$(C_1$–$C_4)$-Haloalkyl" is to be understood as an alkyl group mentioned under the term "$(C_1$–$C_4)$-alkyl" in which one or more hydrogen atoms are replaced by the same number of identical or different halogen atoms, preferably by fluorine or chlorine, such as the trifluoromethyl, the 1-fluoroethyl, the 2,2,2-trifluoroethyl, the chloromethyl, fluoromethyl, the difluoromethyl and the 1,1,2,2-tetrafluoroethyl group.

"$(C_1$–$C_4)$-Alkoxy" is to be understood as an alkoxy group whose hydrocarbon radical has the meaning given under the term "$(C_1$–$C_4)$-alkyl". Alkoxy groups embracing a greater range of carbon atoms are to be understood correspondingly.

The terms "alkenyl" and "alkynyl" having a prefix stating the range of carbon atoms denote a straight-chain or branched hydrocarbon radical having a number of carbon atoms corresponding to the range stated which comprises at least one multiple bond which may be in any position of the unsaturated radical in question. "$(C_2$–$C_4)$-Alkenyl" is thus, for example, the vinyl, allyl, 2-methyl-2-propene or 2-butenyl group; "$(C_2$–$C_6)$-alkenyl" denotes the abovementioned radicals and, for example, the pentenyl, 2-methylpentenyl or the hexenyl group. The term "$(C_2$–$C_{20})$-alkenyl" is to be understood as the abovementioned radicals and, for example, the 2-decenyl or the 2-eicosenyl group. "$(C_2$–$C_4)$-Alkynyl" is, for example, the ethynyl, propargyl, 2-methyl-2-propyne or 2-butynyl group. "$(C_2$–$C_6)$-Alkynyl" is to be understood as the abovementioned radicals and, for example, the 2-pentynyl- or the 2-hexynyl group and "$(C_2$–$C_{20})$-alkynyl" is to be understood as the abovementioned radicals and, for example, the 2-octynyl or the 2-decynyl group.

"$(C_3$–$C_8)$-Cycloalkyl" denotes monocyclic alkyl radicals, such as the cyclopropyl, cyclobutyl, cyclopentyl, cyclohexyl, cycloheptyl or cyclooctyl radical and bicyclic alkyl radicals, such as the norbornyl radical.

The term "$(C_3$–$C_8)$-cycloalkyl-$(C_1$–$C_4)$-alkyl" is to be understood as, for example, the cyclopropylmethyl, cyclopentylmethyl, cyclohexylmethyl, cyclohexylethyl and cyclohexylbutyl radical, and the term "$(C_1$–$C_6)$-alkyl-$(C_3$–$C_8)$-cycloalkyl is to be understood as, for example, the 1-methylcyclopropyl, 1-methylcyclopentyl, 1-methylcyclohexyl, 3-hexylcyclobutyl and 4-tert-butyl-cyclohexyl radical.

"$(C_1$–$C_4)$-Alkoxy-$(C_1$–$C_6)$-alkyloxy" is an alkoxy group as defined above which is substituted by a further alkoxy group, such as, for example, 1-ethoxyethoxy.

"$(C_3$–$C_8)$-Cycloalkoxy" or "$(C_3$–$C_8)$-cycloalkylthio" is to be understood as one of the abovementioned $(C_3$–$C_8)$-cycloalkyl radicals which is linked via an oxygen or sulfur atom.

"$(C_3$–$C_8)$-Cycloalkyl-$(C_1$–$C_6)$-alkoxy" is, for example, the cyclopropylmethoxy, cyclobutylmethoxy, cyclopentylmethoxy, cyclohexylmethoxy, cyclohexylethoxy or the cyclohexylbutoxy group;

The term "$(C_1-C_4)$-alkyl-$(C_3-C_8)$-cycloalkoxy" is, for example, the methylcyclopropyloxy, methylcyclobutyloxy or the butylcyclohexyloxy group.

"$(C_1-C_6)$-Alkylthio" is an alkylthio group whose hydrocarbon radical has the meaning given under the term "$(C_1-C_6)$-alkyl".

Correspondingly, "$(C_1-C_6)$-alkylsulfinyl" is, for example, the methyl-, ethyl-, propyl-, isopropyl-, butyl-, isobutyl-, sec-butyl- or tert-butylsulfinyl group and "$(C_1-C_6)$-alkylsulfonyl" is, for example, the methyl-, ethyl-, propyl-, isopropyl-, butyl-, isobutyl-, sec-butyl- or tert-butylsulfonyl group.

"$(C_1-C_6)$-Alkylamino" is a nitrogen atom which is substituted by one or two identical or different alkyl radicals of the above definition.

The term "$(C_1-C_6)$-mono- or dialkylcarbamoyl" is a carbamoyl group having one or two hydrocarbon radicals which have the meaning given under the term "$(C_1-C_6)$-alkyl)" and which, in the case of two hydrocarbon radicals, may be identical or different.

Correspondingly, "$(C_1-C_6)$-dihaloalkylcarbamoyl" is a carbamoyl group which carries two $(C_1-C_6)$-haloalkyl radicals in accordance with the above definition or one $(C_1-C_6)$-haloalkyl radical and one $(C_1-C_6)$-alkyl radical in accordance with the above definition.

"$(C_1-C_6)$-Alkanoyl" is, for example, the acetyl, propionyl, butyryl or 2-methylbutyryl group.

The term "aryl" is to be understood as an isocyclic aromatic radical preferably having 6 to 14, in particular 6 to 12, carbon atoms, such as, for example, phenyl, naphthyl or biphenylyl, preferably phenyl. "Aroyl" is thus an aryl radical as defined above which is attached via a carbonyl group, such as, for example, the benzoyl group.

The term "heterocyclyl" denotes a cyclic radical which may be fully saturated, partially unsaturated or fully unsaturated and which may be interrupted by at least one or more identical atoms from the group nitrogen, sulfur or oxygen, oxygen atoms, however, not being directly adjacent to one another and at least one carbon atom being present in the ring, such as, for example, a thiophene, furan, pyrrole, thiazole, oxazole, imidazole, isothiazole, isoxazole, pyrazole, 1,3,4-oxadiazole, 1,3,4-thiadiazole, 1,3,4-triazole, 1,2,4-oxadiazole, 1,2,4-thiadiazole, 1,2,4-triazole, 1,2,3-triazole, 1,2,3,4-tetrazole, benzo[b]thiophene, benzo[b]furan, indole, benzo[c]thiophene, benzo[c]furan, isoindole, benzoxazole, benzothiazole, benzimidazole, benzisoxazole, benzisothiazole, benzopyrazole, benzothiadiazole, benzotriazole, dibenzofuran, dibenzothiophene, carbazole, pyridine, pyrazine, pyrimidine, pyridazine, 1,3,5-triazine, 1,2,4-triazine, 1,2,4,5-tetrazine, quinoline, isoquinoline, quinoxaline, quinazoline, cinnoline, 1,8-naphthyridine, 1,5-naphthyridine, 1,6-naphthyridine, 1,7-naphthyridine, phthalazine, pyridopyrimidine, purine, pteridine 4H-quinolizine; piperidine, pyrrolidine, oxazoline, tetrahydrofuran, tetrahydropyran, isoxazolidine or thiazolidine radical. The term "heteroaromatic" thus embraces, from among the meanings mentioned above under "heterocyclyl", in each case the fully unsaturated aromatic heterocyclic compounds.

"Aryl-$(C_1-C_4)$-alkoxy" is an aryl radical which is attached via a $(C_1-C_4)$-alkoxy group, for example the benzyloxy, phenylethoxy, phenylbutoxy or naphthylmethoxy radical.

"Arylthio" is an aryl radical attached via a sulfur atom, for example the phenylthio or the 1- or 2-naphthylthio radical. Correspondingly, "aryloxy" is, for example, the phenoxy or 1- or 2-naphthyloxy radical.

"Aryl-$(C_1-C_4)$-alkylthio" is an aryl radical which is attached via an alkylthio radical, for example the benzylthio, naphthylmethylthio or the phenylethylthio radical.

The term "$(C_1-C_6)$-trialkylsilyl" denotes a silicon atom which carries three identical or different alkyl radicals in accordance with the above definition. Correspondingly "aryl-$(C_1-C_6)$-dialkylsilyl" is a silicon atom which carries one aryl radical and two identical or different radicals in accordance with the above definition, "diaryl-$(C_1-C_6)$-alkylsilyl" is a silicon atom which carries one alkyl radical and two identical or different aryl radicals in accordance with the above definition, and "triarylsilyl" is a silicon atom which carries three identical or different aryl radicals in accordance with the above definition.

In cases where two or more radicals $R^{10}$ are present in a substituent, such as, for example, in $—C(=W)NR^{10}{}_2$, these radicals may be identical or different.

Preference is given to those compounds of the formula I in which

Y is $C_1-C_6$-alkyl which is mono- or polysubstituted by chlorine and/or fluorine;

m is zero;

Q is a 5-membered heterocyclic group

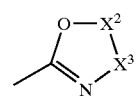

in which
a) $X^2=NR^a$ and $X^3=CR^bR^1$ or
b) $X^2=CR^aR^2$ and $X^3=CR^bR^3$ or
c) $X^2=CR^4R^5$ and $X^3=CR^6R^7$;

$R^a$ and $R^b$ together are a bond;

$R^1$, $R^2$, $R^3$, $R^4$ and $R^6$ are each independently of one another hydrogen, halogen, $C_1-C_{12}$-alkyl, $C_3-C_8$-cycloalkyl, $C_2-C_8$-alkenyl, $C_2-C_8$-alkynyl, where the four last-mentioned hydrocarbon radicals are optionally mono- or polysubstituted by identical or different radicals from a group A1 consisting of $C_1-C_6$-alkylcarbonyl, $C_1-C_6$-alkylaminocarbonyl, $C_1-C_6$-alkoxy, $C_1-C_6$-alkylthio, $C_1-C_6$-alkylamino, $C_1-C_6$-alkylcarbonylamino, $C_1-C_6$-alkylsulfonylamino, phenyl, furyl, pyrryl, thienyl, halogen, cyano, phenyloxy, phenylthio and phenylamino, where the eleven first-mentioned radicals of group A1 are each optionally mono- or polysubstituted by identical or different radicals from a group B1 consisting of halogen, cyano, $C_1-C_3$-alkoxy and phenyl which is optionally mono- or polysubstituted by one or more halogen atoms and where the three last-mentioned radicals of group A1 are each optionally mono- or polysubstituted by identical or different radicals from a group B2 consisting of halogen, cyano, nitro, $C_1-C_3$-alkyl and $C_1-C_3$-alkoxy, or are $C_1-C_6$-alkylcarbonyl, $C_1-C_6$-alkylaminocarbonyl, $C_1-C_6$-alkoxycarbonyl, phenyl, pyridyl, furyl, thienyl, pyrryl, where the eight last-mentioned radicals are optionally mono- or polysubstituted by identical or different radicals from group B1, or are $OR^{10}$, $SR^{10}$ or $N(R^{10})_2$;

$R^5$ and $R^7$ are each independently of one another hydrogen, halogen, $C_1-C_{12}$-alkyl, $C_3-C_8$-cycloalkyl, $C_2-C_8$-alkenyl, $C_2-C_8$-alkynyl, where the four last-mentioned hydrocarbon radicals are optionally mono- or polysubstituted by identical or different radicals from a group A2 consisting of $C_1-C_6$-alkylcarbonyl, $C_1$–$C_6$-alkylaminocarbonyl, $C_1$–$C_6$-alkoxy, $C_1$–$C_6$-alkylthio, $C_1$–$C_6$-alkylamino, $C_1$–$C_6$-alkylcarbonylamino, phenyl, furyl, pyrryl, thienyl, halogen, cyano, phenyloxy, phenylthio and phenylamino, where the ten first-mentioned radicals of group A2 are each optionally mono- or polysubstituted by identical or different radicals from the group B1 and the three last-mentioned radicals of group A2 are each optionally mono- or polysubstituted by identical or different radicals from the group B2, or are $C_1$–$C_6$-alkylcarbonyl, $C_1$–$C_6$-alkylaminocarbonyl, $C_1$–$C_6$-alkoxycarbonyl, phenyl, pyridyl, furyl, thienyl, pyrryl, where the eight last-mentioned radicals are optionally mono- or polysubstituted by identical or different radicals from the group B1, or are $OR^{10}$, $SR^{10}$ or $N(R^{10})_2$;

$R^{10}$ is hydrogen, benzyl, $C_1$–$C_6$-alkyl, $C_1$–$C_6$-cycloalkyl, $C_2$–$C_6$-alkenyl, $C_2$–$C_6$-alkynyl, phenyl, $C_1$–$C_6$-alkylcarbonyl or $C_1$–$C_6$-alkylsulfonyl, where the eight last-mentioned radicals are optionally mono- or polysubstituted by identical or different halogen atoms.

Particular preference is given to compounds of the formula I in which

Y is trifluoromethyl;

$R^1$, $R^2$, $R^3$, $R^4$ and $R^6$ are each independently of one another halogen, $C_1$–$C_{12}$-alkyl, $C_2$–$C_{12}$-alkenyl, where the two last-mentioned radicals are optionally mono- or polysubstituted by identical or different radicals from a group A3 consisting of $C_1$–$C_4$-alkylcarbonyl, $C_1$–$C_4$-alkylaminocarbonyl, $C_1$–$C_4$-alkoxy, $C_1$–$C_4$-alkylthio, $C_1$–$C_4$-alkylamino, $C_1$–$C_4$-alkylcarbonylamino, $C_1$–$C_4$-alkylsulfonylamino, phenyl, furyl, pyrryl, thienyl, fluorine, chlorine, bromine, cyano, phenyloxy, phenylthio and phenylamino, where the eleven first-mentioned radicals of group A3 are each optionally mono- or polysubstituted by identical or different radicals from the group B1 and the three last-mentioned radicals of group A3 are each optionally mono- or polysubstituted by identical or different radicals from the group B2, or are $OR^{10}$, $SR^{10}$ or $N(R^{10})_2$;

$R^5$ and $R^7$ are each independently of one another halogen, $C_1$–$C_{12}$-alkyl, $C_2$–$C_{12}$-alkenyl, where the two last-mentioned radicals are optionally mono- or polysubstituted by identical or different radicals from a group A4 consisting of $C_1$–$C_4$-alkylcarbonyl, $C_1$–$C_4$-alkylaminocarbonyl, $C_1$–$C_4$-alkoxy, $C_1$–$C_4$-alkylthio, $C_1$–$C_4$-alkylamino, $C_1$–$C_4$-alkylcarbonylamino, phenyl, furyl, pyrryl, thienyl, fluorine, chlorine, bromine, cyano, phenyloxy, phenylthio and phenylamino, where the ten first-mentioned radicals of group A4 are each optionally mono- or polysubstituted by identical or different radicals from the group B1 and the three last-mentioned radicals of group A4 are each optionally mono- or polysubstituted by identical or different radicals from the group B2, or are $OR^{10}$, $SR^{10}$ or $N(R^{10})_2$;

$R^{10}$ is hydrogen, $C_1$–$C_6$-alkyl, $C_2$–$C_6$-alkenyl, $C_2$–$C_6$-alkynyl, phenyl, $C_1$–$C_4$-alkylcarbonyl or $C_1$–$C_4$-alkylsulfonyl, where the six last-mentioned radicals are optionally mono- or polysubstituted by identical or different halogen atoms.

Very particular preference is given to compounds of the formula I in which $R^1$, $R^2$, $R^3$, $R^4$ and $R^6$ are each independently of one another $C_1$–$C_{10}$-alkyl, $C_2$-$C_{10}$-alkenyl, where the two last-mentioned radicals are optionally mono- or polysubstituted by identical or different radicals from a group A5 consisting of $C_1$–$C_4$-alkylcarbonyl, $C_1$–$C_4$-alkylaminocarbonyl, $C_1$–$C_4$-alkoxy, $C_1$–$C_4$-alkylthio, $C_1$–$C_4$-alkylamino, $C_1$–$C_4$-alkylcarbonylamino, $C_1$–$C_4$-alkylsulfonylamino, phenyl, fluorine, chlorine, bromine, cyano, phenyloxy, phenylthio and phenylamino, where the eight first-mentioned radicals of group A5 are each optionally mono- or polysubstituted by identical or different radicals from the group B1 and the three last-mentioned radicals of group A5 are each optionally mono- or polysubstituted by identical or different radicals from the group B2;

$R^5$ and $R^7$ are each independently of one another $C_1$–$C_{10}$-alkyl, $C_2$–$C_{10}$-alkenyl, where the two last-mentioned radicals are optionally mono- or polysubstituted by identical or different radicals from a group A6 consisting of $C_1$–$C_4$-alkylcarbonyl, $C_1$–$C_4$-alkylaminocarbonyl, $C_1$–$C_4$-alkoxy, $C_1$–$C_4$-alkylthio, $C_1$–$C_4$-alkylamino, $C_1$–$C_4$-alkylcarbonylamino, phenyl, fluorine, chlorine, bromine, cyano, phenyloxy, phenylthio and phenylamino, where the seven first-mentioned radicals of group A6 are each optionally mono- or polysubstituted by identical or different radicals from the group B1 and the three last-mentioned radicals of group A6 are each optionally mono- or polysubstituted by identical or different radicals from the group B2.

Depending on the nature of the substituents defined above, the compounds of the formula (I) have acidic or basic properties and can form salts. If the compounds of the formula (I) carry, for example, groups such as hydroxyl, carboxyl and other groups inducing acidic properties, these compounds can be reacted with bases to give salts. Suitable bases are, for example, hydroxides, carbonates, bicarbonates of the alkali metals and alkaline earth metals, in particular those of sodium, potassium, magnesium and calcium, further ammonia, primary, secondary and tertiary amines having ($C_1$–$C_4$)-alkyl radicals and also mono-, di- and trialkanolamines of ($C_1$–$C_4$)-alkanols. If the compounds of the formula (I) carry, for example, groups such as amino, alkylamino and other groups inducing basic properties, these compounds can be reacted with acids to give salts. Suitable acids are, for example, mineral acids, such as hydrochloric acid, sulfuric acid and phosphoric acid, organic acids, such as acetic acid, oxalic acid and acidic salts, such as $NaHSO_4$ and $KHSO_4$. The salts which can be obtained in this manner likewise have insecticidal, acaricidal and nematicidal properties.

The compounds of the formula (I) may have one or more asymmetric carbon atoms or stereoisomers on double bonds. Enantiomers or diastereomers may therefore be present. The invention embraces both the pure isomers and mixtures thereof. The mixtures of diastereomers can be separated into the isomers by customary methods, for example by selective crystallization from suitable solvents or by chromatography. Racemates can be separated into the enantiomers by customary methods.

The present invention also provides processes for preparing compounds of the formula I:

To prepare compounds of the formula (I) in which a) $X^1$=W, $X^2$=$NR^a$, $X^3$=$CR^bR^1$ and $R^a$, $R^b$ and $R^1$ are as defined above and W is oxygen, activated derivatives of the acid of the formula (II)

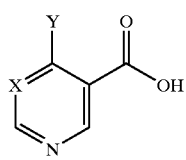
(II)

where X and Y are as defined above, are reacted in the presence of a base with a compound of the formula (III)

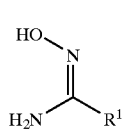
(III)

in which the radical $R^1$ is as defined in formula (I). Suitable activated derivatives are, for example, acyl halides, esters and anhydrides. Suitable bases are amines, such as triethylamine, diisopropylethylamine, pyridine or lutidine, alkali metal hydroxides, alkali metal alkoxides, such as sodium ethoxide or potassium tert-butoxide, or alkylmetal compounds, such as butyllithium.

Depending on the conditions, the reaction described above can be carried out as a one-step process or as a two-step process via intermediates of the formula (IV):

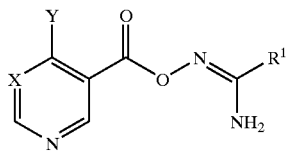
(IV)

Compounds of the formula (IV) can be cyclized to the 1,2,4-oxadiazoles by heating in an inert solvent at temperatures of up to 180° C.

Compounds of the formula (IV) are also directly obtainable from the acid of the formula (II) and amidoximes of the formula (III) by using a dehydrating reagent such as dicyclohexylcarbodiimide, 1-ethyl-3-(3-dimethylaminopropyl)carbodiimide or N,N'-carbonyldiimidazole.

Both acids of the formula (II) and amidoximes of the formula (III) are commercially available or can be prepared by methods known from the literature (see, for example: Houben-Weyl, Methoden der organischen Chemie, Volume X/4, pages 209–212; EP-A 0 580 374; G. F. Holland, J. N. Pereira, J. Med. Chem., 1967, 10, 149).

In the abovementioned case a) where W is sulfur, the compounds of the formula (I) can be obtained in a manner known from the literature by reaction of a compound of the formula (VII) with an electrophilic amination reagent, such as hydroxylamine-O-sulfonic acid (Y. Lin, S. A. Lang, S. R. Petty, J. Org. Chem. 1980, 45, 3750).

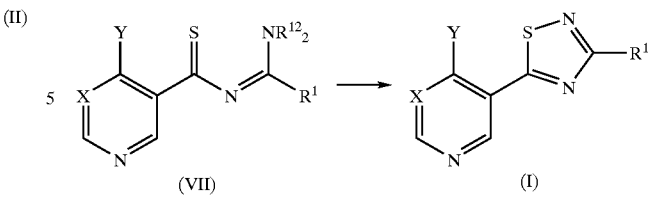
(VII) (I)

The compounds of the formula (VII) required as starting materials for this reaction can be prepared by reacting the thioamides of the formula (VIII) with dialkylamide dialkyl acetals, of formula (IX), where $R^1$ is as defined above and $R^{12}$ and $R^{13}$ are each $C_1$–$C_4$-alkyl.

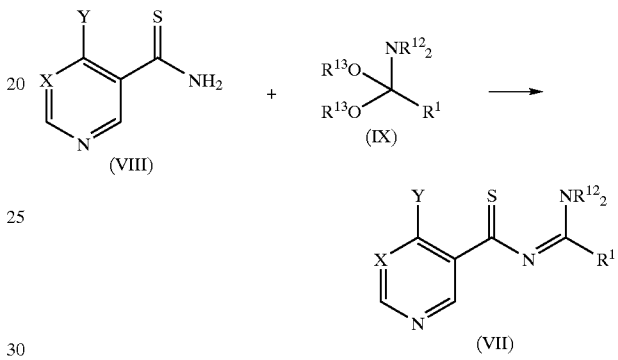

To prepare compounds of the formula (I) in which b) $X^1=NR^a$, $X^2=CR^bR^1$, $X^3=W$ and $R^a$, $R^b$ and $R^1$ are as defined above, and W is oxygen, amidoximes of the formula (V) can be reacted with activated derivatives of the acids of the formula (VI) or with the acids of the formula (VI) themselves.

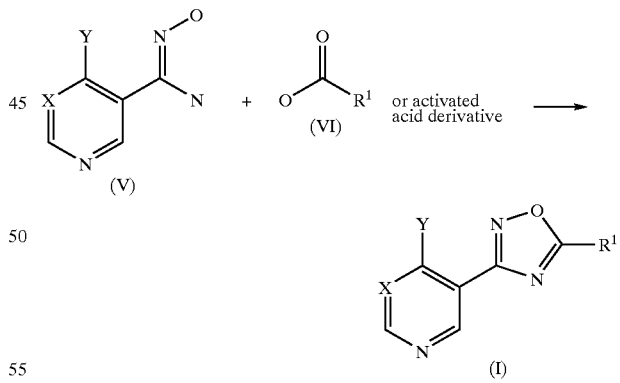

To prepare compounds of the formula (I) in which c) $X^1=V$, $X^2=CR^aR^1$, $X^3=NR^b$ and $R^a$, $R^b$ and $R^1$ are as defined above and V is sulfur, N,N'-diacylhydrazines of the formula (XIII) can be cyclized with a thiolation reagent, such as Lawesson's reagent (A. A. El-Barbary, S. Scheibyl, S. O. Lawesson, H. Fritz, Acta Chem. Scand. 1980, 597), in an inert solvent, such as toluene.

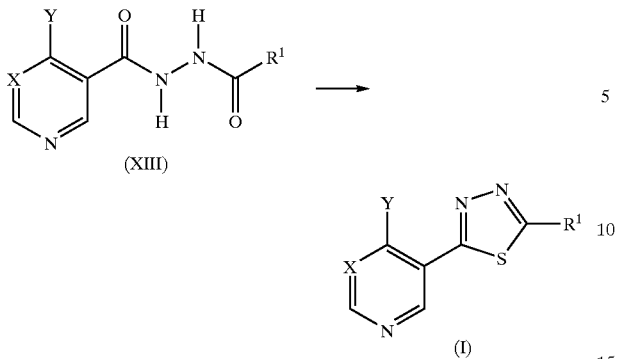

(XIII)

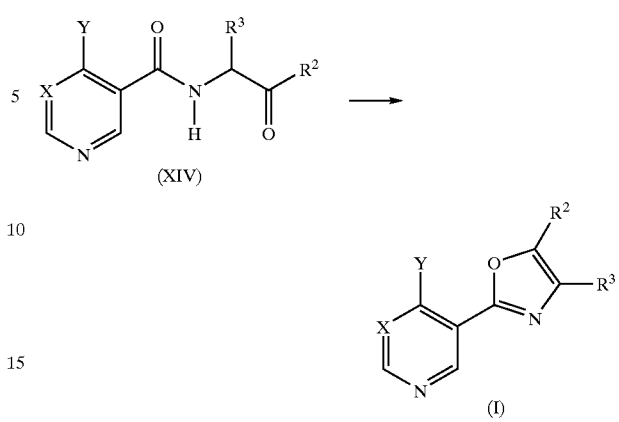

(XIV)

In the abovementioned case b) where W is oxygen, the compounds of the formula (I) can be prepared by reaction of acids of the formula (II) with hydrazines of the formula (X), in which $R^1$ is as defined above, using an activating reagent, such as phosphorus oxychloride or phosphorus pentachloride.

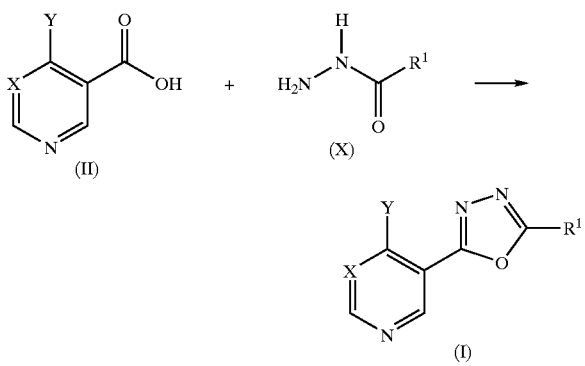

It is also possible to react acid hydrazides of the formula (XI) with ortho esters of the formula (XII) where $R^1$ is as defined above, and $R^{12}$ is $(C_1$–$C_4)$-alkyl.

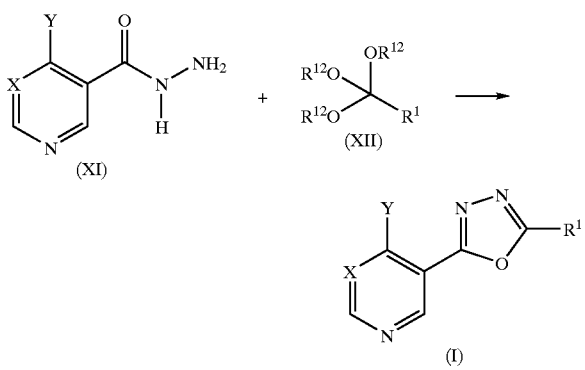

The reaction can be carried out with or without solvent and with or without an activating reagent. Suitable solvents are hydrocarbons, such as toluene, or ethers, such as 1,2-dimethoxyethane. A suitable activating reagent is, for example, phosphorus oxychloride. The reaction temperature is generally the reflux temperature of the solvent.

To prepare compounds of the formula (I) in which d) $X^1$=V, $X^2$=$CR^aR^2$, $X^3$=$CR^bR^3$ and $R^a$, $R^b$ and $R^3$ are as defined above and V is oxygen, compounds of the formula (XIV) are reacted with a dehydrating reagent.

Suitable dehydrating reagents are inorganic acyl chlorides, such as phosphorus oxychloride or thionyl chloride, inorganic acids, such as sulfuric acid or polyphosphoric acid, or a mixture of phosphoric acid and acetic anhydride (Houben-Weyl, Methoden der organischen Chemie, Volume E8a, pages 935–941).

The reaction can be carried out with or without a solvent. Suitable solvents are inert solvents, such as toluene, benzene, dimethoxyethane, dimethylformamide, dimethylacetamide and chlorobenzene. The reaction temperature is advantageously in a range between 50° C. and 150° C.

Compounds of the formula (XIV) can be obtained, for example, by oxidation of the corresponding hydroxyl compound of the formula (XV), it being possible to employ all reagents which are customarily used for this purpose in organic chemistry. (Milos Hudlický, "Oxidations in Organic Chemistry", ACS Monograph 186, American Chemical Society, Washington, D.C., 1990)

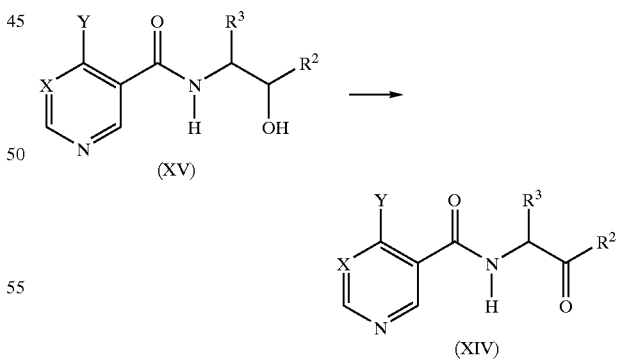

In the abovementioned case d) where V is sulfur, the compounds of the formula (I) can be prepared by condensation of thioamides of the formula (XVII) with carbonyl derivatives of the formula (XVIII), where Z is halogen, in particular chlorine or bromine, acyloxy or sulfonyloxy, in particular methanesulfonyloxy or tolylsulfonyloxy.

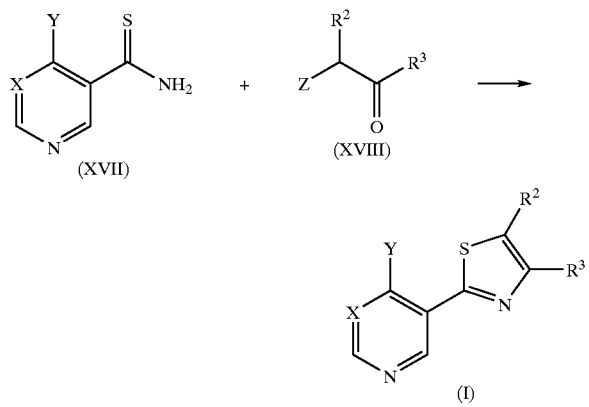

To prepare compounds of the formula (I) in which
e) $X^1=V$, $X^2=CR^4R^5$, $X^3=CR^6R^7$
and $R^4$, $R^5$, $R^6$ and $R^7$ are as defined above and V is oxygen, compounds of the formula (XV) are reacted with cyclization reagents, such as Burgess' reagent (G. M. Atkins, E. M. Burgess, J. Am. Chem. Soc. 1968, 90, 4744.), in a solvent such as tetrahydrofuran and 1,4-dioxane, at a temperature which is in a range between room temperature and the reflux temperature of the solvent.

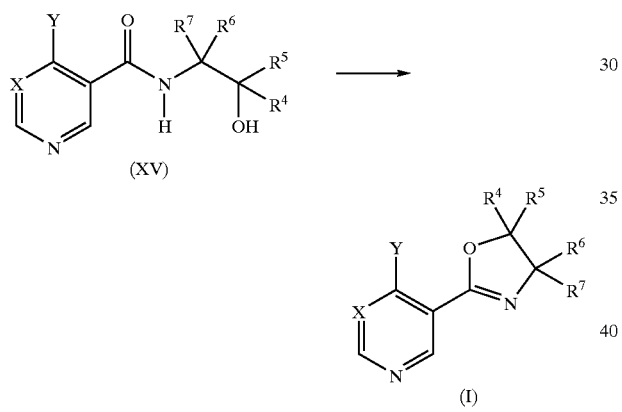

Compounds of the formula (XV) can be obtained by reacting activated derivatives of the acid in formula (II) with β-aminoalcohols of the formula (XVI), if appropriate in the presence of a base, such as, for example, triethylamine, in an inert solvent, such as, for example, dichlormethane.

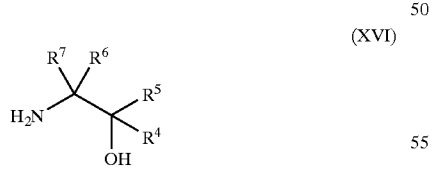

An acyl halide or an anhydride can be used as activated derivative of the acid.

A number of β-aminoalcohols of the formula (XVI) are commercially available. For others, there is a large number of preparation procedures in the literature, for example a reduction of a-amino acids (B. M. Trost "Comprehensive Organic Synthesis, Reduction", Volume 8, Pergamon Press, Oxford, 1991).

In the abovementioned case e) where V is sulfur, the compounds of the formula (I) can be prepared by reaction of thioamides of the formula (XVII) with compounds of the formula (XIX), the two substituents Z being as defined above and either identical or different (A. R. Katritzky "Comprehensive Heterocyclic Chemistry", Volume 6, pages 306–312, Pergamon Press, Oxford).

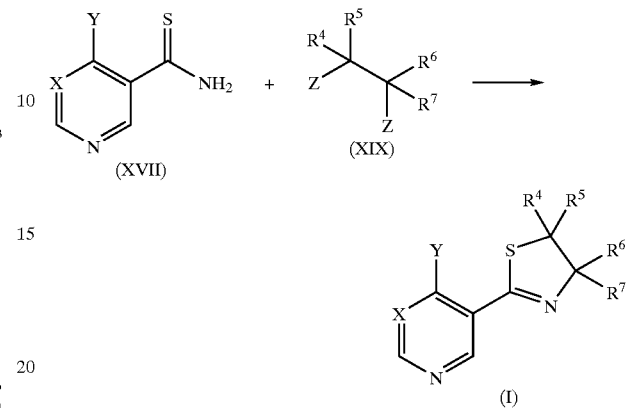

Thioamides of the formula (XVII) are either commercially available or can be obtained by addition of hydrogen sulfide to the corresponding carbonitriles in the presence of a base (A. E. S. Fairfull, J. L. Lowe, D. A. Peak, J. Chem. Soc. 1952, 742).

For preparing compounds of the formula (I) in which
f) $X^1=NR^a$, $X^2=CR^bR^1$, $X^3=NR^8$
and $R^a$, $R^b$, $R^1$ and $R^8$ are as defined above, hydrazides of the formula (XX)

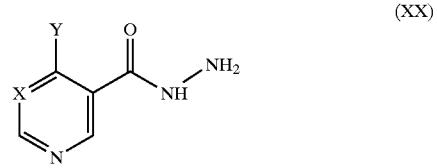

are reacted with a compound of the formula (XXI) or with thioamides of the formula (XXII) (Houben-Weyl, Methoden der organischen Chemie, Volume E8d, pages 510–512).

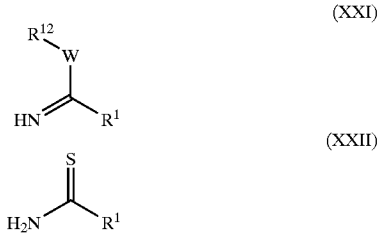

This reaction can be carried out with or without using a solvent, suitable solvents being alcohols, such as ethanol and propanol, or aromatic hydrocarbons, such as toluene and xylene. If the reaction is carried out in a solvent, the reaction temperature to be chosen is advantageously the reflux temperature of the solvent. If, on the other hand, the reaction is carried out without a solvent, it is possible to heat up to 200° C., if appropriate.

Once the group Q has been assembled, for example by condensation, cyclization or cycloaddition reactions, the radicals $R^1$ to $R^9$ may be derivatized further, if desired, employing the extensive arsenal of methods of organochemical synthesis.

To assemble compounds of the formula (I), in which m is 1, compounds of the formula (I) in which m is 0 can be treated with an oxidizing agent, such as, for example, meta-chloroperbenzoic acid.

The compounds of the formula (I) (also referred to as "active compounds" hereinbelow) have good plant tolerance, favorable homotherm toxicity and advantageous properties with respect to aquatic organisms and are suitable for controlling animal pests, in particular insects, arachnids (Acarina), helminths and mollusks, especially preferably for controlling insects and arachnids which are encountered in agriculture, in animal husbandry, in forests, in the preservation of stored products and materials and in the hygiene sector. They are active against normally sensitive and resistant species and all or individual stages of development. It has to be emphasized that the control of animal pests may be the result both of a toxic action of the compounds according to the invention and of a deterrent (repellant) action. The abovementioned pests include:

From the order of the Acarina, for example, *Acarus siro*, Argas spp., Ornithodoros spp., *Dermanyssus gallinae, Eriophyes ribis, Phyllocoptruta oleivora*, Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa*, Panonychus spp., Tetranychus spp., Eotetranychus spp., Oligonychus spp., and Eutetranychus spp.

From the order of the Isopoda, for example, *Oniscus asselus, Armadium vulgar* and *Porcellio scaber.*

From the order of the Diplopoda, for example, *Blaniulus guttulatus.*

From the order of the Chilopoda, for example, *Geophilus carpophagus* and Scutigera spp.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea madeirae, Blatella germanica, Acheta domesticus,* Gryllotalpa spp., *Locusta migratoria migratorioides, Melanoplus differentialis* and *Schistocerca gregaria.*

From the order of the Isoptera, for example, Reticulitermes spp.

From the order of the Anoplura, for example, *Phylloera vastatrix,* Pemphigus spp., *Pediculus humanus corporis,* Haematopinus spp. and Linognathus spp.

From the order of the Mallophaga, for example, Trichodectes spp. and Damalinea spp.

From the order of the Thysanoptera, for example, *Hercinothrips femoralis, Thrips tabaci* and Frankliniella spp.

From the order of the Heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum,* Aphis spp., *Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelus bilobatus, ephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehnielia, Galleria mellonella, Cacoecia podana, Capua reticulana, Choristoneura fumiferana, Clysia ambiguella, Homona magnanima, Tortrix viridana,* Cuaphalocrocis spp. and Manduca spp.

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylloides chrysocephala, Epilachna varivestis,* Atomaria spp., *Oryzaephilus surinamensis,* Anthonumus spp., Sitophilus spp., *Otiorrhynchus sulcatus, Cosmopolites sordidus, Ceuthorrynchus assimilis, Hypera postica,* Dermestes spp., Trogoderma, Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis, Costelytra zealandica* and Lissorhoptus spp.

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hypobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.*

From the order of the Siphonaptera, for example, *Xenopsylla cheopsis* and Ceratophyllus spp. From the order of the Arachnida, for example, *Scorpio maurus* and *Latrodectus mactans.* From the class of helminths, for example, Haemonchus, Trichostrongulus, Ostertagia, Cooperia, Chabertia, Strongyloides, Oesophagostomum, Hyostrongulus, Ancylostoma, Ascaris and Heterakis, as well as Fasciola. From the class of Gastropoda, for example, Deroceras spp., Arion spp., Lymnaea spp., Galba spp., Succinea spp., Biomphalaria spp., Bulinus spp. and Oncomelania spp. From the class of Bivalva, for example, Dreissena spp.

The phytoparasitic nematodes which can be controlled according to the invention include, for example, the root-parasitic soil nematodes, such as, for example, those of the genera Meloidogyne (root gall nematodes, such as *Meloidogyne incognita, Meloidogyne hapla* and *Meloidogyne javanica*), Heterodera and Globodera (cyst-forming nematodes, such as *Globodera rostochiensis, Globodera pallida* and *Heterodera trifolii*) and of the genera Radopholus (such as *Radopholus similis*), Pratylenchus (such as *Pratylenchus neglectus, Pratylenchus penetrans* and *Pratylenchus curvitatus*), Tylenchulus (such as *Tylenchulus semipenetrans*), Tylenchorhynchus (such as *Tylenchorhynchus dubius* and *Tylenchorhynchus claytoni*), Rotylenchus (such as *Rotylencus robustus*), Heliocotylenchus (such as *Heliocotylenchus multicinctus*), Belonoaimus (such as *Belonoaimus longicaudatus*), Longidorus (such as *Longidorus elongatus*), Trichodorus (such as *Trichodorus primitivus*) and Xiphinema (such as *Xiphinema index*).

The nematode genera Ditylenchus (stem parasites, such as *Ditylenchus dipsaci* and *Ditylenchus destructor*), Aphelenchoides (leaf nematodes, such as *Aphelenchoides ritzemabosi*) and Anguina (blossom nematodes, such as *Anguina tritici*) can furthermore be controlled with the compounds according to the invention.

The invention also relates to compositions, in particular insecticidal and acaricidal compositions, which comprise the compounds of the formula (I) in addition to suitable formulation auxiliaries.

The compositions according to the invention in general comprise the active compounds of the formula (I) to the extent of 1 to 95% by weight. They can be formulated in various ways, depending on how this is determined by the biological and/or chemico-physical parameters. Suitable formulation possibilities are therefore: Wettable powders (WP), emulsifiable concentrates (EC), aqueous solutions (SL), emulsions, sprayable solutions, oil- or water-based dispersions, suspension concentrates (SC), suspoemulsions (SE), dusting powders (DP), seed dressings, granules in the form of microgranules, sprayed granules, absorption granules and adsorption granules, water-dispersible granules (WG), ULV formulations, microcapsules, waxes or baits.

These individual types of formulation are known in principle and are described, for example, in: Winnacker-Küchler, "Chemische Technologie" [Chemical Technology], Volume 7, C. Hauser Verlag Munich, 4th Edition 1986; van Falkenberg, "Pesticides Formulations", Marcel Dekker N.Y., 2nd Edition 1972–73; K. Martens, "Spray Drying Handbook", 3rd Edition 1979, G. Goodwin Ltd. London.

The necessary formulation auxiliaries, i.e. carrier substances and surface-acting substances, such as inert materials, surfactants, solvents and further additives, are likewise known and are described, for example, in: Watkins, "Handbook of Insecticide Dust Diluents and Carriers", 2nd Edition, Darland Books, Caldwell N.J.; H. v. Olphen, "Introduction to Clay Colloid Chemistry", 2nd Edition, J. Wiley & Sons, N.Y.; Marsden, "Solvents Guide", 2nd Edition, Interscience, N.Y. 1950; McCutcheon's, "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-active ethylene oxide adducts], Wiss. Verlagsgesell., Stuttgart 1967; Winnacker-Küchler, "Chemische Technologie" [Chemical Technology], Volume 7, C. Hauser Verlag Munich, 4th Edition 1986.

Combinations with other substances having a pesticidal action, fertilizers and/or growth regulators can be prepared on the basis of these formulations, for example in the form of a ready-to-use formulation or as a tank mix. Wettable powders are preparations which are uniformly dispersible in water and which, alongside the active compound, and in addition to a diluent or inert substance, also comprise wetting agents, for example polyethoxylated alkylphenols, polyethoxylated fatty alcohols or alkyl- or alkylphenolsulfonates, and dispersing agents, for example sodium lignininsulfonate or sodium 2,2'-dinaphthylmethane-6,6'-disulfonate. Emulsifiable concentrates are prepared by dissolving the active compound in an organic solvent, for example butanol, cyclohexanone, dimethylformamide, xylene or also higher-boiling aromatics or hydrocarbons, with the addition of one or more emulsifiers. Emulsifiers which can be used are, for example: calcium alkylarylsulfonates, such as Ca dodecylbenzenesulfonate, or nonionic emulsifiers, such as fatty acid polyglycol esters, alkylaryl polyglycol ethers, fatty alcohol polyglycol ethers, propylene oxide/ethylene oxide condensation products, alkyl polyethers, sorbitan fatty acid esters, polyoxyethylene sorbitan fatty acid esters or polyoxyethylene sorbitol esters.

Dusting powders are obtained by grinding the active compound with finely divided solid substances, for example talc, naturally occurring clays, such as kaolin, bentonite and pyrophillite, or diatomaceous earth. Granules can be prepared either by spraying the active compound onto granular inert material capable of adsorption or by applying active compound concentrates to the surface of carrier substances, such as sand, kaolinites or granular inert material, by means of adhesives, for example polyvinyl alcohol, sodium polyacrylate or mineral oils. Suitable active compounds can also be granulated in the manner customary for the preparation of fertilizer granules—if desired as a mixture with fertilizers.

In wettable powders, the active compound concentration is generally about 10 to 90% by weight, the remainder to make up 100% by weight comprising customary formulation constituents. In emulsifiable concentrates, the active compound concentration can be about 5 to 80% by weight. Dust-like formulations usually comprise 5 to 20% by weight of active compound, and sprayable solutions about 2 to 20% by weight. In granules, the content of active compound partly depends on whether the active compound is present in liquid or solid form and what granulating auxiliaries, fillers and the like are used.

In addition, the active compound formulations mentioned comprise, if appropriate, the particular customary tackifiers, wetting agents, dispersing agents, emulsifiers, penetration agents, solvents, fillers or carriers.

For use, the concentrates in the commercially available form are diluted in the customary manner, if appropriate, for example by means of water in the case of wettable powders, emulsifiable concentrates, dispersions and in some cases also microgranules. Dust-like and granular formulations as well as sprayable solutions are usually not diluted further with additional inert substances before use.

The required amount applied varies with external conditions, such as temperature, humidity and the like. It can vary within wide limits, for example between 0.0005 and 10.0 kg/ha or more of active substance, but is preferably between 0.001 and 5 kg/ha.

The active compounds according to the invention can be present in their commercially available formulations and in the use forms prepared from these formulations as mixtures with other active compounds, such as insecticides, attractants, sterilizing agents, acaricides, nematicides, fungicides, growth-regulating substances or herbicides.

The pest control agents include, for example, phosphoric acid esters, carbamates, carboxylic acid esters, formamidines, tin compounds, substances produced by microorganisms and the like.

Preferred partners for the mixtures are 1. from the group of phosphorus compounds acephate, azamethiphos, azinphos-ethyl-, azinphosmethyl, bromophos, bromophos-ethyl, chlorfenvinphos, chlormephos, chlorpyrifos, chlorpyrifos-methyl, demeton, demeton-S-methyl, demeton-S-methyl sulfone, dialifos, diazinon, dichlorvos, dicrotophos, O,O-1,2,2,2-tetrachloroethyl phosphorthioate (SD 208 304), dimethoate, disulfoton, EPN, ethion, ethoprophos, etrimfos, famphur, fenamiphos, fenitriothion, fensulfothion, fenthion, fonofos, formothion, heptenophos, isozophos, isothioate, isoxathion, malathion, methacrifos, methamidophos, methidathion, salithion, mevinphos, monocrotophos, naled, omethoate, oxydemeton-methyl, parathion, parathion-methyl, phenthoate, phorate, phosalone, phosfolan, phosmet, phosphamidon, phoxim, pirimiphos, primiphos-ethyl, pirimiphos-methyl, profenofos, propaphos, proetamphos, prothiofos, pyraclofos, pyridapenthion, quinalphos, sulprofos, temephos, terbufos, tetrachlorvinphos, thiometon, triazophos, trichlorphon, vamidothion;

2. from the group of carbamates aldicarb, 2-sec-butylphenyl methylcarbamate (BPMC), carbaryl, carbofuran, carbosulfan, cloethocarb, benfuracarb, ethiofencarb, furathiocarb, isoprocarb, methomyl, 5-methyl-m-cumenyl butyryl(methyl) carbamate, oxamyl, pirimicarb, propoxur, thiodicarb, thiofanox, ethyl 4,6,9-triaza-4-benzyl-6,10-dimethyl-8-oxa-7-oxo-5,11-dithia-9-dodecenoate (OK 135), 1-methylthio(ethylideneamino) N-methyl-N-(morpholinothio)carbamate (UC 51717);

3. from the group of carboxylic acid esters allethrin, alphametrin, 5-benzyl-3-furylmethyl (E)-(1R)-cis, 2,2-di-methyl-3-(2-oxothiolan-3-ylidenemethyl) cyclopropanecarboxylate, bioallethrin, bioallethrin ((S)-cyclopentyl isomer), bioresmethrin, biphenate, (RS)-1-cyano-1-(6-phenoxy-2-pyridyl)methyl (1RS)-trans-3-(4-tert-butylphenyl)-2,2-dimethylcyclopropanecarboxylate (NCI 85193), cycloprothrin, cyhalothrin, cythithrin, cypermethrin, cyphenothrin, deltamethrin, empenthrin, esfenvalerate, fenfluthrin, fenpropathrin, fenvalerate, flucythrinate, flumethrin, fluvalinate (D isomer), permethrin, pheothrin ((R) isomer), d-pralethrin, pyrethrins (naturally occurring products), resmethrin, tefluthrin, tetramethrin and tralomethrin;

4. from the group of amidines amitraz, chlordimeform;

5. from the group of tin compounds cyhexatin, fenbutatin oxide;

6. others abamectin, Bacillus thuringiensis, bensultap, binapacryl, bromopropylate, buprofezin, camphechlor, cartap, chlorobenzilate, chlorfluazuron, 2-(4-chlorophenyl)-4,5-diphenylthiophene (UBI-T 930), chlorfentezine, 2-naphthylmethyl cyclopropanecarboxylate (Ro 12-0470), cyromazin, N-(3,5-dichloro-4-(1,1,2,3,3,3-hexafluoro-1-propyloxy)phenyl)carbamoyl)-2-chlorobenzocarboximide acid ethyl ester, dicofol, N-(N-(3,5-di-chloro-4-(1,1,2,2-tetrafluoroethoxy) phenylamino)carbonyl)-2,6-difluorobenzamide (XRD 473), diflubenzuron, N-(2,3-dihydro-3-methyl-1,3-thiazol-2-ylidene)-2,4-xylidene, dinobuton, dinocap, endosulfan, ethofenprox, (4-ethoxyphenyl)(dimethyl) (3-(3-phenoxyphenyl)propyl)silane, (4-ethoxyphenyl) (3-(4-fluoro-3-phenoxyphenyl)propyl)dimethylsilane, fenoxycarb, 2-fluoro-5-(4-(4-ethoxyphenyl)-4-methyl-1-pentyl)diphenyl ether (MTI 800), granulosis and nuclear polyhedrosis viruses, fenthiocarb, flubenzimine, flucycloxuron, flufenoxuron, gamma-HCH, hexythiazox, hydramethylnon (AC 217300), ivermectin, 2-nitromethyl-4,5-dihydro-6H-thiazine (DS 52618), 2-nitromethyl-3,4-dihydrothiazole (SD 35651), 2-nitromethylene-1,2-thiazinan-3-ylcarbamaldehyde (WL 108477), propargite, teflubenzuron, tetradifon, tetrasul, thiocyclam, trifumuron, imidacloprid.

The abovementioned combination partners are known active compounds, and most of them are described in Ch. R. Worthing, S. B. Walker, The Pesticide Manual, 7th Edition (1983), British Crop Protection Council.

The active compound content of the use forms prepared from the commercially available formulations can be from 0.00000001 to 95% by weight of active compound, preferably between 0.00001 and 1% by weight.

The active compounds are used in a customary manner appropriate for the use forms.

The active compounds according to the invention are also suitable for controlling endo- and ectoparasites in the veterinary medicine field and in the field of animal husbandry. The active compounds according to the invention are used here in a known manner, such as by oral use in the form of, for example, tablets, capsules, potions or granules, by means of dermal use in the form of, for example, dipping, spraying, pouring-on, spotting-on and dusting, and by parenteral use in the form of, for example, injection.

The novel compounds of the formula (I) can accordingly also particularly advantageously be used in livestock husbandry (for example cattle, sheep, pigs and poultry, such as chickens, geese and the like). In a preferred embodiment of the invention, the compounds are administered orally to the animals, if appropriate in suitable formulations (cf. above) and if appropriate with the drinking water or feed. Since excretion in the faeces takes place in an active manner, the development of insects in the faeces of the animals can be prevented very easily in this way. The dosages and formulations suitable in each case depend in particular on the species and the development stage of the stock animals and also on the pressure of infestation, and can easily be determined and specified by the customary methods. The novel compounds can be employed in cattle, for example, in dosages of 0.01 to 1 mg/kg of body weight.

In addition to the application methods mentioned hereinabove, the active compounds of the formula I according to the invention also have excellent systemic action. The active compounds can therefore also be introduced into the plants via below-ground and above-ground parts of plants (root, stem, leaf), when the active compounds are applied in liquid or solid form to the immediate surroundings of the plants (for example granules in soil application, application in flooded rice fields).

Furthermore, the active compounds according to the invention are particularly useful for treating vegetative and generatative propagation stock, such as, for example, seed of, for example, cereals, vegetables, cotton, rice, sugar beet and other crops and ornamentals, of bulbs, cuttings and tubers of other vegetatively propagated crops and ornamentals. To this end, treatment can be carried out prior to sowing or planting (for example by special seed coating techniques, by seed dressings in liquid or solid form or by seed box treatment), during sowing or planting or after sowing or planting by special application techniques (for example seed row treatment). Depending on the application, the amount of active compound applied can vary within a relatively wide range. In general, the application rates are between 1 g and 10 kg of active compound per hectare of soil area.

In a preferred embodiment, the invention provides 4-trifluoromethyl-3-oxadiazolyl, pyridine derivatives of the formula (I'), (I')

[Chemical structure showing a pyridine ring with CF3 substituent, connected to an oxadiazole ring bearing an X—Y—R substituent, with (O)$_m$ on the pyridine nitrogen]

where the symbols and indices are as defined below:
  m is 0 or 1;
  X is a single bond, a straight-chain alkylene group having 1, 2 or 3 carbon atoms or a branched alkylene group having 3 to 9 carbon atoms, where one or more H atoms may be replaced by F;
  Y is —O—, —S—, —SO—, —SO$_2$—, —O—CO—, —O—CO—O—, —SO$_2$—O—, —O—SO$_2$—, —NR$^1$—, —NR$^2$—CO—, —NR$^3$—CO—O—, —NR$^4$—CO—NR$^5$—, —O—CO—O—, —O—CO—NR$^6$—, —SO$_2$—NR$^7$ or —NR$^8$—SO$_2$—;
  R, R$^1$, R$^2$, R$^3$, R$^4$, R$^5$, R$^6$, R$^7$, R$^8$ are identical or different and are independently of one another H, (C$_1$–C$_{10}$)-alkyl, (C$_2$–C$_{10}$)-alkenyl, (C$_2$–C$_{10}$)-alkynyl, (C$_3$–C$_8$)-cycloalkyl, (C$_4$–C$_8$)-cycloalkenyl, (C$_6$–C$_8$)-cycloalkynyl, heterocyclyl or —(CH$_2$)$_{1-4}$-heterocyclyl, where each of the eight last-mentioned groups is unsubstituted or mono- or polysubstituted, and where, optionally R and R$^1$, R and R$^2$, R and R$^5$, R and R$^6$, R and R$^7$, R and R$^8$ or X and R together form a ring system,
with the proviso, that the compounds in which
  X=-, Y=O, R=H
  X=-, Y=O, R=Me
  X=-, Y=O, R=Et
  X=-, Y=O, R=CHF$_2$
  X=-, Y=O, R=CH$_2$Ph
  X=CH$_2$, Y=O, R=2-furanyl
  X=CH$_2$, Y=O, R=Me
  X=CH$_2$, Y=O, R=5-isoxazolyl
  X=CH$_2$, Y=O, R=5-nitrofuran-2-yl
  X=CH$_2$CH$_2$, Y=O, R=H
  X=CH$_2$CH$_2$; Y=O, R=Me
  X=CH$_2$CH$_2$, Y=O, R = CH$_2$—[epoxide ring structure]

X=CH$_2$CH$_2$, Y=O, R=Et
  X=CH$_2$CH$_2$, Y=O, R=H
  X=CH$_2$CH$_2$; Y=OC(O), R=4-F-phenyl
  X=CH$_2$CH$_2$, Y=OC(O), R=2,6-difluorophenyl
  X=CH$_2$CH$_2$, Y=OC(O), R=4-nitrophenyl
  X=CH$_2$CH$_2$, Y=OC(O), R=t-Bu
  X=CH$_2$CH$_2$, Y=OC(O), R=cyclopropyl
  X=CH$_2$CH$_2$, Y=OC(O), R=Me
  X=CH$_2$CH$_2$CH$_2$, Y=O, R=H
  X=-, Y=S(O), R=4-bromobenzyl
  X=CH$_2$, Y=S, R=Me
  X=CH$_2$, Y=S(O), R=Me
  X=CH$_2$, Y=S(O)$_2$, R=t-Bu
  X=CH$_2$, Y=S, R=2-thienyl
  X=CH$_2$CH$_2$, Y=S, R=Me
  X=CH$_2$CH$_2$, Y=S, R=n-Pr
  X=CH$_2$CH$_2$, Y=S, R=benzyl
  X=CH$_2$CH$_2$, Y=S, R=2-thienylmethyl
  X=CH$_2$CH$_2$CH$_2$, Y=S, R=Me
  X=CH$_2$CH$_2$CH$_2$, Y=S(O), R=Me
  X=CH$_2$CH$_2$CH$_2$CH$_2$, Y=S, R=CH$_2$CH$_2$CH$_2$CH$_2$OMe
are not included.
  m is preferably 0.
  If m is 1 and Y contains an S(O)$_n$ group, n is preferably 2.
  X is preferably a single bond, CH$_2$, CH$_2$—CH$_2$, CH$_2$—CH(CH$_3$) or —CH$_2$—C(CH$_3$)$_2$—.
  Y is preferably —O—, —S—, —SO—, —SO$_2$—, —O—CO—, —O—CO—O—, —O—CO—NR$^6$—, —SO—NR$^7$—, —O—S$\mu_2$— or —SO$_2$—O—.
  R, R$^1$, R$^2$, R$^3$, R$^4$, R$^5$, R$^6$, R$^7$, R$^8$ are preferably identical or different and are independently of one another H, (C$_1$–C$_6$)-alkyl, (C$_2$–C$_6$)-alkenyl, (C$_2$–C$_6$)-alkynyl, (C$_3$–C$_8$)-cycloalkyl, (C$_4$–C$_8$)-cycloalkenyl, (C$_6$–C$_8$)-cycloalkynyl, heterocyclyl or —(CH$_2$)$_{1-4}$-heterocyclyl, where the eight last-mentioned radicals are unsubstituted or substituted by one or more radicals from the group consisting of
    halogen, cyano, citro, hydroxyl, —C(=W)R$^9$, (=W), —C(=NOR$^9$)R$^9$, —C(=NNR$^9_2$)R$^9$, —C(=W)OR$^9$, —C(=W)NR$^9_2$, —OC(=W)R$^9$, —OC(=W)OR$^9$, —NR$^9$C(=W)R$^9$, —N[C(=W)R$^9$]$_2$, —NR$^9$C(=W)OR$^9$, —C(=W)NR$^9$—NR$^9_2$, —C(=W)NR$^9$—NR$^9$[C(=W)R$^9$], —NR$^9$—C(=W)NR$^9_2$, —NR$^9$—NR$^9$C(=W)R$^9$, —NR$^9$—N[C(=W)R$^9$]$_2$, —N[(C=W)R$^9$]—NR$^9_2$, —NR$^9$—N[(C=W)R$^9$]$_2$, —NR$^9$—NR$^9$[(C=W)WR$^9$], —NR$^9$—[(C=W)NR$^9$2], —NR$^9$(C=NR$^9$)R$^9$, —NR$^9$(C=NR$^9$)NR$^9_2$, —O—NR$^9_2$, —O—NR$^9$(C=W)R$^9$, —SO$_2$NR$^9_2$, —NR$^9$SO$_2$R$^9$, —SO$_2$OR$^9$, —OSO$_2$R$^9$, —OR$^9$, —NR$^9_2$, —SR$^9$, —SiR$^9_3$, —SeR$^9$, —PR$^9_2$, —P(=W)R$^9_2$, —SOR$^9$, —SO$_2$R$^9$, —PW$_2$R$^9_2$, —PW$_3$R$^9_2$, aryl and heterocyclyl,
    the two last-mentioned radicals of which are unsubstituted or substituted by one or more radicals from the group consisting of
      (C$_1$–C$_6$)-alkyl, (C$_2$–C$_6$)-alkenyl, (C$_2$–C$_6$)-alkynyl, (C$_3$–C$_8$)-cycloalkyl, (C$_4$–C$_8$)-cycloalkenyl, (C$_6$–C$_8$)-cycloalkynyl, (C$_1$–C$_6$)-haloalkyl, (C$_2$–C$_6$)-haloalkenyl, (C$_2$–C$_6$)-haloalkynyl, halogen, —OR$^{10}$, —NR$^{10}_2$, —SR$^{10}$, —SiR$^{10}_3$, —C(=W)R$^{10}$, —C(=W)OR$^{10}$, —C(=W)NR$^{10}_2$, —SOR$^{10}$, —SO$_2$R$^{10}$, nitro, cyano and hydroxyl,
    and where optionally R and R$^1$, R and R$^5$, R and R$^6$, R and R$^7$ and R and R$^8$ together are —(CH$_2$)$_4$—, —(CH$_2$)$_5$—, —(CH$_2$)$_2$—O—(CH$_2$)$_2$—, (CH$_2$)$_2$—NR$^2$—(CH$_2$)$_2$—
    and where X and R together, if appropriate, may also form a ring system,
    and where optionally R and R$^1$, R and R$^2$, R and R$^5$, R and R$^6$, R and R$^7$, R and R$^8$ or X and R together form a ring system.
  Preferred to form the ring system are —(CH$_2$)$_3$—, —(CH$_2$)$_4$—, —(CH$_2$)$_5$—, —(CH$_2$)$_2$—O—(CH$_2$)$_2$—, —(CH$_2$)$_2$—NR$^3$—(CH$_2$)$_2$—, -(thiophen-3,4-diyl)—C(O)—, CH(imidazolyl-)CF$_2$C(O)—, —CH(Me)CH$_2$C(O)—, —CMe$_2$CH$_2$C(O)—, —CH(Me)CH(Me)C(O)—, —CH$_2$CH$_2$CH$_2$C(O)—, —CH(Me)CH$_2$CH$_2$C(O)—, —CH$_2$CH(Me)CH$_2$C(O)—, —CH$_2$CMe$_2$CH$_2$C(O)—, —CH$_2$C[—(CH$_2$)$_4$—]CH$_2$C(O)—, -(1,2-cyclohexylene)-C(O)—, -(cyclohexene-4,5-diyl)-C(O)—, —CH$_2$—C(H)

Ph—CH$_2$—C(O)—, —CMe=CMe—C(O)—, —CH$_2$—CH$_2$—C(O)—, especially preferred are —(CH$_2$)$_3$—, —(CH$_2$)$_4$—, —(CH$_2$)$_5$—, —(CH$_2$)$_2$—O—(CH$_2$)$_2$—, —(CH$_2$)$_2$—NR$^3$—(CH$_2$)$_2$—.

W is O or S.

R$^9$ is hydrogen, (C$_1$–C$_6$)-alkyl, (C$_2$–C$_6$)-alkenyl, (C$_2$–C$_6$)-alkynyl, (C$_3$–C$_8$)-cycloalkyl, (C$_4$–C$_8$)-cycloalkenyl, (C$_3$–C$_8$)-cycloalkyl-(C$_1$–C$_4$)-alkyl, (C$_4$–C$_8$)-cycloalkenyl-(C$_1$–C$_4$)-alkyl, (C$_3$–C$_8$)-cycloalkyl-(C$_2$–C$_4$)-alkenyl, (C$_4$–C$_8$)-cycloalkenyl-(C$_1$–C$_4$)-alkenyl, (C$_1$–C$_6$)-alkyl-(C$_3$–C$_8$)-cycloalkyl, (C$_2$–C$_6$)-alkenyl-(C$_3$–C$_8$)-cycloalkyl, (C$_2$–C$_6$)-alkynyl-(C$_3$–C$_8$)-cycloalkyl, (C$_1$–C$_6$)-alkyl-(C$_4$–C$_8$)-cycloalkenyl, (C$_2$–C$_6$)-alkenyl-(C$_4$–C$_8$)-cycloalkenyl, where the fourteen last-mentioned radicals are unsubstituted or substituted by one or more radicals from the group consisting of halogen, cyano, nitro, hydroxyl, thio, amino, formyl, (C$_1$–C$_6$)-alkoxy, (C$_2$–C$_6$)-alkenyloxy, (C$_2$–C$_6$)-alkynyloxy, (C$_1$–C$_6$)-haloalkyloxy, (C$_2$–C$_6$)-haloalkenyloxy, (C$_2$–C$_6$)-haloalkynyloxy, (C$_3$–C$_8$)-cycloalkoxy, (C$_4$–C$_8$)-cycloalkenyloxy, (C$_3$–C$_8$)-halocycloalkoxy, (C$_4$–C$_8$)-halocycloalkenyloxy, (C$_3$–C$_8$)-cycloalkyl-(C$_1$–C$_4$)-alkoxy, (C$_4$–C$_8$)-cycloalkenyl-(C$_1$–C$_4$)-alkoxy, (C$_3$–C$_8$)-cycloalkyl-(C$_2$–C$_4$)-alkenyloxy, (C$_4$–C$_8$)-cycloalkenyl-(C$_1$–C$_4$)-alkenyloxy, (C$_1$–C$_6$)-alkyl-(C$_3$–C$_8$)-cycloalkoxy, (C$_2$–C$_6$)-alkenyl-(C$_3$–C$_8$)-cycloalkoxy, (C$_2$–C$_6$)-alkynyl-(C$_3$–C$_8$)-cycloalkoxy, (C$_1$–C$_6$)-alkyl-(C$_4$–C$_8$)-cycloalkenyloxy, (C$_2$–C$_6$)-alkenyl-(C$_4$–C$_8$)-cycloalkenyloxy, (C$_1$–C$_4$)-alkoxy-(C$_1$–C$_6$)-alkoxy, (C$_1$–C$_4$)-alkoxy-(C$_2$–C$_6$)-alkenyloxy, carbamoyl, (C$_1$–C$_6$)-mono- or -dialkylcarbamoyl, (C$_1$–C$_6$)-mono- or dihaloalkylcarbamoyl, (C$_3$–C$_8$)-mono- or dicycloalkylcarbamoyl, (C$_1$–C$_6$)-alkoxycarbonyl, (C$_3$–C$_8$)-cycloalkoxycarbonyl, (C$_1$–C$_6$)-alkanoyloxy, (C$_3$–C$_8$)-cycloalkanoyloxy, (C$_1$–C$_6$)-haloalkoxycarbonyl, (C$_1$–C$_6$)-haloalkanoyloxy, (C$_1$–C$_6$)-alkanamido, (C$_1$–C$_6$)-haloalkanamido, (C$_2$–C$_6$)-alkenamido, (C$_3$–C$_8$)-cycloalkanamido, (C$_3$–C$_8$)-cycloalkyl-(C$_1$–C$_4$)-alkanamido, (C$_1$–C$_6$)-alkylthio, (C$_2$–C$_6$)-alkenylthio, (C$_2$–C$_6$)-alkynylthio, (C$_1$–C$_6$)-haloalkylthio, (C$_2$–C$_6$)-haloalkenylthio, (C$_2$–C$_6$)-haloalkynylthio, (C$_3$–C$_8$)-cycloalkylthio, (C$_4$–C$_8$)-cycloalkenylthio, (C$_3$–C$_8$)-halocycloalkylthio, (C$_4$–C$_8$)-halocycloalkenylthio, (C$_3$–C$_8$)-cycloalkyl-(C$_1$–C$_4$)-alkylthio, (C$_4$–C$_8$)-cycloalkenyl-(C$_1$–C$_4$)-alkylthio, (C$_3$–C$_8$)-cycloalkyl-(C$_2$–C$_4$)-alkenylthio, (C$_4$–C$_8$)-cycloalkenyl-(C$_1$–C$_4$)-alkenylthio, (C$_1$–C$_6$)-alkyl-(C$_3$–C$_8$)-cycloalkylthio, (C$_2$–C$_6$)-alkenyl-(C$_3$–C$_8$)-cycloalkylthio, (C$_2$–C$_6$)-alkynyl-(C$_3$–C$_8$)-cycloalkylthio, (C$_1$–C$_6$)-alkyl-(C$_4$–C$_8$)-cycloalkenylthio, (C$_2$–C$_6$)-alkenyl-(C$_4$–C$_8$)-cycloalkenylthio, (C$_1$–C$_6$)-alkylsulfinyl, (C$_2$–C$_6$)-alkenylsulfinyl, (C$_2$–C$_6$)-alkynylsulfinyl, (C$_1$–C$_6$)-haloalkylsulfinyl, (C$_2$–C$_6$)-haloalkenylsulfinyl, (C$_2$–C$_6$)-haloalkynylsulfinyl, (C$_3$–C$_8$)-cycloalkylsulfinyl, (C$_4$–C$_8$)-cycloalkenylsulfinyl, (C$_3$–C$_8$)-halocycloalkylsulfinyl, (C$_4$–C$_8$)-halocycloalkenylsulfinyl, (C$_3$–C$_8$)-cycloalkyl-(C$_1$–C$_4$)-alkylsulfinyl, (C$_4$–C$_8$)-cycloalkenyl-(C$_1$–C$_4$)-alkylsulfinyl, (C$_3$–C$_8$)-cycloalkyl-(C$_2$–C$_4$)-alkenylsulfinyl, (C$_4$–C$_8$)-cycloalkenyl-(C$_1$–C$_4$)-alkenylsulfinyl, (C$_1$–C$_6$)-alkyl-(C$_3$–C$_8$)-cycloalkylsulfinyl, (C$_2$–C$_6$)-alkenyl-(C$_3$–C$_8$)-cycloalkylsulfinyl, (C$_2$–C$_6$)-alkynyl-(C$_3$–C$_8$)-cycloalkylsulfinyl, (C$_1$–C$_6$)-alkyl-(C$_4$–C$_8$)-cycloalkenylsulfinyl, (C$_2$–C$_6$)-alkenyl-(C$_4$–C$_8$)-cycloalkenylsulfinyl, (C$_1$–C$_6$)-alkylsulfonyl, (C$_2$–C$_6$)-alkenylsulfonyl, (C$_2$–C$_6$)-alkynylsulfonyl, (C$_1$–C$_6$)-haloalkylsulfonyl, (C$_2$–C$_6$)-haloalkenylsulfonyl, (C$_2$–C$_6$)-haloalkynylsulfonyl, (C$_3$–C$_8$)-cycloalkylsulfonyl, (C$_4$–C$_8$)-cycloalkenylsulfonyl, (C$_3$–C$_8$)-halocycloalkylsulfonyl, (C$_4$–C$_8$)-halocycloalkenylsulfonyl, (C$_3$–C$_8$)-cycloalkyl-(C$_1$–C$_4$)-alkylsulfonyl, (C$_4$–C$_8$)-cycloalkenyl-(C$_1$–C$_4$)-alkylsulfonyl, (C$_3$–C$_8$)-cycloalkyl-(C$_2$–C$_4$)-alkenylsulfonyl, (C$_4$–C$_8$)-cycloalkenyl-(C$_1$–C$_4$)-alkenylsulfonyl, (C$_1$–C$_6$)-alkyl-(C$_3$–C$_8$)-cycloalkylsulfonyl, (C$_2$–C$_6$)-alkenyl-(C$_3$–C$_8$)-cycloalkylsulfonyl, (C$_2$–C$_6$)-alkynyl-(C$_3$–C$_8$)-cycloalkylsulfonyl, (C$_1$–C$_6$)-alkyl-(C$_4$–C$_8$)-cycloalkenylsulfonyl, (C$_1$–C$_6$)-alkylamino, (C$_2$–C$_6$)-alkenylamino, (C$_2$–C$_6$)-alkynylamino, (C$_1$–C$_6$)-haloalkylamino, (C$_2$–C$_6$)-haloalkenylamino, (C$_2$–C$_6$)-haloalkynylamino, (C$_3$–C$_8$)-cycloalkylamino, (C$_4$–C$_8$)-cycloalkenylamino, (C$_3$–C$_8$)-halocycloalkylamino, (C$_4$–C$_8$)-halocycloalkenylamino, (C$_3$–C$_8$)-cycloalkyl-(C$_1$–C$_4$)-alkylamino, (C$_4$–C$_8$)-cycloalkenyl-(C$_1$–C$_4$)-alkylamino, (C$_3$–C$_8$)-cycloalkyl-(C$_2$–C$_4$)-alkenylamino, (C$_4$–C$_8$)-cycloalkenyl-(C$_1$–C$_4$)-alkenylamino, (C$_1$–C$_6$)-alkyllkylamino, (C$_2$–C$_6$)-alkenyl-(C$_3$–C$_8$)-cycloalkylamino, (C$_2$–C$_6$)-alkynyl-(C$_3$–C$_8$)-cycloalkylamino, (C$_1$–C$_6$)-alkyl-(C$_4$–C$_8$)-cycloalkenylamino, (C$_2$–C$_6$)-alkenyl-(C$_4$–C$_8$)-cycloalkenylamino, (C$_1$–C$_6$)-trialkylsilyl, aryl, aryloxy, arylthio, arylamino, aryl-(C$_1$–C$_4$)-alkoxy, aryl-(C$_2$–C$_4$)-alkenyloxy, aryl-(C$_1$–C$_4$)-alkylthio, aryl-(C$_2$–C$_4$)-alkenylthio, aryl-(C$_1$–C$_4$)-alkylamino, aryl-(C$_2$–C$_4$)-alkenylamino, aryl-(C$_1$–C$_6$)-dialkylsilyl, diaryl-(C$_1$–C$_6$)-alkylsilyl, triarylsilyl and 5- or 6-membered heterocyclyl, where the cyclic moiety of the fourteen last-mentioned radicals is unsubstituted or substituted by one or more radicals from the group consisting of halogen, cyano, nitro, amino, hydroxyl, thio, (C$_1$–C$_4$)-alkyl, (C$_1$–C$_4$)-haloalkyl, (C$_3$–C$_8$)-cycloalkyl, (C$_1$–C$_4$)-alkoxy, (C$_1$–C$_4$)-haloalkoxy, (C$_1$–C$_4$)-alkylthio, (C$_1$–C$_4$)-haloalkylthio, (C$_1$–C$_4$)-alkylamino, (C$_1$–C$_4$)-haloalkylamino, formyl and (C$_1$–C$_4$)-alkanoyl, aryl, 4-, 5- or 6-membered heterocyclyl, where the two last-mentioned radicals are unsubstituted or substituted by one or more radicals from the group consisting of halogen, cyano, nitro, hydroxyl, thio, amino, formyl, (C$_1$–C$_6$)-alkoxy, (C$_2$–C$_6$)-alkenyloxy, (C$_2$–C$_6$)-alkynyloxy, (C$_1$–C$_6$)-haloalkyloxy, (C$_2$–C$_6$)-haloalkenyloxy, (C$_2$–C$_6$)-haloalkynyloxy, (C$_3$–C$_8$)-cycloalkoxy, (C$_4$–C$_8$)-cycloalkenyloxy, (C$_3$–C$_8$)-halocycloalkoxy, (C$_4$–C$_8$)-halocycloalkenyloxy, carbamoyl, (C$_1$–C$_6$)-mono- or -dialkylcarbamoyl, (C$_1$–C$_6$)-alkoxycarbonyl, (C$_1$–C$_6$)-alkanoyloxy, (C$_1$–C$_6$)-mono- or -dihaloalkylcarbamoyl, (C$_1$–C$_6$)-haloalkoxycarbonyl, (C$_1$–C$_6$)-haloalkanoyloxy, (C$_1$–C$_6$)-alkanamido, (C$_1$–C$_6$)-haloalkanamido, (C$_2$–C$_6$)-alkenamido, (C$_1$–C$_6$)-alkylthio, (C$_2$–C$_6$)-alkenylthio, (C$_2$–C$_6$)-alkynylthio, (C$_1$–C$_6$)- haloalkylthio, $(C_2-C_6)$-haloalkenylthio, $(C_2-C_6)$-haloalkynylthio, $(C_3-C_8)$-cycloalkylthio, $(C_4-C_8)$-cycloalkenylthio, $(C_3-C_8)$-halocycloalkylthio, $(C_4-C_8)$-halocycloalkenylthio, $(C_1-C_6)$-alkylsulfinyl, $(C_2-C_6)$-alkenylsulfinyl, $(C_2-C_6)$-alkynylsulfinyl, $(C_1-C_6)$-haloalkylsulfinyl, $(C_2-C_6)$-haloalkenylsulfinyl, $(C_2-C_6)$-haloalkynylsulfinyl, $(C_3-C_8)$-cycloalkylsulfinyl, $(C_4-C_8)$-cycloalkenylsulfinyl, $(C_3-C_8)$-halocycloalkylsulfinyl, $(C_4-C_8)$-halocycloalkenylsulfinyl, $(C_1-C_6)$-alkylsulfonyl, $(C_2-C_6)$-alkenylsulfonyl, $(C_2-C_6)$-alkynylsulfonyl, $(C_1-C_6)$-haloalkylsulfonyl, $(C_2-C_6)$-haloalkenylsulfonyl, $(C_2-C_6)$-haloalkynylsulfonyl, $(C_3-C_8)$-cycloalkylsulfonyl, $(C_4-C_8)$-cycloalkenylsulfonyl, $(C_3-C_8)$-halocycloalkylsulfonyl, $(C_4-C_8)$-halocycloalkenylsulfonyl, $(C_1-C_6)$-alkylamino, $(C_2-C_6)$-alkenylamino, $(C_2-C_6)$-alkynylamino, $(C_1-C_6)$-haloalkylamino, $(C_2-C_6)$-haloalkenylamino, $(C_2-C_6)$-haloalkynylamino, $(C_3-C_8)$-cycloalkylamino, $(C_4-C_8)$-cycloalkenylamino, $(C_3-C_8)$-halocycloalkylamino and $(C_4-C_8)$-halocycloalkenylamino.

R and $R^1$–$R^8$ are particularly preferably H, $(C_1-C_6)$-alkyl, $(C_2-C_6)$-alkenyl, $(C_2-C_6)$-alkynyl, heterocyclyl, where the four last-mentioned radicals are unsubstituted or substituted by one or more, preferably by one to four, radicals from the group consisting of halogen, preferably F, CN, $SiMe_3$, —O—$(C_1-C_6)$-alkyl, —S—$(C_1-C_6)$-alkyl or —O—CO—$(C_1-C_6)$-alkyl.

Very particular preference is given to compounds of the formulae I'-1 to I'-32, also in the form of their pyridine N-oxides, where the symbols and indices are as defined above:

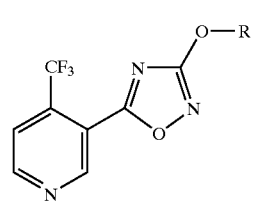

I-1

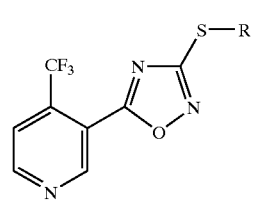

I-2

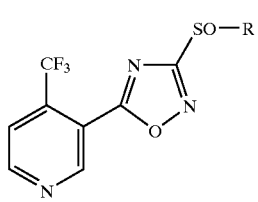

I-3

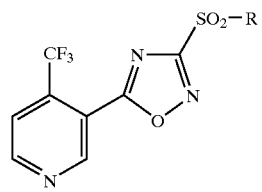

I-4

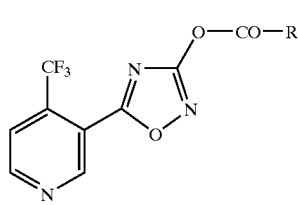

I-5

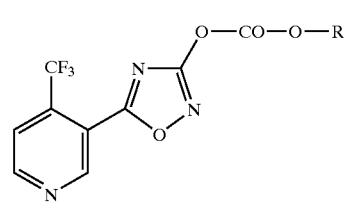

I-6

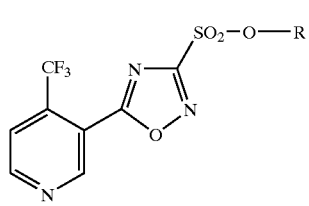

I-7

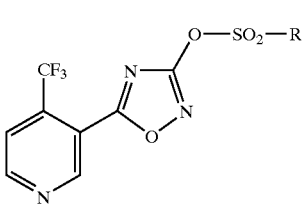

I-8

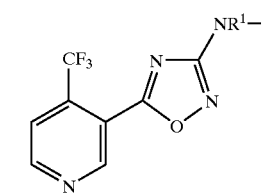

I-9

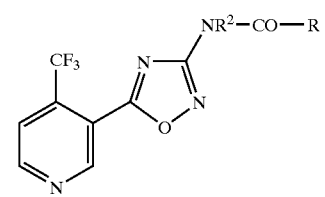

I-10

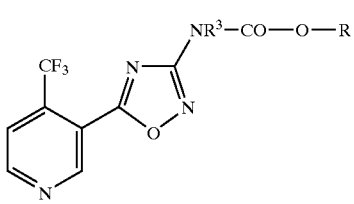

I-11

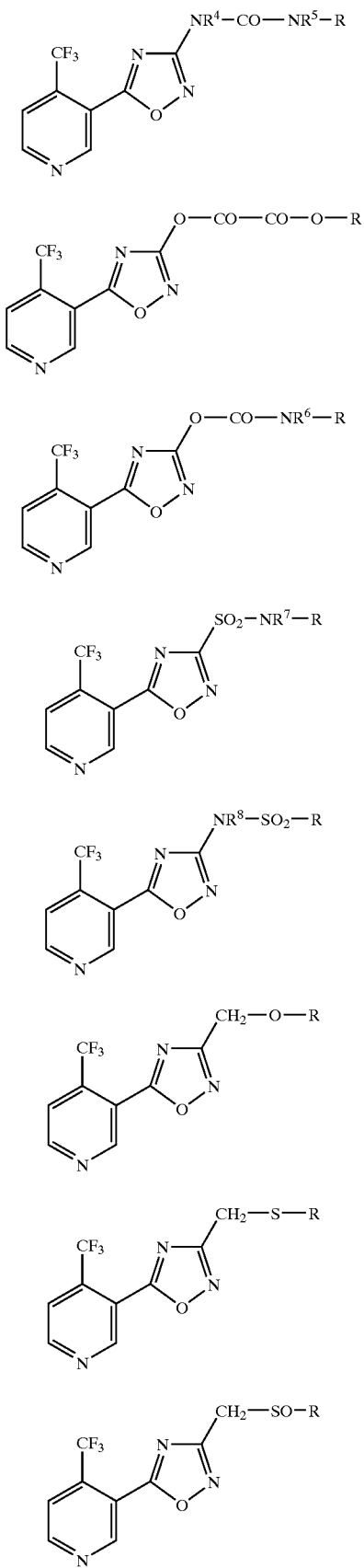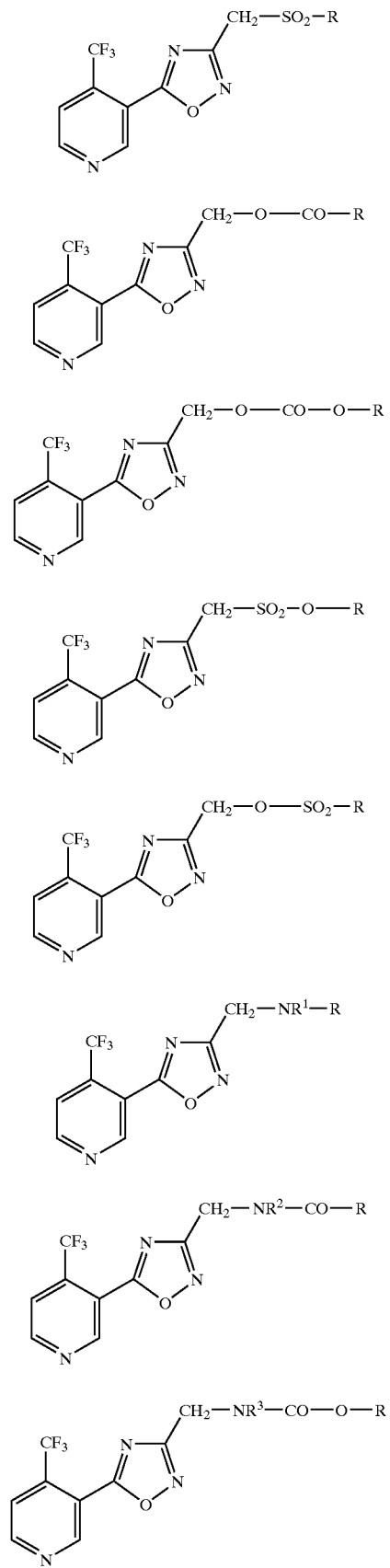

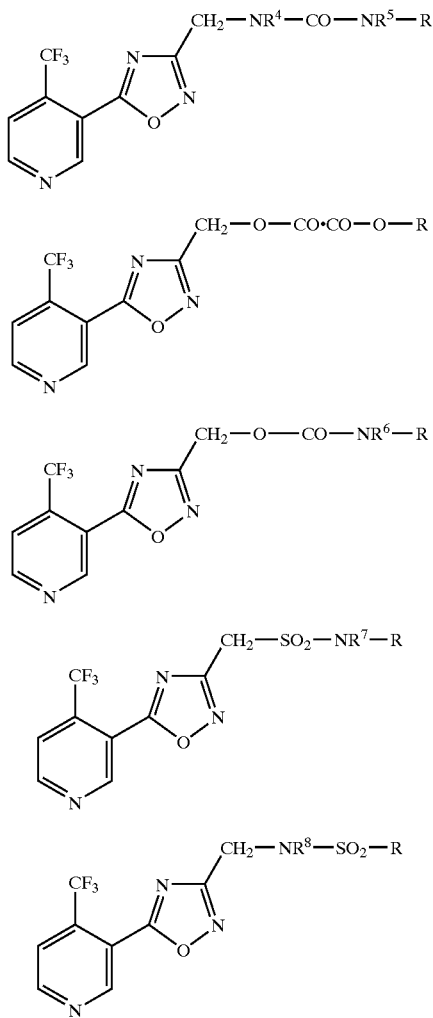

Preference is likewise given to the corresponding formulae I'-33 to I'-96 in which Y is —CH$_2$CH$_2$—, —CH$_2$—CH(CH$_3$)—, —CH$_2$—CH$_2$—CH$_2$— and —CH$_2$—C(CH$_3$)$_2$—.

The term "halogen" includes fluorine, chlorine, bromine and iodine.

The term "(C$_1$–C$_4$)-alkyl" is to be understood as a straight-chain or branched hydrocarbon radical having 1, 2, 3 or 4 carbon atoms, such as, for example, the methyl, ethyl, propyl, isopropyl, 1-butyl, 2-butyl, 2-methylpropyl or tert-butyl radical. Correspondingly, alkyl radicals having a greater range of carbon atoms are to be understood as straight-chain or branched saturated hydrocarbon radicals which contain a number of carbon atoms which corresponds to the range stated. Thus, the term "(C$_1$–C$_6$)-alkyl" includes the abovementioned alkyl radicals, and, for example, the pentyl, 2-methylbutyl, 1,1-dimethylpropyl and hexyl radical. The term "(C$_1$–C$_{10}$)-alkyl" is to be understood as the abovementioned alkyl radicals, and, for example, the nonyl, 1-decyl or 2-decyl radical.

"(C$_1$–C$_4$)-Haloalkyl" is to be understood as an alkyl group mentioned under the term "(C$_1$–C$_4$)-alkyl" in which one or more hydrogen atoms are replaced by the same number of identical or different halogen atoms, preferably chlorine or fluorine, such as the trifluoromethyl, the 1-fluoroethyl, the 2,2,2-trifluoroethyl, the chloromethyl, fluoromethyl, the difluoromethyl and the 1,1,2,2-tetrafluoroethyl group.

"(C$_1$–C$_4$)-Alkoxy" is to be understood as an alkoxy group whose hydrocarbon radical has the meaning given under the term "(C$_1$–C$_4$)-alkyl". Alkoxy groups embracing a greater range of carbon atoms are to be understood correspondingly.

The terms "alkenyl" and "alkynyl" having a prefix stating the range of carbon atoms denote a straight-chain or branched hydrocarbon radical having a number of carbon atoms corresponding to the range stated which comprises at least one multiple bond which may be in any position of the unsaturated radical in question. "(C$_2$–C$_4$)-Alkenyl" is thus, for example, the vinyl, allyl, 2-methyl-2-propene or 2-butenyl group; "(C$_2$–C$_6$)-alkenyl" denotes the abovementioned radicals and, for example, the pentenyl, 2-methylpentenyl or the hexenyl group. "(C$_2$–C$_4$)-Alkynyl" is, for example, the ethynyl, propargyl, 2-methyl-2-propyne or 2-butynyl group. "(C$_2$–C$_6$)-Alkynyl" is to be understood as the abovementioned radicals and, for example, the 2-pentynyl or the 2-hexynyl group and "(C$_2$–C$_{10}$)-alkynyl" is to be understood as the abovementioned radicals and, for example, the 2-octynyl or the 2-decynyl group.

"(C$_3$–C$_8$)-Cycloalkyl" denotes monocyclic alkyl radicals, such as the cyclopropyl, cyclobutyl, cyclopentyl, cyclohexyl, cycloheptyl or cyclooctyl radical and bicyclic alkyl radicals, such as the norbornyl radical.

The term "(C$_3$–C$_8$)-cycloalkyl-(C$_1$–C$_4$)-alkyl" is to be understood as, for example, the cyclopropylmethyl, cyclopentylmethyl, cyclohexylmethyl, cyclohexylethyl and cyclohexylbutyl radical, and the term "(C$_1$–C$_6$)-alkyl-(C$_3$–C$_8$)-cycloalkyl is to be understood as, for example, the 1-methylcyclopropyl, 1-methylcyclopentyl, 1-methylcyclohexyl, 3-hexylcyclobutyl and 4-tert-butylcyclohexyl radical.

"(C$_1$–C$_4$)-Alkoxy-(C$_1$–C$_6$)-alkyloxy" is an alkoxy group as defined above which is substituted by a further alkoxy group, such as, for example, 1-ethoxyethoxy.

"(C$_3$–C$_8$)-Cycloalkoxy" or "(C$_3$–C$_8$)-cycloalkylthio" is to be understood as one of the abovementioned (C$_3$–C$_8$)-cycloalkyl radicals which is linked via an oxygen or sulfur atom.

"(C$_3$–C$_8$)-Cycloalkyl-(C$_1$–C$_6$)-alkoxy" is, for example, the cyclopropylmethoxy, cyclobutylmethoxy, cyclopentylmethoxy, cyclohexylmethoxy, cyclohexylethoxy or the cyclohexylbutoxy group.

The term "(C$_1$–C$_4$)-alkyl-(C$_3$–C$_8$)-cycloalkoxy" is, for example, the methylcyclopropyloxy, methylcyclobutyloxy or the butylcyclohexyloxy group.

"(C$_1$–C$_6$)-Alkylthio" is an alkylthio group whose hydrocarbon radical has the meaning given under the term "(C$_1$–C$_6$)-alkyl".

Correspondingly, "(C$_1$–C$_6$)-alkylsulfinyl" is, for example, the methyl-, ethyl-, propyl-, isopropyl-, butyl-, isobutyl-, sec-butyl- or tert-butylsulfinyl group and "(C$_1$–C$_6$)-alkylsulfonyl" is, for example, the methyl-, ethyl-, propyl-, isopropyl-, butyl-, isobutyl-, sec-butyl- or tert-butylsulfonyl group.

"(C$_1$–C$_6$)-Alkylamino" is a nitrogen atom which is substituted by one or two identical or different alkyl radicals of the above definition.

The term "(C$_1$–C$_6$)-mono- or -dialkylcarbamoyl" is a carbamoyl group having one or two hydrocarbon radicals which have the meaning given under the term "(C$_1$–C$_6$)-alkyl)" and which, in the case of two hydrocarbon radicals, may be identical or different.

Correspondingly, "(C$_1$–C$_6$)-dihaloalkylcarbamoyl" is a carbamoyl group which carries two (C$_1$–C$_6$)-haloalkyl radicals in accordance with the above definition or one (C$_1$–C$_6$)-haloalkyl radical and one (C$_1$–C$_6$)-alkyl radical in accordance with the above definition.

"($C_1$–$C_6$)-Alkanoyl" is, for example, the acetyl, propionyl, butyryl or 2-methylbutyryl group.

The term "aryl" is to be understood as a carbocyclic, i.e. constructed from carbon atoms, aromatic radical preferably having 6 to 14, in particular 6 to 12, carbon atoms, such as, for example, phenyl, naphthyl or biphenylyl, preferably phenyl. "Aroyl" is thus an aryl radical as defined above which is attached via a carbonyl group, such as, for example, the benzoyl group.

The term "heterocyclyl" preferably denotes a cyclic radical which may be fully saturated, partially unsaturated or fully unsaturated and which may be interrupted by at least one or more identical or different atoms from the group consisting of nitrogen, sulfur or oxygen, two oxygen atoms, however, not being allowed to be directly adjacent to one another and at least one carbon atom having to be present in the ring, such as, for example, a thiophene, furan, pyrrole, thiazole, oxazole, imidazole, isothiazole, isoxazole, pyrazole, 1,3,4-oxadiazole, 1,3,4-thiadiazole, 1,3,4-triazole, 1,2,4-oxadiazole, 1,2,4-thiadiazole, 1,2,4-triazole, 1,2,3-triazole, 1,2,3,4-tetrazole, benzo[b]thiophene, benzo[b]furan, indole, benzo[c]thiophene, benzo[c]furan, isoindole, benzoxazole, benzothiazole, benzimidazole, benzisoxazole, benzisothiazole, benzopyrazole, benzothiadiazole, benzotriazole, dibenzofuran, dibenzothiophene, carbazole, pyridine, pyrazine, pyrimidine, pyridazine, 1,3,5-triazine, 1,2,4-triazine, 1,2,4,5-tetrazine, quinoline, isoquinoline, quinoxaline, quinazoline, cinnoline, 1,8-naphthyridine, 1,5-naphthyridine, 1,6-naphthyridine, 1,7-naphthyridine, phthalazine, pyridopyrimidine, purine, pteridine, 4H-quinolizine; piperidine, pyrrolidine, oxazoline, tetrahydrofuran, tetrahydropyran, isoxazolidine or thiazolidine radical. The term "heteroaromatic" thus embraces, from among the meanings mentioned above under "heterocyclyl", in each case the fully unsaturated aromatic heterocyclic compounds.

Heterocyclyl is particularly preferably a saturated, partially saturated or aromatic ring system having 3 to 6 ring members and 1 to 4 heteroatoms from the group consisting of O, S and N, wherein at least one of the ring members is carbon.

Heterocyclyl is very particularly preferably a radical of pyridine, pyrimidine, (1,2,4)-oxadiazole, (1,3,4)-oxadiazole, pyrrole, furan, thiophene, oxazole, thiazole, imidazole, pyrazole, isoxazole, 1,2,4-triazole, tetrazole, pyrazine, pyridazine, oxazoline, thiazoline, tetrahydrofuran, tetrahydropyran, morpholine, piperidine, piperazine, pyrroline, pyrrolidine, oxazolidine, thiazolidine, oxirane and oxetane.

"Aryl-($C_1$–$C_4$)-alkoxy" is an aryl radical which is attached via a ($C_1$–$C_4$)-alkoxy group, for example the benzyloxy, phenylethoxy, phenylbutoxy or naphthylmethoxy radical.

"Arylthio" is an aryl radical attached via a sulfur atom, for example the phenylthio or the 1- or 2-naphthylthio radical. Correspondingly, "aryloxy" is, for example, the phenoxy or 1- or 2-naphthyloxy radical.

"Aryl-($C_1$–$C_4$)-alkylthio" is an aryl radical which is attached via an alkylthio radical, for example the benzylthio, naphthylmethylthio or the phenylethylthio radical.

The term "($C_1$–$C_6$)-trialkylsilyl" denotes a silicon atom which carries three identical or different alkyl radicals in accordance with the above definition. Correspondingly "aryl-($C_1$–$C_6$)-dialkylsilyl" is a silicon atom which carries one aryl radical and two identical or different alkyl radicals in accordance with the above definition, "diaryl-($C_1$–$C_6$)-alkylsilyl" is a silicon atom which carries one alkyl radical and two identical or different aryl radicals in accordance with the above definition, and "triarylsilyl" is a silicon atom which carries three identical or different aryl radicals in accordance with the above definition.

In cases where two or more radicals $R^9$ are present in a substituent, such as, for example, in —C(=W)$NR^9_2$, these radicals may be identical or different.

Depending on the nature of the substituents defined above, the compounds of the formula (I') have acidic or basic properties and can form salts. If the compounds of the formula (I') carry, for example, groups such as hydroxyl, carboxyl or other groups inducing acidic properties, these compounds can be reacted with bases to give salts. Suitable bases are, for example, hydroxides, carbonates, bicarbonates of the alkali metals and alkaline earth metals, in particular those of sodium, potassium, magnesium and calcium, further ammonia, primary, secondary and tertiary amines having ($C_1$–$C_4$)-alkyl radicals and also mono-, di- and trialkanolamines of ($C_1$–$C_4$)-alkanols. If the compounds of the formula (I') carry, for example, groups such as amino, alkylamino or other groups inducing basic properties, these compounds can be reacted with acids to give salts. Suitable acids are, for example, mineral acids, such as hydrochloric acid, sulfuric acid and phosphoric acid, organic acids, such as acetic acid and oxalic acid, and acidic salts, such as $NaHSO_4$ and $KHSO_4$. The salts which can be obtained in this manner likewise have insecticidal, acaricidal and nematicidal properties.

The compounds of the formula (I') may have one or more asymmetric carbon atoms or stereoisomers on double bonds. Enantiomers or diastereomers may therefore be present. The invention embraces both the pure isomers and mixtures thereof. The mixtures of diastereomers can be separated into the isomers by customary methods, for example by selective crystallization from suitable solvents or by chromatography. Racemates can be separated into the enantiomers by customary methods.

The compounds according to the invention are prepared according to methods which are known per se from the literature, as described in standard works on organic synthesis, for example Houben-Weyl, Methoden der Organischen Chemie [Methods of Organic Chemistry], Georg-Thieme-Verlag, Stuttgart.

The preparation is carried out under reaction conditions which are known and suitable for the reactions mentioned. It is also possible to employ variants which are known per se but not mentioned in more detail here.

If desired, the starting materials can also be formed in situ, such that they are not isolated from the reaction mixture but are immediately reacted further to give the compounds of the formula (I').

For preparing compounds of the formula (I'), for example, activated derivatives of the acid of the formula (II'),

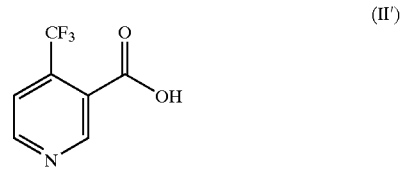

are reacted in the presence of a base with a compound of the formula (III'),

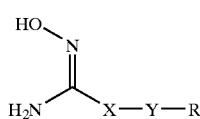

(III')

in which the radical X—Y—R is as defined in formula (I') or corresponds to a precursor of such a radical. The activated derivative used can be, for example, an acyl halide, an ester or an anhydride. Suitable bases are amines, such as triethylamine, diisopropylethylamine, pyridine or lutidine, alkali metal hydroxides, alkali metal alkoxides, such as sodium ethoxide or potassium tert-butoxide, or alkyl metal compounds, such as butyllithium.

Depending on the conditions selected, the described reaction can be carried out as a one-step process or as a two-step process, the intermediates being compounds of the formula (IV'):

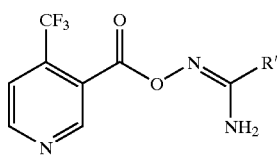

(IV')

Compounds of the formula (IV') can be cyclized to the 1,2,4-oxadiazoles by heating in an inert solvent at temperatures of up to 180° C. and by addition of dehydrating agents (for example Amberlyst).

Compounds of the formula (IV') are also directly obtainable from the acid of the formula (II') and amidoximes of the formula (III') by using a dehydrating agent, such as dicyclohexylcarbodiimide, 1-ethyl-3-(3-dimethylaminopropyl)carbodiimide or N,N'-carbonyldiimidazole.

Both trifluoromethylnicotinic acid (II') and amidoximes of the formula (III') are commercially available or can be prepared by processes known from the literature (see, for example: Houben-Weyl, Methoden der organischen Chemie, Volume X/4, pages 209–212; EP-A 0 580 374; G. F. Holland, J. N. Pereira, J. Med. Chem., 1967, 10, 149).

After the oxadiazolyl group has been constructed, as shown in the following reaction schemes for example by condensation, cyclization or cycloaddition reactions, the radical R can, if desired, be derivatized further, it being possible to employ the broad range of methods of organochemical synthesis.

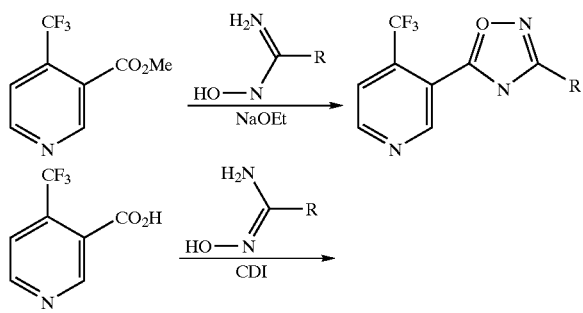

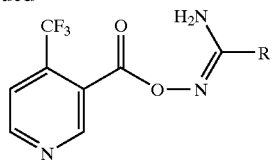

-continued

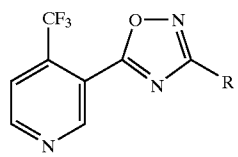

Central intermediates of ethers, thioethers and analogous derivatives are haloalkyl- or hydroxyalkyl-substituted oxadiazole derivatives of the formula (V'), (V')

where V = Cl, Br, I, OH, NH₂ which can then be converted into the corresponding target compounds using standard processes of organic synthesis.

Ethers of the formula (I') are obtainable by etherifying corresponding hydroxyl compounds where the hydroxyl compound is advantageously initially converted into a corresponding metal derivative, for example into the corresponding alkali metal alkoxide by treatment with NaH, NaNH₂, NaOH, KOH, Na₂CO₃. The alkali metal alkoxide or alkali metal phenolate can then be reacted with the appropriate alkyl halide, alkyl sulfonate or dialkyl sulfate, advantageously in an inert solvent, such as acetone, 1,2-dimethoxyethane, DMF or dimethyl sulfoxide, or else in an excess of aqueous or aqueous-alcoholic NaOH or KOH, at temperatures between about 20° C. and 100° C.

Derivatives of the amino compound (VI') can be prepared, for example, by reacting the chloro compound ((V'), V'=Cl) with amines or via the central intermediate ((V'); V'=NH₂).

The synthesis of the central intermediate ((V'); V'=NH₂) is effected by reacting the chloro derivative ((V'; V=Cl) with ammonia in the presence of a suitable base or, preferably by reacting the chloro derivative ((V'); V'=Cl) with potassium phthalimide and subsequent hydrazinolysis. Further derivatisation of this central intermediate ((V'); V'=NH₂) is effected by the reaction with suitable electrophiles.

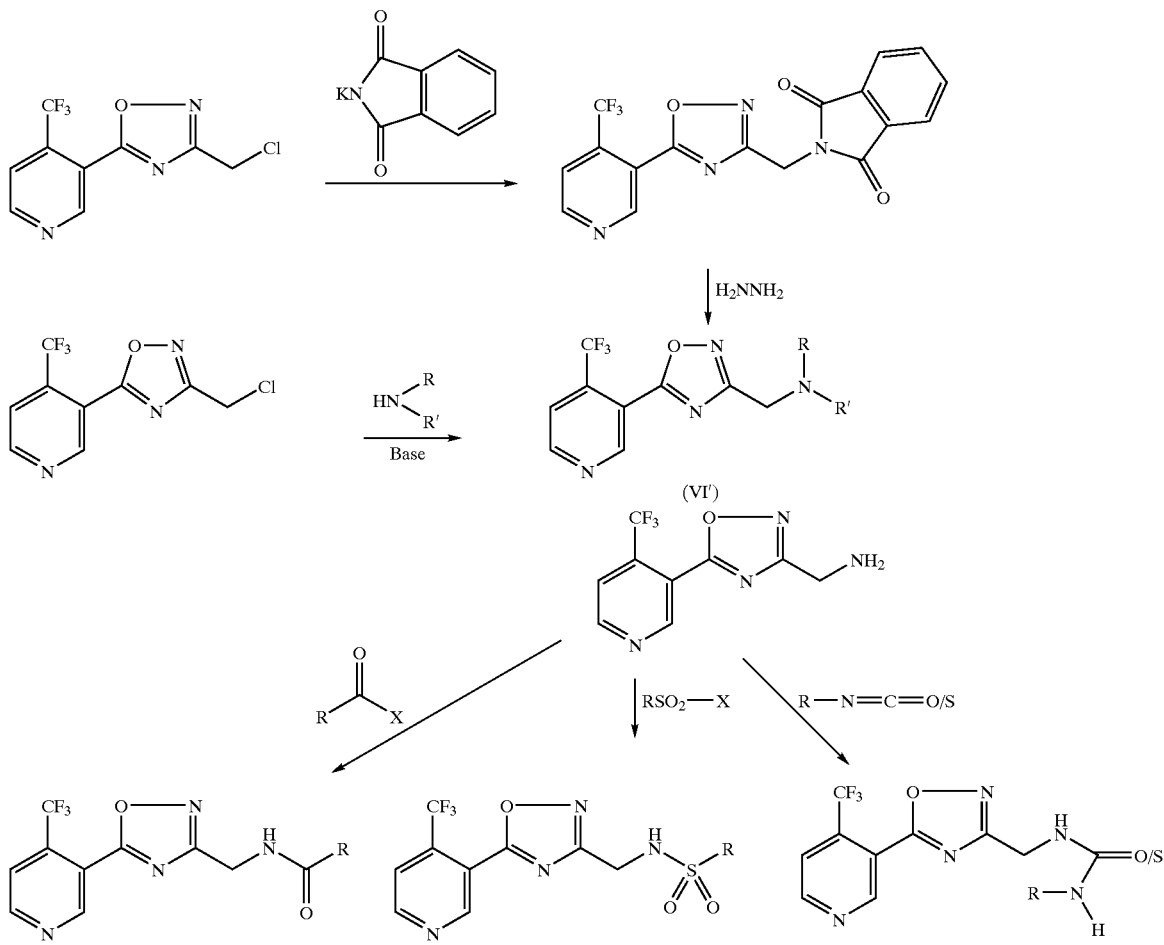

For preparing the sulfoxides ((VII'); n=1) and the sulfones ((VII'); n=2), the corresponding thioethers of the formula (VII') (n=0) are, for example, employed:

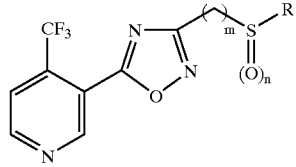

(VII')

The synthesis is carried out by oxidation with an oxidizing agent, for example meta-chloroperbenzoic acid, with an appropriately selected stoichiometry and temperature.

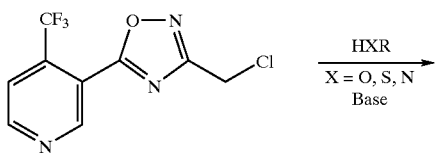

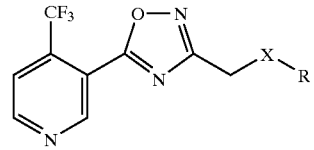

X = S | Oxidation

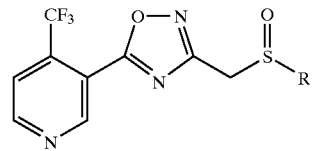

Oxidation

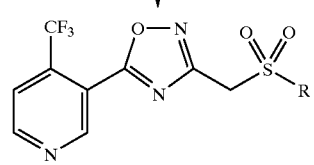

The synthesis of alkylester substituted oxadiazol derivatives (VIII') is effected, e.g. by the substitution of chlorine in ((V'); V'=Cl) by alkalicarboxylates or the esterification of the hydroxyalkyl-oxadiazol ((V'); V'=OH) with activated derivatives of carboxylic acids.

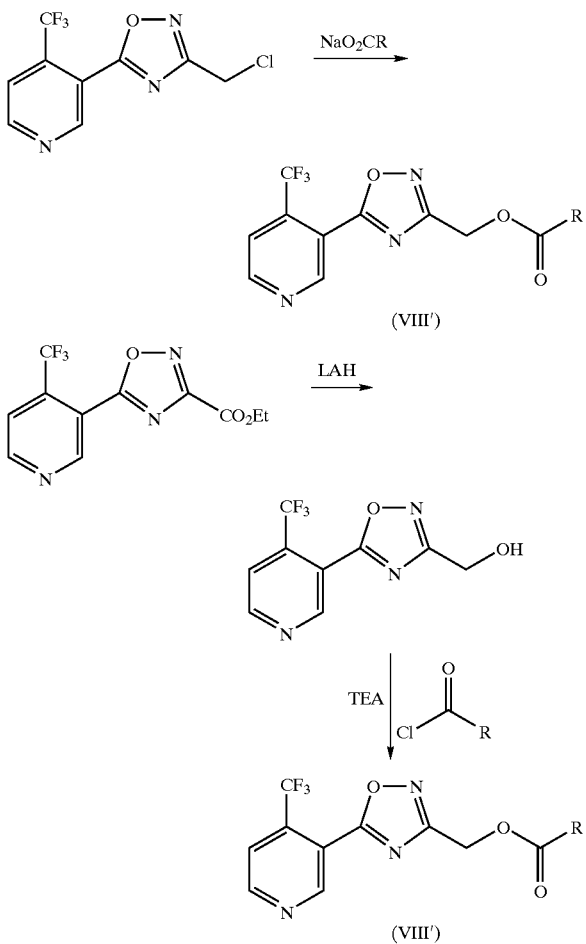

Starting from the hydroxyalkyl oxadiazol ((V'); V'=OH) the respective sulfonates can be prepared analogously:

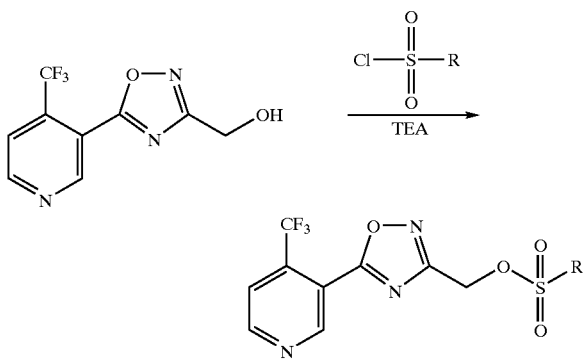

To prepare sulfonamides (X') the chloroalkyl compound ((V'); V'=Cl) is converted to the respective sodium sulfonate (IX') with the acid of sodium sulfite, which the can be further derivatized to the desired sulfonamide (X').

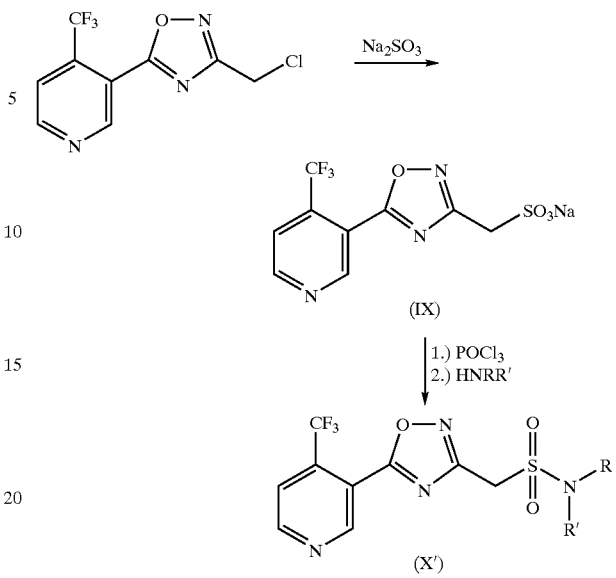

Collections of compounds of the formula (I') which can be synthesized by the abovementioned scheme may also be prepared in a parallel manner and this may be effected manually or in a semiautomated or fully automated manner. In this case, it is possible, for example, to automate the procedure of the reaction, the work-up or the purification of the products or of the intermediates. In total, this is to be understood as meaning a procedure as is described, for example, by S. H. DeWitt in "Annual Reports in Combinatorial Chemistry and Molecular Diversity: Automated Synthesis", Volume 1, Verlag Escom 1997, pages 69 to 77.

A number of commercially available apparatuses as they are offered by, for example, Stem Corporation, Woodrolfe Road, Tollesbury, Essex, CM9 8SE, England, H+P Labortechnik GmbH, Bruckmannring 28, 85764 Oberschleißheim, Germany or Radleys, Shirehill, Saffron Walden, Essex, England may be used for the parallel procedure of the reaction and work-up. For the parallel purification of compounds of the formula (I'), or of intermediates obtained during the preparation, use may be made, inter alia, of chromatography apparatuses, for example those from ISCO, Inc., 4700 Superior Street, Lincoln, Nebr. 68504, USA.

The apparatuses mentioned lead to a modular procedure in which the individual process steps are automated, but manual operations have to be performed between the process steps. This can be avoided by employing semi-integrated or fully integrated automation systems where the automation modules in question are operated by, for example, robots. Such automation systems can be obtained, for example, from Zymark Corporation, Zymark Center, Hopkinton, Mass. 01748, USA.

In addition to what has been described here, compounds of the formula (I') may be prepared in part or fully by solid-phase-supported methods. For this purpose, individual intermediate steps or all intermediate steps of the synthesis or of a synthesis adapted to suit the procedure in question are bound to a synthetic resin. Solid-phase-supported synthesis methods are described extensively in the specialist literature, for example Barry A. Bunin in "The Combinatorial Index", Verlag Academic Press, 1998.

The use of solid-phase-supported synthesis methods permits a series of protocols which are known from the literature and which, in turn, can be performed manually or in an automated manner. For example, the "tea-bag method" (Houghten, U.S. Pat. No. 4,631,211; Houghten et al., Proc. Natl. Acad. Sci, 1985, 82, 5131–5135), in which products from IRORI, 11149 North Torrey Pines Road, La Jolla, Calif. 92037, USA, are employed, may be semiautomated. The automation of solid-phase-supported parallel syntheses is performed successfully, for example, by apparatuses from Argonaut Technologies, Inc., 887 Industrial Road, San Carlos, Calif. 94070, USA or MultiSynTech GmbH, Wullener Feld 4, 58454 Witten, Germany.

The preparation according to the processes described herein yields compounds of the formula (I') in the form of substance collections which are referred to as libraries. The present invention also relates to libraries which comprise at least two compounds of the formula (I').

The compounds of the formula (I') are suitable for controlling animal pests, in particular insects, arachnids, helminths and mollusks, very especially preferably for controlling insects and arachnids, which are encountered in agriculture, in livestock breeding, in forests, in the protection of stored goods and materials and in the hygiene sector, and have good plant tolerance and favorable toxicity to warm-blooded species. They are active against normally sensitive and resistant species and against all or individual development stages. The abovementioned pests include:

From the order of the Acarina, for example, *Acarus siro*, Argas spp., Ornithodoros spp., *Dermanyssus gallinae, Eriophyes ribis, Phyllocoptruta oleivora*, Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa*, Panonychus spp., Tetranychus spp., Eotetranychus spp., Oligonychus spp. and Eutetranychus spp.

From the order of the Isopoda, for example, *Oniscus asselus, Armadium vulgare* and *Porcellio scaber.*

From the order of the Diplopoda, for example, *Blaniulus guttulatus.*

From the order of the Chilopoda, for example, *Geophilus carpophagus* and Scutigera spp.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea madeira, Blattella germanica, Acheta domesticus*, Gryllotalpa spp., *Locusta migratoria migratorioides, Melanoplus differentialis* and *Schistocerca gregaria.*

From the order of the Isoptera, for example, Reticulitermes spp.

From the order of the Anoplura, for example, *Phylloera vastatrix*, Pemphigus spp., *Pediculus humanus corporis*, Haematopinus spp. and Linognathus spp.

From the order of the Mallophaga, for example, Trichodectes spp. and Damalinea spp.

From the order of the Thysanoptera, for example, *Hercinothrips femoralis* and *Thrips tabaci.*

From the order of the Heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae*, Myzus spp., *Phorodon humuli, Rhopalosiphum padi*, Empoasca spp., *Euscelus bilobatus, Nephotettix cincticeps, Lecanium corni, Saissetia oleae, Laodelphax striatellus, Nilaparvata lugens, Aonidiella aurantii, Aspidiotus hederae*, Pseudococcus spp. and Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea*, Lymantria spp., *Bucculatrix thurberiella, Phyllocnistis citrella*, Agrotis spp., Euxoa spp., Feltia spp., *Earias insulana*, Heliothis spp., *Laphygma exigua, Mamestra brassicae, Panolis flammea, Prodenia litura*, Spodoptera spp., *Trichoplusia ni, Carpocapsa pomonella*, Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana.*

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae*, Diabrotica spp., *Psylloides chrysocephala, Epilachna varivestis*, Atomaria spp., *Oryzaephilus surinamensis*, Anthonumus spp., Sitophilus spp., *Otiorrhynchus sulcatus, Cosmopolites sordidus, Ceuthorrynchus assimilis, Hypera postica*, Dermestes spp., Trogoderma, Anthrenus spp., Attagenus spp., Lyctus spp., *Meligethes aeneus*, Ptinus spp., *Niptus hololeucus, Gibbium psylloides*, Tribolium spp., *Tenebrio molitor*, Agriotes spp., Conoderus spp., *Melolontha melolontha, Amphimallon solstitialis* and *Costelytra zealandica.*

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster*, Musca spp., Fannia spp., *Calliphora erythiocephala*, Lucilia spp., Chrysomyia spp., Cuterebra spp., Gastrophilus spp., Hypobosca spp., Stomoxys spp., Oestrus spp., Hypoderma spp., Tabanus spp., Tannia spp., *Bibio hortulanus, Oscinella frit*, Phorbia spp., *Pegomyia hyoscyami, Ceratitis capitata, Dacus oleae* and *Tipula paludosa.*

From the order of the Siphonaptera, for example, *Xenopsylla cheopsis* and Ceratophyllus spp.

From the order of the Arachnida, for example, *Scorpio maurus* and *Latrodectus mactans.*

From the class of helminths, for example, Haemonchus, Trichostrongulus, Ostertagia, Cooperia, Chabertia, Strongyloides, Oesophagostomum, Hyostrongulus, Ancylostoma, Ascaris and Heterakis, as well as Fasciola.

From the class of the Gastropoda, for example, Deroceras spp., Arion spp., Lymnaea spp., Galba spp., Succinea spp., Biomphalaria spp., Bulinus spp. and Oncomelania spp.

From the class of Bivalva, for example, Dreissena spp.

The phytoparasitic nematodes which can be controlled according to the invention include, for example, the root-parasitic soil nematodes, such as, for example, those of the genera Meloidogyne (root gall nematodes, such as *Meloidogyne incognita, Meloidogyne hapla* and *Meloidogyne javanica*), Heterodera and Globodera (cyst-forming nematodes, such as *Globodera rostochiensis, Globodera pallida* and *Heterodera trifolii*) and of the genera Radopholus, such as *Radopholus similis*, Pratylenchus, such as *Pratylenchus neglectus, Pratylenchus penetrans* and *Pratylenchus curvitatus*; Tylenchulus, such as *Tylenchulus semipenetrans*, Tylenchorhynchus, such as *Tylenchorhyn-*

*chus dubius* and *Tylenchorhynchus claytoni*, Rotylenchus, such as *Rotylencus robustus*, Heliocotylenchus, such as *Heliocotylenchus multicinctus*, Belonoaimus, such as *Belonoaimus longicaudatus*, Longidorus, such as *Longidorus elongatus*, Trichodorus, such as *Trichodorus primitivus* and Xiphinema, such as *Xiphinema index*.

The nematode genera Ditylenchus (stem parasites, such as *Ditylenchus dipsaci* and *Ditylenchus destructor*), Aphelenchoides (leaf nematodes, such as *Aphelenchoides ritzemabosi*) and Anguina (blossom nematodes, such as *Anguina tritici*) can furthermore be controlled with the compounds according to the invention.

The invention also relates to compositions, for example crop protection compositions, preferably insecticidal, acaricidal, ixodicidal, nematicidal, molluskidal or fungicidal, particularly preferably insecticidal and acaricidal compositions, which comprise one or more compounds of the formula (I') in addition to suitable formulation auxiliaries.

In general, the compositions according to the invention comprise from 1 to 95% by weight of the active compounds of the formula (I').

For preparing the compositions according to the invention, the active compound and the other additives are combined and formulated as a suitable use form.

The invention also relates to compositions, in particular insecticidal and acaricidal compositions, which comprise the compounds of the formula (I') in addition to suitable formulation auxiliaries.

The compositions according to the invention in general comprise from 1 to 95% by weight the active compounds of the formula (I'). They can be formulated in various ways, depending on how this is determined by the biological and/or chemico-physical parameters. Suitable formulation possibilities are therefore:

Wettable powders (WP), emulsifiable concentrates (EC), aqueous solutions (SL), emulsions, sprayable solutions, oil- or water-based dispersions (SC), suspoemulsions (SE), dusting powders (DP), seed dressings, granules in the form of microgranules, sprayed granules, absorption granules and adsorption granules, water-dispersible granules (WG), ULV formulations, microcapsules, waxes or baits.

These individual types of formulation are known in principle and are described, for example, in: Winnacker-Küchler, "Chemische Technologie" [Chemical Technology], Volume 7, C. Hauser Verlag Munich, 4th Edition 1986; van Falkenberg, "Pesticides Formulations", Marcel Dekker N.Y., 2nd Edition 1972–73; K. Martens, "Spray Drying Handbook", 3rd Edition 1979, G. Goodwin Ltd. London.

The necessary formulation auxiliaries, i.e. carrier substances and/or surface-active substances, such as inert materials, surfactants, solvents and further additives, are likewise known and are described, for example, in: Watkins, "Handbook of Insecticide Dust Diluents and Carriers", 2nd Edition, Darland Books, Caldwell N.J.; H. v. Olphen, "Introduction to Clay Colloid Chemistry", 2nd Edition, J. Wiley & Sons, N.Y.; Marsden, "Solvents Guide", 2nd Edition, Interscience, N.Y. 1950; McCutcheon's, "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflachenaktive Äthylenoxidaddukte" [Surface-active ethylene oxide adducts], Wiss. Verlagsgesell., Stuttgart 1967; Winnacker-Küchler, "Chemische Technologie" [Chemical Technology], Volume 7, C. Hauser Verlag Munich, 4th Edition 1986.

Combinations with other substances having a pesticidal action, fertilizers and/or growth regulators can be prepared on the basis of these formulations, for example in the form of a ready-to-use formulation or as a tank mix. Wettable powders are preparations which are uniformly dispersible in water and which, alongside the active compound, and in addition to a diluent or inert substance, also comprise wetting agents, for example polyethoxylated alkylphenols, polyethoxylated fatty alcohols or alkyl- or alkylphenolsulfonates, and dispersing agents, for example sodium ligninsulfonate or sodium 2,2'-dinaphthylmethane-6,6'-disulfonate. Emulsifiable concentrates are prepared by dissolving the active compound in an organic solvent, for example butanol, cyclohexanone, dimethylformamide, xylene or also higher-boiling aromatics or hydrocarbons, with the addition of one or more emulsifiers.

Emulsifiers which can be used are, for example: calcium alkylarylsulfonates, such as Ca dodecylbenzenesulfonate, or nonionic emulsifiers, such as fatty acid polyglycol esters, alkylaryl polyglycol ethers, fatty alcohol polyglycol ethers, propylene oxide/ethylene oxide condensation products, alkyl polyethers, sorbitan fatty acid esters, polyoxyethylene sorbitan fatty acid esters or polyoxyethylene sorbitol esters.

Dusting powders are obtained by grinding the active compound with finely divided solid substances, for example talc, naturally occurring clays, such as kaolin, bentonite and pyrophillite, or diatomaceous earth. Granules can be prepared either by spraying the active compound onto granular inert material capable of adsorption or by applying active compound concentrates to the surface of carrier substances, such as sand, kaolinites or granular inert material, by means of adhesives, for example polyvinyl alcohol, sodium polyacrylate or mineral oils. Suitable active compounds can also be granulated in the manner customary for the preparation of fertilizer granules—if desired as a mixture with fertilizers.

In wettable powders, the active compound concentration is generally about 10 to 90% by weight, the remainder to make up 100% by weight comprising customary formulation constituents. In emulsifiable concentrates, the active compound concentration can be about 5 to 80% by weight. Dust-like formulations usually comprise 5 to 20% by weight of active compound, and sprayable solutions about 2 to 20% by weight. In granules, the content of active compound partly depends on whether the active compound is present in liquid or solid form and what granulating auxiliaries, fillers and the like are used.

In addition, the active compound formulations mentioned comprise, if appropriate, the particular customary tackifiers, wetting agents, dispersing agents, emulsifiers, penetration agents, solvents, fillers or carrier substances.

For use, the concentrates in the commercially available form are diluted in the customary manner, if appropriate, for example by means of water in the case of wettable powders, emulsifiable concentrates, dispersions and in some cases also microgranules. Dust-like and granular formulations as well as sprayable solutions are usually not diluted further with additional inert substances before use.

The required amount applied varies with the external conditions, such as temperature, humidity and the like. It can vary within wide limits, for example between 0.0005 and 10.0 kg/ha or more of active substance, but is preferably between 0.001 and 5 kg/ha of active compound.

The active compounds according to the invention can be present in their commercially available formulations and in the use forms prepared from these formulations as mixtures with other active compounds, such as insecticides, attractants, sterilizing agents, acaricides, nematicides, fungicides, growth-regulating substances or herbicides.

The pesticides include, for example, phosphoric acid esters, carbamates, carboxylic acid esters, formamidines, tin compounds and substances produced by microorganisms.

Preferred partners for the mixtures are:
1. from the group of phosphorus compounds
   acephate, azamethiphos, azinphos-ethyl, azinphos-methyl, bromophos, bromophos-ethyl, cadusafos (F-67825), chlorethoxyphos, chlorfenvinphos, chlormephos, chlorpyrifos, chlorpyrifos-methyl, demeton, demeton-S-methyl, demeton-S-methyl sulfone, dialifos, diazinon, dichlorvos, dicrotophos, dimethoate, disulfoton, EPN, ethion, ethoprophos, etrimfos, famphur, fenamiphos, fenitrothion, fensulfothion, fenthion, fonofos, formothion, fosthiazate (ASC-66824), heptenophos, isazophos, isothioate, isoxathion, malathion, methacrifos, methamidophos, methidathion, salithion, mevinphos, monocrotophos, naled, omethoate, oxydemeton-methyl, parathion, parathion-methyl, phenthoate, phorate, phosalone, phosfolan, phosphocarb (BAS-301), phosmet, phosphamidon, phoxim, pirimiphos, primiphos-ethyl, pirimiphos-methyl, pro fenofos, propaphos, proetamphos, prothiofos, pyraclofos, pyridapenthion, quinaiphos, sulprofos, temephos, terbufos, tebupirimfos, tetrachlorvinphos, thiometon, triazophos, trichlorphon, vamidothion;
2. from the group of carbamates
   alanycarb (OK-135), aldicarb, 2-sec-butylphenyl methyl-carbamate (BPMC), carbaryl, carbofliran, carbosulfan, cloethocarb, benfuiracarb, ethiofencarb, furathiocarb, HCN-801, isoprocarb, methomyl, 5-methyl-m-cumenyl butyryl(methyl)carbamate, oxamyl, pirimicarb, propoxur, thiodicarb, thiofanox, 1-methylthio(ethylideneamino) N-methyl-N-(morpholinothio)carbamate (UC 51717), triazamate;
3. from the group of carboxylic acid esters
   acrinathrin, allethrin, alphametrin, 5-benzyl-3-furyl methyl (E)-(1R)-cis-2,2-di-methyl-3-(2-oxothiolan-3-ylidenemethyl)cyclopropanecarboxylate, beta-cyfluthrin, beta-cypermethrin, bioallethrin, bioallethrin ((S)-cyclopentyl isomer), bioresmethrin, bifenthrin, (RS)-1-cyano-1-(6-phenoxy-2-pyridyl)methyl (1RS)-trans-3-(4-tert-butylphenyl)-2,2-dimethylcyclopropanecarboxylate (NCI 85193), cycloprothrin, cyfluthrin, cyhalothrin, cythithrin, cypermethrin, cyphenothrin, deltamethrin, empenthrin, esfenvalerate, fenfluthrin, fenpropathrin, fenvalerate, flucythrinate, flumethrin, fluvalinate (D isomer), imiprothrin (S-41311), lambda-cyhalothrin, permethrin, pheothrin ((R) isomer), prallethrin, pyrethrins (natural products), resmethrin, tefluthrin, tetramethrin, theta-cypermethrin (TD-2344), tralomethrin, transfluthrin and zeta-cypermethrin (F-56701);
4. from the group of amidines
   amitraz, chlordimeform;
5. from the group of tin compounds
   cyhexatin, fenbutatin oxide;
6. others
   abamectin, ABG-9008, acetamiprid, *Anagrapha falcitera*, AKD-1022, AKD-3059, ANS-118, *Bacillus thuringiensis, Beauveria bassianea*, bensultap, bifenazate (D-2341), binapacryl, BJL-932, bromopropylate, BTG-504, BTG-505, buprofezin, camphechlor, cartap, chlorobenzilate, chlorfenapyr, chlorfluazuron, 2-(4-chlorophenyl)-4,5-diphenylthiophene (UBI-T 930), chlorfentezine, chromafenozide (ANS-118), CG-216, CG-217, CG-234, A-184699, 2-naphthylmethyl cyclopropanecarboxylate (Ro 12-0470), cyromazin, diacloden (thiamethoxam), diafenthiuron, N-(3,5-dichloro-4-(1,1,2,3,3,3-hexafluoro-1-propyloxy)phenyl)carbamoyl)-2-chlorobenzocarboxamide acid ethyl ester, DDT, dicofol, diflubenzuron, N-(2,3-dihydro-3-methyl-1,3-thiazol-2-ylidene)-2,4-xylidine, dinobuton, dinocap, diofenolan, DPX-062, emamectin-benzoate (MK-244), endosulfan, ethiprole (sulfethiprole), ethofenprox, etoxazole (YI-5301), fenazaquin, fenoxycarb, fipronil, fluazuron, flumite (flufenzine, SZI-121), 2-fluoro-5-(4-(4-ethoxyphenyl)-4-methyl-1-pentyl)diphenyl ether (MTI 800), granulosis and nuclear polyhedrosis viruses, fenpyroximate, fenthiocarb, flubenzimine, flucycloxuron, flufenoxuron, flufenprox (ICI-A5683), fluproxyfen, gamma-HCH, halofenozide (RH-0345), halofenprox (MTI-732), hexaflumuron (DE__473), hexythiazox, HOI-9004, hydramethylnon (AC 217300), lufenuron, imidacloprid, indoxacarb (DPX-MP062), kanemite (AKD-2023), M-020, MTI-446, ivermectin, M-020, methoxyfenozide (Intrepid, RH-2485), milbemectin, NC-196, neemgard, nitenpyram (TI-304), 2-nitromethyl-4,5-dihydro-6H-thiazine (DS 52618), 2-nitromethyl-3,4-dihydrothiazole (SD 35651), 2-nitromethylene-1,2-thiazinan-3-ylcarbamaldehyde (WL 108477), pyriproxyfen (S-71639), NC-196, NC-1111, NNI-9768, novaluron (MCW-275), OK-9701, OK-9601, OK-9602, propargite, pymethrozine, pyridaben, pyrimidifen (SU-8801), RH-0345, RH-2485, RYI-210, S-1283, S-1833, SB7242, SI-8601, silafluofen, silomadine (CG-177), spinosad, SU-9118, tebufenozide, tebufenpyrad (MK-239), teflubenzuron, tetradifon, tetrasul, thiacloprid, thiocyclam, TI-435, tolfenpyrad (OMI-88), triazamate (RH-7988), triflumuron, verbutin, vertalec (Mykotal), YI-5301, The abovementioned combination partners are known active compounds, and most of them are described in Ch. R. Worthing, S. B. Walker, The Pesticide Manual, 11th Edition, British Crop Protection Council Farnham 1997.

The active compound content of the use forms prepared from the commercially available formulations can be from 0.00000001 to 95% by weight of active compound, preferably between 0.00001 and 1% by weight.

The active compounds are used in a customary manner appropriate for the use forms.

The active compounds according to the invention are also suitable for controlling endo- and ectoparasites in the veterinary medicine field and in the field of animal husbandry. The active compounds according to the invention are used here in a known manner, such as by oral use in the form of, for example, tablets, capsules, potions or granules, by means of dermal use in the form of, for example, dipping, spraying, pouring-on, spotting-on and dusting, and by parenteral use in the form of, for example, injection.

The novel compounds of the formula (I') can accordingly also particularly advantageously be used in livestock husbandry (for example cattle, sheep, pigs and poultry, such as chickens, geese and the like). In a preferred embodiment of the invention, the compounds are administered orally to the animals, if appropriate in suitable formulations and if appropriate with the drinking water or feed. Since excretion in the feces takes place in an active manner, the development of insects in the feces of the animals can be prevented very easily in this way. The dosages and formulations suitable in each case depend in particular on the species and the development stage of the stock animals and also on the level of infestation, and can easily be determined and specified by the customary methods. The compounds can be employed in cattle, for example, in dosages of 0.01 to 1 mg/kg of body weight.

In addition to the application methods mentioned hereinabove, the active compounds of the formula (I') according to the invention also have excellent systemic action. The active compounds can therefore also be introduced into the plants via below-ground and above-ground parts of plants (root, stem, leaf), when the active compounds are applied in liquid or solid form to the immediate surroundings of the plants (for example granules in soil application, application in flooded rice fields).

Furthermore, the active compounds according to the invention are particularly useful for treating vegetative and generatative propagation stock, such as, for example, seed of, for example, cereals, vegetables, cotton, rice, sugar beet and other crops and ornamentals, of bulbs, cuttings and tubers of other vegetatively propagated crops and ornamentals. To this end, treatment can be carried out prior to sowing or planting (for example by special seed coating techniques, by seed dressings in liquid or solid form or by seed box treatment), during sowing or planting or after sowing or planting by special application techniques (for example seed row treatment). Depending on the application, the amount of active compound applied can vary within a relatively wide range. In general, the application rates are between 1 g and 10 kg of active compound per hectare of soil area.

The compounds of the formula (I') can also be used for controlling harmful plants in crops of known genetically modified plants or of genetically modified plants still to be developed. The transgenic plants generally have particularly advantageous properties, for example resistance to certain crop protection agents, resistance to plant diseases or pathogens of plant diseases, such as certain insects or microorganisms, such as fungi, bacteria or viruses. Other special properties relate, for example, to the harvested product, with respect to quantity, quality, shelf-life, composition and special ingredients. Thus, transgenic plants having increased starch content or a modified quality of the starch or those having a different fatty acid composition of the harvested product are known.

Preference is given to the use in economically important transgenic crops of useful and ornamental plants, for example cereals, such as wheat, barley, rye, oats, millet, rice, manioc and maize, or else crops of sugar beet, cotton, soya, rapeseed, potato, tomato, pea and other vegetable species.

The use in transgenic crops, in particular crops with resistance to insects, is, in addition to the effects with respect to harmful organisms which can be observed in other crops, frequently associated with effects which are specific for the application in the respective transgenic crop, for example a modified or specifically widened spectrum of pests which can be controlled, or modified application rates which can be used for the application.

The invention therefore also provides the use of compounds of the formula (I') for controlling harmful organisms in transgenic crop plants.

The use of the compounds according to the invention comprises, in addition to direct application to the pests, any other application where the compounds of the formula (I') act on the pests. Such indirect applications may be, for example, the use of compounds which decompose or are degraded to compounds of the formula (I'), for example in the soil, the plant or the pest.

Herewith, express reference is made to the content of German Patent Application 198 581 93.9, the priority of which is claimed by the present application, and to the content of the enclosed summary; they are incorporated into this description by reference.

The examples below serve to illustrate the invention.

EXAMPLES

I. COMPOUNDS OF FORMULA (I)

A. Formulation Examples a) A dusting powder is obtained by mixing 10 parts by weight of active compound and 90 parts by weight of talc, as the inert substance, and comminuting the mixture in an impact mill.

b) A wettable powder which is readily dispersible in water is obtained by mixing 25 parts by weight of active compound, 65 parts by weight of kaolin-containing quartz, as the inert substance, 10 parts by weight of potassium ligninsulfonate and 1 part by weight of sodium oleoylmethyltauride, as wetting and dispersing agent and grinding the mixture in a pinned disk mill.

c) A dispersion concentrate which is readily dispersible in water is prepared by mixing 40 parts by weight of active compound with 7 parts by weight of a sulfosuccinic monoester, 2 parts by weight of a sodium ligninsulfonate and 51 parts by weight of water and grinding the mixture to a fineness of below 5 microns in a grinding bead mill.

d) An emulsifiable concentrate can be prepared from 15 parts by weight of active compound, 75 parts by weight of cyclohexane, as the solvent, and 10 parts by weight of ethoxylated nonylphenol (10 EO), as the emulsifier.

e) Granules can be prepared from 2 to 15 parts by weight of active compound and an inert granule carrier material, such as attapulgite, pumice granules and/or quartz sand. A suspension of the wettable powder from Example b) having a solids content of 30% is expediently used, and this is sprayed onto the surface of attapulgite granules and the components are dried and mixed intimately. The weight content of the wettable powder is approximately 5% and that of the inert carrier material is approximately 95% of the finished granules.

B. Chemical Examples

Example No. 1

3-Isopropyl-5-(4-trifluoromethyl-3-pyridyl)-1,2,4-oxadiazole (Table 1, No. 81)

2 g of methyl 4-trifluoromethylnicotinate and 1.56 g of isobutyramide oxime were initially charged in 15 ml of ethanol and cooled to 0° C. 10 ml of a 1.2 molar sodium ethoxide solution were added dropwise to this solution. The mixture was allowed to warm to room temperature over a period of two hours and stirring was then continued at this temperature until the reaction, according to TLC, had ended.

The reaction mixture was concentrated and the residue was taken up in saturated ammonium chloride solution and extracted with diethyl ether. Chromatographic purification of the crude product gave the desired compound as a yellowish oil.

$^1$H-NMR (CDCl$_3$, 300 MHz): d=1.41 (d, J=6.9 Hz, 6H), 3.22 (m, 1H), 7.78 (d, J=5 Hz, 1H), 9.02 (d, J=5 Hz, 1H), 9.34 (s, 1H) ppm.

Example No. 2

3-Isopropyl-5-(4-trifluoromethyl-5-pyrimidyl)-1,2,4-oxadiazole (Table 1, No. 189)

2 g of ethyl 4-trifluoromethylpyrimidine-5-carboxylate and 1.56 g of isobutyramide oxime were initially charged in 15 ml of ethanol and cooled to 0° C. 10 ml of a 1.2 molar sodium ethoxide solution were added dropwise to this solution. The mixture was allowed to warm to room temperature over a period of one hour and then heated under reflux until the reaction, according to TLC, had ended. The reaction mixture was concentrated and the residue was taken up in saturated ammonium chloride solution and extracted with diethyl ether. Chromatographic purification of the crude product gave the desired compound as a yellowish oil.

$^1$H-NMR (CDCl$_3$, 300 MHz): d=1.43 (d, J=7 Hz, 6H), 3.22 (hept., J=7 Hz, 1H), 9.52 (s, 1H), 9.58 (s, 1H) ppm.

Example No. 3

2-Methyl-5-(4-trifluoromethyl-3-pyridyl)-1,3,4-oxadiazole (Table 3, No. 549)

500 mg of 4-trifluoromethylnicotinic hydrazide were heated under reflux in 3.5 ml of triethyl orthoacetate for 2 hours. The reaction mixture was subsequently concentrated and the residue was carefully admixed with 2 ml of phosphorus oxychloride. The mixture was stirred at room temperature for 1 hour and then poured on ice and extracted with ethyl acetate. Chromatographic purification of the crude product obtained after drying and concentrating gave the desired compound as a yellowish oil.

$^1$H-NMR (CDCl$_3$, 300 MHz): d=2.67 (s, 3H), 7.75 (d, J=5 Hz, 1H), 8.99 (d, J=5 Hz, 1H), 9.34 (s, 1H) ppm.

Example No. 4

4-(Ethoxycarbonylmethyl)-2-(4-trifluoromethyl-3-pyridyl) thiazole (Table 4, No. 688)

500 mg of 4-trifluoromethylpyridine-3-thiocarboxamide and 440 mg of ethyl 4-chloroacetate were dissolved in 5 ml of dimethylformamide and heated at 100° C. for 4 hours. After cooling, the reaction mixture was poured onto ice-water and extracted with diethyl ether. The diethyl ether phase was dried (MgSO$_4$), filtered and concentrated and the residue was purified by chromatography. This gave the desired product in pure form as a colorless oil.

$^1$H-NMR (CDCl$_3$, 300 MHz): d=1.28 (t, J=7.5 Hz, 3H), 3.92 (s, 2H), 4.22 (q, J=7.5 Hz, 2H), 7.43 (s, 1H), 7.68 (d, J=5 Hz, 1H), 8.86 (d, J=5 Hz, 1H), 8.97 (s, 1H) ppm.

Example No. 5

4-Ethyl-2-(4-trifluoromethyl-3-pyridyl)oxazole (Table 4, No. 762)

2.6 g of 4-trifluoromethylnicotinic acid were admixed with 20 ml of thionyl chloride and heated at reflux temperature for 1 hour. After cooling, excess thionyl chloride was distilled off and the acyl chloride which remained as a pale yellow oil was taken up in 30 ml of dichloromethane. This solution was subsequently added dropwise to a solution of 2.4 g of 2-amino-1-butanol and 2.75 g of triethylamine in 30 ml of dichloromethane cooled in an ice bath. After the addition had ended, stirring was continued at room temperature for approximately 2 hours. The mixture was poured into ammonium chloride solution and extracted with ethyl acetate. The crude N-(1-hydroxy-2-butyl)-4-trifluoromethylnicotinamide (2.3 g) obtained after drying and concentrating the ethyl acetate phase was dissolved at room temperature in 100 ml dichloromethane and mixed with 4.6 g of periodinan (Dess-Martin reagent). After the reaction had ended, according to TLC, the reaction mixture was concentrated and purified by column chromatography. The resulting 2-(trifluoromethylpyridin-3-amido)butanal (1.5 g) was dissolved in 30 ml of dimethylformamide, admixed with 2.72 g of phosphorus oxychloride and heated at 90° C. for 15 minutes. The solution was then poured onto ice and extracted with diethyl ether. Drying and concentration of the diethyl ether phase and chromatographic purification of the residue gave the product as a brownish oil.

$^1$H-NMR (CDCl$_3$, 300 MHz): d=1.3 (t, J=7.4 Hz, 3H), 2.66 (qd, J=7.4 Hz, J<1 Hz, 2H), 7.58 (t, J<1 Hz, 1H), 7.65 (d, J=5 Hz, 1H), 8.83 (d, J=5 Hz, 1H), 9.33 (d, J=5 Hz, 1H) ppm.

Example No. 6

4-Ethyl-2-(4-trifluoromethyl-3-pyridyl)-4,5-dihydrooxazole (Table 5, No 876)

1 g of 4-trifluoromethylnicotinic acid was admixed with 8 ml of thionyl chloride and heated at reflux temperature for 1 hour. After cooling, excess thionyl chloride was distilled off and the acyl chloride which remained as a pale yellow oil was taken up in 10 ml of dichloromethane. This solution was subsequently added dropwise to a solution of 930 mg of 2-amino-1-butanol and 1.06 g of triethylamine in 10 ml of dichloromethane cooled in an ice bath. After the addition had ended, stirring was continued for approximately 2 hours at room temperature. The mixture was poured into an ammonium chloride solution and extracted with ethyl acetate. The crude N-(1-hydroxy-2-butyl)-4-trifluoromethylnicotinamide (1.03 g) obtained after drying and concentration of the ethyl acetate phase was dissolved at room temperature in 6 ml of tetrahydrofuran and admixed with 1.09 g of N-[(triethylammonio)sulfonyl]-methylcarbamate (Burgess' reagent). The mixture was stirred at 60° C. for 3 hours. After cooling, the batch was concentrated and the residue was taken up in water and extracted with ethyl acetate. Chromatographic purification of the crude product gave the product as a colorless oil.

$^1$H-NMR (CDCl$_3$, 200 MHz): d=1.03 (t, J=7.6 Hz, 3H), 1.72 (m, 2H), 4.15 (t, J=7.5 Hz, 1H), 4.32 (m, 1H), 4.58 (t, J=7.5 Hz, 1H), 7.6 (d, J=5 Hz, 1H), 8.87 (d, J=5 Hz, 1H), 9.06 (s, 1H) ppm.

Example No. 7

2-(3-Thienylmethyl)-5-(4-trifluoromethyl-3-pyridyl)-1,3,4-oxadiazole (Table 3, No. 572)

880 mg of thiophene-3-acetic hydrazide were added to a solution of 960 mg of 4-trifluoromethylpyridine-3-carboxylic acid in 5 ml of phosphorus oxychloride, and the mixture was heated at reflux for 2 hours. The reaction mixture was subsequently added dropwise to ice-water, made neutral using concentrated ammonia solution and extracted with ethyl acetate. Drying (Na$_2$SO$_4$), concentration and chromatographic purification gave 624 mg of the desired product as a slightly brown oil.

$^1$H-NMR (CDCl$_3$, 200 MHz): d=4.38 (s, 2H), 7.1 (d, J=5 Hz, 1H), 7.23 (s, 1H), 7.37 (dd, J=5 Hz, J=3 Hz, 1H), 7.75 (d, J=6 Hz, 1H), 8.98 (d, J=6 Hz, 1H), 9.36 (s, 1H) ppm.

Example No. 8

5-Methyl-3-(4-trifluoromethyl-3-pyridyl)-1H-1,2,4-triazole (Table 6, No. 947)

A mixture of 290 mg of ethylacetimidate hydrochloride and 100 mg of sodium hydroxide in 2 ml of ethanol was filtered and added to 500 mg of 4-trifluoromethyl-3-pyridinecarbohydrazide, and the mixture was heated under reflux for 3 hours. The reaction mixture was concentrated and the residue was suspended in xylene and refluxed for 4 hours. For work-up, the batch was diluted with ethyl acetate and washed with water. Chromatographic purification gave the pure product as a colorless solid.

$^1$H-NMR (CDCl$_3$, 300 MHz): d=2.58 (s, 3H), 7.64 (d, J=5 Hz, 1H), 8.85 (d, J=5 Hz, 1H), 9.19 (s, 1H) ppm.

Example No. 9
3-(N-Isopropylcarbamoylmethyl)-5-(4-trifluoromethyl-3-pyridyl)-1,2,4-oxadiazole Step 1: Tert-butyl 3-Amino-3-(4-trifluoromethyl-3-pyridinecarbonyloxy-imino)propionate 30 g of 4-trifluoromethyl-3-pyridinecarboxylic acid is initially charged in 150 ml of dry THF and, a little at a time, admixed with 25.3 g of carbonyl-diimidazole. The mixture is stirred at room temperature for 30 min. 27.2 g of tert-butoxycarbonylacetamide oxime dissolved in 150 ml of THF are then added dropwise. The mixture is stirred overnight, the solvent is evaporated and the residue is taken up in ethyl acetate, washed three times with 1 M sulfuric acid and once with saturated sodium bicarbonate solution. Concentration of the ethyl acetate phase gives 28 g of the product as a pale yellow solid.

$^1$H-NMR (CDCl$_3$, 300MHz): d=1.5 (s, 9H), 3.3 (s, 2H), 5.55 (br.s, 2H), 7.83 (d, J=5 Hz, 1H), 8.97 (d, J=5 Hz, 1H), 9.13 (s, 1H) ppm.

Step 2: 3-(Tert-butoxycarbonylmethyl)-5-(4-trifluoromethyl-3-pyridyl)-1,2,4-oxadiazole 28 g of tert-butyl 3-amino-3-(4-trifluoromethyl-3-pyridinecarbonyloxy-imino)propionate are dissolved in 380 ml of toluene and heated under reflux for 17 hours. Concentration and chromatographic purification of the residue over silica gel gives 14.4 g of the product as a pale brown oil.

$^1$H-NMR (CDCl$_3$, 300MHz): d=1.5 (s, 9H), 3.88 (s, 2H), 7.79 (d, J=5 Hz, 1H), 9.02 (d, J=5 Hz, 1H), 9.33 (s, 1H) ppm.

Step 3: 3-(Hydroxycarbonylmethyl)-5-(4-trifluoromethyl-3-pyridyl)-1,2,4-oxadiazole 12.4 g of 3-(tert-butoxycarbonylmethyl)-5-(4-trifluoromethyl-3-pyridyl)-1,2,4-oxadiazole are dissolved in 110 ml of dichloromethane and admixed with 57 ml of trifluoroacetic acid. The reaction mixture is stirred at room temperature for 1.5 hours and subsequently concentrated under reduced pressure. The residue is repeatedly taken up in dichloromethane and reconcentrated to remove any remaining trifluoroacetic acid. The mixture is finally triturated with diethyl ether, giving 8.1 g of the product as a white solid.

Step 4: 3-(N-Isopropylcarbamoylmethyl)-5-(4-trifluoromethyl-3-pyridyl)-1,2,4-oxadiazole 1 g of the product of the previous step are dissolved in 10 ml of THF and is mixed with 0.59 g of carbonyldiimidazole. The mixture is stirred at room temperature for 10 minutes, 0.22 g of isopropylamine are added dropwise and the mixture is allowed to react for a further 1.5 hours at room temperature with stirring. The reaction mixture is subsequently concentrated and the residue is taken up in ethyl acetate and washed three times with 1 M sulfuric acid and once with saturated sodium bicarbonate solution. The solid residue obtained after drying and concentrating the ethyl acetate phase is recrystallized from tert-butyl methyl ether, giving 0.46 g of the pure product as a pale yellow solid.

$^1$H-NMR (CDCl$_3$, 300MHz): d=1.20 (d, J=7.6 Hz, 6H), 3.82 (s, 2H), 4.12 (m, 1H), 6.50 (br.s, 1H), 7.81 (d, J=5 Hz, 1H), 9.02 (d, J=5 Hz, 1H), 9.37 (s, 1H) ppm.

Example No. 10
3-(N,N-Dimethylaminocarbamoyl)-5-(4-trifluoromethyl-3-pyridyl)-1,2,4-oxadiazole (Table 1, No. 502)

Step 1: Ethyl 2-Amino-2-(4-trifluoromethyl-3-pyridinecarbonyloxyimino)acetate 17.3 g of carbonyldiimidazole are initially charged in 200 ml of 1,4-dioxane and, a little at a time, admixed with 20 g of 4-trifluoromethyl-3-pyridinecarboxylic acid. The mixture is stirred at room temperature for 1 h and subsequently heated to 45° C. for 2 h. After cooling to 30° C., 14.5 g of ethoxycarbonylformamide oxime are added and the mixture is stirred at 45° C. for 3 h. The precipitated solid is filtered off with suction and the filtrate is concentrated to 50 ml and, together with the solid, added to 250 ml of ice-water. The solid is filtered off with suction and dried at 50° C. under reduced pressure. This gives 28.7 g of the product as a white solid of mp. 172–174° C.

Step 2: 3-Ethoxycarbonyl-5-(4-trifluoromethyl-3-pyridyl)-1,2,4-oxadiazole 20 g of ethyl 2-amino-2-(4-trifluormethyl-3-pyridinecarbonyloxyimino)-acetate are dissolved in 200 ml of a mixture of xylene and toluene and admixed with 5 g of Amberlyst 15. The mixture is boiled at 125–130° C. for 6 h using a Dean-Stark apparatus. After the reaction has ended, the mixture is cooled and admixed with a small amount of diethyl ether. The mixture is filtered with suction through a glass filter frit, and the solution is then concentrated. This gives 15.8 g of the product as a yellow oil.

Step 3: 5-(4-Trifluoromethyl-3-pyridyl)-1,2,4-oxadiazole-3-carboxylic Acid 15.8 g of 3-ethoxycarbonyl-5-(4-trifluoromethyl-3-pyridyl)-1,2,4-oxadiazole are initially charged in 13 ml of methanol, and, with ice-cooling at 0° C., a solution of 2.8 g of lithium hydroxide in 50 ml of water is added dropwise. The mixture is stirred at room temperature for 2 h, 20 ml of ice-water are added and the mixture is extracted with 200 ml of diethyl ether. The aqueous phase is adjusted to pH=2 using dil. HCl, and the precipitated product is filtered off with suction. After drying, 13.8 g of 5-(4-trifluoromethyl-3-pyridyl)-1,2,4-oxadiazole-3-carboxylic acid are obtained as a white solid of mp. 157–159° C.

Step 4: N,N-Dimethyl-5-(4-trifluoromethyl-3-pyridyl)-1,2,4-oxadiazole-3-carboxamide 5.8 g of carbonyldiimidazole are initially charged in 90 ml of tetrahydrofuran and, a little at a time, admixed with 9 g of 5-(4-trifluoromethyl-3-pyridyl)-1,2,4-oxadiazole-3-carboxylic acid. The mixture is stirred at room temperature for 15 min and then heated at 50° C. for 2 h. After cooling to room temperature, 2.3 g of dimethylamine are introduced in a very gentle gas stream over a period of 2 h. After a reaction time of 12 h, the mixture is concentrated and taken up in 200 ml of diethyl ether. The mixture is washed with ice-cold half conc. hydrochloric acid solution, washed neutral with sat. sodium bicarbonate sol., dried over magnesium sulfate and concentrated under reduced pressure. This gives a slightly yellow oil which solidifies after a number of days to a solid of mp. 52–54° C.

In a similar manner, it is possible to prepare the compounds shown in Tables 1 to 6 below. The abbreviations used denote Ph: phenyl THP: 2-tetrahydropyranyl

TABLE 1

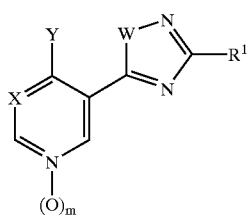

| No. | X | Y | m | W | R¹ | m.p. [° C.] |
|---|---|---|---|---|---|---|
| 1 | N | CCl$_3$ | 0 | O | CH$_3$ | |
| 2 | N | CCl$_3$ | 0 | O | CH$_2$CH$_3$ | |
| 3 | N | CCl$_3$ | 0 | O | COOCH$_2$CH$_3$ | |
| 4 | CH | CCl$_3$ | 0 | O | CH$_3$ | |
| 5 | CH | CCl$_3$ | 0 | O | COOCH$_2$CH$_3$ | |
| 6 | N | (CF$_2$)$_3$CHCF$_2$ | 0 | O | CH$_3$ | |
| 7 | N | (CF$_2$)$_3$CHCF$_2$ | 0 | O | COOCH$_2$CH$_3$ | |
| 8 | CH | (CF$_2$)$_3$CHCF$_2$ | 0 | O | CH$_3$ | |
| 9 | CH | (CF$_2$)$_3$CHCF$_2$ | 0 | O | COOCH$_2$CH$_3$ | |
| 10 | N | (CF$_2$)$_3$CHCF$_2$ | 0 | S | CH$_2$COOC(CH$_3$)$_3$ | |
| 11 | N | (CF$_2$)$_3$CHCF$_2$ | 0 | S | CH$_2$CONHCH$_3$ | |
| 12 | CH | (CF$_2$)$_3$CHCF$_2$ | 0 | S | (CH$_2$)$_2$CH$_3$ | |
| 13 | CH | (CF$_2$)$_3$CHCF$_2$ | 0 | S | COOCH$_2$CH$_3$ | |
| 14 | N | (CF$_2$)$_2$CHCF$_2$ | 0 | O | CH$_2$CH$_3$ | |
| 15 | N | (CF$_2$)$_2$CHCF$_2$ | 0 | O | COOCH$_2$CH$_3$ | |
| 16 | N | (CF$_2$)$_2$CHCF$_2$ | 0 | O | OH | |
| 17 | N | (CF$_2$)$_2$CHCF$_2$ | 0 | O | OCH$_3$ | |
| 18 | CH | (CF$_2$)$_2$CHCF$_2$ | 0 | O | CH$_3$ | |
| 19 | CH | (CF$_2$)$_2$CHCF$_2$ | 0 | O | COOCH$_2$CH$_3$ | |
| 20 | CH | (CF$_2$)$_2$CHCF$_2$ | 0 | O | OH | |
| 21 | CH | (CF$_2$)$_2$CHCF$_2$ | 0 | O | NHCH$_3$ | |
| 22 | N | CF$_2$CF$_3$ | 0 | O | CH$_3$ | |
| 23 | N | CF$_2$CF$_3$ | 0 | O | CH$_2$CH$_3$ | |
| 24 | N | CF$_2$CF$_3$ | 0 | O | (CH$_2$)$_2$CH$_3$ | |
| 25 | N | CF$_2$CF$_3$ | 0 | O | CH(CH$_3$)$_2$ | |
| 26 | N | CF$_2$CF$_3$ | 0 | O | Cyclo-C$_6$H$_{11}$ | |
| 27 | N | CF$_2$CF$_3$ | 0 | O | CH$_2$C=CH$_2$ | |
| 28 | N | CF$_2$CF$_3$ | 0 | O | CH$_2$C≡CH | |
| 29 | N | CF$_2$CF$_3$ | 0 | O | CH$_2$CH$_2$C≡CH | |
| 30 | N | CF$_2$CF$_3$ | 0 | O | CH$_2$C≡CCH$_2$CH$_3$ | |
| 31 | N | CF$_2$CF$_3$ | 0 | O | (CH$_2$)$_4$C≡CH | |
| 32 | N | CF$_2$CF$_3$ | 0 | O | CHFCF$_3$ | |
| 33 | N | CF$_2$CF$_3$ | 0 | O | COOCH$_2$CH$_3$ | |
| 34 | N | CF$_2$CF$_3$ | 0 | O | CH$_2$COOC(CH$_3$)$_3$ | |
| 35 | N | CF$_2$CF$_3$ | 0 | O | CH$_2$CONHCH$_3$ | |
| 36 | N | CF$_2$CF$_3$ | 0 | O | NH$_2$ | |
| 37 | N | CF$_2$CF$_3$ | 0 | O | NHCH$_2$CH$_3$ | |
| 38 | CH | CF$_2$CF$_3$ | 0 | O | CH$_3$ | |
| 39 | CH | CF$_2$CF$_3$ | 0 | O | CH$_2$CH$_3$ | |
| 40 | CH | CF$_2$CF$_3$ | 0 | O | (CH$_2$)$_2$CH$_3$ | |
| 41 | CH | CF$_2$CF$_3$ | 0 | O | CH(CH$_3$)$_2$ | |
| 42 | CH | CF$_2$CF$_3$ | 0 | O | Cyclo-C$_6$H$_{11}$ | |
| 43 | CH | CF$_2$CF$_3$ | 0 | O | CH$_2$C=CH$_2$ | |
| 44 | CH | CF$_2$CF$_3$ | 0 | O | CH$_2$COOC(CH$_3$)$_3$ | |
| 45 | CH | CF$_2$CF$_3$ | 0 | O | NH$_2$ | |
| 46 | CH | CF$_2$CF$_3$ | 0 | O | NHCOCH$_3$ | |
| 47 | CH | CF$_2$CF$_3$ | 0 | O | NHCOCH$_2$CH$_3$ | |
| 48 | N | CF$_2$CF$_3$ | 0 | S | CH$_3$ | |
| 49 | N | CF$_2$CF$_3$ | 0 | S | CH$_2$CH$_3$ | |
| 50 | N | CF$_2$CF$_3$ | 0 | S | (CH$_2$)$_2$CH$_3$ | |
| 51 | N | CF$_2$Cl | 0 | O | CH$_3$ | |
| 52 | N | CF$_2$Cl | 0 | O | CH$_2$CH$_3$ | |
| 53 | N | CF$_2$Cl | 0 | O | (CH$_2$)$_2$CH$_3$ | |
| 54 | N | CF$_2$Cl | 0 | O | CH(CH$_3$)$_2$ | |
| 55 | N | CF$_2$Cl | 0 | O | CH$_2$COOC(CH$_3$)$_3$ | |
| 56 | N | CF$_2$Cl | 0 | O | CH$_2$CONHCH$_3$ | |
| 57 | N | CF$_2$Cl | 0 | O | OH | |
| 58 | N | CF$_2$Cl | 0 | O | OCH$_3$ | |
| 59 | N | CF$_2$Cl | 0 | O | OCH$_2$CH$_3$ | |
| 60 | N | CF$_2$Cl | 0 | O | NHCH$_3$ | |
| 61 | CH | CF$_2$Cl | 0 | O | CH$_3$ | |
| 62 | CH | CF$_2$Cl | 0 | O | CH$_2$CH$_3$ | |
| 63 | CH | CF$_2$Cl | 0 | O | (CH$_2$)$_2$CH$_3$ | |
| 64 | CH | CF$_2$Cl | 0 | O | CH(CH$_3$)$_2$ | |
| 65 | CH | CF$_2$Cl | 0 | O | CH$_2$COOC(CH$_3$)$_3$ | |

TABLE 1-continued

| No. | X | Y | m | W | R¹ | m.p. [° C.] |
|---|---|---|---|---|---|---|
| 66 | CH | CF$_2$Cl | 0 | O | CH$_2$CONHCH$_3$ | |
| 67 | CH | CF$_2$Cl | 0 | O | OH | |
| 68 | CH | CF$_2$Cl | 0 | O | OCH$_3$ | |
| 69 | CH | CF$_2$Cl | 0 | O | OCH$_2$CH$_3$ | |
| 70 | CH | CF$_2$Cl | 0 | O | NHCH$_3$ | |
| 71 | CH | CF$_2$Cl | 0 | O | Cyclo-C$_6$H$_{11}$ | |
| 72 | CH | CF$_2$Cl | 0 | O | CH$_2$C=CH$_2$ | |
| 73 | CH | CF$_2$Cl | 0 | O | COOCH$_2$CH$_3$ | |
| 74 | CH | CF$_2$Cl | 0 | O | CH$_2$COOC(CH$_3$)$_3$ | |
| 75 | CH | CF$_2$Cl | 0 | O | CH$_2$CONHCH$_3$ | |
| 76 | CH | CF$_2$Cl | 0 | O | OCH$_3$ | |
| 77 | CH | CF$_2$Cl | 0 | O | NHCH$_3$ | |
| 78 | CH | CF$_3$ | 0 | O | CH$_3$ | oil |
| 79 | CH | CF$_3$ | 0 | O | CH$_2$CH$_3$ | oil |
| 80 | CH | CF$_3$ | 0 | O | (CH$_2$)$_2$CH$_3$ | oil |
| 81 | CH | CF$_3$ | 0 | O | CH(CH$_3$)$_2$ | oil |
| 82 | CH | CF$_3$ | 0 | O | Cyclo-C$_3$H$_5$ | oil |
| 83 | CH | CF$_3$ | 0 | O | (CH$_2$)$_3$CH$_3$ | oil |
| 84 | CH | CF$_3$ | 0 | O | CH(CH$_3$)CH$_2$CH$_3$ | oil |
| 85 | CH | CF$_3$ | 0 | O | CH$_2$CH(CH$_3$)$_2$ | oil |
| 86 | CH | CF$_3$ | 0 | O | C(CH$_3$)$_3$ | oil |
| 87 | CH | CF$_3$ | 0 | O | Cyclo-C$_4$H$_7$ | |
| 88 | CH | CF$_3$ | 0 | O | (CH$_2$)$_4$CH$_3$ | oil |
| 89 | CH | CF$_3$ | 0 | O | CH(CH$_3$)(CH$_2$)$_2$CH$_3$ | |
| 90 | CH | CF$_3$ | 0 | O | (CH$_2$)$_2$CH(CH$_3$)$_2$ | |
| 91 | CH | CF$_3$ | 0 | O | CH$_2$C(CH$_3$)$_3$ | |
| 92 | CH | CF$_3$ | 0 | O | Cyclo-C$_5$H$_9$ | oil |
| 93 | CH | CF$_3$ | 0 | O | (CH$_2$)$_5$CH$_3$ | |
| 94 | CH | CF$_3$ | 0 | O | C(CH$_2$CH$_3$)$_2$CH$_3$ | |
| 95 | CH | CF$_3$ | 0 | O | Cyclo-C$_6$H$_{11}$ | |
| 96 | CH | CF$_3$ | 0 | O | (CH$_2$)$_6$CH$_3$ | |
| 97 | CH | CF$_3$ | 0 | O | CH(CH$_3$)(CH$_2$)$_4$CH$_3$ | |
| 98 | CH | CF$_3$ | 0 | O | Cyclo-C$_7$H$_{13}$ | |
| 99 | CH | CF$_3$ | 0 | O | CH$_2$-cyclo-C$_6$H$_{11}$ | |
| 100 | CH | CF$_3$ | 0 | O | 2-Norbornyl | |
| 101 | CH | CF$_3$ | 0 | O | (CH$_2$)$_7$CH$_3$ | |
| 102 | CH | CF$_3$ | 0 | O | CH(CH$_2$CH$_3$)(CH$_2$)$_5$CH$_3$ | |
| 103 | CH | CF$_3$ | 0 | O | (CH$_2$)$_8$CH$_3$ | |
| 104 | CH | CF$_3$ | 0 | O | (CH$_2$)$_3$-cyclo-C$_6$H$_{11}$ | |
| 105 | CH | CF$_3$ | 0 | O | (CH$_2$)$_9$CH$_3$ | |
| 106 | CH | CF$_3$ | 0 | O | 1-Adamantyl | |
| 107 | CH | CF$_3$ | 0 | O | (CH$_2$)$_{10}$CH$_3$ | |
| 108 | CH | CF$_3$ | 0 | O | (CH$_2$)$_{11}$CH$_3$ | |
| 109 | CH | CF$_3$ | 0 | O | CH(CH$_3$)(CH$_2$)$_9$CH$_3$ | |
| 110 | CH | CF$_3$ | 0 | O | (CH$_2$)$_{12}$CH$_3$ | |
| 111 | CH | CF$_3$ | 0 | O | (CH$_2$)$_{13}$CH$_3$ | |
| 112 | CH | CF$_3$ | 0 | O | (CH$_2$)$_{14}$CH$_3$ | |
| 113 | CH | CF$_3$ | 0 | O | (CH$_2$)$_{15}$CH$_3$ | |
| 114 | CH | CF$_3$ | 0 | O | (CH$_2$)$_{17}$CH$_3$ | |
| 115 | CH | CF$_3$ | 0 | O | (CH$_2$)$_{19}$CH$_3$ | |
| 116 | CH | CF$_3$ | 0 | O | CHO | |
| 117 | CH | CF$_3$ | 0 | O | CH=CH$_2$ | oil |
| 118 | CH | CF$_3$ | 0 | O | CH$_2$C=C(CH$_3$)$_2$ | |
| 119 | CH | CF$_3$ | 0 | O | CH$_2$CH$_2$C=CH$_2$ | |
| 120 | CH | CF$_3$ | 0 | O | CH$_2$C=CH$_2$ | |
| 121 | CH | CF$_3$ | 0 | O | C(CH$_3$)=CH$_2$ | |
| 122 | CH | CF$_3$ | 0 | O | (E)-CH$_2$CH=CHCH$_2$CH$_3$ | |
| 123 | CH | CF$_3$ | 0 | O | (Z)-CH$_2$CH=CHCH$_2$CH$_3$ | |
| 124 | CH | CF$_3$ | 0 | O | (CH$_2$)$_5$C=CH$_2$ | |
| 125 | CH | CF$_3$ | 0 | O | C(=CHCH$_3$)CH$_3$ | 62–64 |
| 126 | CH | CF$_3$ | 0 | O | Geranyl | |
| 127 | CH | CF$_3$ | 0 | O | 3-Menthyl | |
| 128 | CH | CF$_3$ | 0 | O | C≡CH | |
| 129 | CH | CF$_3$ | 0 | O | CH$_2$C≡CH | |
| 130 | CH | CF$_3$ | 0 | O | CH$_2$CH$_2$C≡CH | |

TABLE 1-continued

| No. | X | Y | m | W | R¹ | m.p. [° C.] |
|---|---|---|---|---|---|---|
| 131 | CH | CF₃ | 0 | O | CH₂CH₂C≡CH | |
| 132 | CH | CF₃ | 0 | O | (CH₂)₄C≡CH | |
| 133 | CH | CF₃ | 0 | O | CHFCF₃ | oil |
| 134 | CH | CF₃ | 0 | O | COOCH₂CH₃ | oil |
| 135 | CH | CF₃ | 0 | O | CH₂CH₂OH | oil |
| 136 | CH | CF₃ | 0 | O | CH₂CH₂OCH₃ | oil |
| 137 | CH | CF₃ | 0 | O | CH₂COOC(CH₃)₃ | oil |
| 138 | CH | CF₃ | 0 | O | CH₂SC₆H₅ | oil |
| 139 | CH | CF₃ | 0 | O | CH₂CONHCH₃ | 109–111 |
| 140 | CH | CF₃ | 0 | O | CH₂CH(OH)CH₂OH | |
| 141 | CH | CF₃ | 0 | O | CH₂COCH₃ | |
| 142 | CH | CF₃ | 0 | O | COCH3 | |
| 143 | CH | CF₃ | 0 | O | CH₂OC₆H₅ | |
| 144 | CH | CF₃ | 0 | O | COC₆H₅ | |
| 145 | CH | CF₃ | 0 | O | CO(4-Cl)—C₆H₄ | |
| 146 | CH | CF₃ | 0 | O | CF₂CH₃ | |
| 147 | CH | CF₃ | 0 | O | CH₂CN | |
| 148 | CH | CF₃ | 0 | O | CH₂CH₂CN | |
| 149 | CH | CF₃ | 0 | O | CH₂CH(—O—)CH₂ | |
| 150 | CH | CF₃ | 0 | O | CH₂(4-OCH₃)C₆H₄ | |
| 151 | CH | CF₃ | 0 | O | CH₂-cyclo-(4-Oxo)-C₆H₈ | |
| 152 | CH | CF₃ | 0 | O | CH₂CH(OH)CH₂SC₆H₅ | |
| 153 | CH | CF₃ | 0 | O | CH₂CH₂Si(CH₃)₃ | |
| 154 | CH | CF₃ | 0 | O | CH=CF₂ | |
| 155 | CH | CF₃ | 0 | O | CCl=CHCl | |
| 156 | CH | CF₃ | 0 | O | 2-Pyridyl | 99–101 |
| 157 | CH | CF₃ | 0 | O | 2-Furyl | |
| 158 | CH | CF₃ | 0 | O | 2-Thienyl | 106–108 |
| 159 | CH | CF₃ | 0 | O | CH₂C≡CCH₂CH₂OTHP | |
| 160 | CH | CF₃ | 0 | O | CH₂CH₂Cl | oil |
| 161 | CH | CF₃ | 0 | O | Si(CH₃)₃ | |
| 162 | CH | CF₃ | 0 | O | OC₆H₅ | |
| 163 | CH | CF₃ | 0 | O | OH | |
| 164 | CH | CF₃ | 0 | O | OCH₃ | |
| 165 | CH | CF₃ | 0 | O | OCH₂CH₃ | |
| 166 | CH | CF₃ | 0 | O | OCHF₂ | |
| 167 | CH | CF₃ | 0 | O | OCH₂C₆H₅ | |
| 168 | CH | CF₃ | 0 | O | CH₂SCH₃ | 48–49 |
| 169 | CH | CF₃ | 0 | O | SC₆H₅ | |
| 170 | CH | CF₃ | 0 | O | SeC₆H₅ | |
| 171 | CH | CF₃ | 0 | O | NH₂ | 116–118 |
| 172 | CH | CF₃ | 0 | O | NHCH₃ | |
| 173 | CH | CF₃ | 0 | O | NHCH₂CH₃ | |
| 174 | CH | CF₃ | 0 | O | N(CH₂CH₃)₂ | |
| 175 | CH | CF₃ | 0 | O | CONHCH₂C=CH₂ | 105–107 |
| 176 | CH | CF₃ | 0 | O | Cl | |
| 177 | CH | CF₃ | 0 | O | Br | |
| 178 | CH | CF₃ | 0 | O | CONH₂ | 206–208 |
| 179 | CH | CF₃ | 0 | O | NHCOCH₃ | 129–131 |
| 180 | CH | CF₃ | 0 | O | NHCOCH₂CH₃ | |
| 181 | CH | CF₃ | 0 | O | OSO₂CH₃ | |
| 182 | CH | CF₃ | 0 | O | SOCH₂(4-Br)—C₆H₄ | |
| 183 | CH | CF₃ | 0 | O | N(CH₃)COOCH₂C₆H₅ | |
| 184 | CH | CF₃ | 0 | O | NHNH₂ | |
| 185 | CH | CF₃ | 0 | O | NHN(CH₃)₂ | |
| 186 | N | CF₃ | 0 | O | CH₃ | |
| 187 | N | CF₃ | 0 | O | CH₂CH₃ | oil |
| 188 | N | CF₃ | 0 | O | (CH₂)₂CH₃ | oil |
| 189 | N | CF₃ | 0 | O | CH(CH₃)₂ | oil |
| 190 | N | CF₃ | 0 | O | (CH₂)₃CH₃ | oil |
| 191 | N | CF₃ | 0 | O | CH₂CH(CH₃)₂ | oil |
| 192 | N | CF₃ | 0 | O | C(CH₃)₃ | |
| 193 | N | CF₃ | 0 | O | (CH₂)₄CH₃ | oil |
| 194 | N | CF₃ | 0 | O | CH(CH₃)(CH₂)₂CH₃ | |
| 195 | N | CF₃ | 0 | O | CH₂C(CH₃)₃ | |

TABLE 1-continued

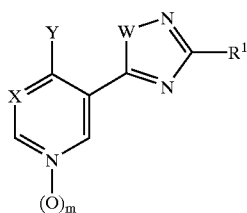

| No. | X | Y | m | W | R¹ | m.p. [° C.] |
|---|---|---|---|---|---|---|
| 196 | N | $CF_3$ | 0 | O | Cyclo-$C_5H_9$ | |
| 197 | N | $CF_3$ | 0 | O | $(CH_2)_5CH_3$ | |
| 198 | N | $CF_3$ | 0 | O | Cyclo-$C_6H_{11}$ | |
| 199 | N | $CF_3$ | 0 | O | $CH(CH_3)(CH_2)_4CH_3$ | |
| 200 | N | $CF_3$ | 0 | O | $CH_2$-cyclo-$C_6H_{11}$ | |
| 201 | N | $CF_3$ | 0 | O | $(CH_2)_7CH_3$ | |
| 202 | N | $CF_3$ | 0 | O | $(CH_2)_8CH_3$ | |
| 203 | N | $CF_3$ | 0 | O | $(CH_2)_9CH_3$ | |
| 204 | N | $CF_3$ | 0 | O | $CH(CH_3)(CH_2)_9CH_3$ | |
| 205 | N | $CF_3$ | 0 | O | $(CH_2)_{15}CH_3$ | |
| 206 | N | $CF_3$ | 0 | O | $(CH_2)_{17}CH_3$ | |
| 207 | N | $CF_3$ | 0 | O | $(CH_2)_{19}CH_3$ | |
| 208 | N | $CF_3$ | 0 | O | $CH_2CH{=}C(CH_3)_2$ | |
| 209 | N | $CF_3$ | 0 | O | $CH_2CH_2CH{=}CH_2$ | |
| 210 | N | $CF_3$ | 0 | O | $CH_2CH{=}CH_2$ | |
| 211 | N | $CF_3$ | 0 | O | (Z)-$CH_2CH{=}CHCH_2CH_3$ | |
| 212 | N | $CF_3$ | 0 | O | $(CH_2)_5CH{=}CH_2$ | |
| 213 | N | $CF_3$ | 0 | O | $CH_2C{\equiv}CH$ | |
| 214 | N | $CF_3$ | 0 | O | $CH_2C{\equiv}CCH_2CH_3$ | |
| 215 | N | $CF_3$ | 0 | O | $CHFCF_3$ | |
| 216 | N | $CF_3$ | 0 | O | $COOCH_2CH_3$ | |
| 217 | N | $CF_3$ | 0 | O | $CH_2CH_2OH$ | |
| 218 | N | $CF_3$ | 0 | O | $CH_2CH_2OCH_3$ | |
| 219 | N | $CF_3$ | 0 | O | $CH_2COOC(CH_3)_3$ | |
| 220 | N | $CF_3$ | 0 | O | $CH_2SC_6H_5$ | |
| 221 | N | $CF_3$ | 0 | O | $CH_2CONHCH_3$ | |
| 222 | N | $CF_3$ | 0 | O | $CH_2CH(OH)CH_2OH$ | |
| 223 | N | $CF_3$ | 0 | O | CHO | |
| 224 | N | $CF_3$ | 0 | O | $COCH_3$ | |
| 225 | N | $CF_3$ | 0 | O | $CH_2OC_6H_5$ | |
| 226 | N | $CF_3$ | 0 | O | $COC_6H_5$ | |
| 227 | N | $CF_3$ | 0 | O | $CF_2CH_3$ | |
| 228 | N | $CF_3$ | 0 | O | $CH_2CN$ | |
| 229 | N | $CF_3$ | 0 | O | $CH_2CH_2CN$ | |
| 230 | N | $CF_3$ | 0 | O | $CH{=}CF_2$ | |
| 231 | N | $CF_3$ | 0 | O | 2-Furyl | |
| 232 | N | $CF_3$ | 0 | O | $CH_2C{\equiv}C{-}I$ | |
| 233 | N | $CF_3$ | 0 | O | OH | |
| 234 | N | $CF_3$ | 0 | O | $OCH_3$ | |
| 235 | N | $CF_3$ | 0 | O | $OCH_2CH_3$ | |
| 236 | N | $CF_3$ | 0 | O | $OCHF_2$ | |
| 237 | N | $CF_3$ | 0 | O | $OCH_2C_6H_5$ | |
| 238 | N | $CF_3$ | 0 | O | $SC_6H_5$ | |
| 239 | N | $CF_3$ | 0 | O | $NH_2$ | |
| 240 | N | $CF_3$ | 0 | O | $NHCH_3$ | |
| 241 | N | $CF_3$ | 0 | O | $NHCH_2CH_3$ | |
| 242 | N | $CF_3$ | 0 | O | $N(CH_2CH_3)_2$ | |
| 243 | N | $CF_3$ | 0 | O | $N(CH_2CN)_2$ | |
| 244 | N | $CF_3$ | 0 | O | $N(CH_3)_2$ | |
| 245 | N | $CF_3$ | 0 | O | $NHCOCH_3$ | |
| 246 | N | $CF_3$ | 0 | O | $NHCOCH_2CH_3$ | |
| 247 | N | $CF_3$ | 0 | O | $OSO_2CH_3$ | |
| 248 | N | $CF_3$ | 0 | O | $NHNH_2$ | |
| 249 | CH | $CF_3$ | 0 | S | $CH_3$ | |
| 250 | CH | $CF_3$ | 0 | S | $CH_2CH_3$ | |
| 251 | CH | $CF_3$ | 0 | S | $(CH_2)_2CH_3$ | |
| 252 | CH | $CF_3$ | 0 | S | CHO | |
| 253 | CH | $CF_3$ | 0 | S | $CHFCF_3$ | |
| 254 | CH | $CF_3$ | 0 | S | $CH_2C{\equiv}CH$ | |
| 255 | CH | $CF_3$ | 0 | S | $COOCH_2CH_3$ | |
| 256 | CH | $CF_3$ | 0 | S | $CH_2COOC(CH_3)_3$ | |
| 257 | CH | $CF_3$ | 0 | S | $CH_2CN$ | |
| 258 | CH | $CF_3$ | 0 | S | $SeC_6H_5$ | |
| 259 | N | $CF_3$ | 0 | S | $CH_3$ | |
| 260 | N | $CF_3$ | 0 | S | $CH_2CH_3$ | |

TABLE 1-continued

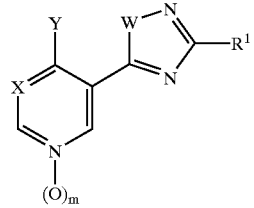

| No. | X | Y | m | W | R¹ | m.p. [° C.] |
|---|---|---|---|---|---|---|
| 261 | N | $CF_3$ | 0 | S | $(CH_2)_2CH_3$ | |
| 262 | N | $CF_3$ | 0 | S | $CHFCF_3$ | |
| 263 | N | $CF_3$ | 0 | S | $CH_2CH_2OH$ | |
| 264 | N | $CF_3$ | 0 | S | $CH_2COOC(CH_3)_3$ | |
| 265 | CH | $CH_2CH_2Cl$ | 0 | O | $CH_3$ | |
| 266 | CH | $CH_2CH_2Cl$ | 0 | O | $CH_2CH_3$ | |
| 267 | CH | $CH_2CH_2Cl$ | 0 | O | $(CH_2)_2CH_3$ | |
| 268 | CH | $CH_2CH_2Cl$ | 0 | O | $CH(CH_3)_2$ | |
| 269 | CH | $CH_2CH_2Cl$ | 0 | O | $CH_2SC_6H_5$ | |
| 270 | CH | $CH_2CH_2Cl$ | 0 | O | $CH_2CONHCH_3$ | |
| 271 | CH | $CH_2CH_2Cl$ | 0 | O | $NH_2$ | |
| 272 | CH | $CH_2CH_2Cl$ | 0 | O | $NHCH_2CH_3$ | |
| 273 | N | $CH_2CH_2Cl$ | 0 | O | $CH_2CH_3$ | |
| 274 | N | $CH_2CH_2Cl$ | 0 | O | $NH_2$ | |
| 275 | N | $CH_2Cl$ | 0 | O | $CH_3$ | |
| 276 | CH | $CH_2Cl$ | 0 | O | $CH_3$ | |
| 277 | CH | $CHF_2$ | 0 | O | $CH_3$ | |
| 278 | CH | $CHF_2$ | 0 | O | $CH_2CH_3$ | |
| 279 | CH | $CHF_2$ | 0 | O | $(CH_2)_2CH_3$ | |
| 280 | CH | $CHF_2$ | 0 | O | $CH_2CH=CH_2$ | |
| 281 | CH | $CHF_2$ | 0 | O | $C(CH_3)=CH_2$ | |
| 282 | CH | $CHF_2$ | 0 | O | $COOCH_2CH_3$ | |
| 283 | CH | $CHF_2$ | 0 | O | $CH_2CONHCH_3$ | |
| 284 | CH | $CHF_2$ | 0 | O | $CF_2CH_3$ | |
| 285 | CH | $CHF_2$ | 0 | O | $CHO$ | |
| 286 | CH | $CHF_2$ | 0 | O | $NH_2$ | |
| 287 | CH | $CHF_2$ | 0 | O | $Cl$ | |
| 288 | CH | $CHF_2$ | 0 | O | $NHCOCH_3$ | |
| 289 | CH | $CHF_2$ | 0 | O | $NHNH_2$ | |
| 290 | N | $CHF_2$ | 0 | O | $CH_3$ | |
| 291 | N | $CHF_2$ | 0 | O | $CH_2CH_3$ | |
| 292 | N | $CHF_2$ | 0 | O | $CH(CH_3)(CH_2)_4CH_3$ | |
| 293 | N | $CHF_2$ | 0 | O | $CH_2CH=CH_2$ | |
| 294 | N | $CHF_2$ | 0 | O | $COOCH_2CH_3$ | |
| 295 | N | $CHF_2$ | 0 | O | $NH_2$ | |
| 296 | CH | $CF_3$ | 1 | O | $CH_3$ | |
| 297 | CH | $CF_3$ | 1 | O | $COOCH_2CH_3$ | |
| 298 | CH | $CF_3$ | 1 | O | $CH_2COOC(CH_3)_3$ | |
| 299 | CH | $CF_3$ | 1 | O | $CHFCF_3$ | |
| 300 | N | $CF_3$ | 0 | O | $CH_2NHSO_2CH_3$ | |
| 301 | N | $CF_3$ | 0 | O | $(CH_2)_2NHSO_2CH_3$ | |
| 302 | N | $CF_3$ | 0 | O | $CH_2NHSO_2CH_2CH_3$ | |
| 303 | N | $CF_3$ | 0 | O | $CH_2NHSO_2CH_2C_6H_5$ | |
| 304 | CH | $CF_3$ | 0 | O | $(CH_2)_4NHSO_2CF_3$ | |
| 305 | CH | $CF_3$ | 0 | O | $(CH_2)_2S(CH_2)_2CH_3$ | |
| 306 | CH | $CF_3$ | 0 | O | $(CH_2)_4S(CH_2)_4OCH_3$ | |
| 307 | CH | $CF_3$ | 0 | S | $(CH_2)_2S(CH_2)_2CN$ | |
| 308 | CH | $CF_3$ | 0 | S | $CH_2NHSO_2CH_2CH_3$ | |
| 309 | CH | $CF_3$ | 0 | S | $CH_2NHSO_2CH_2C_6H_5$ | |
| 310 | CH | $CF_3$ | 0 | S | $(CH_2)_2NHSO_2CH_3$ | |
| 311 | CH | $CF_3$ | 0 | S | $CH_2NHSO_2CH_3$ | |
| 312 | CH | $CF_3$ | 0 | S | $CH(CH_3)CH_2NHC_6H_5$ | |
| 313 | CH | $CF_3$ | 0 | S | $(CH_2)_2S(2-F)—C_6H_4$ | |
| 314 | CH | $CF_3$ | 0 | S | $(CH_2)_6NHCH_2)_6OCH_3$ | |
| 315 | CH | $CF_3$ | 0 | S | $(CH_2)_2NH—(2-F)—C_6H_4$ | |
| 316 | CH | $CF_3$ | 0 | S | $(CH_2)_3NHCH_2CN$ | |
| 317 | CH | $CF_3$ | 0 | S | $(CH_2)_2O(3-Cl)—C_6H_4$ | |
| 318 | CH | $CF_3$ | 0 | S | $(CH_2)_6NHCH_2CF_3$ | |
| 319 | CH | $CF_3$ | 0 | S | $(CH_2)_2O(3-CH_3)—C_6H_4$ | |
| 320 | CH | $CF_3$ | 0 | O | $CH_2NHC_6H_5$ | |
| 321 | CH | $CF_3$ | 0 | O | $(CH_2)_4S(2-Br)—C_6H_4$ | |
| 322 | CH | $CF_3$ | 0 | O | $(CH_2)_6NH(CH_2)_2OCH_3$ | |
| 323 | CH | $CF_3$ | 0 | O | $(CH_2)_2NH(CH_2)_4OCH_3$ | |
| 324 | CH | $CF_3$ | 0 | O | $(CH_2)_3NH—(4-CN)—C_6H_4$ | |
| 325 | CH | $CF_3$ | 0 | O | $(CH_2)_2O(3-CH_3)—C_6H_4$ | |

TABLE 1-continued

| No. | X | Y | m | W | R¹ | m.p. [° C.] |
|---|---|---|---|---|---|---|
| 326 | CH | CF$_3$ | 0 | O | (CH$_2$)$_4$NHCH$_2$CF$_3$ | |
| 327 | CH | CF$_3$ | 0 | O | (CH$_2$)$_4$NHCH$_2$CN | |
| 328 | CH | CF$_3$ | 0 | O | (CH$_2$)$_3$O(4-OCH$_3$)—C$_6$H$_4$ | |
| 329 | CH | CF$_3$ | 0 | O | CH$_2$SO$_2$-tert-C$_4$H$_9$ | oil |
| 330 | CH | CF$_3$ | 0 | O | CH$_2$SO$_2$—(4-F)—C$_6$H$_4$ | oil |
| 331 | CH | CF$_3$ | 0 | O | CH$_2$SO$_2$—C$_6$H$_5$ | oil |
| 332 | CH | CF$_3$ | 0 | O | CH$_2$SOCH$_3$ | 63 |
| 333 | CH | CF$_3$ | 0 | O | CH$_2$SO—C$_6$H$_5$ | oil |
| 334 | CH | CF$_3$ | 0 | O | CH$_2$CONH(CH$_2$)$_2$CH$_3$ | 80–82 |
| 335 | CH | CF$_3$ | 0 | O | (4-OCF$_3$)—C$_6$H$_4$ | 57–59 |
| 336 | CH | CF$_3$ | 0 | O | CH$_2$OCH$_3$ | oil |
| 337 | CH | CF$_3$ | 0 | O | CH$_2$-piperidinyl | 53–54 |
| 338 | CH | CF$_3$ | 0 | O | CH$_2$-(2-thienyl) | oil |
| 339 | CH | CF$_3$ | 0 | O | CH$_2$CH$_2$OCH$_2$CH$_3$ | oil |
| 340 | CH | CF$_3$ | 0 | O | CH$_2$CH$_2$NC$_6$H$_5$ | 80–83 |
| 341 | CH | CF$_3$ | 0 | O | CH$_2$-(1-methylpyrrol-2-yl) | 80–81 |
| 342 | CH | CF$_3$ | 0 | O | CH$_2$-(benzo[1,3]dioxol-5-yl) | 110–111 |
| 343 | CH | CF$_3$ | 0 | O | CH$_2$CH$_2$O(CO)—(4-Cl)—C$_6$H$_4$ | 80–82 |
| 344 | CH | CF$_3$ | 0 | O | CH$_2$—(4-OCH$_3$)—C$_6$H$_4$ | 54–55 |
| 345 | CH | CF$_3$ | 0 | O | CH$_2$—(3-Cl)—C$_6$H$_4$ | 51–52 |
| 346 | CH | CF$_3$ | 0 | O | CH$_2$-cyclo-C$_3$H$_5$ | oil |
| 347 | CH | CF$_3$ | 0 | O | CH$_2$—(4-C$_6$H$_5$)—C$_6$H$_4$ | oil |
| 348 | CH | CF$_3$ | 0 | O | CH$_2$-(benzimidazol-2-yl) | 143–144 |
| 349 | CH | CF$_3$ | 0 | O | CH$_2$CH$_2$O(CO)—(2,6-F$_2$)—C$_6$H$_3$ | 57–58 |
| 350 | CH | CF$_3$ | 0 | O | CH$_2$CH$_2$O(CO)—(4-NO$_2$)—C$_6$H$_4$ | 80–81 |
| 351 | CH | CF$_3$ | 0 | O | CH$_2$—(2,6-Cl$_2$)—C$_6$H$_3$ | 91–92 |
| 352 | CH | CF$_3$ | 0 | O | CH$_2$CH$_2$OSO$_2$CH$_3$ | oil |
| 353 | CH | CF$_3$ | 0 | O | CH$_2$CH$_2$O(CO)-tert-C$_4$H$_9$ | oil |
| 354 | CH | CF$_3$ | 0 | O | CH$_2$—(3-F)—C$_6$H$_4$ | 50–51 |
| 355 | CH | CF$_3$ | 0 | O | CH$_2$CONCH$_2$C≡CH | 129–131 |
| 356 | CH | CF$_3$ | 0 | O | CH$_2$CH$_2$O(CO)-cyclo-C$_3$H$_7$ | oil |
| 357 | CH | CF$_3$ | 0 | O | CH$_2$CH$_2$O(CO)CH$_3$ | oil |
| 358 | CH | CF$_3$ | 0 | O | CH$_2$—[2,4-(CH$_3$)$_2$]—C$_6$H$_3$ | 85–86 |
| 359 | CH | CF$_3$ | 0 | O | CH$_2$CONCH$_2$CH═CH$_2$ | 210–212 |
| 360 | CH | CF$_3$ | 0 | O | CH$_2$CON(CH$_2$CH$_3$)$_2$ | oil |
| 361 | CH | CF$_3$ | 0 | O | CH$_2$CON(CH$_2$)$_3$CH$_3$ | 77–79 |

TABLE 1-continued

| No. | X | Y | m | W | R¹ | m.p. [° C.] |
|---|---|---|---|---|---|---|
| 362 | CH | CF₃ | 0 | O | CH₂CONCH₂-(2-furyl) | 139–141 |
| 363 | CH | CF₃ | 0 | O | CH₂CONCH(CH₃)₂ | 112–114 |
| 364 | CH | CF₃ | 0 | O | CH₂CONCH(CH₃)[(CH₂)₄CH₃] | 73–75 |
| 365 | CH | CF₃ | 0 | O | CH₂CONCH₂CH₂C₆H₅ | 120–122 |
| 366 | CH | CF₃ | 0 | O | CH₂CONCH₂CH₂OCH₂CH₃ | 78 |
| 367 | CH | CF₃ | 0 | O | CH₂CONCH₂CF₃ | 176–178 |
| 368 | CH | CF₃ | 0 | O | CH₂CONCH(CH₃)[(CH₂)₅CH₃] | 85–86 |
| 369 | CH | CF₃ | 0 | O | H₂C—(4-(1,1,2,2-tetrafluoroethoxy)phenyl) | oil |
| 370 | CH | CF₃ | 0 | O | H₂C—(2-piperidinyl) | oil |
| 371 | CH | CF₃ | 0 | O | CH₂CH2-(1-pyrryl) | oil |
| 372 | CH | CF₃ | 0 | O | CH₂CH₂C₆H₅ | oil |
| 373 | CH | CF₃ | 0 | O | CH₂Cl | 53–54 |
| 374 | CH | CF₃ | 0 | O | (CH₂)₃OH | 38–39 |
| 375 | CH | CF₃ | 0 | O | CH₂CONCH(CH₃)[(CH₂)₂]CH₃ | 68–69 |
| 376 | CH | CF₃ | 0 | O | CH₂CH(OCH₃)₂ | oil |
| 377 | CH | CF₃ | 0 | O | CH₂CONCH₂C(CH₃)₃ | oil |
| 378 | CH | CF₃ | 0 | O | CH₂CONC(CH₃)₂(CH₂CH₃) | oil |
| 379 | CH | CF₃ | 0 | O | CH₂CONCH₂CH₂-cyclo-C₆H₁₁ | 82–85 |
| 380 | CH | CF₃ | 0 | O | CH₂CONCH(CH₃)(1-naphthyl) | 142–146 |
| 381 | CH | CF₃ | 0 | O | (CH₂)₃Cl | oil |
| 382 | CH | CF₃ | 0 | O | CH₂CON-tert-C₄H₉ | oil |
| 383 | CH | CF₃ | 0 | O | CH₂CON(iso-C₃H₇)₂ | 70–72 |
| 384 | CH | CF₃ | 0 | O | CH₂CON(CH₂)₇CH₃ | 79–81 |
| 385 | CH | CF₃ | 0 | O | CH₂CON-cyclo-C₆H₁₁ | 119–121 |
| 386 | CH | CF₃ | 0 | O | CH₂CONCH₂CH₂—(4-Cl)—C₆H₄ | 120–121 |
| 387 | CH | CF₃ | 0 | O | CH₂CONCH₂-(2-thienyl) | 137–139 |
| 388 | CH | CF₃ | 0 | O | H₂C—C(=O)NH—(4-(4-fluorobenzylidene)cyclohexyl) | 151–153 |
| 389 | CH | CF₃ | 0 | O | CH₂CONHCH(CH₃)(CH₂CH₃) | 87–89 |
| 390 | CH | CF₃ | 0 | O | (CH₂)₃SCH₃ | oil |
| 391 | CH | CF₃ | 0 | O | (CH₂)₃SOCH₃ | oil |
| 392 | CH | CF₃ | 0 | O | CH₂CONC(CH₃)₂(C≡CH) | 111–113 |
| 393 | CH | CF₃ | 0 | O | CH₂CONCH(CH₃)CH₂CH₂CH(CH₃)₂ | 72–74 |
| 394 | CH | CF₃ | 0 | O | CH₃CH₂—C(=O)NH—(4-(2-methylbutan-2-yl)cyclohexyl) | oil |
| 395 | CH | CF₃ | 0 | O | CH₂CON-cyclo-C₅H₉ | 110–112 |
| 396 | CH | CF₃ | 0 | O | CH₂CON(CH₂)₄CH₃ | 75–77 |

TABLE 1-continued

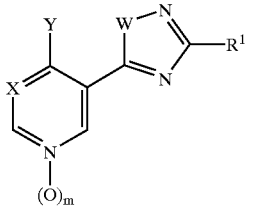

| No. | X | Y | m | W | R¹ | m.p. [° C.] |
|---|---|---|---|---|---|---|
| 397 | CH | CF$_3$ | 0 | O | 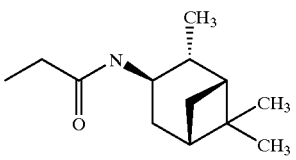 | 190–192 |
| 398 | CH | CF$_3$ | 0 | O | CH$_2$CON(3-CF$_3$)C$_6$H$_4$ | 136–138 |
| 399 | CH | CF$_3$ | 0 | O | CH$_2$CON-cyclo-C$_8$H$_{17}$ | 115–117 |
| 400 | CH | CF$_3$ | 0 | O | 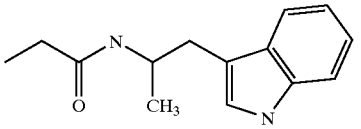 | oil |
| 401 | CH | CF$_3$ | 0 | O | CH$_2$CON-Adamantyl | oil |
| 402 | CH | CF$_3$ | 0 | O | CH$_2$CON(CH$_2$CH$_2$CH$_3$)$_2$ | oil |
| 403 | CH | CF$_3$ | 0 | O | CH$_2$CONCH(CH$_3$)[(4-F)—C$_6$H$_4$] | 111–113 |
| 404 | CH | CF$_3$ | 0 | O | CH$_2$CONCH$_2$CH(CH$_3$)$_2$ | 91–93 |
| 405 | CH | CF$_3$ | 0 | O | 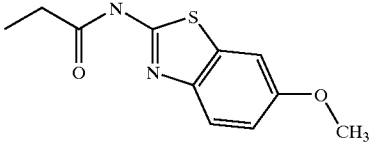 | Oil |
| 406 | CH | CF$_3$ | 0 | O | CH$_2$CONCH$_2$CH$_2$OC$_6$H$_5$ | 99–101 |
| 407 | CH | CF$_3$ | 0 | O | CH$_2$CH=NOCH$_3$ | oil |
| 408 | CH | CF$_3$ | 0 | O | CH$_2$CONCH$_2$CH$_2$—[3,4-(OCH$_3$)$_2$]C$_6$H$_3$ | 123–125 |
| 409 | CH | CF$_3$ | 0 | O | CH$_2$CON—(2-Cl)C$_6$H$_4$ | 138–140 |
| 410 | CH | CF$_3$ | 0 | O | CH$_2$CON—(2-SCH$_3$)C$_6$H$_4$ | 136–138 |
| 411 | CH | CF$_3$ | 0 | O | 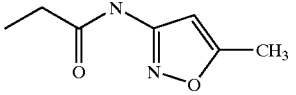 | 222–225 |
| 412 | CH | CF$_3$ | 0 | O |  | 207–209 |
| 413 | CH | CF$_3$ | 0 | O | CH$_2$CON—(3-Br)C$_6$H$_4$ | 129–131 |
| 414 | CH | CF$_3$ | 0 | O | CH$_2$CON—N—(2,4,6-Cl$_3$)C$_6$H$_2$ | 153–155 |
| 415 | CH | CF$_3$ | 0 | O | CH$_2$CON—(4-I)C$_6$H$_4$ | 143–145 |
| 416 | CH | CF$_3$ | 0 | O | CH$_2$CON—NCOCH$_2$(3-Thienyl) | 185–187 |
| 417 | CH | CF$_3$ | 0 | O | CH$_2$CH$_2$CHO | oil |
| 418 | CH | CF$_3$ | 0 | O | CH$_2$CON(CH$_3$)[(CH$_2$)$_3$CH$_3$] | oil |
| 419 | CH | CF$_3$ | 0 | O | CH$_2$CON—(3,5-Cl$_2$-2,4-F$_2$)C$_6$H | 166–167 |
| 420 | CH | CF$_3$ | 0 | O | CH$_2$CON—C$_6$H$_5$ | 215–217 |
| 421 | CH | CF$_3$ | 0 | O | CH$_2$CON(CH$_3$)(C$_6$H$_{11}$) | oil |
| 422 | CH | CF$_3$ | 0 | O | CH$_2$CON(CH$_2$CH$_3$)(CH$_2$CH=CH$_2$) | oil |
| 423 | CH | CF$_3$ | 0 | O | CH$_2$CON(CH$_2$CH$_3$)[CH(CH$_3$)$_2$] | oil |
| 424 | CH | CF$_3$ | 0 | O | CH$_2$CONCH(CH$_3$)[(CH$_3$)$_2$] | 108–110 |
| 425 | CH | CF$_3$ | 0 | O | CH$_2$CON(CH$_2$CH$_3$)[CH$_2$C(=CH$_2$)(CH$_3$)] | oil |
| 426 | CH | CF$_3$ | 0 | O | CH$_2$CONCH$_2$(4-tert-C$_4$H$_9$)C$_6$H$_4$ | oil |
| 427 | CH | CF$_3$ | 0 | O | CH$_2$CONCH(CH$_3$)(tert-C$_4$H$_9$) | oil |

TABLE 1-continued

[Structure: pyridine ring with X, Y substituents, N-oxide (O)$_m$, connected to 1,2,4-triazole with W and R$^1$]

| No. | X | Y | m | W | R$^1$ | m.p. [° C.] |
|---|---|---|---|---|---|---|
| 428 | CH | CF$_3$ | 0 | O | CH$_2$CONCH(CH$_3$)[CH$_2$CH(CH$_3$)(CH$_2$CH$_3$)] | oil |
| 429 | CH | CF$_3$ | 0 | O | CH$_2$CONCH$_2$COOCH$_2$CH$_3$ | 103–105 |
| 430 | CH | CF$_3$ | 0 | O | CH$_2$CON[(CH$_2$)$_2$CH$_3$](CH$_2$-cyclo-C$_3$H$_7$) | oil |
| 431 | CH | CF$_3$ | 0 | O | CH$_2$CONCH(CH$_3$)CH$_2$CH$_2$CH(CH$_3$)$_2$ | 80–82 |
| 432 | CH | CF$_3$ | 0 | O | CH$_2$CONCH(CH$_2$CH$_3$)[CH$_2$CH(CH$_3$)$_2$] | oil |
| 433 | CH | CF$_3$ | 0 | O | CH$_2$C=O-(1-Piperidinyl) | oil |
| 434 | CH | CF$_3$ | 0 | O | [2-ethyl-3-(2-chloroethyl)-4,5-dihydrooxazolium chloride structure] | 180–182 |
| 435 | CH | CF$_3$ | 0 | O | CH$_2$CONCH$_2$C(=CH2)(CH$_3$) | 86–87 |
| 436 | CH | CF$_3$ | 0 | O | CH$_2$CONCH[CH(CH$_3$)$_2$](COOCH$_3$) | oil |
| 437 | CH | CF$_3$ | 0 | O | CH$_2$CONCH$_2$-cyclo-C$_3$H$_7$ | oil |
| 438 | CH | CF$_3$ | 0 | O | CH$_2$CON(CH$_2$)$_5$OH | oil |
| 439 | CH | CF$_3$ | 0 | O | CH$_2$CON(CH$_3$)(CH$_2$CO$_2$CH$_3$) | oil |
| 440 | CH | CF$_3$ | 0 | O | CH$_2$CON(CH$_3$)(CH$_2$CN) | oil |
| 441 | CH | CF$_3$ | 0 | O | CH$_2$CONCH[CH$_2$CH(CH$_3$)$_2$](CO$_2$CH$_3$) | oil |
| 442 | CH | CF$_3$ | 0 | O | CH$_2$CON-(1-Piperidinyl) | oil |
| 443 | CH | CF$_3$ | 0 | O | CH$_2$CONCH$_2$CH$_2$OCH$_3$ | 97–99 |
| 444 | CH | CF$_3$ | 0 | O | CH$_2$CH$_2$SC$_6$H$_5$ | oil |
| 445 | CH | CF$_3$ | 0 | O | CH$_2$CH$_2$SCH$_3$ | oil |
| 446 | CH | CF$_3$ | 0 | O | CH$_2$CH$_2$SCH$_2$C$_6$H$_5$ | oil |
| 447 | CH | CF$_3$ | 0 | O | [1-propyl-2-pyrrolidinone structure] | oil |
| 448 | CH | CF$_3$ | 0 | O | CH$_2$CON—(2-OH)C$_6$H$_4$ | 162–164 |
| 449 | CH | CF$_3$ | 0 | O | CH$_2$CON—(3-OH)C$_6$H$_4$ | oil |
| 450 | CH | CF$_3$ | 0 | O | CH$_2$CON—(2-CH$_3$)C$_6$H$_4$ | 163–164 |
| 451 | CH | CF$_3$ | 0 | O | CH$_2$CON—(3-NO$_2$)C$_6$H$_4$ | 176–178 |
| 452 | CH | CF$_3$ | 0 | O | CH$_2$CON—(3-OCF$_2$CHFCl)C$_6$H$_4$ | 120–121 |
| 453 | CH | CF$_3$ | 0 | O | CH$_2$CON—(3-CF$_3$-4-F)C$_6$H$_3$ | 168–170 |
| 454 | CH | CF$_3$ | 0 | O | CH$_2$CON—(2,4-Cl$_2$)C$_6$H$_3$ | 120–122 |
| 455 | CH | CF$_3$ | 0 | O | CH$_2$CON—(2-F-4-Cl)C$_6$H$_3$ | 148–151 |
| 456 | CH | CF$_3$ | 0 | O | CH$_2$CON—[2,4-(CH$_3$)$_2$]C$_6$H$_3$ | 123–125 |
| 457 | CH | CF$_3$ | 0 | O | CH$_2$CON—[2,3-(CH$_3$)$_2$]C$_6$H$_3$ | waxy |
| 458 | CH | CF$_3$ | 0 | O | [propanoyl-benzo[1,3]dioxol-5-ylamide structure] | waxy |
| 459 | CH | CF$_3$ | 0 | O | CH$_2$CON—(2-CH$_3$-3-Cl)C$_6$H$_3$ | 160–162 |
| 460 | CH | CF$_3$ | 0 | O | CH$_2$CON(CH$_2$CH$_3$)(C$_6$H$_5$) | oil |
| 461 | CH | CF$_3$ | 0 | O | [1-propanoyl-2-methylindoline structure] | 124–126 |

TABLE 1-continued

| No. | X | Y | m | W | R¹ | m.p. [° C.] |
|---|---|---|---|---|---|---|
| 462 | CH | CF₃ | 0 | O | CH₂CON(2-OCH₃-5-Ph)C₆H₃ | 167–169 |
| 463 | CH | CF₃ | 0 | O | (propanoyl-5,6,7,8-tetrahydronaphthalen-1-yl-amide) | 157–158 |
| 464 | CH | CF₃ | 0 | O | CH₂CON—(3-NO₂-4-Cl)C₆H₃ | oil |
| 465 | CH | CF₃ | 0 | O | CH₂CON—(2-Cl-4-CH₃)C₆H₃ | 106–108 |
| 466 | CH | CF₃ | 0 | O | CH₂CON—(3-OCH₂CH₃)C₆H₄ | waxy |
| 467 | CH | CF₃ | 0 | O | (propanoyl-4-phenoxyphenyl-amide) | 169–171 |
| 468 | CH | CF₃ | 0 | O | CH₂CON—(4-CH₃)C₆H₄ | 139–141 |
| 469 | CH | CF₃ | 0 | O | CH₂CON-(1-Naphthyl) | 155–157 |
| 470 | CH | CF₃ | 0 | O | CH₂CON—(3-I)C₆H₄ | 135–137 |
| 471 | CH | CF₃ | 0 | O | CH₂CON—(2-OCH₂CH₃)C₆H₄ | 138 |
| 472 | CH | CF₃ | 0 | O | CH₂CON—(2-OCH₃)C₆H₄ | 130–132 |
| 473 | CH | CF₃ | 0 | O | CH₂CON—[3,5-(OCH₃)₂]C₆H₃ | 130–132 |
| 474 | CH | CF₃ | 0 | O | CH₂CON—(4-Cl)C₆H₄ | 139–141 |
| 475 | CH | CF₃ | 0 | O | CH₂CON—(3-CH₃)C₆H₄ | oil |
| 476 | CH | CF₃ | 0 | O | CH₂CON—(3-OCH₃)C₆H₄ | oil |
| 477 | CH | CF₃ | 0 | O | CH₂CON—(4-CH₂CH₃)C₆H₄ | 122–123 |
| 478 | CH | CF₃ | 0 | O | CH₂CON—(4-CF₃)C₆H₄ | 151–152 |
| 479 | CH | CF₃ | 0 | O | CH₂CON—(2-CH₃-4-Cl)C₆H₃ | 165–167 |
| 480 | CH | CF₃ | 0 | O | CH₂CH₂NCH₂C₆H₅ | oil |
| 481 | CH | CF₃ | 0 | O | CH₂CH₂NCH₂-(3-Pyridyl) | oil |
| 482 | CH | CF₃ | 0 | O | CH₂CH=NOCH₂CH₃ | oil |
| 483 | CH | CF₃ | 0 | O | CH₂CH=NOC₆H₅ | oil |
| 484 | CH | CF₃ | 0 | O | CH₂CON—(4-NO₂)C₆H₄ | 181–183 |
| 485 | CH | CF₃ | 0 | O | CH₂CON—(2-CH₃-4-NO₂)C₆H₃ | 129–131 |
| 486 | CH | CF₃ | 0 | O | CH₂CON—(2-Cl-3-CF₃)C₆H₃ | 136 |
| 487 | CH | CF₃ | 0 | O | CH₂CON—(2-CN-4-Cl)C₆H₃ | 157–159 |
| 488 | CH | CF₃ | 0 | O | CH₂CON—(3,5-Cl₂)C₆H₃ | 167–169 |
| 489 | CH | CF₃ | 0 | O | CH₂CON—(3,5-Cl₂-4-OCF₂CHF₂)C₆H₂ | 132–134 |
| 490 | CH | CF₃ | 0 | O | CH₂CON—(2,4,5-Cl₃)C₆H₂ | 146 |
| 491 | CH | CF₃ | 0 | O | CH₂CON—(3,5-Cl₂-4-OCF₂CHFCF₃)C₆H₂ | 124–126 |
| 492 | CH | CF₃ | 0 | O | CH₂CON—(2-CF₃-4-Cl)C₆H₃ | 136 |
| 493 | CH | CF₃ | 0 | O | (propanoyl-2-benzoylphenyl-amide) | oil |
| 494 | CH | CF₃ | 0 | O | (3,5-dimethylisoxazol-4-yl) | 91–93 |

TABLE 1-continued

| No. | X | Y | m | W | R¹ | m.p. [° C.] |
|---|---|---|---|---|---|---|
| 495 | CH | CF₃ | 0 | O | (3-methylpyrazin-2-yl) | 123–125 |
| 496 | CH | CF₃ | 0 | O | (5-methylisoxazol-3-yl) | 81–83 |
| 497 | CH | CF₃ | 0 | O | (3-chloro-6-methylpyrazin-2-yl) | 113–115 |
| 498 | CH | CF₃ | 0 | O | COOH | 155–157 |
| 499 | CH | CF₃ | 0 | O | 4-F—C₆H₄ | 104–106 |
| 500 | CH | CF₃ | 0 | O | CON(C₂H₅)₂ | oil |
| 501 | CH | CF₃ | 0 | O | CONCH(CH₃)₂ | oil |
| 502 | CH | CF₃ | 0 | O | CON(CH₃)₂ | 52–54 |
| 503 | CH | CF₃ | 0 | O | CONHCH₂CCH | 105–107 |
| 504 | CH | CF₃ | 0 | O | CONH-cyclo-C₃H₅ | 101–103 |
| 505 | CH | CF₃ | 0 | O | CONH₂ | 206–208 |
| 506 | CH | CF₃ | 0 | O | (3-methyl-4-trifluoromethylpyridin-2-yl) | 72–74 |
| 507 | CH | CF₃ | 0 | O | (6-methyl-3-trifluoromethylpyridin-2-yl) | 98–100 |
| 508 | CH | CF₃ | 0 | O | (5-methyl-2-nitrofuran-3-yl) | 108–110 |
| 509 | CH | CF₃ | 0 | O | (3-(2,6-dichlorophenyl)-5-methyl-4-isoxazolyl) | 140–142 |
| 510 | CH | CF₃ | 0 | O | CONHCH₃ | 127–129 |
| 511 | CH | CF₃ | 0 | O | CONHCH₂CH=CH₂ | oil |
| 512 | CH | CF₃ | 0 | O | CON(CH₂CN)₂ | 90–92 |
| 513 | CH | CF₃ | 0 | O | 4-(t-C₄H₉)—C₆H₄ | 64–66 |
| 514 | CH | CF₃ | 0 | O | 4-CF₃-C₆H₄ | 89–91 |

TABLE 1-continued

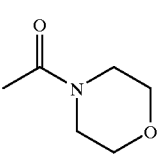

| No. | X | Y | m | W | R¹ | m.p. [° C.] |
|---|---|---|---|---|---|---|
| 515 | CH | CF₃ | 0 | O | 4-CH₃-3-F—C₆H₃ | 104–106 |
| 516 | CH | CF₃ | 0 | O | 2,4-di-Cl—C₆H₃ | 70–72 |
| 517 | CH | CF₃ | 0 | O | 4-(NHSO₂CH₃)—C₆H₄ | 204–206 |
| 518 | CH | CF₃ | 0 | O | 2,6-di-Cl—C₆H₃ | 139–141 |
| 519 | CH | CF₃ | 0 | O | COOCH₂C₆H₅ | 83–85 |
| 520 | CH | CF₃ | 0 | O | CONHC₃H₇ | oil |
| 521 | CH | CF₃ | 0 | O | 3,5-di-Br-4-(OCH₃)—C₆H₂ | 132–134 |
| 522 | CH | CF₃ | 0 | O | CHCl₂ | oil |
| 523 | CH | CF₃ | 0 | O | CCl₃ | oil |
| 524 | CH | CF₃ | 0 | O | CH(OCH3)₂ | oil |
| 525 | CH | CF₃ | 0 | O | 3-CF₃—C₆H₄ | 57–59 |
| 526 | CH | CF₃ | 0 | O | CON(CH₂)₅ | oil |
| 527 | CH | CF₃ | 0 | O | CON(CH₃)CH₂C₆H₅ | oil |
| 528 | CH | CF₃ | 0 | O | CONHCH₂C₆H₅ | 96–98 |
| 529 | CH | CF₃ | 0 | O | 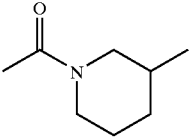 | oil |
| 530 | CH | CF₃ | 0 | O | CONH-n-C₆H₁₃ | oil |
| 531 | CH | CF₃ | 0 | O | CON(CH₂CH₃)CH₂C₆H₅ | oil |
| 532 | CH | CF₃ | 0 | O | CONH-c-C₆H₁₁ | 115–117 |
| 533 | CH | CF₃ | 0 | O | CON(n-C₄H₉)₂ | oil |
| 534 | CH | CF₃ | 0 | O | 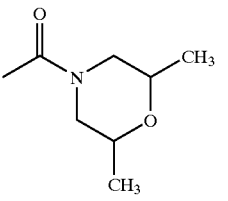 | oil |
| 535 | CH | CF₃ | 0 | O | CONH-i-C₄H₉ | oil |
| 536 | CH | CF₃ | 0 | O | 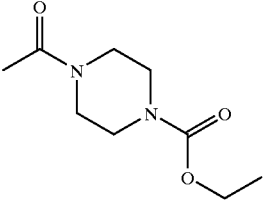 | oil |
| 537 | CH | CF₃ | 0 | O | CON(CH₂)₄ | 68–70 |
| 538 | CH | CF₃ | 0 | O | CON(CH₃)-n-C₆H₁₃ | oil |
| 539 | CH | CF₃ | 0 | O |  | oil |
| 540 | CH | CF₃ | 0 | O | CON(CH₃)CH₂CH₃ | oil |
| 541 | CH | CF₃ | 0 | O | CONHOCH₃ | oil |

TABLE 1-continued

| No. | X | Y | m | W | R¹ | m.p. [° C.] |
|---|---|---|---|---|---|---|
| 542 | CH | CF₃ | 0 | O | [4-tert-butylcyclohexyl-NH-C(=O)-CH₂-] | oil |
| 543 | CH | CF₃ | 0 | O | CON(CH₃)CH₂CH₂CH₃ | oil |
| 544 | CH | CF₃ | 0 | O | CONHCH₂CH(OCH₃)₂ | oil |
| 545 | CH | CF₃ | 0 | O | CONH-t-C₄H₉ | 113–115 |
| 546 | CH | CF₃ | 0 | O | CONHCH₂-4-Cl—C₆H₄ | oil |
| 547 | CH | CF₃ | 0 | O | CONHCH(CH₃)C₆H₅ | oil |
| 548 | CH | CF₃ | 0 | O | CONHCH₂CH₂OCH₃ | 92–94 |
| 549 | CH | CF₃ | 0 | O | [4H-1,2,4-triazol-4-yl-NH-C(=O)-CH₂-] | 190–192 |
| 550 | CH | CF₃ | 0 | O | CONHC(CH₃)₂CCH | 90–92 |
| 551 | CH | CF₃ | 0 | O | CONHCH₂-2-Furyl | 93–95 |
| 552 | CH | CF₃ | 0 | O | CON(CH₂)₃ | 91–93 |
| 553 | CH | CF₃ | 0 | O | CONHCH₂-c-C₃H₅ | oil |
| 554 | CH | CF₃ | 0 | O | CONHC(CH₃)₂CH₂CH₃ | oil |
| 555 | CH | CF₃ | 0 | O | CONH(CH₂)₃C₆H₅ | oil |
| 556 | CH | CF₃ | 0 | O | CONHCH₂-3-Pyridyl | 132–134 |
| 557 | CH | CF₃ | 0 | O | CON(CH₃)-n-C₄H₉ | oil |
| 558 | CH | CF₃ | 0 | O | CON(CH₂CH3)-i-C₃H₇ | oil |
| 559 | CH | CF₃ | 0 | O | [4-methylpiperazin-1-yl-C(=O)-CH₂-] | oil |
| 560 | CH | CF₃ | 0 | O | CONHCH₂CH₂Cl | oil |
| 561 | CH | CF₃ | 0 | O | CONHCH₂CN | 152–157 |
| 562 | CH | CF₃ | 0 | O | CON(CH₃)OCH₃ | oil |
| 563 | CH | CF₃ | 0 | O | CON(CH₃)CH₂CH=CH₂ | oil |
| 564 | CH | CF₃ | 0 | O | CONHCH₂COOCH₃ | oil |
| 565 | CH | CF₃ | 0 | O | CON(CH₃)-i-C₃H₇ | oil |
| 566 | CH | CF₃ | 0 | O | CON(CH₃)CH₂CH₂CN | oil |
| 567 | CH | CF₃ | 0 | O | CON(CH₃)CH₂CH(OCH₃)₂ | oil |
| 568 | CH | CF₃ | 0 | O | CON(CH₃)CH₂CH(—CH₂CH₂O—) | oil |
| 569 | CH | CF₃ | 0 | O | CONHCH₂C(=CH₂)CHH₃ | oil |
| 570 | CH | CF₃ | 0 | O | CON(CH₂CH₃)CH₂CH=CH₂ | oil |
| 571 | CH | CF₃ | 0 | O | CONHC₆H₅ | 83–85 |
| 572 | CH | CF₃ | 0 | O | CON(CH₃)CH₂CCH | oil |
| 573 | CH | CF₃ | 0 | O | CON(CH₃)CH₂CN | oil |
| 574 | CH | CF₃ | 0 | O | CON(CH₃)CH₂CH₂N(CH₃)₂ | oil |
| 575 | CH | CF₃ | 0 | O | CONHOCH₂CH₃ | 114–116 |
| 576 | CH | CF₃ | 0 | O | CONHCH₂CF₃ | 74–76 |
| 577 | CH | CF₃ | 0 | O | CON(CH₂CH₂Cl)₂ | oil |
| 578 | CH | CF₃ | 0 | O | CONH-c-C₄H₇ | oil |
| 579 | CH | CF₃ | 0 | O | CON(CH₂CH₂CH₃)CH₂-c-C₃H₅ | oil |
| 580 | CH | CF₃ | 0 | O | CON(CH₃)-c-C₆H₁₁ | oil |
| 581 | CH | CF₃ | 0 | O | CON(CH₂CH₃)CH₂C(=CH₂)CH₃ | oil |
| 582 | CH | CF₃ | 0 | O | CONHOCH₂CH=CH₂ | 90–92 |
| 583 | CH | CF₃ | 0 | O | CONHOCH₂C₆H₅ | 126–128 |
| 584 | CH | CF₃ | 0 | O | CON(CH₃)CH₂COOCH₃ | oil |
| 585 | CH | CF₃ | 0 | O | COONHCH₃ | 230–232 |
| 586 | CH | CF₃ | 0 | O | CONHCH₂CH₃ | 83–85 |

TABLE 1-continued

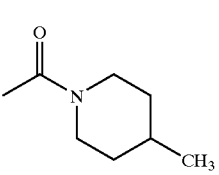

| No. | X | Y | m | W | R¹ | m.p. [° C.] |
|---|---|---|---|---|---|---|
| 587 | CH | CF₃ | 0 | O | CONHCH(CH₃)COOCH₃ | 104–106 |
| 588 | CH | CF₃ | 0 | O | CONHCH(i-C₃H₇)COOCH₃ | oil |
| 589 | CH | CF₃ | 0 | O | CON(CH₃)CH₂CON(CH₃)₂ | oil |
| 590 | CH | CF₃ | 0 | O | CON(CH₃)-t-C₄H₉ | oil |
| 591 | CH | CF₃ | 0 | O | CONHO-t-C₄H₉ | 103–105 |
| 592 | CH | CF₃ | 0 | O | CON(CH₃)CH(i-C₃H₇)COOCH₃ | oil |
| 593 | CH | CF₃ | 0 | O | CH(OCH₂CH₃)₂ | oil |
| 594 | CH | CF₃ | 0 | O | 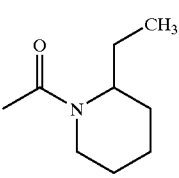 | oil |
| 595 | CH | CF₃ | 0 | O | 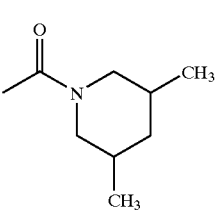 | oil |
| 596 | CH | CF₃ | 0 | O | 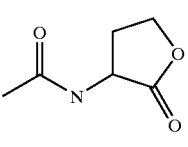 | oil |
| 597 | CH | CF₃ | 0 | O | 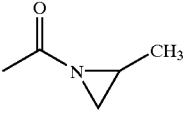 | oil |
| 598 | CH | CF₃ | 0 | O | 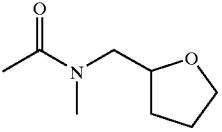 | oil |
| 599 | CH | CF₃ | 0 | O | CONHCH₂CONHCH₃ | 101–103 |
| 600 | CH | CF₃ | 0 | O | CON(CH₂)₇ | oil |
| 601 | CH | CF₃ | 0 | O | CON(CH₂)₆ | oil |
| 602 | CH | CF₃ | 0 | O | CON(CH₂CH₃)CH₂CH₂OCH₃ | oil |
| 603 | CH | CF₃ | 0 | O |  | oil |

TABLE 1-continued

[Structure: pyridine ring with X, Y substituents, N-oxide (O)_m, connected to 1,2,4-triazole/oxadiazole (W) with R¹]

| No. | X | Y | m | W | R¹ | m.p. [° C.] |
|---|---|---|---|---|---|---|
| 604 | CH | CF₃ | 0 | O | [N-acetyl thiazolidine] | oil |
| 605 | CH | CF₃ | 0 | O | [N-acetyl aziridine-2-carboxylic acid methyl ester] | oil |
| 606 | CH | CF₃ | 0 | O | CON(CH₂CH₃)CH₂CH₂CN | oil |
| 607 | CH | CF₃ | 0 | O | [N-acetyl thiomorpholine] | oil |
| 608 | CH | CF₃ | 0 | O | CON(CH₂CH₃)-n-C₄H₉ | oil |
| 609 | CH | CF₃ | 0 | O | [2-(1-hydroxy-1-methyl-2-nitroethylidene)-thiazolidine] | 179–181 |
| 610 | CH | CF₃ | 0 | O | CONHCH(CH₃)CONHCH₃ | 136–138 |
| 611 | CH | CF₃ | 0 | O | COON(CH₂)₄ | 64–66 |
| 612 | CH | CF₃ | 0 | O | CONHCH₂CON(CH₃)₂ | 107–109 |
| 613 | CH | CF₃ | 0 | O | CON(CH₂COOCH₂CH₃)₂ | oil |
| 614 | CH | CF₃ | 0 | O | [N-acetyl-3-amino-5-methylisoxazole] | 180–182 |
| 615 | CH | CF₃ | 0 | O | [N-acetyl-2-aminothiazole] | 221–223 |
| 616 | CH | CF₃ | 0 | O | [N-acetyl-2-amino-5-methyl-1,3,4-thiadiazole] | 234–236 |
| 617 | CH | CF₃ | 0 | O | [N-acetyl-5-amino-3,4-dimethylisoxazole] | oil |
| 618 | CH | CF₃ | 0 | O | CON(CH₃)CH₂-6-Cl-3-pyridyl | oil |

TABLE 1-continued

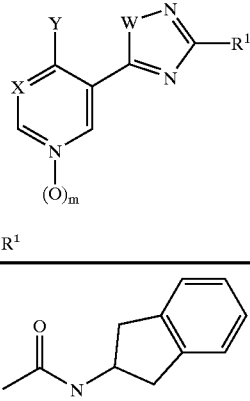

| No. | X | Y | m | W | R¹ | m.p. [° C.] |
|---|---|---|---|---|---|---|
| 619 | CH | CF₃ | 0 | O | 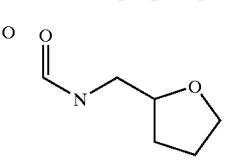 | 105–107 |
| 620 | CH | CF₃ | 0 | O | CONHCH(CH₃)CH(OCH₃)₂ | oil |
| 621 | CH | CF₃ | 0 | O | CONHCH₂CH₂SCH₃ | oil |
| 622 | CH | CF₃ | 0 | O | CONHCH(CH₃)CH₂OCH₃ | 70–72 |
| 623 | CH | CF₃ | 0 | O | CONHCH₂CH₂NHCOCH₃ | 124–126 |
| 624 | CH | CF₃ | 0 | O | CONH(CH₂)₃OCH₂CH₃ | oil |
| 625 | CH | CF₃ | 0 | O | CON(CH₂CH₃)CH₂CH₂CH₃ | oil |
| 626 | CH | CF₃ | 0 | O | CON(CH₂CH₃)CH₂OCH₃ | oil |
| 627 | CH | CF₃ | 0 | O | CONHCH₂CH₂SCH₂CH₃ | oil |
| 628 | CH | CF₃ | 0 | O | CONHCH₂CH₂OCH₂CH₃ | 59–61 |
| 629 | CH | CF₃ | 0 | O | 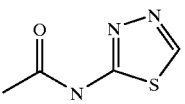 | oil |
| 630 | CH | CF₃ | 0 | O | 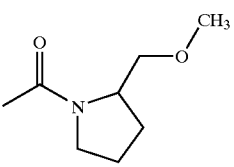 | 174–176 |
| 631 | CH | CF₃ | 0 | O | CONHCH(CH₃)CH(OCH₃)₂ | oil |
| 632 | CH | CF₃ | 0 | O | CONHCH₂CH₂SCH₃ | oil |
| 633 | CH | CF₃ | 0 | O | CONHCH(CH₃)CH₂OCH₃ | 70–72 |
| 634 | CH | CF₃ | 0 | O | CONHCH₂CH₂NHCOCH₃ | 124–126 |
| 635 | CH | CF₃ | 0 | O | CONH(CH₂)₃OCH₂CH₃ | oil |
| 636 | CH | CF₃ | 0 | O | CON(CH₂CH₃)CH2CH₂CH₃ | oil |
| 637 | CH | CF₃ | 0 | O | CON(CH₂CH₃)CH₂OCH₃ | oil |
| 638 | CH | CF₃ | 0 | O | CONHCH₂CH₂SCH₂CH₃ | oil |
| 639 | CH | CF₃ | 0 | O | CONHCH(CH₃)CH₂COOCH₂CH₃ | oil |
| 640 | CH | CF₃ | 0 | O | CONH-4-COOCH₃—C₆H₄ | 189–191 |
| 641 | CH | CF₃ | 0 | O | CONH-4-CONH₂—C₆H₄ | 265–267 |
| 642 | CH | CF₃ | 0 | O | CONHCH₂CH₂Br | oil |
| 643 | CH | CF₃ | 0 | O | CONHCH₂CH=CHCH₂Cl | oil |
| 644 | CH | CF₃ | 0 | O | CONH-4-CONHCH₃—C₆H₄ | 219–221 |
| 645 | CH | CF₃ | 0 | O | CONHCH₂CH₂CH₂Br | oil |
| 646 | CH | CF₃ | 0 | O | CONHCH₂CH₂OCH₃ | oil |
| 647 | CH | CF₃ | 0 | O | CONH-4-CH₂CH₃—C₆H₄ | 97–99 |
| 648 | CH | CF₃ | 0 | O | CONHCH₂CH₂OCH(CH₃)₂ | oil |
| 649 | CH | CF₃ | 0 | O | CONHCH₂CH₂CH₂OCH₂CH₃ | oil |
| 650 | CH | CF₃ | 0 | O | 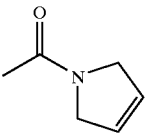 | oil |
| 651 | CH | CF₃ | 0 | O |  | 64–66 |

TABLE 1-continued

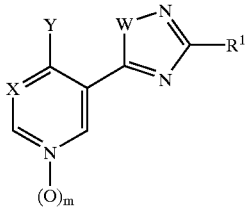

| No. | X | Y | m | W | R¹ | m.p. [° C.] |
|---|---|---|---|---|---|---|
| 652 | CH | CF$_3$ | 0 | O | 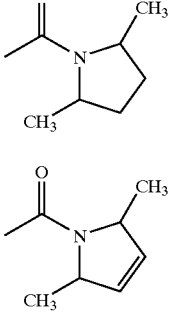 | oil |
| 653 | CH | CF$_3$ | 0 | O | 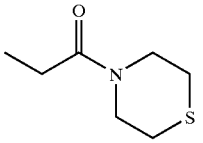 | oil |
| 654 | CH | CF$_3$ | 0 | O | CH$_2$CON(CH$_3$)CH$_2$CH$_3$ | oil |
| 655 | CH | CF$_3$ | 0 | O | CH$_2$CON(CH$_3$)$_2$ | 58–60 |
| 656 | CH | CF$_3$ | 0 | O | CH$_2$CON(CH$_2$)$_4$ | 101–103 |
| 657 | CH | CF$_3$ | 0 | O | 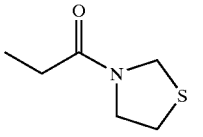 | oil |
| 658 | CH | CF$_3$ | 0 | O | 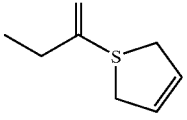 | 90–92 |
| 659 | CH | CF$_3$ | 0 | O | CH$_2$CONHCH$_2$CH$_3$ | 104–106 |
| 660 | CH | CF$_3$ | 0 | O | CH$_2$CON(CH$_3$)CH$_2$CH$_2$OH | oil |
| 661 | CH | CF$_3$ | 0 | O | CH$_2$CON(CH$_3$)CH$_2$CH$_2$CH$_3$ | oil |
| 662 | CH | CF$_3$ | 0 | O | CH$_2$CON(CH$_3$)CH$_2$CH(—OCH$_2$CH$_2$O—) | oil |
| 663 | CH | CF$_3$ | 0 | O | CH$_2$CONHCH$_2$CH$_3$ | 104–106 |
| 664 | CH | CF$_3$ | 0 | O | CH$_2$CON(CH$_3$)CH$_2$CH$_2$OH | oil |
| 665 | CH | CF$_3$ | 0 | O | CH$_2$CON(CH$_3$)CH$_2$CH$_2$CH$_3$ | oil |
| 667 | CH | CF$_3$ | 0 | O | CH$_2$CON(CH$_3$)CH$_2$CH(—OCH$_2$CH$_2$O—) | oil |
| 668 | CH | CF$_3$ | 0 | O |  | 79–81 |
| 669 | CH | CF$_3$ | 0 | O | CH$_2$CONHCH$_2$CH$_2$SCH$_3$ | 65–67 |
| 670 | CH | CF$_3$ | 0 | O | CH$_2$CONHCH(CH$_3$)CH$_2$OCH$_3$ | 86–88 |
| 671 | CH | CF$_3$ | 0 | O | CON(CH$_3$)CH$_2$CH2OCO-c-C$_4$H$_7$ | oil |
| 672 | CH | CF$_3$ | 0 | O | CH$_2$CONHCH$_2$CH$_2$Br | 87–89 |
| 673 | CH | CF$_3$ | 0 | O | CON(CH$_3$)CH$_2$CH$_2$OCOC$_6$H$_5$ | oil |
| 674 | CH | CF$_3$ | 0 | O | CON(CH$_3$)CH$_2$CH$_2$OCO-c-C$_3$H$_5$ | oil |
| 675 | CH | CF$_3$ | 0 | O | CONH-2-CH$_3$—C$_6$H$_4$ | 104–106 |
| 676 | CH | CF$_3$ | 0 | O | CH$_2$CON(i-C$_3$H$_7$)-4-F—C$_6$H$_4$ | 102–104 |

TABLE 1-continued

| No. | X | Y | m | W | R¹ | m.p. [° C.] |
|---|---|---|---|---|---|---|
| 677 | CH | CF₃ | 0 | O | (1-acetylpyrrolidine-2-carboxamide) | oil |
| 678 | CH | CF₃ | 0 | O | (methyl 1-acetylpyrrolidine-2-carboxylate) | oil |
| 679 | CH | CF₃ | 0 | O | CON(CH₃)CH₂CH₂OCONHC₆H₅ | 100–102 |
| 680 | CH | CF₃ | 0 | O | CON(CH₃)CH₂CH₂OCONHCH₂CH₃ | oil |
| 681 | CH | CF₃ | 0 | O | CON(CH₃)CH₂CH₂OSO₂CH₃ | oil |
| 682 | CH | CF₃ | 0 | O | CH₂CONH-c-C₄H₇ | 133–135 |
| 683 | CH | CF₃ | 0 | O | CH₂CONHCH₂CN | 158–160 |

TABLE 2

| No. | X | Y | W | R¹ | m.p. [° C.] |
|---|---|---|---|---|---|
| 684 | N | (CF₂)₃CHF₂ | O | CH₃ | |
| 685 | N | (CF₂)₂CF₃ | O | CH₂CH₃ | |
| 686 | N | (CF₂)₂CF₃ | O | COOCH₂CH₃ | |
| 687 | N | (CF₂)₂CF₃ | O | OH | |
| 688 | N | (CF₂)₂CF₃ | O | OCH₃ | |
| 689 | N | CF₂CF₃ | O | CH₃ | |
| 690 | N | CF₂CF₃ | O | CH₂CH₃ | |
| 691 | N | CF₂CF₃ | S | CH₃ | |
| 692 | N | CF₂CF₃ | S | CH₂CH₃ | |
| 693 | N | CF₂CF₃ | S | (CH₂)₂CH₃ | |
| 694 | CH | CF₃ | O | CH₃ | oil |
| 695 | CH | CF₃ | O | CH₂CH₃ | |
| 696 | CH | CF₃ | O | (CH₂)₂CH₃ | |
| 697 | CH | CF₃ | O | CH(CH₃)₂ | |
| 698 | CH | CF₃ | O | (CH₂)₃CH₃ | |
| 699 | CH | CF₃ | O | CH(CH₃)CH₂CH₃ | |
| 700 | CH | CF₃ | O | CH₂CH(CH₃)₂ | |
| 701 | CH | CF₃ | O | C(CH₃)₃ | oil |
| 702 | CH | CF₃ | O | (CH₂)₄CH₃ | |
| 703 | CH | CF₃ | O | CH(CH₃)(CH₂)₂CH₃ | |
| 704 | CH | CF₃ | O | (CH₂)₂CH(CH₃)₂ | |
| 705 | CH | CF₃ | O | CH₂C(CH₃)₃ | |
| 706 | CH | CF₃ | O | Cyclo-C₅H₉ | |
| 707 | CH | CF₃ | O | Cyclo-C₆H₁₁ | |
| 708 | CH | CF₃ | O | CHO | |
| 709 | CH | CF₃ | O | CH=CH₂ | |
| 710 | CH | CF₃ | O | CH₂CH=C(CH₃)₂ | |
| 711 | CH | CF₃ | O | CH₂CH=CH₂ | |
| 712 | CH | CF₃ | O | C(CH₃)=CH₂ | |
| 713 | CH | CF₃ | O | (CH₂)₅C=CH₂ | |
| 714 | CH | CF₃ | O | C(=CHCH₃)CH₃ | |
| 715 | CH | CF₃ | O | CH₂C≡CH | |
| 716 | CH | CF₃ | O | CH₂CH₂C≡CH | |
| 717 | CH | CF₃ | O | CH₂C≡CCH₂CH₃ | |
| 718 | CH | CF₃ | O | (CH₂)₄C≡CH | |
| 719 | CH | CF₃ | O | CHFCF₃ | |
| 720 | CH | CF₃ | O | COOCH₂CH₃ | |
| 721 | CH | CF₃ | O | CH₂CH₂OH | |
| 722 | CH | CF₃ | O | CH₂CH₂OCH₃ | |
| 723 | CH | CF₃ | O | CH₂COOC(CH₃)₃ | |
| 724 | CH | CF₃ | O | CH₂SC₆H₅ | |
| 725 | CH | CF₃ | O | CH₂CONHCH₃ | |
| 726 | CH | CF₃ | O | CH₂CH(OH)CH₂OH | |
| 727 | CH | CF₃ | O | CH₂COCH₃ | |
| 728 | CH | CF₃ | O | COCH3 | |
| 729 | CH | CF₃ | O | CH₂OC₆H₅ | |
| 730 | CH | CF₃ | O | COC₆H₅ | |
| 731 | CH | CF₃ | O | CF₂CH₃ | |

TABLE 2-continued

| No. | X | Y | W | R¹ | m.p. [° C.] |
|---|---|---|---|---|---|
| 732 | CH | CF₃ | O | CH₂CN | |
| 733 | CH | CF₃ | O | CH₂CH(—O—)CH₂ | |
| 734 | CH | CF₃ | O | CH₂(4-OCH₃)C₆H₅ | |
| 735 | CH | CF₃ | O | CH₂CH(OH)CH₂SC₆H₅ | |
| 736 | CH | CF₃ | O | CH=CF₂ | |
| 737 | CH | CF₃ | O | CCl=CHCl | |
| 738 | CH | CF₃ | O | 2-Pyridyl | |
| 739 | CH | CF₃ | O | OC₆H₅ | |
| 740 | CH | CF₃ | O | OH | |
| 741 | CH | CF₃ | O | OCH₃ | |
| 742 | CH | CF₃ | O | OCH₂CH₃ | |
| 743 | CH | CF₃ | O | OCHF₂ | |
| 744 | CH | CF₃ | O | OCH₂C₆H₅ | |
| 745 | CH | CF₃ | O | SCH₃ | |
| 746 | CH | CF₃ | O | SC₆H₅ | |
| 747 | CH | CF₃ | O | NH₂ | |
| 748 | CH | CF₃ | O | NHCH₃ | |
| 749 | CH | CF₃ | O | NHCH₂CH₃ | |
| 750 | CH | CF₃ | O | N(CH₂CH₃)₂ | |
| 751 | CH | CF₃ | O | N(CH₂CN)₂ | |
| 752 | CH | CF₃ | O | N(CH₃)₂ | |
| 753 | CH | CF₃ | O | NHCOCH₃ | |
| 754 | CH | CF₃ | O | NHCOCH₂CH₃ | |
| 755 | CH | CF₃ | O | OSO₂CH₃ | |
| 756 | CH | CF₃ | O | SOCH₂(4-Br)—C₆H₄ | |
| 757 | CH | CF₃ | O | N(CH₃)COOCH₂C₆H₅ | |
| 758 | N | CF₃ | O | CH₃ | |
| 759 | N | CF₃ | O | CH₂CH₃ | |
| 760 | N | CF₃ | O | (CH₂)₂CH₃ | |
| 761 | N | CF₃ | O | CH(CH₃)₂ | |
| 762 | N | CF₃ | O | (CH₂)₃CH₃ | |
| 763 | N | CF₃ | O | CH₂CH(CH₃)₂ | |
| 764 | N | CF₃ | O | C(CH₃)₃ | |
| 765 | N | CF₃ | O | CH₂C(CH₃)₃ | |
| 766 | N | CF₃ | O | Cyclo-C₅H₉ | |
| 767 | N | CF₃ | O | Cyclo-C₆H₁₁ | |
| 768 | N | CF₃ | O | CH₂C=C(CH₃)₂ | |
| 769 | N | CF₃ | O | CH₂CH₂C=CH₂ | |
| 770 | N | CF₃ | O | CH₂CH=CH₂ | |
| 771 | N | CF₃ | O | (CH₂)₅CH=CH₂ | |
| 772 | N | CF₃ | O | CH₂C≡CH | |
| 773 | N | CF₃ | O | CH₂C≡CCH₂CH₃ | |
| 774 | N | CF₃ | O | CHFCF₃ | |
| 775 | N | CF₃ | O | COOCH₂CH₃ | |
| 776 | N | CF₃ | O | CH₂CH₂OH | |
| 777 | N | CF₃ | O | CH₂CH₂OCH₃ | |
| 778 | N | CF₃ | O | CH₂COOC(CH₃)₃ | |
| 779 | N | CF₃ | O | CH₂SC₆H₅ | |
| 780 | N | CF₃ | O | CH₂CONHCH₃ | |
| 781 | N | CF₃ | O | CH₂CH(OH)CH₂OH | |
| 782 | N | CF₃ | O | CHO | |
| 783 | N | CF₃ | O | COCH₃ | |
| 784 | N | CF₃ | O | CH₂OC₆H₅ | |
| 785 | N | CF₃ | O | COC₆H₅ | |
| 786 | N | CF₃ | O | CF₂CH₃ | |
| 787 | N | CF₃ | O | CH₂CN | |
| 788 | N | CF₃ | O | CH₂CH₂CN | |
| 789 | N | CF₃ | O | CH=CF₂ | |
| 790 | N | CF₃ | O | 2-Furyl | |
| 791 | N | CF₃ | O | OH | |
| 792 | N | CF₃ | O | OCH₃ | |
| 793 | N | CF₃ | O | OCH₂CH₃ | |
| 794 | N | CF₃ | O | OCHF₂ | |
| 795 | N | CF₃ | O | OCH₂C₆H₅ | |
| 796 | N | CF₃ | O | NH₂ | |
| 797 | N | CF₃ | O | NHCH₃ | |
| 798 | N | CF₃ | O | NHCH₂CH₃ | |
| 799 | N | CF₃ | O | N(CH₂CH₃)₂ | |
| 800 | N | CF₃ | O | N(CH₂CN)₂ | |
| 801 | N | CF₃ | O | N(CH₃)₂ | |
| 802 | N | CF₃ | O | NHCOCH₃ | |
| 803 | N | CF₃ | O | NHCOCH₂CH₃ | |
| 804 | N | CF₃ | O | OSO₂CH₃ | |
| 805 | CH | CF₃ | S | CH₃ | |
| 806 | CH | CF₃ | S | CH₂CH₃ | |
| 807 | CH | CF₃ | S | (CH₂)₂CH₃ | |
| 808 | CH | CF₃ | S | CHO | |
| 809 | CH | CF₃ | S | CHFCF₃ | |
| 810 | CH | CF₃ | S | CH₂C≡CH | |
| 811 | CH | CF₃ | S | COOCH₂CH₃ | |
| 812 | CH | CF₃ | S | CH₂COOC(CH₃)₃ | |
| 813 | CH | CF₃ | S | CH₂CN | |
| 814 | N | CF₃ | S | CH₃ | |
| 815 | N | CF₃ | S | CH₂CH₃ | |
| 816 | N | CF₃ | S | (CH₂)₂CH₃ | |
| 817 | N | CF₃ | S | CHFCF₃ | |
| 818 | N | CF₃ | S | CH₂CH₂OH | |
| 819 | N | CF₃ | S | CH₂COOC(CH₃)₃ | |
| 820 | N | CH₂CH₂Cl | O | CH₃ | |
| 821 | N | CH₂CH₂Cl | O | NH₂ | |
| 822 | N | CH₂Cl | O | CH₃ | |
| 823 | CH | CHF₂ | O | CH₃ | |
| 824 | CH | CHF₂ | O | CH₂CH₃ | |
| 825 | CH | CHF₂ | O | (CH₂)₂CH₃ | |
| 826 | CH | CHF₂ | O | CH₂C=CH₂ | |
| 827 | CH | CHF₂ | O | C(CH₃)=CH₂ | |
| 828 | CH | CHF₂ | O | COOCH₂CH₃ | |
| 829 | CH | CHF₂ | O | CH₂CONHCH₃ | |
| 830 | CH | CHF₂ | O | CF₂CH₃ | |
| 831 | CH | CHF₂ | O | CHO | |
| 832 | CH | CHF₂ | O | NH₂ | |
| 833 | CH | CHF₂ | O | NHCOCH₃ | |
| 834 | N | CHF₂ | O | CH₃ | |
| 835 | N | CHF₂ | O | CH₂CH₃ | |
| 836 | N | CHF₂ | O | CH(CH₃)(CH₂)₄CH₃ | |
| 837 | N | CHF₂ | O | CH₂CH=CH₂ | |
| 838 | N | CHF₂ | O | COOCH₂CH₃ | |
| 839 | N | CHF₂ | O | NH₂ | |

TABLE 3

| No. | X | Y | m | V | R$^1$ | m.p. [° C.] |
|---|---|---|---|---|---|---|
| 840 | N | (CF$_2$)$_3$CHF$_2$ | 0 | O | CH$_3$ | |
| 841 | N | (CF$_2$)$_2$CF$_3$ | 0 | O | CH$_2$CH$_3$ | |
| 842 | N | (CF$_2$)$_2$CF$_3$ | 0 | O | COOCH$_2$CH$_3$ | |
| 843 | N | (CF$_2$)$_2$CF$_3$ | 0 | O | SH | |
| 844 | N | (CF$_2$)$_2$CF$_3$ | 0 | O | SCH$_3$ | |
| 845 | N | (CF$_2$)$_2$CF$_3$ | 0 | O | SCH$_2$C≡CH | |
| 846 | N | CF$_2$CF$_3$ | 0 | O | CH$_3$ | |
| 847 | N | CF$_2$CF$_3$ | 0 | O | CH$_2$CH$_3$ | |
| 848 | N | CF$_3$ | 0 | O | CH$_3$ | |
| 849 | N | CF$_3$ | 0 | O | CH$_2$CH$_3$ | |
| 850 | N | CF$_3$ | 0 | O | (CH$_2$)$_2$CH$_3$ | |
| 851 | N | CF$_3$ | 0 | O | CH(CH$_3$)$_2$ | |
| 852 | N | CF$_3$ | 0 | O | (CH$_2$)$_3$CH$_3$ | |
| 853 | N | CF$_3$ | 0 | O | CH$_2$CH(CH$_3$)$_2$ | |
| 854 | N | CF$_3$ | 0 | O | C(CH$_3$)$_3$ | |
| 855 | N | CF$_3$ | 0 | O | CH$_2$C(CH$_3$)$_3$ | |
| 856 | N | CF$_3$ | 0 | O | Cyclo-C$_5$H$_9$ | |
| 857 | N | CF$_3$ | 0 | O | Cyclo-C$_6$H$_{11}$ | |
| 858 | N | CF$_3$ | 0 | O | CH$_2$CH=C(CH$_3$)$_2$ | |
| 859 | N | CF$_3$ | 0 | O | CH$_2$CH$_2$CH=CH$_2$ | |
| 860 | N | CF$_3$ | 0 | O | CH$_2$CH=CH$_2$ | |
| 861 | N | CF$_3$ | 0 | O | (CH$_2$)$_5$CH=CH$_2$ | |
| 862 | N | CF$_3$ | 0 | O | CH$_2$C≡CH | |
| 863 | N | CF$_3$ | 0 | O | CH$_2$C≡CCH$_2$CH$_3$ | |
| 864 | N | CF$_3$ | 0 | O | CHFCF$_3$ | |
| 865 | N | CF$_3$ | 0 | O | COOCH$_2$CH$_3$ | |
| 866 | N | CF$_3$ | 0 | O | CH$_2$CH$_2$OH | |
| 867 | N | CF$_3$ | 0 | O | CH$_2$CH$_2$OCH$_3$ | |
| 868 | N | CF$_3$ | 0 | O | CH$_2$COOC(CH$_3$)$_3$ | |
| 869 | N | CF$_3$ | 0 | O | CH$_2$SPh | |
| 870 | N | CF$_3$ | 0 | O | CH$_2$CONHCH$_3$ | |
| 871 | N | CF$_3$ | 0 | O | CH$_2$CH(OH)CH$_2$OH | |
| 872 | N | CF$_3$ | 0 | O | CHO | |
| 873 | N | CF$_3$ | 0 | O | COCH$_3$ | |
| 874 | N | CF$_3$ | 0 | O | CH$_2$OC$_6$H$_5$ | |
| 875 | N | CF$_3$ | 0 | O | COPh | |
| 876 | N | CF$_3$ | 0 | O | CF$_2$CH$_3$ | |
| 877 | N | CF$_3$ | 0 | O | CH$_2$CN | |
| 878 | N | CF$_3$ | 0 | O | CH$_2$CH$_2$CN | |
| 879 | N | CF$_3$ | 0 | O | CH=CF$_2$ | |
| 880 | N | CF$_3$ | 0 | O | 2-Furyl | |
| 881 | N | CF$_3$ | 0 | O | OH | |
| 882 | N | CF$_3$ | 0 | O | OCH$_3$ | |
| 883 | N | CF$_3$ | 0 | O | OCH$_2$CH$_3$ | |
| 884 | N | CF$_3$ | 0 | O | OCHF$_2$ | |
| 885 | N | CF$_3$ | 0 | O | OCH$_2$Ph | |
| 886 | N | CF$_3$ | 0 | O | NH$_2$ | |
| 887 | N | CF$_3$ | 0 | O | NHCH$_3$ | |
| 888 | N | CF$_3$ | 0 | O | NHCH$_2$CH$_3$ | |
| 889 | N | CF$_3$ | 0 | O | N(CH$_2$CH$_3$)$_2$ | |
| 890 | N | CF$_3$ | 0 | O | N(CH$_2$CN)$_2$ | |
| 891 | N | CF$_3$ | 0 | O | N(CH$_3$)$_2$ | |
| 892 | N | CF$_3$ | 0 | O | NHCOCH$_3$ | |
| 893 | N | CF$_3$ | 0 | O | NHCOCH$_2$CH$_3$ | |
| 894 | N | CF$_3$ | 0 | O | OSO$_2$CH$_3$ | |
| 895 | N | CH$_2$CH$_2$Cl | 0 | O | CH$_2$CH$_3$ | |
| 896 | N | CH$_2$CH$_2$Cl | 0 | O | NH$_2$ | |
| 897 | N | CH$_2$Cl | 0 | O | CH$_3$ | |
| 898 | N | CHF$_2$ | 0 | O | CH$_3$ | |
| 899 | N | CHF$_2$ | 0 | O | CH$_2$CH$_3$ | |
| 900 | N | CHF$_2$ | 0 | O | CH(CH$_3$)(CH$_2$)$_4$CH$_3$ | |
| 901 | N | CHF$_2$ | 0 | O | CH$_2$CH=CH$_2$ | |
| 902 | N | CHF$_2$ | 0 | O | COOCH$_2$CH$_3$ | |
| 903 | N | CHF$_2$ | 0 | O | NH$_2$ | |
| 904 | CH | CF$_3$ | 0 | O | CH$_3$ | 60–61 |

TABLE 3-continued

| No. | X | Y | m | V | R¹ | m.p. [° C.] |
|---|---|---|---|---|---|---|
| 905 | CH | CF$_3$ | 1 | O | CH$_3$ | |
| 906 | CH | CF$_3$ | 0 | O | CH$_2$CH$_3$ | oil |
| 907 | CH | CF$_3$ | 1 | O | CH$_2$CH$_3$ | oil |
| 908 | CH | CF$_3$ | 0 | O | (CH$_2$)$_2$CH$_3$ | oil |
| 909 | CH | CF$_3$ | 1 | O | (CH$_2$)$_2$CH$_3$ | oil |
| 910 | CH | CF$_3$ | 0 | O | CH(CH$_3$)$_2$ | |
| 911 | CH | CF$_3$ | 1 | O | CH(CH$_3$)$_2$ | |
| 912 | CH | CF$_3$ | 0 | O | (CH$_2$)$_3$CH$_3$ | |
| 913 | CH | CF$_3$ | 1 | O | (CH$_2$)$_3$CH$_3$ | |
| 914 | CH | CF$_3$ | 0 | O | CH(CH$_3$)CH$_2$CH$_3$ | |
| 915 | CH | CF$_3$ | 1 | O | CH(CH$_3$)CH$_2$CH$_3$ | |
| 916 | CH | CF$_3$ | 0 | O | CH$_2$CH(CH$_3$)$_2$ | |
| 917 | CH | CF$_3$ | 1 | O | CH$_2$CH(CH$_3$)$_2$ | |
| 918 | CH | CF$_3$ | 0 | O | C(CH$_3$)$_3$ | |
| 919 | CH | CF$_3$ | 1 | O | C(CH$_3$)$_3$ | |
| 920 | CH | CF$_3$ | 0 | O | (CH$_2$)$_4$CH$_3$ | |
| 921 | CH | CF$_3$ | 1 | O | (CH$_2$)$_4$CH$_3$ | |
| 922 | CH | CF$_3$ | 0 | O | CH(CH$_3$)(CH$_2$)$_2$CH$_3$ | |
| 923 | CH | CF$_3$ | 0 | O | (CH$_2$)$_2$CH(CH$_3$)$_2$ | |
| 924 | CH | CF$_3$ | 0 | O | CH$_2$C(CH$_3$)$_3$ | |
| 925 | CH | CF$_3$ | 0 | O | cyclo-C$_5$H$_9$ | |
| 926 | CH | CF$_3$ | 0 | O | cyclo-C$_6$H$_{11}$ | |
| 927 | CH | CF$_3$ | 0 | O | CH$_2$(3-Thienyl) | oil |
| 928 | CH | CF$_3$ | 0 | O | CHO | |
| 929 | CH | CF$_3$ | 0 | O | CH=CH$_2$ | |
| 930 | CH | CF$_3$ | 0 | O | CH$_2$Ph | 61–63 |
| 931 | CH | CF$_3$ | 0 | O | CH$_2$CH=C(CH$_3$)$_2$ | |
| 932 | CH | CF$_3$ | 0 | O | CH$_2$CH=CH$_2$ | |
| 933 | CH | CF$_3$ | 0 | O | C(CH$_3$)=CH$_2$ | |
| 934 | CH | CF$_3$ | 0 | O | (CH$_2$)$_5$C=CH$_2$ | |
| 935 | CH | CF$_3$ | 0 | O | C(=CHCH$_3$)CH$_3$ | |
| 936 | CH | CF$_3$ | 0 | O | CH$_2$C≡CH | |
| 937 | CH | CF$_3$ | 0 | O | CH$_2$CH$_2$C≡CH$_2$ | |
| 938 | CH | CF$_3$ | 0 | O | CH$_2$C≡CCH$_2$CH$_3$ | |
| 939 | CH | CF$_3$ | 0 | O | (CH$_2$)$_4$C≡CH | |
| 940 | CH | CF$_3$ | 0 | O | CHFCF$_3$ | |
| 941 | CH | CF$_3$ | 0 | O | COOCH$_2$CH$_3$ | |
| 942 | CH | CF$_3$ | 0 | O | CH$_2$CH$_2$OH | |
| 943 | CH | CF$_3$ | 0 | O | CH$_2$CH$_2$OCH$_3$ | |
| 944 | CH | CF$_3$ | 0 | O | CH$_2$COOC(CH$_3$)$_3$ | |
| 945 | CH | CF$_3$ | 0 | O | CH$_2$SPh | |
| 946 | CH | CF$_3$ | 0 | O | CH$_2$CONHCH$_3$ | |
| 947 | CH | CF$_3$ | 0 | O | CH$_2$CH(OH)CH$_2$OH | |
| 948 | CH | CF$_3$ | 0 | O | CH$_2$COCH$_3$ | |
| 949 | CH | CF$_3$ | 0 | O | COCH3 | |
| 950 | CH | CF$_3$ | 0 | O | CH$_2$Oph | |
| 951 | CH | CF$_3$ | 0 | O | COPh | |
| 952 | CH | CF$_3$ | 0 | O | CF$_2$CH$_3$ | |
| 953 | CH | CF$_3$ | 0 | O | CH$_2$CN | oil |
| 954 | CH | CF$_3$ | 0 | O | CH$_2$CH(—O—)CH$_2$ | |
| 955 | CH | CF$_3$ | 0 | O | CH$_2$(4-OCH$_3$)Ph | |
| 956 | CH | CF$_3$ | 0 | O | CH$_2$CH(OH)CH$_2$SPh | |
| 957 | CH | CF$_3$ | 0 | O | CH=CF$_2$ | |
| 958 | CH | CF$_3$ | 0 | O | CCl=CHCl | |
| 959 | CH | CF$_3$ | 0 | O | Ph | 120–121 |
| 960 | CH | CF$_3$ | 0 | O | 2-Thienyl | 87–89 |
| 961 | CH | CF$_3$ | 0 | O | OPh | |
| 962 | CH | CF$_3$ | 0 | O | OH | |
| 963 | CH | CF$_3$ | 0 | O | OCH$_3$ | |
| 964 | CH | CF$_3$ | 0 | O | OCH$_2$CH$_3$ | |
| 965 | CH | CF$_3$ | 0 | O | OCHF$_2$ | |
| 966 | CH | CF$_3$ | 0 | O | OCH$_2$Ph | |
| 967 | CH | CF$_3$ | 0 | O | SCH$_3$ | |
| 968 | CH | CF$_3$ | 0 | O | SPh | |
| 969 | CH | CF$_3$ | 0 | O | NH$_2$ | 190–191 |

TABLE 3-continued

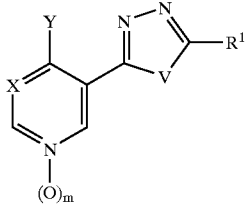

| No. | X | Y | m | V | R¹ | m.p. [° C.] |
|---|---|---|---|---|---|---|
| 970 | CH | $CF_3$ | 0 | O | $NHCH_3$ | |
| 971 | CH | $CF_3$ | 0 | O | $NHCH_2CH_3$ | |
| 972 | CH | $CF_3$ | 0 | O | $N(CH_2CH_3)_2$ | |
| 973 | CH | $CF_3$ | 0 | O | $N(CH_2CN)_2$ | |
| 974 | CH | $CF_3$ | 0 | O | $N(CH_3)_2$ | |
| 975 | CH | $CF_3$ | 0 | O | $NHCOCH_3$ | |
| 976 | CH | $CF_3$ | 0 | O | $NHCOCH_2CH_3$ | |
| 977 | CH | $CF_3$ | 0 | O | $OSO_2CH_3$ | |
| 978 | CH | $CF_3$ | 0 | O | $SOCH_2(4\text{-}Br)\text{---}C_6H_4$ | |
| 979 | CH | $CF_3$ | 0 | O | $N(CH_3)COOCH_2Ph$ | |
| 980 | CH | $CF_3$ | 0 | $NCH_3$ | $CH_3$ | |
| 981 | CH | $CF_3$ | 0 | $NCH_2CH_3$ | $CH_3$ | |
| 982 | CH | $CF_3$ | 0 | $NCH_2CH_3$ | $CH_2CH_3$ | |
| 983 | CH | $CF_3$ | 0 | $NCH_2CN$ | $CH_2CH_3$ | |
| 984 | CH | $CF_3$ | 0 | $NCH_2OCH_3$ | $NHCH_3$ | |
| 985 | CH | $CF_3$ | 0 | $NCH_2OCH_2CH_3$ | CN | |
| 986 | CH | $CF_3$ | 0 | $NCH_2CH\text{=}CH_2$ | $CH_3$ | |
| 987 | CH | $CF_3$ | 0 | $NCH_2CH\text{=}CF_2$ | $SCH_3$ | |
| 988 | CH | $CF_3$ | 0 | $NCH_2OCH_3$ | $SCH_2CH_3$ | |
| 989 | CH | $CF_3$ | 0 | $NCH_2OCH_3$ | $SCH_2Ph$ | |
| 990 | CH | $CHF_2$ | 0 | O | $CH_3$ | |
| 991 | CH | $CHF_2$ | 0 | O | $CH_2CH_3$ | |
| 992 | CH | $CHF_2$ | 0 | O | $(CH_2)_2CH_3$ | |
| 993 | CH | $CHF_2$ | 0 | O | $CH_2CH\text{=}CH_2$ | |
| 994 | CH | $CHF_2$ | 0 | O | $C(CH_3)\text{=}CH_2$ | |
| 995 | CH | $CHF_2$ | 0 | O | $COOCH_2CH_3$ | |
| 996 | CH | $CHF_2$ | 0 | O | $CH_2CONHCH_3$ | |
| 997 | CH | $CHF_2$ | 0 | O | $CF_2CH_3$ | |
| 998 | CH | $CHF_2$ | 0 | O | CHO | |
| 999 | CH | $CHF_2$ | 0 | O | $NH_2$ | |
| 1000 | CH | $CHF_2$ | 0 | O | $NHCOCH_3$ | |
| 1001 | N | $CF_2CF_3$ | 0 | S | $CH_3$ | |
| 1002 | N | $CF_2CF_3$ | 0 | S | $CH_2CH_3$ | |
| 1003 | N | $CF_2CF_3$ | 0 | S | $(CH_2)_2CH_3$ | |
| 1004 | N | $CF_3$ | 0 | S | $CH_3$ | |
| 1005 | N | $CF_3$ | 0 | S | $CH_2CH_3$ | |
| 1006 | N | $CF_3$ | 0 | S | $(CH_2)_2CH_3$ | |
| 1007 | N | $CF_3$ | 0 | S | $CHFCF_3$ | |
| 1008 | N | $CF_3$ | 0 | S | $CH_2CH_2OH$ | |
| 1009 | N | $CF_3$ | 0 | S | $CH_2COOC(CH_3)_3$ | |
| 1010 | CH | $CF_3$ | 0 | S | $CH_3$ | |
| 1011 | CH | $CF_3$ | 0 | S | $CH_2CH_3$ | |
| 1012 | CH | $CF_3$ | 0 | S | $(CH_2)_2CH_3$ | |
| 1013 | CH | $CF_3$ | 0 | S | CHO | |
| 1014 | CH | $CF_3$ | 0 | S | $CHFCF_3$ | |
| 1015 | CH | $CF_3$ | 0 | S | $CH_2C\equiv CH$ | |
| 1016 | CH | $CF_3$ | 0 | S | $COOCH_2CH_3$ | |
| 1017 | CH | $CF_3$ | 0 | S | $CH_2COOC(CH_3)_3$ | |
| 1018 | CH | $CF_3$ | 0 | S | $CH_2CN$ | |

TABLE 4

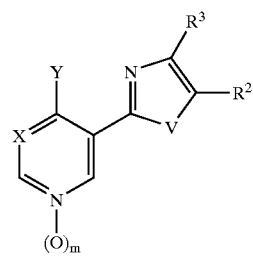

| No. | X | Y | m | V | R² | R³ | m.p. [° C.] |
|---|---|---|---|---|---|---|---|
| 1019 | N | (CF₂)₃CHF₂ | 0 | S | H | CH₂CH₃ | |
| 1020 | N | CF₂CF₂CF₃ | 0 | S | H | CH₂CH₃ | |
| 1021 | N | CF₂CF₃ | 0 | S | H | CH₂CH₃ | |
| 1022 | N | CH₂CH₂Cl | 0 | S | H | CH₂CH₃ | |
| 1023 | N | CH₂Cl | 0 | S | H | CH₂CH₃ | |
| 1024 | N | CF₃ | 0 | S | CH₂CH₃ | CH₂CH₃ | |
| 1025 | N | CF₃ | 0 | S | (CH₂)₂CH₃ | H | |
| 1026 | N | CF₃ | 0 | S | CH(CH₃)₂ | H | |
| 1027 | N | CF₃ | 0 | S | CH₂CH(CH₃)₂ | H | |
| 1028 | N | CF₃ | 0 | S | C(CH₃)₃ | H | |
| 1029 | CH | CF₃ | 0 | S | H | CH₃ | oil |
| 1030 | CH | CF₃ | 0 | S | H | CH₂CH₃ | oil |
| 1031 | CH | CF₃ | 0 | S | H | C(CH₃)₃ | oil |
| 1032 | CH | CF₃ | 0 | S | CH₂CH₃ | COOCH₂CH₃ | |
| 1033 | CH | CF₃ | 0 | S | (CH₂)₂CH₃ | COOCH₂CH₃ | |
| 1034 | CH | CF₃ | 0 | S | CH(CH₃)₂ | COOCH₂CH₃ | |
| 1035 | CH | CF₃ | 0 | S | CH(CH₃)₂ | CONHCH₂CH₃ | |
| 1036 | CH | CF₃ | 0 | S | CH(CH₃)₂ | CONHCH₂CH₃ | |
| 1037 | CH | CF₃ | 0 | S | CH(CH₃)₂ | CON(CH₂CH₃)₂ | |
| 1038 | CH | CF₃ | 0 | S | CH(CH₃)₂ | CONH-cyclo-C₃H₇ | |
| 1039 | CH | CF₃ | 0 | S | C(CH₃)₃ | COOCH₂CH₃ | |
| 1040 | CH | CF₃ | 0 | S | H | CONHCH₂CH₃ | |
| 1041 | CH | CF₃ | 0 | S | H | CON(CH₂CH₃)₂ | |
| 1042 | CH | CF₃ | 0 | S | H | COOCH₂CH₃ | oil |
| 1043 | CH | CF₃ | 0 | S | H | CH₂COOCH₂CH₃ | oil |
| 1044 | CH | CF₃ | 0 | S | H | CH₂CHO | |
| 1045 | CH | CF₃ | 0 | S | H | CH₂OCH₃ | |
| 1046 | CH | CF₃ | 0 | S | H | CH₂OCH₂Ph | |
| 1047 | CH | CF₃ | 0 | S | H | H | |
| 1048 | CH | CF₃ | 0 | S | Cyclo-C₅H₉ | H | |
| 1049 | CH | CF₃ | 0 | S | CON(CH₃)₂ | CH₃ | oil |
| 1050 | CH | CF₃ | 0 | S | CH₃ | CH₂CH₂OH | |
| 1051 | CH | CF₃ | 0 | S | CH₃ | CH₂CH₂OCH₃ | |
| 1052 | CH | CF₃ | 0 | S | CH₃ | CH₂CH₂OCH₂Ph | |
| 1053 | CH | CF₃ | 0 | S | CH₃ | CH₂CH₂SPh | |
| 1054 | CH | CF₃ | 0 | S | CH₃ | CH₃ | oil |
| 1055 | CH | CF₃ | 0 | S | CH₃ | CH₂CH₂CHO | |
| 1055 | CH | CF₃ | 0 | S | CH₃ | CH₂CH₂CHNPh | |
| 1057 | CH | CF₃ | 0 | S | CH₃ | CH₂CH₂CONH₂ | |
| 1058 | CH | CF₃ | 0 | S | H | (4-CF₃O)C₆H₄ | 120–121 |
| 1059 | CH | CF₃ | 0 | S | CH₂C≡CH | H | |
| 1060 | CH | CF₃ | 0 | S | CH₂CH₂C≡CH | H | |
| 1061 | CH | CF₃ | 0 | S | CH₂C≡CCH₂CH₃ | H | |
| 1062 | CH | CF₃ | 0 | S | CH₂CH=C(CH₃)₂ | H | |
| 1063 | CH | CF₃ | 0 | S | CH₂CH₂CH=CH₂ | H | |
| 1064 | CH | CF₃ | 0 | S | CH₂CH=CH₂ | H | |
| 1065 | CH | CF₃ | 0 | S | C(CH₃)=CH₂ | H | |
| 1066 | CH | CF₃ | 0 | S | CHFCF₃ | H | |
| 1067 | CH | CF₃ | 0 | S | COOCH₂CH₃ | H | |
| 1068 | CH | CF₃ | 0 | S | CH₂CH₂OH | H | |
| 1069 | CH | CF₃ | 0 | S | CH₂CH₂OCH₃ | H | |
| 1070 | CH | CF₃ | 0 | S | CH₂COOC(CH₃)₃ | H | |
| 1071 | CH | CF₃ | 0 | S | CH₂COCH₃ | H | |
| 1072 | CH | CF₃ | 0 | S | COCH3 | H | |
| 1073 | CH | CF₃ | 0 | S | CH₂Oph | H | |
| 1074 | CH | CF₃ | 0 | S | COPh | H | |
| 1075 | CH | CF₃ | 0 | S | CO(4-Cl)—C₆H₄ | H | |
| 1076 | CH | CF₃ | 0 | S | CF₂CH₃ | H | |
| 1077 | CH | CF₃ | 0 | S | CH₂CN | H | |
| 1078 | CH | CF₃ | 0 | S | CH₂CH₂CN | H | |
| 1079 | N | CF₃ | 0 | S | H | H | |
| 1080 | N | CF₃ | 0 | S | H | CH₂CH₂CN | |
| 1081 | N | CF₃ | 0 | S | H | CH₂CO₂C(CH₃)₃ | |

TABLE 4-continued

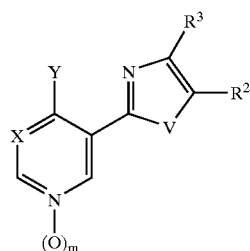

| No. | X | Y | m | V | R² | R³ | m.p. [° C.] |
|---|---|---|---|---|---|---|---|
| 1082 | N | CF₃ | 0 | S | H | CH₂CHO | |
| 1083 | N | CF₃ | 0 | S | H | CH₂CH₂OH | |
| 1084 | N | CF₃ | 0 | S | H | CH₂CH₂OCH₃ | |
| 1085 | N | CF₃ | 0 | S | Cyclo-C₅H₉ | H | |
| 1086 | N | CF₃ | 0 | S | CH₃ | COOCH₂CH₃ | |
| 1087 | N | CF₃ | 0 | S | CH₃ | COOH | |
| 1088 | N | CF₃ | 0 | S | CH₃ | CONH₂ | |
| 1089 | N | CF₃ | 0 | S | CH₃ | CONHCH₂CH₃ | |
| 1090 | N | CF₃ | 0 | S | CH₃ | CON(CH₂CH₃)₂ | |
| 1091 | N | CF₃ | 0 | S | CH₃ | CONHCH₃ | |
| 1092 | N | CF₃ | 0 | S | CH₃ | CONHCH₂CN | |
| 1093 | N | CF₃ | 0 | S | CH₃ | CON(CH₂CN)₂ | |
| 1094 | N | CF₃ | 0 | S | CH₃ | CON(CH₃)₂ | |
| 1095 | N | CF₃ | 0 | S | CH₂C≡CH | OCH₂CH₃ | |
| 1096 | N | CF₃ | 0 | S | CH₂CH₂C≡CH | OCH₂CH₃ | |
| 1097 | N | CF₃ | 0 | S | CH₂C≡CCH₂CH₃ | OCH₂CH₃ | |
| 1098 | N | CF₃ | 0 | S | CH₂CH=C(CH₃)₂ | OCH₂CH₃ | |
| 1099 | N | CF₃ | 0 | S | CH₂CH₂CH=CH₂ | OCH₂CH₃ | |
| 1100 | N | CF₃ | 0 | S | CH₂CH=CH₂ | OCH₂CH₃ | |
| 1101 | N | CF₃ | 0 | S | C(CH₃)=CH₂ | OCH₂CH₃ | |
| 1102 | N | CF₃ | 0 | S | CHFCF₃ | OCH₂CH₃ | |
| 1103 | N | CF₃ | 0 | S | COOCH₂CH₃ | OCH₂CH₃ | |
| 1104 | N | CF₃ | 0 | S | CH₂CH₂OH | OCH₂CH₃ | |
| 1105 | N | CF₃ | 0 | S | CH₂CH₂OCH₃ | OCH₂CH₃ | |
| 1106 | N | CF₃ | 0 | S | CH₂COOC(CH₃)₃ | OCH₂CH₃ | |
| 1107 | N | CF₃ | 0 | S | CH₂COCH₃ | H | |
| 1108 | N | CF₃ | 0 | S | COCH3 | H | |
| 1109 | N | CF₃ | 0 | S | CH₂Oph | H | |
| 1110 | N | CF₃ | 0 | S | COPh | H | |
| 1111 | N | CF₃ | 0 | S | CO(4-Cl)—C₆H₄ | H | |
| 1112 | N | CF₃ | 0 | S | CF₂CH₃ | H | |
| 1113 | N | CF₃ | 0 | S | CH₂CN | H | |
| 1114 | N | CF₃ | 0 | S | CH₂CH₂CN | H | |
| 1115 | CH | CF₃ | 0 | O | CH₂CH₃ | CH₂CH₃ | |
| 1116 | CH | CF₃ | 0 | O | (CH₂)₂CH₃ | H | |
| 1117 | CH | CF₃ | 0 | O | H | CH₂CH₃ | oil |
| 1118 | CH | CF₃ | 0 | O | CH(CH₃)₂ | COOCH₂CH₃ | |
| 1119 | CH | CF₃ | 0 | O | CH(CH₃)₂ | COOH | |
| 1120 | CH | CF₃ | 0 | O | CH(CH₃)₂ | CONH₂ | |
| 1121 | CH | CF₃ | 0 | O | CH(CH₃)₂ | CH₃ | |
| 1122 | CH | CF₃ | 0 | O | C(CH₃)₃ | H | |
| 1123 | CH | CF₃ | 0 | O | H | CH₃ | |
| 1124 | CH | CF₃ | 0 | O | H | cyclo-C₅H₉ | |
| 1125 | CH | CF₃ | 0 | O | H | CH₂CH₂CH₃ | |
| 1126 | CH | CF₃ | 0 | O | H | Ph | 103–1041 |
| 1127 | CH | CF₃ | 0 | O | H | 2-Pyridyl | |
| 1128 | CH | CF₃ | 0 | O | H | 2-Furyl | |
| 1129 | CH | CF₃ | 0 | O | Cyclo-C₅H₉ | H | |
| 1130 | CH | CF₃ | 0 | O | CH₃ | COOCH₂CH₃ | |
| 1131 | CH | CF₃ | 0 | O | CH₃ | COOH | |
| 1132 | CH | CF₃ | 0 | O | CH₃ | CONH₂ | |
| 1133 | CH | CF₃ | 0 | O | CH₃ | CONHCH₂CH₃ | |
| 1134 | CH | CF₃ | 0 | O | CH₃ | CON(CH₂CH₃)₂ | |
| 1135 | CH | CF₃ | 0 | O | CH₃ | CONHCH₃ | |
| 1136 | CH | CF₃ | 0 | O | CH₃ | CONHCH₂CN | |
| 1137 | CH | CF₃ | 0 | O | CH₃ | CON(CH₂CN)₂ | |
| 1138 | CH | CF₃ | 0 | O | CH₃ | CON(CH₃)₂ | |
| 1139 | CH | CF₃ | 0 | O | CH₂C≡CH | H | |
| 1140 | CH | CF₃ | 0 | O | CH₂CH₂C≡CH | H | |
| 1141 | CH | CF₃ | 0 | O | CH₂C≡CCH₂CH₃ | H | |
| 1142 | CH | CF₃ | 0 | O | CH₂CH=C(CH₃)₂ | H | |
| 1143 | CH | CF₃ | 0 | O | CH₂CH₂C=CH | H | |
| 1144 | CH | CF₃ | 0 | O | CH₂CH=CH₂ | H | |

TABLE 4-continued

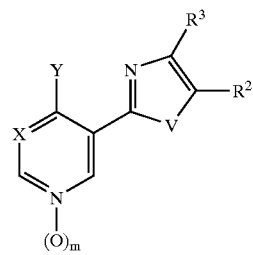

| No. | X | Y | m | V | R² | R³ | m.p. [° C.] |
|---|---|---|---|---|---|---|---|
| 1145 | CH | CF₃ | 0 | O | C(CH₃)=CH₂ | H | |
| 1146 | CH | CF₃ | 0 | O | CHFCF₃ | H | |
| 1147 | CH | CF₃ | 0 | O | COOCH₂CH₃ | H | |
| 1148 | CH | CF₃ | 0 | O | CH₂CH₂OH | H | |
| 1149 | CH | CF₃ | 0 | O | CH₂CH₂OCH₃ | H | |
| 1150 | CH | CF₃ | 0 | O | CH₂COOC(CH₃)₃ | H | |
| 1151 | CH | CF₃ | 0 | O | CH₂COCH₃ | H | |
| 1152 | CH | CF₃ | 0 | O | COCH3 | H | |
| 1153 | CH | CF₃ | 0 | O | CH₂Oph | H | |
| 1154 | CH | CF₃ | 0 | O | COPh | H | |
| 1155 | CH | CF₃ | 0 | O | CO(4-Cl)—C₆H₄ | H | |
| 1156 | CH | CF₃ | 0 | O | CF₂CH₃ | H | |
| 1157 | CH | CF₃ | 0 | O | CH₂CN | H | |
| 1158 | CH | CF₃ | 0 | O | CH₂CH₂CN | H | |
| 1159 | N | CF₃ | 0 | O | CH₂CH₃ | CH₂CH₃ | |
| 1160 | N | CF₃ | 0 | O | (CH₂)₂CH₃ | H | |
| 1161 | N | CF₃ | 0 | O | CH(CH₃)₂ | CONH₂ | |
| 1162 | N | CF₃ | 0 | O | CH(CH₃)₂ | CH₃ | |
| 1163 | N | CF₃ | 0 | O | C(CH₃)₃ | H | |
| 1164 | N | CF₃ | 0 | O | H | CH₃ | |
| 1165 | N | CF₃ | 0 | O | H | CH₂CH₃ | |
| 1166 | N | CF₃ | 0 | O | H | CH₂CH₂CH₃ | |
| 1167 | N | CF₃ | 0 | O | H | Ph | |
| 1168 | N | CF₃ | 0 | O | H | 2-Pyridyl | |
| 1169 | N | CF₃ | 0 | O | H | 2-Furyl | |
| 1170 | N | CF₃ | 0 | O | Cyclo-C₅H₉ | H | |
| 1171 | N | CF₃ | 0 | O | CH₃ | COOCH₂CH₃ | |
| 1172 | N | CF₃ | 0 | O | CH₃ | COOH | |
| 1173 | N | CF₃ | 0 | O | CH₃ | CONH₂ | |
| 1174 | N | CF₃ | 0 | O | CH₃ | CONHCH₂CH₃ | |
| 1175 | N | CF₃ | 0 | O | CH₃ | CON(CH₂CH₃)₂ | |
| 1176 | N | CF₃ | 0 | O | CH₃ | CONHCH₃ | |
| 1177 | N | CF₃ | 0 | O | CH₃ | CONHCH₂CN | |
| 1178 | N | CF₃ | 0 | O | CH₃ | CON(CH₂CN)₂ | |
| 1179 | N | CF₃ | 0 | O | CH₃ | CON(CH₃)₂ | |
| 1180 | N | CF₃ | 0 | O | CH₂C≡CH | H | |
| 1181 | N | CF₃ | 0 | O | CH₂CH₂C≡CH | H | |
| 1182 | N | CF₃ | 0 | O | CH₂C≡CCH₂CH₃ | H | |
| 1183 | N | CF₃ | 0 | O | CH₂CH=C(CH₃)₂ | H | |
| 1184 | N | CF₃ | 0 | O | CH₂CH₂CH=CH₂ | H | |
| 1185 | N | CF₃ | 0 | O | CH₂CH=CH₂ | H | |
| 1186 | N | CF₃ | 0 | O | C(CH₃)=CH₂ | H | |
| 1187 | N | CF₃ | 0 | O | CHFCF₃ | H | |
| 1188 | N | CF₃ | 0 | O | COOCH₂CH₃ | H | |
| 1189 | N | CF₃ | 0 | O | CH₂CH₂OH | H | |
| 1190 | N | CF₃ | 0 | O | CH₂CH₂OCH₃ | H | |
| 1191 | N | CF₃ | 0 | O | CH₂COOC(CH₃)₃ | H | |
| 1192 | N | CF₃ | 0 | O | CH₂COCH₃ | H | |
| 1193 | N | CF₃ | 0 | O | COCH3 | H | |
| 1194 | N | CF₃ | 0 | O | OCH₂Oph | H | |
| 1195 | N | CF₃ | 0 | O | COPh | H | |
| 1196 | N | CF₃ | 0 | O | CO(4-Cl)—C₆H₄ | H | |
| 1197 | N | CF₃ | 0 | O | CF₂CH₃ | H | |
| 1198 | N | CF₃ | 0 | O | CH₂CN | H | |
| 1199 | N | CF₃ | 0 | O | CH₂CH₂CN | H | |
| 1200 | N | CF₃ | 0 | O | CH₂NHSO₂CH₃ | CH₃ | |
| 1201 | N | CF₃ | 0 | O | (CH₂)₂NHSO₂CH₃ | CH₃ | |
| 1202 | N | CF₃ | 0 | O | CH₂NHSO₂CH₂CH₃ | CH₃ | |
| 1203 | N | CF₃ | 0 | O | H | CH₂NHSO₂CH₂Ph | |
| 1204 | CH | CF₃ | 0 | O | (CH₂)₄NHSO₂CF₃ | CH₃ | |
| 1205 | CH | CF₃ | 0 | O | (CH₂)₂S(CH₂)₂CH₃ | CH₂CH₂CH₃ | |
| 1206 | CH | CF₃ | 0 | O | (CH₂)₄S(CH₂)₄OCH₃ | CH₃ | |
| 1207 | CH | CF₃ | 0 | S | CH₃ | (CH₂)₂S(CH₂)₂CN | |

TABLE 4-continued

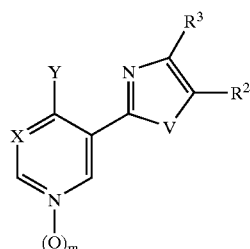

| No. | X | Y | m | V | R² | R³ | m.p. [° C.] |
|---|---|---|---|---|---|---|---|
| 1208 | CH | CF₃ | 0 | S | CH₂NHSO₂CH₂CH₃ | CH₃ | |
| 1209 | CH | CF₃ | 0 | S | CH₂NHSO₂CH₂Ph | CH₂CH₂CH₃ | |
| 1210 | CH | CF₃ | 0 | S | (CH₂)₂NHSO₂CH₃ | CF₃ | |
| 1211 | CH | CF₃ | 0 | S | H | CH₂NHSO₂CH₃ | |
| 1212 | CH | CF₃ | 0 | S | CH(CH₃)CH₂NHPh | CF₃ | |
| 1213 | CH | CF₃ | 0 | S | (CH₂)₂S(2-F)—C₆H₄ | CH₂CH₂CH₃ | |
| 1214 | CH | CF₃ | 0 | S | (CH₂)₆NHCH₂)₆OCH₃ | CF₃ | |
| 1215 | CH | CF₃ | 0 | S | H | (CH₂)₂NH—(2-F)—C₆H₄ | |
| 1216 | CH | CF₃ | 0 | S | (CH₂)₃NHCH₂CN | H | |
| 1217 | CH | CF₃ | 0 | S | (CH₂)₂O(3-Cl)—C₆H₄ | CH₃ | |
| 1218 | CH | CF₃ | 0 | S | CF₃ | (CH₂)₆NHCH₂CF₃ | |
| 1219 | CH | CF₃ | 0 | S | CH₃ | (CH₂)₂O(3-CH₃)—C₆H₄ | |
| 1220 | CH | CF₃ | 0 | O | H | CH₂NHPh | |
| 1221 | CH | CF₃ | 0 | O | CH₃ | (CH₂)₄S(2-Br)—C₆H₄ | |
| 1222 | CH | CF₃ | 0 | O | (CH₂)₆NH(CH₂)₂OCH₃ | CH₃ | |
| 1223 | CH | CF₃ | 0 | O | (CH₂)₂NH(CH₂)₄OCH₃ | H | |
| 1224 | CH | CF₃ | 0 | O | CF₃ | (CH₂)₃NH—(4-CN)—C₆H₄ | |
| 1225 | CH | CF₃ | 0 | O | (CH₂)₄NHCH₂CF₃ | CH₃ | |
| 1226 | CH | CF₃ | 0 | O | C₂F₅ | (CH₂)₂O(3-CH₃)—C₆H₄ | |
| 1227 | CH | CF₃ | 0 | O | (CH₂)₄NHCH₂CN | H | |
| 1228 | CH | CF₃ | 0 | O | (CH₂)₃O(4-Cl)—C₆H₄ | C₂F₅ | |

TABLE 5

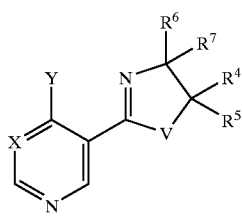

| No. | X | Y | V | R⁴ | R⁵ | R⁶ | R⁷ | m.p. [° C.] |
|---|---|---|---|---|---|---|---|---|
| 1229 | CH | CF₃ | O | H | H | H | H | oil |
| 1230 | CH | CF₃ | O | H | H | CH₃ | H | oil |
| 1231 | CH | CF₃ | O | H | H | CH₂CH₃ | H | oil |
| 1232 | CH | CF₃ | O | H | H | CH(CH₃)₂ | H | |
| 1233 | CH | CF₃ | O | H | H | CH₂CH(CH₃)₂ | H | |
| 1234 | CH | CF₃ | O | H | H | CH(CH₃)CH₂CH₃ | H | |
| 1235 | CH | CF₃ | O | H | H | CH₂OH | H | |
| 1236 | CH | CF₃ | O | H | H | CH(OH)CH₃ | H | |
| 1237 | CH | CF₃ | O | H | H | CH₂SH | H | |
| 1238 | CH | CF₃ | O | H | H | CH₂CH₂SCH₃ | H | |
| 1239 | CH | CF₃ | O | H | H | (CH₂)₃NH₂ | H | |
| 1240 | CH | CF₃ | O | H | H | (CH₂)₄NH₂ | H | |
| 1241 | CH | CF₃ | O | H | H | CH=CH₂ | H | |
| 1242 | CH | CF₃ | O | H | H | (CH₂)₂COOCH₃ | H | |
| 1243 | CH | CF₃ | O | H | H | (CH₂)₂COOH | H | |
| 1244 | CH | CF₃ | O | H | H | (CH₂)₂CONH₂ | H | |
| 1245 | CH | CF₃ | S | CH₃ | CH₃ | H | H | |
| 1246 | CH | CF₃ | O | H | H | CH₃ | CH₃ | oil |
| 1247 | CH | CF₃ | O | H | H | CH₂COOCH₃ | H | |
| 1248 | CH | CF₃ | O | H | H | CH₂COOH | H | |
| 1249 | CH | CF₃ | O | H | H | CH₂CONH₂ | H | |
| 1250 | CH | CF₃ | O | H | H | CH₂Ph | H | |
| 1251 | CH | CF₃ | O | H | H | CH₂—(4-OH)—C₆H₄ | H | |

TABLE 5-continued

| No. | X | Y | V | R⁴ | R⁵ | R⁶ | R⁷ | m.p. [° C.] |
|---|---|---|---|---|---|---|---|---|
| 1252 | CH | CF₃ | O | H | H | CH₂—(3-Indolyl) | H | |
| 1253 | CH | CF₃ | O | CH₃ | CH₃ | H | H | oil |
| 1254 | CH | CF₃ | O | CH₃ | H | H | H | oil |
| 1255 | CH | CF₃ | O | CH₃ | H | H | Ph | |
| 1256 | CH | CF₃ | O | H | | (CH₂)₄ | H | |
| 1257 | CH | CF₃ | NH | H | | (CH₂)₄ | H | |
| 1258 | CH | CF₃ | NCH₃ | H | | (CH₂)₄ | H | |
| 1259 | CH | CF₃ | NCH₂C₆H₄ | H | | (CH₂)₄ | H | |
| 1260 | CH | CF₃ | NCH(CH₃)₂ | H | | (CH₂)₄ | H | |
| 1261 | CH | CF₃ | O | Ph | H | Ph | H | |
| 1262 | CH | CF₃ | NH | Ph | H | Ph | H | |
| 1263 | CH | CF₃ | NCH₃ | Ph | H | Ph | H | |
| 1264 | CH | CF₃ | NCH₂C₆H₄ | Ph | H | Ph | H | |
| 1265 | N | CF₃ | O | H | H | CH₂CH₃ | H | oil |
| 1266 | N | CF₃ | O | H | H | CH(CH₃)₂ | H | |
| 1267 | N | CF₃ | O | H | H | CH₂CH(CH₃)₂ | H | |
| 1268 | N | CF₃ | O | H | H | CH₂COOH | H | |
| 1269 | N | CF₃ | O | H | H | CH₂COOCH₃ | H | |
| 1270 | N | CF₃ | O | H | H | CH₂CONH₂ | H | |
| 1271 | N | CF₃ | O | CH₃ | CH₃ | H | H | |
| 1272 | N | CF₃ | O | H | (CH₂ | | H | |
| 1273 | N | CF₃ | O | H | H | CH₂CH₂SCH₃ | H | |
| 1274 | CH | CF₃ | S | H | H | H | H | oil |

TABLE 6

| No. | X | Y | R⁸ | R¹ | m.p. [° C.] |
|---|---|---|---|---|---|
| 1275 | CH | CF₃ | CH₃ | SH | 209–210 |
| 1276 | CH | CF₃ | CH₃ | SCH₃ | |
| 1277 | CH | CF₃ | CH₃ | SCH₂CH₃ | |
| 1278 | CH | CF₃ | CH₃ | S(CH₂)₂CH₃ | |
| 1279 | CH | CF₃ | CH₃ | SCH(CH₃)₂ | |
| 1280 | CH | CF₃ | CH₃ | SPh | |
| 1281 | CH | CF₃ | CH₃ | S(CH₂)₃CH₃ | |
| 1282 | CH | CF₃ | CH₃ | SCH(CH₃)CH₂CH₃ | |
| 1283 | CH | CF₃ | CH₃ | SCH₂CH(CH₃)₂ | |
| 1284 | CH | CF₃ | CH₃ | OH | 119–120 |
| 1285 | CH | CF₃ | CH₃ | OCH₃ | |
| 1286 | CH | CF₃ | CH₃ | OCH₂CH₃ | |
| 1287 | CH | CF₃ | CH₃ | OCHF₂ | |
| 1288 | CH | CF₃ | CH₃ | OCH₂Ph | |
| 1289 | CH | CF₃ | CH₃ | OCONHPh | |
| 1290 | CH | CF₃ | CH₃ | OCONH—(4-F)—C₆H₄ | |
| 1291 | CH | CF₃ | CH₃ | OCONH—(3,5-di-Cl)—C₆H₃ | |
| 1292 | CH | CF₃ | CH₂CN | OCH₃ | |
| 1293 | CH | CF₃ | CH₂CN | OCH₂CH₃ | |
| 1294 | CH | CF₃ | CH₂CN | OCHF₂ | |
| 1295 | CH | CF₃ | CH₂CN | OCH₂Ph | |
| 1296 | CH | CF₃ | CH₂CN | OCONHPh | |
| 1297 | CH | CF₃ | CH₂CN | OCONH—(4-F)—C₆H₄ | |

TABLE 6-continued

| No. | X | Y | R⁸ | R¹ | m.p. [° C.] |
|---|---|---|---|---|---|
| 1298 | CH | CF₃ | CH₂OCH₂CH₃ | OCH₃ | |
| 1299 | CH | CF₃ | CH₂OCH₂CH₃ | OCH₂CH₃ | |
| 1300 | CH | CF₃ | CH₂OCH₂CH₃ | OCHF₂ | |
| 1301 | CH | CF₃ | CH₂OCH₂CH₃ | OCH₂Ph | |
| 1302 | CH | CF₃ | CH₂OCH₂CH₃ | OCONHPh | |
| 1303 | CH | CF₃ | H | CH₃ | 203–204 |
| 1304 | CH | CF₃ | H | CH₂CH₃ | 134–135 |
| 1305 | CH | CF₃ | H | (CH₂)₂CH₃ | |
| 1306 | CH | CF₃ | H | CH(CH₃)₂ | |
| 1307 | CH | CF₃ | H | Cyclo-C₃H₅ | |
| 1308 | CH | CF₃ | H | (CH₂)₃CH₃ | |
| 1309 | CH | CF₃ | H | CH(CH₃)CH₂CH₃ | |
| 1310 | CH | CF₃ | H | CH₂CH(CH₃)₂ | |
| 1311 | CH | CF₃ | H | CH=CH₂ | |
| 1312 | CH | CF₃ | H | CH₂CH=C(CH₃)₂ | |
| 1313 | CH | CF₃ | H | CH₂CH₂CH=CH₂ | |
| 1314 | CH | CF₃ | H | CH₂CH=CH₂ | |
| 1315 | CH | CF₃ | H | C(CH₃)=CH₂ | |
| 1316 | CH | CF₃ | H | CHFCF₃ | |
| 1317 | CH | CF₃ | H | COOCH₂CH₃ | |
| 1318 | CH | CF₃ | H | CH₂CH₂OH | |
| 1319 | CH | CF₃ | H | CH₂CH₂OCH₃ | |
| 1320 | CH | CF₃ | H | CH₂COOC(CH₃)₃ | |
| 1321 | CH | CF₃ | CH₃ | CH₂COOC(CH₃)₃ | |
| 1322 | CH | CF₃ | CH₂CN | CH₂COOC(CH₃)₃ | |
| 1323 | CH | CF₃ | CH₂OCH₂CH₃ | CH₂COOC(CH₃)₃ | |
| 1324 | CH | CF₃ | H | CH₂SPh | |
| 1325 | CH | CF₃ | H | CH₂CONHCH₃ | |
| 1326 | CH | CF₃ | H | CH₂COCH₃ | |
| 1327 | CH | CF₃ | H | COCH3 | |
| 1328 | CH | CF₃ | H | CH₂Oph | |
| 1329 | CH | CF₃ | H | COPh | |
| 1330 | CH | CF₃ | H | CO(3-Cl)—C₆H₄ | |
| 1331 | CH | CF₃ | H | CF₂CH₃ | |
| 1332 | CH | CF₃ | H | CH₂CN | |
| 1333 | CH | CF₃ | H | CH₂CH₂CN | |
| 1334 | CH | CF₃ | H | CH₂CH(—O—)CH₂ | |
| 1336 | CH | CF₃ | H | CH₂(4-OCH₃)Ph | |
| 1337 | N | CF₃ | CH₃ | SH | |
| 1338 | N | CF₃ | CH₃ | SCH₃ | |
| 1339 | N | CF₃ | CH₃ | SCH₂CH₃ | |
| 1340 | N | CF₃ | CH₃ | SPh | |
| 1341 | N | CF₃ | CH₃ | SCH₂CH(CH₃)₂ | |
| 1342 | N | CF₃ | CH₃ | OH | |
| 1343 | N | CF₃ | CH₃ | OCH₃ | |
| 1344 | N | CF₃ | CH₃ | OCH₂CH₃ | |
| 1345 | N | CF₃ | CH₃ | OCH₂Ph | |
| 1346 | N | CF₃ | CH₃ | OCONHPh | |
| 1347 | N | CF₃ | CH₂CN | OCH₃ | |
| 1348 | N | CF₃ | CH₂CN | OCH₂CH₃ | |
| 1349 | N | CF₃ | CH₂CN | OCH₂Ph | |
| 1350 | N | CF₃ | CH₂CN | OCONHPh | |
| 1351 | N | CF₃ | CH₂OCH₂CH₃ | OCH₃ | |
| 1352 | N | CF₃ | CH₂OCH₂CH₃ | OCH₂Ph | |
| 1353 | N | CF₃ | CH₂OCH₂CH₃ | OCONHPh | |
| 1354 | N | CF₃ | H | CH₃ | |
| 1355 | N | CF₃ | H | CH₂CH₃ | |
| 1356 | N | CF₃ | H | (CH₂)₂CH₃ | |
| 1357 | N | CF₃ | H | CH(CH₃)₂ | |
| 1358 | N | CF₃ | H | (CH₂)₃CH₃ | |
| 1359 | N | CF₃ | H | CH(CH₃)CH₂CH₃ | |
| 1360 | N | CF₃ | H | CH₂CH(CH₃)₂ | |
| 1361 | N | CF₃ | H | CH₂C=C(CH₃)₂ | |
| 1362 | N | CF₃ | H | CH₂CH=CH₂ | |
| 1363 | N | CF₃ | H | C(CH₃)H=CH₂ | |

TABLE 6-continued

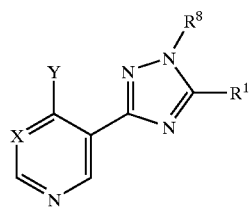

| No. | X | Y | R⁸ | R¹ | m.p. [° C.] |
|---|---|---|---|---|---|
| 1364 | N | CF₃ | H | COOCH₂CH₃ | |
| 1365 | N | CF₃ | H | CH₂CH₂OH | |
| 1366 | N | CF₃ | H | CH₂CH₂OCH₃ | |
| 1367 | N | CF₃ | H | CH₂COOC(CH₃)₃ | |
| 1368 | N | CF₃ | H | CH₂SPh | |
| 1369 | N | CF₃ | H | CH₂CONHCH₃ | |
| 1370 | N | CF₃ | H | CH₂COCH₃ | |
| 1371 | N | CF₃ | H | COCH3 | |
| 1372 | N | CF₃ | H | CH₂Oph | |
| 1373 | N | CF₃ | H | COPh | |
| 1374 | N | CF₃ | H | CH₂CN | |
| 1375 | N | CF₃ | H | CH₂CH₂CN | |
| 1376 | CH | CF₃ | CH₃ | CH₂CH₃ | oil |

C. Biological Examples

Example 1

A Petri dish whose bottom is covered with filter paper and which contains about 5 ml of culture medium is prepared. Pieces of filter paper with about 30, 24-hour-old eggs of the American tobacco budworm (Heliothis virescens) are dipped into an aqueous solution of the formulated preparation to be examined for 5 seconds and subsequently placed in the Petri dish. A further 200 µl of the aqueous solution are spread over the culture medium. The Petri dish is closed and then kept at about 25° C. in a climatized chamber. After 6 days' storage, the effect of the preparation on the eggs and the larvae which may have hatched from these is determined. At a concentration of 300 ppm (based on the content of active compound), the preparations of Example Nos. 79 and 88 effect a mortality of 90–100%.

Example 2

Germinated broad bean seeds (Vicia faba) with radicles are transferred into brown glass bottles filled with tap water and subsequently populated with approximately 100 black bean aphids (Aphis fabae) belegt. Plants and aphids are then dipped for 5 seconds into an aqueous solution of the formulated preparation to be examined. After the solution has dripped off, plant and animals are kept in a climatized chamber (16 hours of light/day, 25° C., 40–60% relative atmospheric humidity. After 3 and 6 days' storage, the effect of the preparation on the aphids is determined. At a concentration of 300 ppm (based on the content of active compound), the preparations of Example Nos. 79, 78, 80, 81, 83, 84, 88, 133, 135, 136, 137, 138, 139, 1117, 1229, 1230, 1231, 1246 and 1254 effect a mortality of 90–100% among the aphids.

Example 3

The leaves of 12 rice plants having a stem length of 8 cm are dipped for 5 seconds into an aqueous solution of the formulated preparation to be examined. After the solution has dripped off, the rice plants treated in this manner are placed in a Petri dish and populated with approximately 20 larvae (L3 stage) of the rice leaf hopper species Nilaparvata lugens. The Petri dish is closed and stored in a climatized chamber (16 hours of light/day, 25° C., 40–60% relative atmospheric humidity). After 6 days' storage, the mortality among the leaf hopper larvae is determined. At a concentration of 300 ppm (based on the content of active compound), the preparations of Example Nos. 88, 139 and 927 effect a mortality of 90–100%.

Example 4

Germinated broad bean seeds (Vicia faba) with radicles are transferred into brown glass bottles filled with tap water. Four milliliters of an aqueous solution of the formulated preparation to be examined are pipetted into the brown glass bottle. The broad bean is subsequently heavily populated with approximately 100 black bean aphids (Aphis fabae). Plant and animals are then stored in a climatized chamber (16 hours of light/day, 25° C., 40–60% relative atmospheric humidity). After 3 and 6 days' storage, the root-systemic activity of the preparation on the aphids is determined. At a concentration of of 30 ppm (based on the content of active compound), the Preparations of Example Nos. 78, 79, 80, 81, 83, 84, 88, 133, 135, 136, 137, 138, 139, 187, 1117, 1229, 1230, 1231, 1246 and 1254 effect a mortality of 90–100% among the aphids by root-systemic action.

II. COMPOUNDS OF THE FORMULA (I')

A. Chemical Examples

Example 1

At room temperature, a solution of 4-tridiimidfluoromethylnicotinic acid (2.2 g) in 40 ml of THF was admixed with 1,1-carbonyldiimidazole (1.9 g), and the mixture was heated at 40° C. for 30 min. Furfurylsulfonylacetamidoxime (2.5 g) was then added, and the mixture was stirred at 40° C. for a further 5 h. The reaction mixture was then concentrated under reduced pressure and poured onto ice-water. The resulting precipitate was filtered off with suction and subsequently dried in a drying cabinet. This gave 4-trifluoromethylnicotinic acid furfurylsulfonylacetamidoxime ester in the form of a colorless solid (melting point 171° C.).

$^1$H-NMR (DMSO-d$^6$, 300 MHz): 4.09 (s, 2H), 4.86 (s, 2H), 6.55 (m, 1H), 6.63 (m, 1H), 7.08 (s, 2H), 7.75 (m, 1H), 7.94 (d, J=5 Hz, 1H), 9.07 (d, J=5 Hz, 1H), 9.30 (s, 1H).

Example 2

The amidoxime ester described above (4.0 g) was admixed with 80 ml of toluene and 60 ml of xylene and Amberlyst 15 (1.0 g). The reaction mixture was heated at 125° C. for 6 h. The mixture was subsequently filtered off with suction and the filtrate was concentrated under reduced pressure and purified by chromatography (silica gel, ethyl acetate/petroleum ether, 4:1). Subsequent trituration with n-heptane gave [5-(4'-trifluoromethylpyridin-3'-yl)-[1,2,4]-oxadiazole-3-methyl]furfurylsulfone as a pale yellow solid (melting point 99° C.).

$^1$H-NMR (CDCl$_3$, 300 MHz): 4.53 (s, 2H), 4.62 (s, 2H), 6.44 (m, 1H), 6.69 (m, 1H), 7.54 (m, 1H), 7.82 (d, J=5 Hz, 1H), 9.08 (d, J=5 Hz, 1H), 9.40 (s, 1H).

Example 3

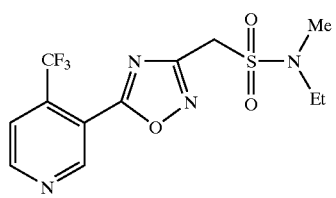

A mixture of 3-chloromethyl-5-(4-trifluoromethyl-3-pyridyl)-1,2,4-oxadiazole (1.0 g), sodium sulfite (0.9 g), water (18 ml) and methanol (18 ml) was stirred at 50° C. for 6 hours. The reaction mixture was then concentrated and the residue was taken up in methanol and filtered. The methanol solution was then concentrated and the residue was triturated with diethyl ether. This gave

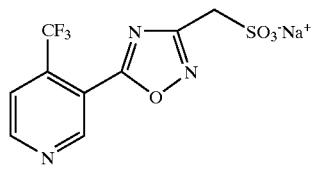

as a slightly yellowish solid (m.p.=214° C.).

$^1$H-NMR (DMSO-d$^6$, 300 MHz): 4.02 (s, 2H), 8.09 (d, J=5H, 1H), 9.15 (d, J=5 Hz, 1H), 9.33 (s, 1H).

The sodium sulfonate described above (0.95 g) was suspended in phosphorus oxychloride (30 ml), and the mixture was heated at reflux temperature for 5 hours. The excess phosphorus oxychloride was then distilled off and the sulfonyl chloride which remained was taken up in dichloromethane (10 ml). This suspension was admixed with ethylmethylamine (150 ml), and stirring at room temperature was continued for one hour.

The mixture was subsequently washed with water, 5% strength aqueous potassium hydrogen-sulfate solution and saturated sodium bicarbonate solution. The crude product which was obtained after drying (MgSO$_4$) and concentration of the dichloromethane phase was purified chromatographically. This gave the desired sulfonamide as a colorless oil.

$^1$H-NMR (CDCl$_3$, 300 MHz): 1.23 (6, J=7 Hz, 3H), 2.92 (s, 3H), 3.25 (Q, J=7Hz, 2H), 4.54 (s, 2H), 7.90 (d, J=5 Hz, 1H), 9.06 (d, J=5 Hz, 1H), 9.35 (s, 1H).

The sulfonamides listed in Table 1 are prepared in an analogous manner.

Example 4

3-[(2-Hydroxyethyl)thiomethyl]-5-(4-trifluoromethyl-3-pyridyl)-1,2,4-oxadiazole

A solution of sodium methoxide (0.31 ml, 30% in methanol) was added to a solution of 3-chloromethyl-5-(4-trifluoromethyl-3-pyridyl)-1,2,4-oxadiazole (0.5 g) and 2-mercaptoethanol (0.13 g) in methanol (5 ml), and the mixture was stirred at room temperature for 5 hours.

Water was then added and the mixture was extracted with ethyl acetate. The organic phase was washed with water, dried (MgSO$_4$), filtered and concentrated. Chromatographic purification was carried out over silica gel using heptane/ethyl acetate. The crude product gave the desired compound as a slightly brown oil.

$^1$H-NMR (CDCl$_3$, 300 MHz): 2.88 (t, J=7 Hz, 2H), 3.04 (b, s, 1H), 3.82 (t, J=7 Hz, 2H), 3.94 (s, 2H), 7.80 (d, J=5 Hz, 1H), 9.04 (d, J=5 Hz, 1H), 9.35 (s, 1H).

Example 5

3-Ethoxymethyl-5-(4-trifluoromethyl-3-pyridyl)-1,2,4-oxadiazole

3-Iodomethyl-5-(4-trifluoromethyl-3-pyridyl)-1,2,4-oxadiazole (0.5 g) was dissolved in a freshly prepared solution of sodium ethoxide (30 mg of sodium in 7 ml of ethanol), and the mixture was stirred at room temperature for 6 hours.

The reaction mixture was then concentrated, the residue was taken up in ethyl acetate, washed with water, dried (MgSO$_4$), filtered and concentrated.

Chromatographic purification of the crude product gave the desired ether as a yellowish oil.

$^1$H-NMR (CDCl$_3$, 300 MHz): 1.31 (t, J=7 Hz, 3H), 3.72 (t, J=7 Hz, 2H), 4.76 (s, 2H), 7.70 (d, J=5 Hz, 1H), 9.03 (d, J=5 Hz, 1H), 9.33 (s, 1H).

The ethers listed in Table 1 are prepared in an analogous manner.

Example 6

Ethyl [(4'-(Trifluoromethyl)pyridin-3'-yl)-5-[1,2,4]-oxadiazole-3-methyl]carbonate 3-Hydroxymethyl-5-(4'-(trifluoromethyl)pyridin-3'-yl)-[1,2,4]-oxadiazole (1.0 g) was initially charged in acetonitrile (10 ml), and the mixture was admixed with triethylamine (0.5 g). Ethyl chloroformate (0.5 g) was added, and the mixture was then stirred at room temperature for 6 h. The reaction mixture was then mixed with ethyl acetate (5 ml), washed with 2N sodium carbonate solution and dried over MgSO$_4$. The crude product which was obtained after the drying agent had been filtered off and the solution had been concentrated under reduced pressure was purified by column chromatography (silica gel, n-heptane/ethyl acetate, 1:1). This gave the target product as an oil.

$^1$H-NMR (CDCl$_3$, 300 MHz): 1.38 (t, J=7 Hz, 3H), 4.31 (q, J=7 Hz, 2H), 5.43 (s, 2H), 7.80 (d, J=5 Hz, 1H), 9.04 (d, J=5 Hz, 1H), 9.37 (s, 1H).

TABLE 1

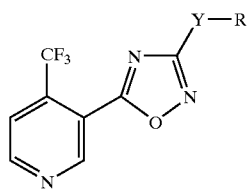 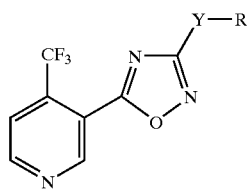

| Ex. No. | Y | R | R' | m.p. [° C.] |
|---|---|---|---|---|
| 1 | O | n-Pr | | |
| 2 | O | i-Pr | | |
| 3 | O | n-Bu | | |
| 4 | O | i-Bu | | oil |
| 5 | O | allyl | | |
| 6 | O | CH$_2$C≡CH | | |
| 7 | O | CH=CH$_2$ | | |
| 8 | O | CH$_2$CH$_2$F | | |
| 9 | O | CF$_3$ | | |
| 10 | O | CH$_2$CF$_3$ | | |
| 11 | O | CH$_2$CN | | |
| 12 | O | cyclopropyl | | |
| 13 | O | cyclopropylmethyl | | |
| 14 | O | CH$_2$CO$_2$Me | | |
| 15 | O | CH$_2$CH$_2$NMe$_2$ | | |
| 16 | O | CH$_2$-(N-morpholinyl) | | |
| 17 | O | 2-chloropyridin-5-yl-methyl | | |
| 18 | O | 2-furanyl | | |
| 19 | O | 2-pyrimidinyl | | |
| 20 | O | 2-oxazolyl | | |
| 21 | O | 5-[1,2,4]-oxadiazolyl | | |
| 22 | O | tetrazolyl | | |
| 23 | S | H | | |
| 24 | S | Me | | |
| 25 | S | Et | | |
| 26 | S | n-Pr | | |
| 27 | S | i-Pr | | |
| 28 | S | n-Bu | | |
| 29 | S | i-Bu | | |
| 30 | S | allyl | | |
| 31 | S | CH$_2$C≡CH | | |
| 32 | S | CH=CH$_2$ | | |
| 33 | S | CH$_2$CH$_2$F | | |
| 34 | S | CF$_3$ | | |
| 35 | S | CH$_2$CF$_3$ | | |
| 36 | S | CH$_2$CN | | |
| 37 | S | cyclopropyl | | |
| 38 | S | cyclopropylmethyl | | |
| 39 | S | CH$_2$CO$_2$Me | | |
| 40 | S | CH$_2$CH$_2$NMe$_2$ | | |
| 41 | S | CH$_2$-(N-morpholinyl) | | |
| 42 | S | 2-chloropyridin-5-yl-methyl | | |
| 43 | S | 2-furanyl | | |
| 44 | S | 2-pyrimidinyl | | |
| 45 | S | 2-oxazolyl | | |
| 46 | S | 5-[1,2,4]-oxadiazolyl | | |
| 47 | S | tetrazolyl | | |
| 48 | S(O) | Me | | |
| 49 | S(O) | Et | | |
| 50 | S(O) | n-Pr | | |
| 51 | S(O) | i-Pr | | |
| 52 | S(O) | n-Bu | | |
| 53 | S(O) | i-Bu | | |
| 54 | S(O) | allyl | | |
| 55 | S(O) | CH$_2$C≡CH | | |
| 56 | S(O) | CH=CH$_2$ | | |
| 57 | S(O) | CH$_2$CH$_2$F | | |
| 58 | S(O) | CF$_3$ | | |
| 59 | S(O) | CH$_2$CF$_3$ | | |
| 60 | S(O) | CH$_2$CN | | |
| 61 | S(O) | cyclopropyl | | |
| 62 | S(O) | cyclopropylmethyl | | |
| 63 | S(O) | CH$_2$CO$_2$Me | | |
| 64 | S(O) | CH$_2$CH$_2$NMe$_2$ | | |
| 65 | S(O) | CH$_2$-(N-morpholinyl) | | |
| 66 | S(O) | 2-chloropyridin-5-yl-methyl | | |
| 67 | S(O) | 2-furanyl | | |
| 68 | S(O) | 2-pyrimidinyl | | |
| 69 | S(O) | 2-oxazolyl | | |
| 70 | S(O) | 5-[1,2,4]-oxadiazolyl | | |
| 71 | S(O) | tetrazolyl | | |
| 72 | S(O)$_2$ | Me | | |
| 73 | S(O)$_2$ | Et | | |
| 74 | S(O)$_2$ | n-Pr | | |
| 75 | S(O)$_2$ | i-Pr | | |
| 76 | S(O)$_2$ | n-Bu | | |
| 77 | S(O)$_2$ | i-Bu | | |
| 78 | S(O)$_2$ | allyl | | |
| 79 | S(O)$_2$ | CH$_2$C≡CH | | |
| 80 | S(O)$_2$ | CH=CH$_2$ | | |
| 81 | S(O)$_2$ | CH$_2$CH$_2$F | | |
| 82 | S(O)$_2$ | CF$_3$ | | |
| 83 | S(O)$_2$ | CH$_2$CF$_3$ | | |
| 84 | S(O)$_2$ | CH$_2$CN | | |
| 85 | S(O)$_2$ | cyclopropyl | | |
| 86 | S(O)$_2$ | cyclopropylmethyl | | |
| 87 | S(O)$_2$ | CH$_2$CO$_2$Me | | |
| 88 | S(O)$_2$ | CH$_2$CH$_2$NMe$_2$ | | |
| 89 | S(O)$_2$ | CH$_2$-(N-morpholinyl) | | |
| 90 | S(O)$_2$ | 2-chloropyridin-5-yl-methyl | | |
| 91 | S(O)$_2$ | 2-furanyl | | |
| 92 | S(O)$_2$ | 2-pyrimidinyl | | |
| 93 | S(O)$_2$ | 2-oxazolyl | | |
| 94 | S(O)$_2$ | 5-[1,2,4]-oxadiazolyl | | |
| 94a | S(O)$_2$ | tetrazolyl | | |
| 95 | OC(O) | H | | |
| 96 | OC(O) | Me | | |
| 97 | OC(O) | Et | | |
| 98 | OC(O) | n-Pr | | |
| 99 | OC(O) | i-Pr | | |
| 100 | OC(O) | n-Bu | | |
| 101 | OC(O) | i-Bu | | |
| 102 | OC(O) | allyl | | |
| 103 | OC(O) | CH$_2$C≡CH | | |
| 104 | OC(O) | CH=CH$_2$ | | |
| 105 | OC(O) | CH$_2$CH$_2$F | | |
| 106 | OC(O) | CF$_3$ | | |
| 107 | OC(O) | CH$_2$CF$_3$ | | |
| 108 | OC(O) | CH$_2$CN | | |
| 109 | OC(O) | cyclopropyl | | |
| 110 | OC(O) | cyclopropylmethyl | | |
| 111 | OC(O) | CH$_2$CO$_2$Me | | |
| 112 | OC(O) | CH$_2$CH$_2$NMe$_2$ | | |
| 113 | OC(O) | CH$_2$-(N-morpholinyl) | | |
| 114 | OC(O) | 2-chloropyridin-5-yl-methyl | | |
| 115 | OC(O) | 2-furanyl | | |
| 116 | OC(O) | 2-pyrimidinyl | | |
| 117 | OC(O) | 2-oxazolyl | | |
| 118 | OC(O) | 5-[1,2,4]-oxadiazolyl | | |
| 119 | OC(O) | tetrazolyl | | |
| 120 | OC(O)O | Me | | |
| 121 | OC(O)O | Et | | |
| 122 | OC(O)O | n-Pr | | |
| 123 | OC(O)O | i-Pr | | |
| 124 | OC(O)O | n-Bu | | |
| 125 | OC(O)O | i-Bu | | |
| 126 | OC(O)O | allyl | | |
| 127 | OC(O)O | CH$_2$C≡CH | | |
| 128 | OC(O)O | CH=CH$_2$ | | |
| 129 | OC(O)O | CH$_2$CH$_2$F | | |
| 130 | OC(O)O | CF$_3$ | | |
| 131 | OC(O)O | CH$_2$CF$_3$ | | |

TABLE 1-continued

| Ex. No. | Y | R | R' | m.p. [° C.] |
|---|---|---|---|---|
| 132 | OC(O)O | CH₂CN | | |
| 133 | OC(O)O | cyclopropyl | | |
| 134 | OC(O)O | cyclopropylmethyl | | |
| 135 | OC(O)O | CH₂CO₂Me | | |
| 136 | OC(O)O | CH₂CH₂NMe₂ | | |
| 137 | OC(O)O | CH₂-(N-morpholinyl) | | |
| 138 | OC(O)O | 2-chloropyridin-5-yl-methyl | | |
| 139 | OC(O)O | 2-furanyl | | |
| 140 | OC(O)O | 2-pyrimidinyl | | |
| 141 | OC(O)O | 2-oxazolyl | | |
| 142 | OC(O)O | 5-[1,2,4]-oxadiazolyl | | |
| 143 | OC(O)O | tetrazolyl | | |
| 144 | OC(O)O | CH₂CH₂OMe | | |
| 145 | OC(O)NR' | H | H | |
| 146 | OC(O)NR' | Me | H | |
| 147 | OC(O)NR' | Et | H | |
| 148 | OC(O)NR' | n-Pr | H | |
| 149 | OC(O)NR' | i-Pr | H | |
| 150 | OC(O)NR' | n-Bu | H | |
| 151 | OC(O)NR' | i-Bu | H | |
| 152 | OC(O)NR' | allyl | H | |
| 153 | OC(O)NR' | CH₂C≡CH | H | |
| 154 | OC(O)NR' | CH=CH₂ | H | |
| 155 | OC(O)NR' | CH₂CH₂F | H | |
| 156 | OC(O)NR' | CF₃ | H | |
| 157 | OC(O)NR" | CH₂CF₃ | H | |
| 158 | OC(O)NR' | CH₂CN | H | |
| 159 | OC(O)NR' | cyclopropyl | H | |
| 160 | OC(O)NR' | cyclopropylmethyl | H | |
| 161 | OC(O)NR' | CH₂CO₂Me | H | |
| 162 | OC(O)NR' | CH₂CH₂NMe₂ | H | |
| 163 | OC(O)NR' | CH₂-(N-morpholinyl) | H | |
| 164 | OC(O)NR' | 2-chloropyridin-5-yl-methyl | H | |
| 165 | OC(O)NR' | 2-furanyl | H | |
| 166 | OC(O)NR' | 2-pyrimidinyl | H | |
| 167 | OC(O)NR' | 2-oxazolyl | H | |
| 168 | OC(O)NR' | 5-[1,2,4]-oxadiazolyl | H | |
| 169 | OC(O)NR' | tetrazolyl | H | |
| 170 | OC(O)NR' | H | Me | |
| 171 | OC(O)NR' | Me | Me | |
| 172 | OC(O)NR' | Et | Me | |
| 173 | OC(O)NR' | n-Pr | Me | |
| 174 | OC(O)NR' | i-Pr | Me | |
| 175 | OC(O)NR' | n-Bu | Me | |
| 176 | OC(O)NR' | i-Bu | Me | |
| 177 | OC(O)NR' | allyl | Me | |
| 178 | OC(O)NR' | CH₂C≡CH | Me | |
| 179 | OC(O)NR' | CH=CH₂ | Me | |
| 180 | OC(O)NR' | CH₂CH₂F | Me | |
| 181 | OC(O)NR' | CF₃ | Me | |
| 182 | OC(O)NR" | CH₂CF₃ | Me | |
| 183 | OC(O)NR' | CH₂CN | Me | |
| 184 | OC(O)NR' | cyclopropyl | Me | |
| 185 | OC(O)NR' | cyclopropylmethyl | Me | |
| 186 | OC(O)NR' | CH₂CO₂Me | Me | |
| 187 | OC(O)NR' | CH₂CH₂NMe₂ | Me | |
| 188 | OC(O)NR' | CH₂-(N-morpholinyl) | Me | |
| 189 | OC(O)NR' | 2-chloropyridin-5-yl-methyl | Me | |
| 190 | OC(O)NR' | 2-furanyl | Me | |
| 191 | OC(O)NR' | 2-pyrimidinyl | Me | |
| 192 | OC(O)NR' | 2-oxazolyl | Me | |
| 193 | OC(O)NR' | 5-[1,2,4]-oxadiazolyl | Me | |
| 194 | OC(O)NR' | tetrazolyl | Me | |
| 195 | OC(O)NR' | H | Et | |
| 196 | OC(O)NR' | Me | Et | |
| 197 | OC(O)NR' | Et | Et | |
| 198 | OC(O)NR' | n-Pr | Et | |
| 199 | OC(O)NR' | i-Pr | Et | |
| 200 | OC(O)NR' | n-Bu | Et | |
| 201 | OC(O)NR' | i-Bu | Et | |
| 202 | OC(O)NR' | allyl | Et | |
| 203 | OC(O)NR' | CH₂C≡CH | Et | |
| 204 | OC(O)NR' | CH=CH₂ | Et | |
| 205 | OC(O)NR' | CH₂CH₂F | Et | |
| 206 | OC(O)NR' | CF₃ | Et | |
| 207 | OC(O)NR" | CH₂CF₃ | Et | |
| 208 | OC(O)NR' | CH₂CN | Et | |
| 209 | OC(O)NR' | cyclopropyl | Et | |
| 210 | OC(O)NR' | cyclopropylmethyl | Et | |
| 211 | OC(O)NR' | CH₂CO₂Me | Et | |
| 212 | OC(O)NR' | CH₂CH₂NMe₂ | Et | |
| 213 | OC(O)NR' | CH₂-(N-morpholinyl) | Et | |
| 214 | OC(O)NR' | 2-chloropyridin-5-yl-methyl | Et | |
| 215 | OC(O)NR' | 2-furanyl | Et | |
| 216 | OC(O)NR' | 2-pyrimidinyl | Et | |
| 217 | OC(O)NR' | 2-oxazolyl | Et | |
| 218 | OC(O)NR' | 5-[1,2,4]-oxadiazolyl | Et | |
| 219 | OC(O)NR' | tetrazolyl | Et | |
| 220 | OC(O)C(O)O | H | | |
| 221 | OC(O)C(O)O | Me | | |
| 222 | OC(O)C(O)O | Et | | |
| 223 | OC(O)C(O)O | n-Pr | | |
| 224 | OC(O)C(O)O | i-Pr | | |
| 225 | OC(O)C(O)O | n-Bu | | |
| 226 | OC(O)C(O)O | i-Bu | | |
| 227 | OC(O)C(O)O | allyl | | |
| 228 | OC(O)C(O)O | CH₂C≡CH | | |
| 229 | OC(O)C(O)O | CH=CH₂ | | |
| 230 | OC(O)C(O)O | CH₂CH₂F | | |
| 231 | OC(O)C(O)O | CF₃ | | |
| 232 | OC(O)C(O)O | CH₂CF₃ | | |
| 234 | OC(O)C(O)O | CH₂CN | | |
| 235 | OC(O)C(O)O | cyclopropyl | | |
| 236 | OC(O)C(O)O | cyclopropylmethyl | | |
| 237 | OC(O)C(O)O | CH₂CO₂Me | | |
| 238 | OC(O)C(O)O | CH₂CH₂NMe₂ | | |
| 239 | OC(O)C(O)O | CH₂-(N-morpholinyl) | | |
| 240 | OC(O)C(O)O | 2-chloropyridin-5-yl-methyl | | |
| 241 | OC(O)C(O)O | 2-furanyl | | |
| 242 | OC(O)C(O)O | 2-pyrimidinyl | | |
| 243 | OC(O)C(O)O | 2-oxazolyl | | |
| 244 | OC(O)C(O)O | 5-[1,2,4]-oxadiazolyl | | |
| 245 | OC(O)C(O)O | tetrazolyl | | |
| 246 | S(O)₂NR' | H | H | |
| 247 | S(O)₂NR' | Me | H | |
| 248 | S(O)₂NR' | Et | H | |
| 249 | S(O)₂NR' | n-Pr | H | |
| 250 | S(O)₂NR' | i-Pr | H | |
| 251 | S(O)₂NR' | n-Bu | H | |
| 252 | S(O)₂NR' | i-Bu | H | |
| 253 | S(O)₂NR' | allyl | H | |
| 254 | S(O)₂NR' | CH₂C≡CH | H | |
| 255 | S(O)₂NR' | CH=CH₂ | H | |
| 256 | S(O)₂NR' | CH₂CH₂F | H | |
| 257 | S(O)₂NR' | CF₃ | H | |
| 258 | S(O)₂NR' | CH₂CF₃ | H | |
| 259 | S(O)₂NR' | CH₂CN | H | |
| 260 | S(O)₂NR' | cyclopropyl | H | |
| 261 | S(O)₂NR' | cyclopropylmethyl | H | |
| 262 | S(O)₂NR' | CH₂CO₂Me | H | |
| 263 | S(O)₂NR' | CH₂CH₂NMe₂ | H | |
| 264 | S(O)₂NR' | CH₂-(N-morpholinyl) | H | |

TABLE 1-continued

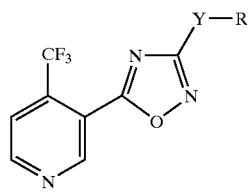

| Ex. No. | Y | R | R' | m.p. [° C.] |
|---|---|---|---|---|
| 265 | S(O)₂NR' | 2-chloropyridin-5-yl-methyl | H | |
| 266 | S(O)₂NR' | 2-furanyl | H | |
| 267 | S(O)₂NR' | 2-pyrimidinyl | H | |
| 268 | S(O)₂NR' | 2-oxazolyl | H | |
| 269 | S(O)₂NR' | 5-[1,2,4]-oxadiazolyl | H | |
| 270 | S(O)₂NR' | tetrazolyl | H | |
| 271 | S(O)₂NR' | H | Me | |
| 272 | S(O)₂NR' | Me | Me | |
| 273 | S(O)₂NR' | Et | Me | |
| 274 | S(O)₂NR' | n-Pr | Me | |
| 275 | S(O)₂NR' | i-Pr | Me | |
| 276 | S(O)₂NR' | n-Bu | Me | |
| 277 | S(O)₂NR' | i-Bu | Me | |
| 278 | S(O)₂NR' | allyl | Me | |
| 279 | S(O)₂NR' | CH₂C≡CH | Me | |
| 280 | S(O)₂NR' | CH=CH₂ | Me | |
| 281 | S(O)₂NR' | CH₂CH₂F | Me | |
| 282 | S(O)₂NR' | CF₃ | Me | |
| 283 | S(O)₂NR' | CH₂CF₃ | Me | |
| 284 | S(O)₂NR' | CH₂CN | Me | |
| 285 | S(O)₂NR' | cyclopropyl | Me | |
| 286 | S(O)₂NR' | cyclopropylmethyl | Me | |
| 287 | S(O)₂NR' | CH₂CO₂Me | Me | |
| 288 | S(O)₂NR' | CH₂CH₂NMe₂ | Me | |
| 289 | S(O)₂NR' | CH₂-(N-morpholinyl) | Me | |
| 289 | S(O)₂NR' | 2-chloropyridin-5-yl-methyl | Me | |
| 290 | S(O)₂NR' | 2-furanyl | Me | |
| 291 | S(O)₂NR' | 2-pyrimidinyl | Me | |
| 292 | S(O)₂NR' | 2-oxazolyl | Me | |
| 293 | S(O)₂NR' | 5-[1,2,4]-oxadiazolyl | Me | |
| 294 | S(O)₂NR' | tetrazolyl | Me | |
| 295 | S(O)₂NR' | H | Et | |
| 296 | S(O)₂NR' | Me | Et | |
| 297 | S(O)₂NR' | Et | Et | |
| 298 | S(O)₂NR' | n-Pr | Et | |
| 299 | S(O)₂NR' | i-Pr | Et | |
| 300 | S(O)₂NR' | n-Bu | Et | |
| 301 | S(O)₂NR' | i-Bu | Et | |
| 302 | S(O)₂NR' | allyl | Et | |
| 303 | S(O)₂NR' | CH₂C≡CH | Et | |
| 304 | S(O)₂NR' | CH=CH₂ | Et | |
| 305 | S(O)₂NR' | CH₂CH₂F | Et | |
| 306 | S(O)₂NR' | CF₃ | Et | |
| 307 | S(O)₂NR' | CH₂CF₃ | Et | |
| 308 | S(O)₂NR' | CH₂CN | Et | |
| 309 | S(O)₂NR' | cyclopropyl | Et | |
| 310 | S(O)₂NR' | cyclopropylmethyl | Et | |
| 311 | S(O)₂NR' | CH₂CO₂Me | Et | |
| 312 | S(O)₂NR' | CH₂CH₂NMe₂ | Et | |
| 313 | S(O)₂NR' | CH₂-(N-morpholinyl) | Et | |
| 314 | S(O)₂NR' | 2-chloropyridin-5-yl-methyl | Et | |
| 315 | S(O)₂NR' | 2-furanyl | Et | |
| 316 | S(O)₂NR' | 2-pyrimidinyl | Et | |
| 317 | S(O)₂NR' | 2-oxazolyl | Et | |
| 318 | S(O)₂NR' | 5-[1,2,4]-oxadiazolyl | Et | |
| 319 | S(O)₂NR' | tetrazolyl | Et | |

TABLE 2

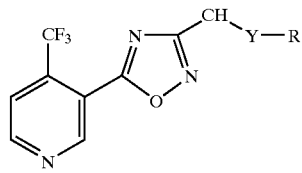

| Ex. No. | Y | R | R' | m.p. [° C.] |
|---|---|---|---|---|
| 1 | O | H | | 128 |
| 2 | O | Et | | oil |
| 3 | O | n-Pr | | |
| 4 | O | i-Pr | | oil |
| 5 | O | n-Bu | | oil |
| 6 | O | i-Bu | | oil |
| 7 | O | allyl | | oil |
| 8 | O | CH₂C≡CH | | oil |
| 9 | O | CH=CH₂ | | |
| 10 | O | CH₂CH₂F | | |
| 11 | O | CF₃ | | |
| 12 | O | CH₂CF₃ | | oil |
| 13 | O | CH₂CN | | |
| 14 | O | cyclopropyl | | |
| 15 | O | cyclopropylmethyl | | oil |
| 16 | O | CH₂CO₂Me | | |
| 17 | O | CH₂CH₂NMe₂ | | |
| 18 | O | CH₂-(N-morpholinyl) | | oil |
| 19 | O | 2-chloropyridin-5-yl-methyl | | |
| 20 | O | 2-furanyl | | |
| 21 | O | 2-pyrimidinyl | | |
| 22 | O | 2-oxazolyl | | |
| 23 | O | 5-[1,2,4]-oxindazolyl | | |
| 24 | O | tetrazolyl | | |
| 25 | O | 1,3-oxindol-2-yl | | oil |
| 26 | O | CH₂CH₂OMe | | oil |
| 27 | O | CH₂CH₂OCH₂CH₂OMe | | oil |
| 28 | O | CH₂CH₂SCH₂CH₃ | | oil |
| 29 | S | H | | |
| 30 | S | Et | | oil |
| 31 | S | n-Pr | | oil |
| 32 | S | i-Pr | | |
| 33 | S | n-Bu | | |
| 34 | S | i-Bu | | oil |
| 35 | S | allyl | | oil |
| 36 | S | CH₂C≡CH | | |
| 37 | S | CH=CH₂ | | |
| 38 | S | CH₂CH₂F | | |
| 39 | S | CF₃ | | oil |
| 40 | S | CH₂CF₃ | | oil |
| 41 | S | CH₂CN | | |
| 42 | S | cyclopropyl | | |
| 43 | S | cyclopropylmethyl | | |
| 44 | S | CH₂CO₂Me | | oil |
| 45 | S | CH₂CO₂Et | | oil |
| 46 | S | CH₂CH₂CO₂Me | | oil |
| 47 | S | CH₂CH₂NMe₂ | | |
| 48 | S | CH₂-(N-morpholinyl) | | |
| 49 | S | 2-chloropyridin-5-yl-methyl | | |
| 50 | S | 2-furanyl | | |
| 51 | S | 2-pyridinyl | | oil |
| 52 | S | 2-pyrimidinyl | | crystal-line |
| 53 | S | 2-oxazolyl | | |
| 54 | S | 5-[1,2,4]-oxadiazolyl | | |
| 55 | S | tetrazolyl | | |
| 56 | S | CH₂CH₂OH | | oil |
| 57 | S | Ac | | oil |
| 58 | S | | | |

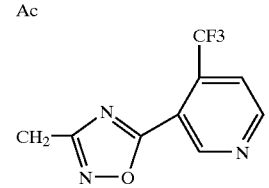

TABLE 2-continued

[Structure: 4-(trifluoromethyl)pyridin-3-yl connected to 1,2,4-oxadiazole with CH₂—Y—R substituent]

| Ex. No. | Y | R | R' | m.p. [°C.] |
|---|---|---|---|---|
| 59 | NR'(CO) | (phenyl)-C(O)- | | 136 |
| 60 | NR'C(O)O | CMe₃ | H | Öl |
| 61 | NR' | CH₂-[3-(4-trifluoromethylpyridin-3-yl)-1,2,4-oxadiazol-5-yl] | CO₂allyl | Öl |
| 62 | NR'SO₂ | C(H)Cl₂ | Me | Öl |
| 63 | NR'SO₂ | Bu | Me | Öl |
| 64 | NR'SO₂ | Pr | Me | Öl |
| 65 | S | N-Me-imidazol-2-yl | | solid |
| 66 | S | [1,2,4]-triazol-3-yl | | solid |
| 67 | S | 4-Me-[1,2,4]-triazol-3-yl | | crystalline |
| 68 | S | 4-Me-tetrazol-5-yl | | solid |
| 69 | S | 2-thiazolin-2-yl | | crystalline |
| 70 | S | cyclohexyl | | wax |
| 71 | S(O) | Et | | |
| 72 | S(O) | n-Pr | | |
| 73 | S(O) | i-Pr | | oil |
| 74 | S(O) | n-Bu | | |
| 75 | S(O) | i-Bu | | |
| 76 | S(O) | allyl | | |
| 77 | S(O) | CH₂C≡CH | | |
| 78 | S(O) | CH=CH₂ | | |
| 79 | S(O) | CH₂CH₂F | | |
| 80 | S(O) | CF₃ | | solid |
| 81 | S(O) | CH₂CF₃ | | |
| | | CH₂CN | | 129 |
| 82 | S(O) | cyclopropyl | | |
| 83 | S(O) | cyclopropylmethyl | | |
| 84 | S(O) | CH₂CO₂Me | | |
| 85 | S(O) | CH₂CH₂NMe₂ | | |
| 86 | S(O) | CH₂-(N-morpholinyl) | | |
| 87 | S(O) | 2-chloropyridin-5-yl-methyl | | |
| 88 | S(O) | 2-furanyl | | |
| 89 | S(O) | 2-pyrimidinyl | | |
| 90 | S(O) | 2-oxazolyl | | |
| 91 | S(O) | 5-[1,2,4]-oxadiazolyl | | |
| 92 | S(O) | tetrazolyl | | |
| 93 | S(O) | | | |
| 94 | S(O)₂ | Me | | 92 |
| 95 | S(O)₂ | Et | | |
| 96 | S(O)₂ | n-Pr | | 73 |
| 97 | S(O)₂ | i-Pr | | 109 |
| 98 | S(O)₂ | n-Bu | | |
| 99 | S(O)₂ | n-Hex | | 87 |
| 100 | S(O)₂ | i-Bu | | |
| 101 | S(O)₂ | allyl | | |
| 102 | S(O)₂ | CH₂C≡CH | | |
| 103 | S(O)₂ | CH=CH₂ | | |
| 104 | S(O)₂ | CH₂CH₂F | | |
| 105 | S(O)₂ | CF₃ | | |
| 106 | S(O)₂ | CH₂CF₃ | | crystalline |
| 107 | S(O)₂ | CH₂CN | | |
| 108 | S(O)₂ | cyclopropyl | | |
| 109 | S(O)₂ | cyclopropylmethyl | | |
| 110 | S(O)₂ | CH₂CO₂Me | | |
| 111 | S(O)₂ | CH₂CH₂NMe₂ | | |
| 112 | S(O)₂ | CH₂-(N-morpholinyl) | | |
| 113 | S(O)₂ | 2-chloropyridin-5-yl-methyl | | |
| 114 | S(O)₂ | 2-furanyl | | |
| 115 | S(O)₂ | 2-furfuryl | | 99 |
| 116 | S(O)₂ | 2-thienyl | | 100 |
| 117 | S(O)₂ | 2-pyrimidinyl | | |
| 118 | S(O)₂ | 2-oxazolyl | | |
| 119 | S(O)₂ | 5-[1,2,4]-oxadiazolyl | | |
| 120 | S(O)₂ | tetrazolyl | | |
| 121 | S(O)₂ | ONa | | 214 |
| 122 | S(O)₂ | p-F-benzyl | | 156 |
| 123 | OC(O) | H | | |
| 124 | OC(O) | Me | | |
| 125 | OC(O) | Et | | oil |
| 126 | OC(O) | n-Pr | | |
| 127 | OC(O) | i-Pr | | |
| 128 | OC(O) | n-Bu | | |
| 129 | OC(O) | i-Bu | | oil |
| 130 | OC(O) | t-Bu | | oil |
| 131 | OC(O) | allyl | | |
| 132 | OC(O) | CH₂C≡CH | | |
| 133 | OC(O) | CH=CH₂ | | oil |
| 134 | OC(O) | CH₂CH₂F | | |
| 135 | OC(O) | CF₃ | | |
| 136 | OC(O) | CH₂CF₃ | | |
| 137 | OC(O) | CH₂CH₂SiMe₃ | | oil |
| 138 | OC(O) | CH₂CN | | oil |
| 139 | OC(O) | cyclopropyl | | |
| 140 | OC(O) | cyclopropylmethyl | | |
| 141 | OC(O) | CH₂CO₂Me | | oil |
| 142 | OC(O) | CH₂CH₂NMe₂ | | |
| 143 | OC(O) | CH₂OMe | | |
| 144 | OC(O) | CH₂-(N-morpholinyl) | | |
| 145 | OC(O) | 2-chloropyridin-5-yl-methyl | | |
| 146 | OC(O) | 2-furanyl | | |
| 147 | OC(O) | 2-pyrimidinyl | | |
| 148 | OC(O) | 2-oxazolyl | | |
| 149 | OC(O) | 5-[1,2,4]-oxadiazolyl | | |
| 150 | OC(O) | tetrazolyl | | |
| 151 | OC(O) | 2-oxopyrrolidin-5-yl | | oil |
| 152 | OC(O)O | H | | |
| 153 | OC(O)O | Me | | oil |
| 154 | OC(O)O | Et | | oil |
| 155 | OC(O)O | n-Pr | | oil |
| 156 | OC(O)O | i-Pr | | |
| 157 | OC(O)O | n-Bu | | |
| 158 | OC(O)O | i-Bu | | |
| 159 | OC(O)O | allyl | | |
| 160 | OC(O)O | CH₂C≡CH | | |
| 161 | OC(O)O | CH=CH₂ | | |
| 162 | OC(O)O | CH₂CH₂F | | |
| 163 | OC(O)O | CF₃ | | |
| 164 | OC(O)O | CH₂CF₃ | | |
| 165 | OC(O)O | CH₂CN | | |
| 166 | OC(O)O | cyclopropyl | | |
| 167 | OC(O)O | cyclopropylmethyl | | |
| 168 | OC(O)O | CH₂CO₂Me | | |
| 169 | OC(O)O | CH₂CH₂NMe₂ | | |
| 170 | OC(O)O | CH₂-(N-morpholinyl) | | |
| 171 | OC(O)O | 2-chloropyridin-5-yl-methyl | | |
| 172 | OC(O)O | 2-furanyl | | |
| 173 | OC(O)O | 2-pyrimidinyl | | |

TABLE 2-continued

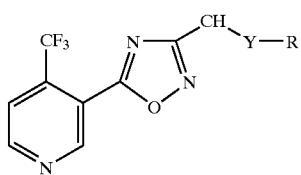

| Ex. No. | Y | R | R' | m.p. [° C.] |
|---|---|---|---|---|
| 174 | OC(O)O | 2-oxazolyl | | |
| 175 | OC(O)O | 5-[1,2,4]-oxadiazolyl | | |
| 176 | OC(O)O | tetrazolyl | | |
| 177 | OC(O)NR' | H | H | |
| 178 | OC(O)NR' | Me | H | |
| 179 | OC(O)NR' | Et | H | |
| 180 | OC(O)NR' | n-Pr | H | |
| 181 | OC(O)NR' | i-Pr | H | |
| 182 | OC(O)NR' | n-Bu | H | |
| 183 | OC(O)NR' | i-Bu | H | |
| 184 | OC(O)NR' | allyl | H | |
| 185 | OC(O)NR' | CH$_2$C≡CH | H | |
| 186 | OC(O)NR' | CH=CH$_2$ | H | |
| 187 | OC(O)NR' | CH$_2$CH$_2$F | H | |
| 188 | OC(O)NR' | CF$_3$ | H | |
| 189 | OC(O)NR' | CH$_2$CF$_3$ | H | |
| 190 | OC(O)NR' | CH$_2$CN | H | |
| 191 | OC(O)NR' | cyclopropyl | H | |
| 192 | OC(O)NR' | cyclopropylmethyl | H | |
| 193 | OC(O)NR' | CH$_2$CO$_2$Me | H | |
| 194 | OC(O)NR' | CH$_2$CH$_2$NMe$_2$ | H | |
| 195 | OC(O)NR' | CH$_2$-(N-morpholinyl) | H | |
| 196 | OC(O)NR' | 2-chloropyridin-5-yl-methyl | H | |
| 197 | OC(O)NR' | 2-furanyl | H | |
| 198 | OC(O)NR' | 2-pyrimidinyl | H | |
| 199 | OC(O)NR' | 2-oxazolyl | H | |
| 200 | OC(O)NR' | 5-[1,2,4]-oxadiazolyl | H | |
| 201 | OC(O)NR' | tetrazolyl | H | |
| 202 | OC(O)NR' | H | Me | |
| 203 | OC(O)NR' | Me | Me | oil |
| 204 | OC(O)NR' | Et | Me | |
| 205 | OC(O)NR' | n-Pr | Me | |
| 206 | OC(O)NR' | i-Pr | Me | |
| 207 | OC(O)NR' | n-Bu | Me | |
| 208 | OC(O)NR' | i-Bu | Me | |
| 209 | OC(O)NR' | allyl | Me | |
| 210 | OC(O)NR' | CH$_2$C≡CH | Me | |
| 211 | OC(O)NR' | CH=CH$_2$ | Me | |
| 212 | OC(O)NR' | CH$_2$CH$_2$F | Me | |
| 213 | OC(O)NR' | CF$_3$ | Me | |
| 214 | OC(O)NR' | CH$_2$CF$_3$ | Me | |
| 215 | OC(O)NR' | CH$_2$CN | Me | |
| 216 | OC(O)NR' | cyclopropyl | Me | |
| 217 | OC(O)NR' | cyclopropylmethyl | Me | |
| 218 | OC(O)NR' | CH$_2$CO$_2$Me | Me | |
| 219 | OC(O)NR' | CH$_2$CH$_2$NMe$_2$ | Me | |
| 220 | OC(O)NR' | CH$_2$-(N-morpholinyl) | Me | |
| 221 | OC(O)NR' | 2-chloropyridin-5-yl-methyl | Me | |
| 222 | OC(O)NR' | 2-furanyl | Me | |
| 223 | OC(O)NR' | 2-pyrimidinyl | Me | |
| 224 | OC(O)NR' | 2-oxazolyl | Me | |
| 225 | OC(O)NR' | 5-[1,2,4]-oxadiazolyl | Me | |
| 226 | OC(O)NR' | tetrazolyl | Me | |
| 227 | OC(O)NR' | n-Hex | Me | |
| 228 | OC(O)NR' | H | Et | |
| 229 | OC(O)NR' | Me | Et | |
| 230 | OC(O)NR' | Et | Et | |
| 231 | OC(O)NR' | n-Pr | Et | |
| 232 | OC(O)NR' | i-Pr | Et | |
| 233 | OC(O)NR' | n-Bu | Et | |
| 234 | OC(O)NR' | i-Bu | Et | |
| 235 | OC(O)NR' | allyl | Et | |
| 236 | OC(O)NR' | CH$_2$C≡CH | Et | |
| 237 | OC(O)NR' | CH=CH$_2$ | Et | |
| 238 | OC(O)NR' | CH$_2$CH$_2$F | Et | |
| 239 | OC(O)NR' | CF$_3$ | Et | |

TABLE 2-continued

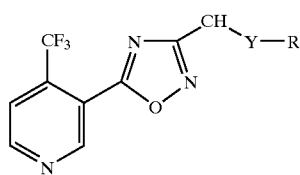

| Ex. No. | Y | R | R' | m.p. [° C.] |
|---|---|---|---|---|
| 240 | OC(O)NR' | CH$_2$CF$_3$ | Et | |
| 241 | OC(O)NR' | CH$_2$CN | Et | |
| 242 | OC(O)NR' | cyclopropyl | Et | |
| 243 | OC(O)NR' | cyclopropylmethyl | Et | |
| 244 | OC(O)NR' | CH$_2$CO$_2$Me | Et | |
| 245 | OC(O)NR' | CH$_2$CH$_2$NMe$_2$ | Et | |
| 246 | OC(O)NR' | CH$_2$-(N-morpholinyl) | Et | |
| 247 | OC(O)NR' | 2-chloropyridin-5-yl-methyl | Et | |
| 248 | OC(O)NR' | 2-furanyl | Et | |
| 249 | OC(O)NR' | 2-pyrimidinyl | Et | |
| 250 | OC(O)NR' | 2-oxazolyl | Et | |
| 251 | OC(O)NR' | 5-[1,2,4]-oxadiazolyl | Et | |
| 252 | OC(O)NR' | tetrazolyl | Et | |
| 253 | OC(O)NR' | H | Et | |
| 254 | OC(O)C(O)O | H | | |
| 255 | OC(O)C(O)O | Me | | oil |
| 256 | OC(O)C(O)O | Et | | oil |
| 257 | OC(O)C(O)O | n-Pr | | |
| 258 | OC(O)C(O)O | i-Pr | | |
| 259 | OC(O)C(O)O | n-Bu | | |
| 260 | OC(O)C(O)O | i-Bu | | |
| 261 | OC(O)C(O)O | allyl | | |
| 262 | OC(O)C(O)O | CH$_2$C≡CH | | |
| 263 | OC(O)C(O)O | CH=CH$_2$ | | |
| 264 | OC(O)C(O)O | CH$_2$CH$_2$F | | |
| 265 | OC(O)C(O)O | CF$_3$ | | |
| 266 | OC(O)C(O)O | CH$_2$CF$_3$ | | |
| 267 | OC(O)C(O)O | CH$_2$CN | | |
| 268 | OC(O)C(O)O | cyclopropyl | | |
| 269 | OC(O)C(O)O | cyclopropylmethyl | | |
| 270 | OC(O)C(O)O | CH$_2$CO$_2$Me | | |
| 271 | OC(O)C(O)O | CH$_2$CH$_2$NMe$_2$ | | |
| 272 | OC(O)C(O)O | CH$_2$-(N-morpholinyl) | | |
| 273 | OC(O)C(O)O | 2-chloropyridin-5-yl-methyl | | |
| 274 | OC(O)C(O)O | 2-furanyl | | |
| 275 | OC(O)C(O)O | 2-pyrimidinyl | | |
| 276 | OC(O)C(O)O | 2-oxazolyl | | |
| 277 | OC(O)C(O)O | 5-[1,2,4]-oxadiazolyl | | |
| 278 | OC(O)C(O)O | tetrazolyl | | |
| 279 | S(O)$_2$NR' | H | H | |
| 280 | S(O)$_2$NR' | Me | H | |
| 281 | S(O)$_2$NR' | Et | H | |
| 282 | S(O)$_2$NR' | n-Pr | H | |
| 283 | S(O)$_2$NR' | i-Pr | H | 93 |
| 284 | S(O)$_2$NR' | n-Bu | H | |
| 285 | S(O)$_2$NR' | i-Bu | H | |
| 286 | S(O)$_2$NR' | allyl | H | 83 |
| 287 | S(O)$_2$NR' | CH$_2$C≡CH | H | |
| 288 | S(O)$_2$NR' | CH=CH$_2$ | H | |
| 289 | S(O)$_2$NR' | CH$_2$CH$_2$F | H | |
| 290 | S(O)$_2$NR' | CF$_3$ | H | |
| 291 | S(O)$_2$NR' | CH$_2$CF$_3$ | H | |
| 292 | S(O)$_2$NR' | CH$_2$CN | H | |
| 293 | S(O)$_2$NR' | cyclopropyl | H | |
| 294 | S(O)$_2$NR' | cyclopropylmethyl | H | solid |
| 295 | S(O)$_2$NR' | CH$_2$CO$_2$Me | H | |
| 296 | S(O)$_2$NR' | CH$_2$CH$_2$NMe$_2$ | H | |
| 297 | S(O)$_2$NR' | CH$_2$-(N-morpholinyl) | H | |
| 298 | S(O)$_2$NR' | 2-chloropyridin-5-yl-methyl | H | |
| 299 | S(O)$_2$NR' | 2-furanyl | H | |
| 300 | S(O)$_2$NR' | 2-pyrimidinyl | H | |
| 301 | S(O)$_2$NR' | 2-oxazolyl | H | |
| 302 | S(O)$_2$NR' | 5-[1,2,4]-oxadiazolyl | H | |
| 303 | S(O)$_2$NR' | tetrazolyl | H | |
| 304 | S(O)$_2$NR' | H | Me | |
| 305 | S(O)$_2$NR' | Me | Me | |

TABLE 2-continued

[Structure: 4-(trifluoromethyl)pyridin-3-yl attached to 1,2,4-oxadiazole with CH(R')—Y—R substituent]

| Ex. No. | Y | R | R' | m.p. [° C.] |
|---|---|---|---|---|
| 306 | S(O)$_2$NR' | Et | Me | oil |
| 307 | S(O)$_2$NR' | n-Pr | Me | |
| 308 | S(O)$_2$NR' | i-Pr | Me | oil |
| 309 | S(O)$_2$NR' | n-Bu | Me | |
| 310 | S(O)$_2$NR' | i-Bu | Me | |
| 311 | S(O)$_2$NR' | allyl | Me | |
| 312 | S(O)$_2$NR' | CH$_2$C≡CH | Me | 94 |
| 313 | S(O)$_2$NR' | CH=CH$_2$ | Me | |
| 314 | S(O)$_2$NR' | CH$_2$CH$_2$F | Me | |
| 315 | S(O)$_2$NR' | CF$_3$ | Me | |
| 316 | S(O)$_2$NR' | CH$_2$CF$_3$ | Me | |
| 317 | S(O)$_2$NR' | CH$_2$CN | Me | |
| 318 | S(O)$_2$NR' | cyclopropyl | Me | |
| 319 | S(O)$_2$NR' | cyclopropylmethyl | Me | |
| 320 | S(O)$_2$NR' | CH$_2$CO$_2$Me | Me | |
| 321 | S(O)$_2$NR' | CH$_2$CH$_2$NMe$_2$ | Me | |
| 322 | S(O)$_2$NR' | CH$_2$-(N-morpholinyl) | Me | |
| 323 | S(O)$_2$NR' | 2-chloropyridin-5-yl-methyl | Me | |
| 324 | S(O)$_2$NR' | furanyl | Me | |
| 325 | S(O)$_2$NR' | 2-pyrimidinyl | Me | |
| 326 | S(O)$_2$NR' | 2-oxazolyl | Me | |
| 327 | S(O)$_2$NR' | 5-[1,2,4]-oxadiazolyl | Me | |
| 328 | S(O)$_2$NR' | tetrazolyl | Me | |
| 329 | S(O)$_2$NR' | H | Et | |
| 330 | S(O)$_2$NR' | Me | Et | |
| 331 | S(O)$_2$NR' | Et | Et | |
| 332 | S(O)$_2$NR' | n-Pr | Et | |
| 333 | S(O)$_2$NR' | i-Pr | Et | 70 |
| 334 | S(O)$_2$NR' | n-Bu | Et | |
| 335 | S(O)$_2$NR' | i-Bu | Et | |
| 336 | S(O)$_2$NR' | allyl | Et | oil |
| 337 | S(O)$_2$NR' | CH$_2$C≡CH | Et | |
| 338 | S(O)$_2$NR' | CH=CH$_2$ | Et | |
| 339 | S(O)$_2$NR' | CH$_2$CH$_2$F | Et | |
| 340 | S(O)$_2$NR' | CF$_3$ | Et | |
| 341 | S(O)$_2$NR' | CH$_2$CF$_3$ | Et | |
| 342 | S(O)$_2$NR' | CH$_2$CN | Et | |
| 343 | S(O)$_2$NR' | cyclopropyl | Et | |
| 344 | S(O)$_2$NR' | cyclopropylmethyl | Et | |
| 345 | S(O)$_2$NR' | CH$_2$CO$_2$Me | Et | |
| 346 | S(O)$_2$NR' | CH$_2$CH$_2$NMe$_2$ | Et | |
| 347 | S(O)$_2$NR' | CH$_2$-(N-morpholinyl) | Et | |
| 348 | S(O)$_2$NR' | 2-chloropyridin-5-yl-methyl | Et | |
| 349 | S(O)$_2$NR' | furanyl | Et | |
| 350 | S(O)$_2$NR' | 2-pyrimidinyl | Et | |
| 351 | S(O)$_2$NR' | 2-oxazolyl | Et | |
| 352 | S(O)$_2$NR' | 5-[1,2,4]-oxadiazolyl | Et | |
| 353 | S(O)$_2$NR' | tetrazolyl | Et | |
| 354 | S(O)$_2$NR' | n-Pr | n-Pr | oil |
| 355 | S(O)$_2$NR' | CH$_2$SCH$_2$CH$_3$ | n-Pr | |
| 356 | S(O)$_2$NR' | CH$_2$CH$_2$CH$_2$CH$_2$CH$_2$ | n-Pr | 152 |
| 357 | S(O)$_2$NR' | CH$_2$CH=CHCH$_2$CH$_2$ | n-Pr | 138 |
| 358 | S | 2-methylmercapto-1,3,4-thiadiazol-5-yl | | 92 |
| 359 | S | 5-(trifluoromethyl)-pyridin-2-yl | | 78 |
| 360 | S | 5-(trifluoromethyl)-pyridin-2-yl | | 68 |
| 361 | S | 4-methylthiazol-2-yl | | oil |
| 362 | S | 3-(methylmercapto)-1,2,4-thiadiazol-5-yl | | oil |
| 363 | S | 4-pyridinyl | | 88 |
| 364 | S | 2-methylfuran-3-yl | | oil |
| 365 | S | 4-(trifluoromethoxy)-phenyl | | 57 |
| 366 | S | 2-imidazolyl | | 171 |
| 367 | S | 5-methyl-1,2,4-triazol-3-yl | | 95 |
| 368 | S | 2-thiazolyl | | oil |
| 369 | S | dimethylaminothiocarbonyl | | solid |
| 370 | S | 4,6-dimethylpyrimidin-2-yl | | oil |

TABLE 2-continued

[Structure: 4-(trifluoromethyl)pyridin-3-yl attached to 1,2,4-oxadiazole with CH(R')—Y—R substituent]

| Ex. No. | Y | R | R' | m.p. [° C.] |
|---|---|---|---|---|
| 371 | S | 5-methyl-1,3,4-thiadiazol-2-yl | | 98 |
| 372 | NR'C(S)NH | CO$_2$Et | H | 136 |
| 373 | NR'C(O) | CH(imidazolyl-)CF$_2$C(O) | | oil |
| 374 | NR'C(O) | CH(Me)CH$_2$C(O) | | oil |
| 375 | NR'C(O) | CMe$_2$CH$_2$C(O) | | oil |
| 376 | NR'C(O) | CH(Me)CH(Me)C(O) | | oil |
| 377 | NR'C(O) | CH$_2$CH$_2$CH$_2$C(O) | | oil |
| 378 | NR'C(O) | CH(Me)CH$_2$CH$_2$C(O) | | oil |
| 379 | NR'C(O) | CH$_2$CH(Me)CH$_2$C(O) | | oil |
| 380 | NR'C(O) | CH$_2$CMe$_2$CH$_2$C(O) | | oil |
| 381 | NR'C(O) | CH$_2$C[—(CH$_2$)$_4$—]CH$_2$C(O) | | oil |
| 382 | NR'C(O) | (cyclopentyl-C(O)) | | 192 |
| 383 | NR'C(O)N(H) | CH(CHMe$_2$)CO$_2$Et | H | oil |
| 384 | NR'C(S)N(H) | Et | H | oil |
| 385 | NR'C(S)N(H) | CMe$_3$ | H | 113 |
| 386 | NR'C(S)N(H) | -p-Tol | H | oil |
| 387 | NR'C(O) | (4-CF$_3$-3-methylpyridin-... ) | H | 148 |
| 388 | NR'C(O)N(H) | Et | H | 144 |
| 389 | NR'C(O)N(H) | C(H)Me$_2$ | H | 159 |
| 390 | NR'C(O)N(H) | Bu | H | 117 |
| 391 | NR'C(O)N(H) | (CH$_2$)$_4$Me | H | 118 |
| 392 | NR'C(O)N(H) | cyclohexyl | H | 160 |
| 393 | NR'C(O)N(H) | C(H)MeCO$_2$Et | H | 157 |
| 394 | NR'C(O)N(H) | C(O)Ph | H | 182 |
| 395 | NR'C(O)N(H) | (4-CF$_3$-Ph) | H | 170 |
| 396 | NR'C(O)N(H) | (2,6-C$_6$H$_3$F$_2$) | H | 193 |
| 397 | NR'C(O) | (cyclohexyl-C(O)) | | oil |
| 398 | NR'C(O) | CH$_2$C(H)PhCH$_2$C(O) | | oil |
| 399 | NR'C(O) | CMe=CMeC(O) | | oil |
| 400 | NR'C(O) | (cyclohexenyl-C(O)) | | oil |
| 401 | NR'(CO)N(H) | CMe$_3$ | H | 120 |
| 402 | NR'C(O)O | CH$_2$C≡CH | H | solid |
| 403 | NR'SO$_2$ | C(H)Me$_2$ | H | oil |
| 404 | NR'C(O) | CH$_2$OC(O)Me | H | 80 |
| 405 | NR'C(O) | (CH$_2$)$_3$Cl | H | 56 |
| 406 | NR'C(O) | (CH$_2$)$_2$SMe | H | 96 |
| 407 | NR'C(O)O | Bu | H | oil |
| 408 | NR'C(O)O | cyclopentyl | H | oil |
| 409 | NR'C(O) | CH$_2$CH$_2$C(O) | | 87 |
| 410 | NR'C(O)N(H) | Ph | H | 129 |
| 411 | NR'H$^+$HSO$_4$$^-$ | H | H | solid |

TABLE 3

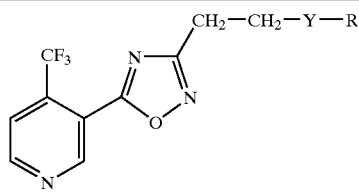

| Ex. No. | Y | R | R' | m.p. [° C.] |
|---|---|---|---|---|
| 1 | O | n-Pr | | oil |
| 2 | O | i-Pr | | oil |
| 3 | O | n-Bu | | |
| 4 | O | i-Bu | | |
| 5 | O | allyl | | oil |
| 6 | O | CH₂C≡CH | | oil |
| 7 | O | CH=CH₂ | | |
| 8 | O | CH₂CH₂F | | |
| 9 | O | CF₃ | | |
| 10 | O | CH₂CF₃ | | |
| 11 | O | CH₂CN | | |
| 12 | O | cyclopropyl | | |
| 13 | O | cyclopropylmethyl | | |
| 14 | O | CH₂CO₂Me | | |
| 15 | O | CH₂CH₂NMe₂ | | |
| 16 | O | CH₂-(N-morpholinyl) | | |
| 17 | O | 2-chloropyridin-5-yl-methyl | | |
| 18 | O | n-Hex | | |
| 19 | O | 2-furanyl | | |
| 20 | O | 2-pyrimidinyl | | |
| 21 | O | 2-oxazolyl | | |
| 22 | O | 5-[1,2,4]-oxadiazolyl | | |
| 23 | O | tetrazolyl | | |
| 24 | O | 2-hexahydropropanyl | | |
| 25 | S | H | | |
| 26 | S | Et | | |
| 27 | S | i-Pr | | oil |
| 28 | S | n-Bu | | |
| 29 | S | i-Bu | | |
| 30 | S | allyl | | |
| 31 | S | CH₂C≡CH | | |
| 32 | S | CH=CH₂ | | |
| 33 | S | CH₂CH₂F | | |
| 34 | S | CF₃ | | |
| 35 | S | CH₂CF₃ | | oil |
| 36 | S | CH₂CN | | |
| 37 | S | cyclopropyl | | |
| 38 | S | cyclopropylmethyl | | |
| 39 | S | CH₂CO₂Me | | |
| 40 | S | CH₂CH₂NMe₂ | | |
| 41 | S | CH₂-(N-morpholinyl) | | |
| 42 | S | 2-chloropyridin-5-yl-methyl | | |
| 43 | S | n-Hex | | |
| 44 | S | 2-furanyl | | |
| 45 | S | 2-pyrimidinyl | | |
| 46 | S | 2-oxazolyl | | |
| 47 | S | 5-[1,2,4]-oxadiazolyl | | |
| 48 | | tetrazolyl | | |
| 49 | S | | | oil |
| 50 | S(O) | Me | | |
| 51 | S(O) | Et | | |
| 52 | S(O) | n-Pr | | |
| 53 | S(O) | i-Pr | | |
| 54 | S(O) | n-Bu | | |
| 55 | S(O) | i-Bu | | |
| 56 | S(O) | allyl | | |
| 57 | S(O) | CH₂C≡CH | | |

TABLE 3-continued

Structure: 4-CF₃-pyridin-3-yl substituted 1,2,4-oxadiazole with CH₂—CH₂—Y—R at 3-position

| Ex. No. | Y | R | R' | m.p. [° C.] |
|---|---|---|---|---|
| 58 | S(O) | CH=CH₂ | | |
| 59 | S(O) | CH₂CH₂F | | |
| 60 | S(O) | CF₃ | | |
| 61 | S(O) | CH₂CF₃ | | |
| 62 | S(O) | CH₂CN | | |
| 63 | S(O) | cyclopropyl | | |
| 64 | S(O) | cyclopropylmethyl | | |
| 65 | S(O) | CH₂CO₂Me | | |
| 66 | S(O) | CH₂CH₂NMe₂ | | |
| 67 | S(O) | CH₂-(N-morpholinyl) | | |
| 68 | S(O) | 2-chloropyridin-5-yl-methyl | | |
| 69 | S(O) | n-Hex | | |
| 70 | S(O) | 2-furanyl | | |
| 71 | S(O) | 2-pyrimidinyl | | |
| 72 | S(O) | 2-oxazolyl | | |
| 73 | S(O) | 5-[1,2,4]-oxadiazolyl | | |
| 74 | S(O) | tetrazolyl | | |
| 75 | S(O)₂ | Me | | 84 |
| 76 | S(O)₂ | Et | | |
| 77 | S(O)₂ | n-Pr | | |
| 78 | S(O)₂ | i-Pr | | |
| 79 | S(O)₂ | n-Bu | | |
| 80 | S(O)₂ | i-Bu | | |
| 81 | S(O)₂ | allyl | | |
| 82 | S(O)₂ | CH₂C≡CH | | |
| 83 | S(O)₂ | CH=CH₂ | | |
| 84 | S(O)₂ | CH₂CH₂F | | |
| 85 | S(O)₂ | CF₃ | | |
| 86 | S(O)₂ | CH₂CF₃ | | |
| 87 | S(O)₂ | CH₂CN | | |
| 88 | S(O)₂ | cyclopropyl | | |
| 89 | S(O)₂ | cyclopropylmethyl | | |
| 90 | S(O)₂ | CH₂CO₂Me | | |
| 91 | S(O)₂ | CH₂CH₂NMe₂ | | |
| 92 | S(O)₂ | CH₂-(N-morpholinyl) | | |
| 93 | S(O)₂ | 2-chloropyridin-5-yl-methyl | | |
| 94 | S(O)₂ | n-Hex | | |
| 95 | S(O)₂ | furanyl | | |
| 96 | S(O)₂ | 2-pyrimidinyl | | |
| 97 | S(O)₂ | 2-oxazolyl | | |
| 98 | S(O)₂ | 5-[1,2,4]-oxadiazolyl | | |
| 99 | S(O)₂ | tetrazolyl | | |
| 100 | OC(O) | H | | |
| 101 | OC(O) | Et | | |
| 102 | OC(O) | n-Pr | | |
| 103 | OC(O) | i-Pr | | |
| 104 | OC(O) | n-Bu | | |
| 105 | OC(O) | i-Bu | | |
| 106 | OC(O) | allyl | | |
| 107 | OC(O) | CH₂C≡CH | | |
| 108 | OC(O) | CH=CH₂ | | |
| 109 | OC(O) | CH₂CH₂F | | |
| 110 | OC(O) | CF₃ | | |
| 111 | OC(O) | CH₂CF₃ | | |
| 112 | OC(O) | CH₂CN | | |
| 113 | OC(O) | cyclopropyl | | |
| 114 | OC(O) | cyclopropylmethyl | | |
| 115 | OC(O) | CH₂CO₂Me | | |
| 116 | OC(O) | CH₂CH₂NMe₂ | | |
| 117 | OC(O) | CH₂-(N-morpholinyl) | | |
| 118 | OC(O) | 2-chloropyridin-5-yl-methyl | | |
| 119 | OC(O) | n-Hex | | |
| 120 | OC(O) | 2-furanyl | | |
| 121 | OC(O) | 2-pyrimidinyl | | |
| 122 | OC(O) | 2-oxazolyl | | |
| 123 | OC(O) | 5-[1,2,4]-oxadiazolyl | | |

TABLE 3-continued

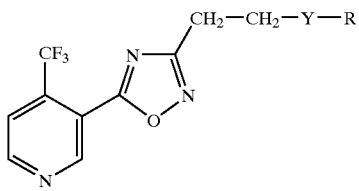

| Ex. No. | Y | R | R' | m.p. [° C.] |
|---|---|---|---|---|
| 124 | OC(O) | tetrazolyl | | |
| 125 | OC(O)O | Me | | |
| 126 | OC(O)O | Et | | |
| 127 | OC(O)O | n-Pr | | |
| 128 | OC(O)O | i-Pr | | |
| 129 | OC(O)O | n-Bu | | |
| 130 | OC(O)O | i-Bu | | |
| 131 | OC(O)O | allyl | | |
| 132 | OC(O)O | $CH_2C\equiv CH$ | | |
| 133 | OC(O)O | $CH=CH_2$ | | |
| 134 | OC(O)O | $CH_2CH_2F$ | | |
| 135 | OC(O)O | $CF_3$ | | |
| 136 | OC(O)O | $CH_2CF_3$ | | |
| 137 | OC(O)O | $CH_2CN$ | | |
| 138 | OC(O)O | cyclopropyl | | |
| 139 | OC(O)O | cyclopropylmethyl | | |
| 140 | OC(O)O | $CH_2CO_2Me$ | | |
| 141 | OC(O)O | $CH_2CH_2NMe_2$ | | |
| 142 | OC(O)O | $CH_2$-(N-morpholinyl) | | |
| 143 | OC(O)O | 2-chloropyridin-5-yl-methyl | | |
| 144 | OC(O)O | n-Hex | | |
| 145 | OC(O)O | 2-furanyl | | |
| 146 | OC(O)O | 2-pyrimidinyl | | |
| 147 | OC(O)O | 2-oxazolyl | | |
| 148 | OC(O)O | 5-[1,2,4]-oxadiazolyl | | |
| 149 | OC(O)O | tetrazolyl | | |
| 150 | OC(O)NR' | H | H | |
| 151 | OC(O)NR' | Me | H | |
| 152 | OC(O)NR' | Et | H | |
| 154 | OC(O)NR' | n-Pr | H | |
| 155 | OC(O)NR' | i-Pr | H | |
| 156 | OC(O)NR' | n-Bu | H | |
| 157 | OC(O)NR' | i-Bu | H | |
| 158 | OC(O)NR' | allyl | H | |
| 159 | OC(O)NR' | $CH_2C\equiv CH$ | H | |
| 160 | OC(O)NR' | $CH=CH_2$ | H | |
| 161 | OC(O)NR' | $CH_2CH_2F$ | H | |
| 162 | OC(O)NR' | $CF_3$ | H | |
| 163 | OC(O)NR' | $CH_2CF_3$ | H | |
| 164 | OC(O)NR' | $CH_2CN$ | H | |
| 165 | OC(O)NR' | cyclopropyl | H | |
| 166 | OC(O)NR' | cyclopropylmethyl | H | |
| 167 | OC(O)NR' | $CH_2CO_2Me$ | H | |
| 168 | OC(O)NR' | $CH_2CH_2NMe_2$ | H | |
| 169 | OC(O)NR' | $CH_2$-(N-morpholinyl) | H | |
| 170 | OC(O)NR' | 2-chloropyridin-5-yl-methyl | H | |
| 171 | OC(O)NR' | n-Hex | H | |
| 172 | OC(O)NR' | 2-furanyl | H | |
| 173 | OC(O)NR' | 2-pyrimidinyl | H | |
| 174 | OC(O)NR' | 2-oxazolyl | H | |
| 175 | OC(O)NR' | 5-[1,2,4]-oxadiazolyl | H | |
| 176 | OC(O)NR' | tetrazolyl | H | |
| 177 | OC(O)NR' | H | Me | |
| 178 | OC(O)NR' | Me | Me | |
| 179 | OC(O)NR' | Et | Me | |
| 180 | OC(O)NR' | n-Pr | Me | |
| 181 | OC(O)NR' | i-Pr | Me | |
| 182 | OC(O)NR' | n-Bu | Me | |
| 183 | OC(O)NR' | i-Bu | Me | |
| 184 | OC(O)NR' | allyl | Me | |
| 185 | OC(O)NR' | $CH_2C\equiv CH$ | Me | |
| 186 | OC(O)NR' | $CH=CH_2$ | Me | |
| 187 | OC(O)NR' | $CH_2CH_2F$ | Me | |
| 188 | OC(O)NR' | $CF_3$ | Me | |
| 189 | OC(O)NR' | $CH_2CF_3$ | Me | |
| 190 | OC(O)NR' | $CH_2CN$ | Me | |

TABLE 3-continued

Structure: pyridine with CF₃ at 4-position and 3-position attached to 1,2,4-oxadiazole bearing CH₂—CH₂—Y—R substituent

| Ex. No. | Y | R | R' | m.p. [° C.] |
|---|---|---|---|---|
| 191 | OC(O)NR' | cyclopropyl | Me | |
| 192 | OC(O)NR' | cyclopropylmethyl | Me | |
| 193 | OC(O)NR' | CH$_2$CO$_2$Me | Me | |
| 194 | OC(O)NR' | CH$_2$CH$_2$NMe$_2$ | Me | |
| 195 | OC(O)NR' | CH$_2$-(N-morpholinyl) | Me | |
| 196 | OC(O)NR' | 2-chloropyridin-5-yl-methyl | Me | |
| 197 | OC(O)NR' | n-Hex | Me | |
| 198 | OC(O)NR' | 2-furanyl | Me | |
| 199 | OC(O)NR' | 2-pyrimidinyl | Me | |
| 200 | OC(O)NR' | 2-oxazolyl | Me | |
| 201 | OC(O)NR' | 5-[1,2,4]-oxadiazolyl | Me | |
| 202 | OC(O)NR' | tetrazolyl | Me | |
| 203 | OC(O)NR' | H | Et | |
| 204 | OC(O)NR' | Me | Et | |
| 205 | OC(O)NR' | Et | Et | |
| 206 | OC(O)NR' | n-Pr | Et | |
| 207 | OC(O)NR' | i-Pr | Et | |
| 208 | OC(O)NR' | n-Bu | Et | |
| 209 | OC(O)NR' | i-Bu | Et | |
| 210 | OC(O)NR' | allyl | Et | |
| 211 | OC(O)NR' | CH$_2$C≡CH | Et | |
| 212 | OC(O)NR' | CH=CH$_2$ | Et | |
| 213 | OC(O)NR' | CH$_2$CH$_2$F | Et | |
| 214 | OC(O)NR' | CF$_3$ | Et | |
| 215 | OC(O)NR' | CH$_2$CF$_3$ | Et | |
| 216 | OC(O)NR' | CH$_2$CN | Et | |
| 217 | OC(O)NR' | cyclopropyl | Et | |
| 218 | OC(O)NR' | cyclopropylmethyl | Et | |
| 219 | OC(O)NR' | CH$_2$CO$_2$Me | Et | |
| 220 | OC(O)NR' | CH$_2$CH$_2$NMe$_2$ | Et | |
| 221 | OC(O)NR' | CH$_2$-(N-morpholinyl) | Et | |
| 222 | OC(O)NR' | 2-chloropyridin-5-yl-methyl | Et | |
| 223 | OC(O)NR' | n-Hex | Et | |
| 224 | OC(O)NR' | 2-furanyl | Et | |
| 225 | OC(O)NR' | 2-pyrimidinyl | Et | |
| 226 | OC(O)NR' | 2-oxazolyl | Et | |
| 227 | OC(O)NR' | 5-[1,2,4]-oxadiazolyl | Et | |
| 228 | OC(O)NR' | tetrazolyl | Et | |
| 229 | OC(O)C(O)O | H | | |
| 230 | OC(O)C(O)O | Me | | |
| 231 | OC(O)C(O)O | Et | | |
| 232 | OC(O)C(O)O | n-Pr | | |
| 233 | OC(O)C(O)O | i-Pr | | |
| 234 | OC(O)C(O)O | n-Bu | | |
| 235 | OC(O)C(O)O | i-Bu | | |
| 236 | OC(O)C(O)O | allyl | | |
| 237 | OC(O)C(O)O | CH$_2$C≡CH | | |
| 238 | OC(O)C(O)O | CH=CH$_2$ | | |
| 239 | OC(O)C(O)O | CH$_2$CH$_2$F | | |
| 240 | OC(O)C(O)O | CF$_3$ | | |
| 241 | OC(O)C(O)O | CH$_2$CF$_3$ | | |
| 242 | OC(O)C(O)O | CH$_2$CN | | |
| 243 | OC(O)C(O)O | cyclopropyl | | |
| 244 | OC(O)C(O)O | cyclopropylmethyl | | |
| 245 | OC(O)C(O)O | CH$_2$CO$_2$Me | | |
| 246 | OC(O)C(O)O | CH$_2$CH$_2$NMe$_2$ | | |
| 247 | OC(O)C(O)O | CH$_2$-(N-morpholinyl) | | |
| 248 | OC(O)C(O)O | 2-chloropyridin-5-yl-methyl | | |
| 249 | OC(O)C(O)O | n-Hex | | |
| 250 | OC(O)C(O)O | furanyl | | |
| 251 | OC(O)C(O)O | 2-pyrimidinyl | | |
| 252 | OC(O)C(O)O | 2-oxazolyl | | |
| 253 | OC(O)C(O)O | 5-[1,2,4]-oxadiazolyl | | |
| 254 | OC(O)C(O)O | tetrazolyl | | |
| 255 | S(O)$_2$NR' | H | H | |
| 256 | S(O)$_2$NR' | Me | H | |

TABLE 3-continued

[Structure: pyridine with CF₃ substituent connected to 1,2,4-oxadiazole bearing CH₂—CH₂—Y—R substituent]

| Ex. No. | Y | R | R' | m.p. [° C.] |
|---|---|---|---|---|
| 257 | S(O)₂NR' | Et | H | |
| 258 | S(O)₂NR' | n-Pr | H | |
| 259 | S(O)₂NR' | i-Pr | H | |
| 260 | S(O)₂NR' | n-Bu | H | |
| 261 | S(O)₂NR' | i-Bu | H | |
| 262 | S(O)₂NR' | allyl | H | |
| 263 | S(O)₂NR' | CH₂C≡CH | H | |
| 264 | S(O)₂NR' | CH=CH₂ | H | |
| 265 | S(O)₂NR' | CH₂CH₂F | H | |
| 266 | S(O)₂NR' | CF₃ | H | |
| 267 | S(O)₂NR' | CH₂CF₃ | H | |
| 268 | S(O)₂NR' | CH₂CN | H | |
| 269 | S(O)₂NR' | cyclopropyl | H | |
| 270 | S(O)₂NR' | cyclopropylmethyl | H | |
| 271 | S(O)₂NR' | CH₂CO₂Me | H | |
| 272 | S(O)₂NR' | CH₂CH₂NMe₂ | H | |
| 273 | S(O)₂NR' | CH₂-(N-morpholinyl) | H | |
| 274 | S(O)₂NR' | 2-chloropyridin-5-yl-methyl | H | |
| 275 | S(O)₂NR' | n-Hex | H | |
| 276 | S(O)₂NR' | furanyl | H | |
| 277 | S(O)₂NR' | 2-pyrimidinyl | H | |
| 278 | S(O)₂NR' | 2-oxazolyl | H | |
| 279 | S(O)₂NR' | 5-[1,2,4]-oxadiazolyl | | |
| 280 | S(O)₂NR' | tetrazolyl | | |
| 281 | S(O)₂NR' | H | Me | |
| 282 | S(O)₂NR' | Me | Me | |
| 283 | S(O)₂NR' | Et | Me | |
| 284 | S(O)₂NR' | n-Pr | Me | |
| 285 | S(O)₂NR' | i-Pr | Me | |
| 286 | S(O)₂NR' | n-Bu | Me | |
| 287 | S(O)₂NR' | i-Bu | Me | |
| 288 | S(O)₂NR' | allyl | Me | |
| 289 | S(O)₂NR' | CH₂C≡CH | Me | |
| 290 | S(O)₂NR' | CH=CH₂ | Me | |
| 291 | S(O)₂NR' | CH₂CH₂F | Me | |
| 292 | S(O)₂NR' | CF₃ | Me | |
| 293 | S(O)₂NR' | CH₂CF₃ | Me | |
| 294 | S(O)₂NR' | CH₂CN | Me | |
| 295 | S(O)₂NR' | cyclopropyl | Me | |
| 296 | S(O)₂NR' | cyclopropylmethyl | Me | |
| 297 | S(O)₂NR' | CH₂CO₂Me | Me | |
| 298 | S(O)₂NR' | CH₂CH₂NMe₂ | Me | |
| 299 | S(O)₂NR' | CH₂-(N-morpholinyl) | Me | |
| 300 | S(O)₂NR' | 2-chloropyridin-5-yl-methyl | Me | |
| 301 | S(O)₂NR' | n-Hex | Me | |
| 302 | S(O)₂NR' | furanyl | Me | |
| 303 | S(O)₂NR' | 2-pyrimidinyl | Me | |
| 304 | S(O)₂NR' | 2-oxazolyl | Me | |
| 305 | S(O)₂NR' | 5-[1,2,4]-oxadiazolyl | Me | |
| 306 | S(O)₂NR' | tetrazolyl | Me | |
| 307 | S(O)₂NR' | H | Et | |
| 308 | S(O)₂NR' | Me | Et | |
| 309 | S(O)₂NR' | Et | Et | |
| 310 | S(O)₂NR' | n-Pr | Et | |
| 311 | S(O)₂NR' | i-Pr | Et | |
| 312 | S(O)₂NR' | n-Bu | Et | |
| 313 | S(O)₂NR' | i-Bu | Et | |
| 314 | S(O)₂NR' | allyl | Et | |
| 315 | S(O)₂NR' | CH₂C≡CH | Et | |
| 316 | S(O)₂NR' | CH=CH₂ | Et | |
| 317 | S(O)₂NR' | CH₂CH₂F | Et | |
| 318 | S(O)₂NR' | CF₃ | Et | |
| 319 | S(O)₂NR' | CH₂CF₃ | Et | |
| 320 | S(O)₂NR' | CH₂CN | Et | |
| 321 | S(O)₂NR' | cyclopropyl | Et | |
| 322 | S(O)₂NR' | cyclopropylmethyl | Et | |

TABLE 3-continued

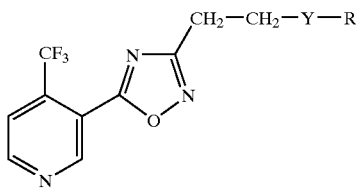

| Ex. No. | Y | R | R' | m.p. [° C.] |
|---|---|---|---|---|
| 323 | S(O)₂NR' | CH₂CO₂Me | Et | |
| 324 | S(O)₂NR' | CH₂CH₂NMe₂ | Et | |
| 325 | S(O)₂NR' | CH₂-(N-morpholinyl) | Et | |
| 326 | S(O)₂NR' | 2-chloropyridin-5-yl-methyl | Et | |
| 327 | S(O)₂NR' | n-Hex | Et | |
| 328 | S(O)₂NR' | furanyl | Et | |
| 329 | S(O)₂NR' | n-Hex | Et | |
| 330 | S(O)₂NR' | 2-pyrimidinyl | Et | |
| 331 | S(O)₂NR' | 2-oxazolyl | Et | |
| 332 | S(O)₂NR' | 5-[1,2,4]-oxadiazolyl | Et | |
| 333 | S(O)₂NR' | tetrazolyl | Et | |

TABLE 4

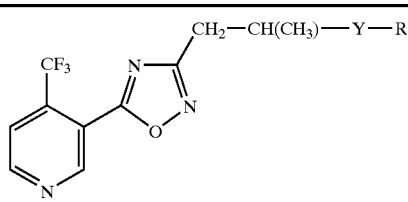

| Ex. No. | Y | R | R' | m.p. [° C.] |
|---|---|---|---|---|
| 1 | O | H | | |
| 2 | O | Me | | |
| 3 | O | Et | | oil |
| 4 | O | n-Pr | | |
| 5 | O | i-Pr | | |
| 6 | O | n-Bu | | |
| 7 | O | i-Bu | | |
| 8 | O | allyl | | |
| 9 | O | CH₂C≡CH | | |
| 10 | O | CH=CH₂ | | |
| 11 | O | CH₂CH₂F | | |
| 12 | O | CF₃ | | |
| 13 | O | CH₂CF₃ | | |
| 14 | O | CH₂CN | | |
| 15 | O | cyclopropyl | | |
| 16 | O | cyclopropylmethyl | | |
| 17 | O | CH₂CO₂Me | | |
| 18 | O | CH₂CH₂NMe₂ | | |
| 19 | O | CH₂-(N-morpholinyl) | | |
| 20 | O | 2-chloropyridin-5-yl-methyl | | |
| 21 | O | n-Hex | | |
| 22 | O | 2-furanyl | | |
| 23 | O | 2-pyrimidinyl | | |
| 24 | O | 2-oxazolyl | | |
| 25 | O | 5-[1,2,4]-oxadiazolyl | | |
| 26 | O | tetrazolyl | | |
| 27 | S | H | | |
| 28 | S | Me | | |
| 29 | S | Et | | |
| 30 | S | n-Pr | | |
| 31 | S | i-Pr | | |
| 32 | S | n-Bu | | |
| 33 | S | i-Bu | | |
| 34 | S | allyl | | |
| 35 | S | CH₂C≡CH | | |
| 36 | S | CH=CH₂ | | |

TABLE 4-continued

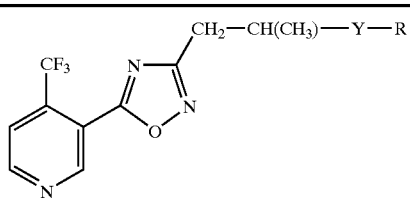

| Ex. No. | Y | R | R' | m.p. [° C.] |
|---|---|---|---|---|
| 37 | S | CH₂CH₂F | | |
| 38 | S | CF₃ | | |
| 39 | S | CH₂CF₃ | | |
| 40 | S | CH₂CN | | |
| 41 | S | cyclopropyl | | |
| 42 | S | cyclopropylmethyl | | |
| 43 | S | CH₂CO₂Me | | |
| 44 | S | CH₂CH₂NMe₂ | | |
| 45 | S | CH₂-(N-morpholinyl) | | |
| 46 | S | 2-chloropyridin-5-yl-methyl | | |
| 47 | S | n-Hex | | |
| 48 | S | 2-furanyl | | |
| 49 | S | 2-pyrimidinyl | | |
| 50 | S | 2-oxazolyl | | |
| 51 | S | 5-[1,2,4]-oxadiazolyl | | |
| 52 | S | tetrazolyl | | |
| 53 | S(O) | H | | |
| 54 | S(O) | Me | | |
| 55 | S(O) | Et | | |
| 56 | S(O) | n-Pr | | |
| 57 | S(O) | i-Pr | | |
| 58 | S(O) | n-Bu | | |
| 59 | S(O) | i-Bu | | |
| 60 | S(O) | allyl | | |
| 61 | S(O) | CH₂C≡CH | | |
| 62 | S(O) | CH=CH₂ | | |
| 63 | S(O) | CH₂CH₂F | | |
| 64 | S(O) | CF₃ | | |
| 65 | S(O) | CH₂CF₃ | | |
| 66 | S(O) | CH₂CN | | |
| 67 | S(O) | cyclopropyl | | |
| 68 | S(O) | cyclopropylmethyl | | |
| 69 | S(O) | CH₂CO₂Me | | |
| 70 | S(O) | CH₂CH₂NMe₂ | | |
| 71 | S(O) | CH₂-(N-morpholinyl) | | |
| 72 | S(O) | 2-chloropyridin-5-yl-methyl | | |

TABLE 4-continued

Structure (left and right, same):

CF$_3$ substituted pyridine connected to 1,2,4-oxadiazole with CH$_2$—CH(CH$_3$)—Y—R substituent

| Ex. No. | Y | R | R' | m.p. [° C.] |
|---|---|---|---|---|
| 73 | S(O) | n-Hex | | |
| 74 | S(O) | 2-furanyl | | |
| 75 | S(O) | 2-pyrimidinyl | | |
| 76 | S(O) | 2-oxazolyl | | |
| 77 | S(O) | 5-[1,2,4]-oxadiazolyl | | |
| 78 | S(O) | tetrazolyl | | |
| 79 | S(O)$_2$ | n-Hex | | |
| 80 | S(O)$_2$ | Me | | |
| 81 | S(O)$_2$ | Et | | |
| 82 | S(O)$_2$ | n-Pr | | |
| 83 | S(O)$_2$ | i-Pr | | |
| 84 | S(O)$_2$ | n-Bu | | |
| 85 | S(O)$_2$ | i-Bu | | |
| 86 | S(O)$_2$ | allyl | | |
| 87 | S(O)$_2$ | CH$_2$C≡CH | | |
| 88 | S(O)$_2$ | CH=CH$_2$ | | |
| 89 | S(O)$_2$ | CH$_2$CH$_2$F | | |
| 90 | S(O)$_2$ | CF$_3$ | | |
| 91 | S(O)$_2$ | CH$_2$CF$_3$ | | |
| 92 | S(O)$_2$ | CH$_2$CN | | |
| 93 | S(O)$_2$ | cyclopropyl | | |
| 94 | S(O)$_2$ | cyclopropylmethyl | | |
| 95 | S(O)$_2$ | CH$_2$CO$_2$Me | | |
| 96 | S(O)$_2$ | CH$_2$CH$_2$NMe$_2$ | | |
| 97 | S(O)$_2$ | CH$_2$-(N-morpholinyl) | | |
| 98 | S(O)$_2$ | 2-chloropyridin-5-yl-methyl | | |
| 99 | S(O)$_2$ | n-Hex | | |
| 100 | S(O)$_2$ | 2-furanyl | | |
| 101 | S(O)$_2$ | 2-pyrimidinyl | | |
| 102 | S(O)$_2$ | 2-oxazolyl | | |
| 103 | S(O)$_2$ | 5-[1,2,4]-oxadiazolyl | | |
| 104 | | tetrazolyl | | |
| 105 | OC(O) | H | | |
| 106 | OC(O) | Me | | |
| 107 | OC(O) | Et | | |
| 108 | OC(O) | n-Pr | | |
| 109 | OC(O) | i-Pr | | |
| 110 | OC(O) | n-Bu | | |
| 111 | OC(O) | i-Bu | | |
| 112 | OC(O) | allyl | | |
| 113 | OC(O) | CH$_2$C≡CH | | |
| 114 | OC(O) | CH=CH$_2$ | | |
| 115 | OC(O) | CH$_2$CH$_2$F | | |
| 116 | OC(O) | CF$_3$ | | |
| 117 | OC(O) | CH$_2$CF$_3$ | | |
| 118 | OC(O) | CH$_2$CN | | |
| 119 | OC(O) | cyclopropyl | | |
| 120 | OC(O) | cyclopropylmethyl | | |
| 121 | OC(O) | CH$_2$CO$_2$Me | | |
| 122 | OC(O) | CH$_2$CH$_2$NMe$_2$ | | |
| 123 | OC(O) | CH$_2$-(N-morpholinyl) | | |
| 124 | OC(O) | 2-chloropyridin-5-yl-methyl | | |
| 125 | OC(O) | n-Hex | | |
| 126 | OC(O) | 2-furanyl | | |
| 127 | OC(O) | 2-pyrimidinyl | | |
| 128 | OC(O) | 2-oxazolyl | | |
| 129 | OC(O) | 5-[1,2,4]-oxadiazolyl | | |
| 130 | OC(O) | tetrazolyl | | |
| 131 | OC(O)O | n-Hex | | |
| 132 | OC(O)O | Me | | |
| 133 | OC(O)O | Et | | |
| 134 | OC(O)O | n-Pr | | |
| 135 | OC(O)O | i-Pr | | |
| 136 | OC(O)O | n-Bu | | |
| 137 | OC(O)O | i-Bu | | |
| 138 | OC(O)O | allyl | | |
| 139 | OC(O)O | CH$_2$C≡CH | | |
| 140 | OC(O)O | CH=CH$_2$ | | |
| 141 | OC(O)O | CH$_2$CH$_2$F | | |
| 142 | OC(O)O | CF$_3$ | | |
| 143 | OC(O)O | CH$_2$CF$_3$ | | |
| 144 | OC(O)O | CH$_2$CN | | |
| 145 | OC(O)O | cyclopropyl | | |
| 146 | OC(O)O | cyclopropylmethyl | | |
| 147 | OC(O)O | CH$_2$CO$_2$Me | | |
| 148 | OC(O)O | CH$_2$CH$_2$NMe$_2$ | | |
| 149 | OC(O)O | CH$_2$-(N-morpholinyl) | | |
| 150 | OC(O)O | 2-chloropyridin-5-yl-methyl | | |
| 151 | OC(O)O | n-Hex | | |
| 152 | OC(O)O | 2-furanyl | | |
| 153 | OC(O)O | 2-pyrimidinyl | | |
| 154 | OC(O)O | 2-oxazolyl | | |
| 155 | OC(O)O | 5-[1,2,4]-oxadiazolyl | | |
| 156 | OC(O)O | tetrazolyl | | |
| 157 | OC(O)NR' | H | H | |
| 158 | OC(O)NR' | Me | H | |
| 159 | OC(O)NR' | Et | H | |
| 160 | OC(O)NR' | n-Pr | H | |
| 161 | OC(O)NR' | i-Pr | H | |
| 162 | OC(O)NR' | n-Bu | H | |
| 163 | OC(O)NR' | i-Bu | H | |
| 164 | OC(O)NR' | allyl | H | |
| 165 | OC(O)NR' | CH$_2$C≡CH | H | |
| 166 | OC(O)NR' | CH=CH$_2$ | H | |
| 167 | OC(O)NR' | CH$_2$CH$_2$F | H | |
| 168 | OC(O)NR' | CF$_3$ | H | |
| 169 | OC(O)NR' | CH$_2$CF$_3$ | H | |
| 170 | OC(O)NR' | CH$_2$CN | H | |
| 171 | OC(O)NR' | cyclopropyl | H | |
| 172 | OC(O)NR' | cyclopropylmethyl | H | |
| 173 | OC(O)NR' | CH$_2$CO$_2$Me | H | |
| 174 | OC(O)NR' | CH$_2$CH$_2$NMe$_2$ | H | |
| 175 | OC(O)NR' | CH$_2$-(N-morpholinyl) | H | |
| 176 | OC(O)NR' | 2-chloropyridin-5-yl-methyl | H | |
| 177 | OC(O)NR' | n-Hex | H | |
| 178 | OC(O)NR' | 2-furanyl | H | |
| 179 | OC(O)NR' | 2-pyrimidinyl | H | |
| 180 | OC(O)NR' | 2-oxazolyl | H | |
| 181 | OC(O)NR' | 5-[1,2,4]-oxadiazolyl | H | |
| 182 | OC(O)NR' | tetrazolyl | H | |
| 183 | OC(O)NR' | H | Me | |
| 184 | OC(O)NR' | Me | Me | |
| 185 | OC(O)NR' | Et | Me | |
| 186 | OC(O)NR' | n-Pr | Me | |
| 187 | OC(O)NR' | i-Pr | Me | |
| 188 | OC(O)NR' | n-Bu | Me | |
| 189 | OC(O)NR' | i-Bu | Me | |
| 190 | OC(O)NR' | allyl | Me | |
| 191 | OC(O)NR' | CH$_2$C≡CH | | |
| 192 | OC(O)NR' | CH=CH$_2$ | Me | |
| 193 | OC(O)NR' | CH$_2$CH$_2$F | Me | |
| 194 | OC(O)NR' | CF$_3$ | Me | |
| 195 | OC(O)NR' | CH$_2$CF$_3$ | Me | |
| 196 | OC(O)NR' | CH$_2$CN | Me | |
| 197 | OC(O)NR' | cyclopropyl | Me | |
| 198 | OC(O)NR' | cyclopropylmethyl | Me | |
| 199 | OC(O)NR' | CH$_2$CO$_2$Me | Me | |
| 200 | OC(O)NR' | CH$_2$CH$_2$NMe$_2$ | Me | |
| 201 | OC(O)NR' | CH$_2$-(N-morpholinyl) | Me | |
| 202 | OC(O)NR' | 2-chloropyridin-5-yl-methyl | Me | |
| 203 | OC(O)NR' | n-Hex | Me | |
| 204 | OC(O)NR' | 2-furanyl | Me | |

TABLE 4-continued

Structure: 4-CF3-pyridin-3-yl connected to 1,2,4-oxadiazole with CH2—CH(CH3)—Y—R substituent

| Ex. No. | Y | R | R' | m.p. [° C.] |
|---|---|---|---|---|
| 205 | OC(O)NR' | 2-pyrimidinyl | Me | |
| 206 | OC(O)NR' | 2-oxazolyl | Me | |
| 207 | OC(O)NR' | 5-[1,2,4]-oxadiazolyl | Me | |
| 208 | OC(O)NR' | tetrazolyl | Me | |
| 209 | OC(O)NR' | H | Et | |
| 210 | OC(O)NR' | Me | Et | |
| 211 | OC(O)NR' | Et | Et | |
| 212 | OC(O)NR' | n-Pr | Et | |
| 213 | OC(O)NR' | i-Pr | Et | |
| 214 | OC(O)NR' | n-Bu | Et | |
| 215 | OC(O)NR' | i-Bu | Et | |
| 216 | OC(O)NR' | allyl | Et | |
| 217 | OC(O)NR' | CH$_2$C≡CH | Et | |
| 218 | OC(O)NR' | CH=CH$_2$ | Et | |
| 219 | OC(O)NR' | CH$_2$CH$_2$F | Et | |
| 220 | OC(O)NR' | CF$_3$ | Et | |
| 221 | OC(O)NR' | CH$_2$CF$_3$ | Et | |
| 222 | OC(O)NR' | CH$_2$CN | Et | |
| 223 | OC(O)NR' | cyclopropyl | Et | |
| 224 | OC(O)NR' | cyclopropylmethyl | Et | |
| 225 | OC(O)NR' | CH$_2$CO$_2$Me | Et | |
| 226 | OC(O)NR' | CH$_2$CH$_2$NMe$_2$ | Et | |
| 227 | OC(O)NR' | CH$_2$-(N-morpholinyl) | Et | |
| 228 | OC(O)NR' | 2-chloropyridin-5-yl-methyl | Et | |
| 229 | OC(O)NR' | 2-furanyl | Et | |
| 230 | OC(O)NR' | 2-pyrimidinyl | Et | |
| 231 | OC(O)NR' | 2-oxazolyl | Et | |
| 232 | OC(O)NR' | 5-[1,2,4]-oxadiazolyl | Et | |
| 234 | OC(O)NR' | tetrazolyl | Et | |
| 235 | OC(O)NR' | n-Hex | Et | |
| 236 | OC(O)C(O)O | cyclobutyl | | |
| 237 | OC(O)C(O)O | Me | | |
| 238 | OC(O)C(O)O | Et | | |
| 239 | OC(O)C(O)O | n-Pr | | |
| 240 | OC(O)C(O)O | i-Pr | | |
| 241 | OC(O)C(O)O | n-Bu | | |
| 242 | OC(O)C(O)O | i-Bu | | |
| 243 | OC(O)C(O)O | allyl | | |
| 244 | OC(O)C(O)O | CH$_2$C≡CH | | |
| 245 | OC(O)C(O)O | CH=CH$_2$ | | |
| 246 | OC(O)C(O)O | CH$_2$CH$_2$F | | |
| 247 | OC(O)C(O)O | CF$_3$ | | |
| 248 | OC(O)C(O)O | CH$_2$CF$_3$ | | |
| 249 | OC(O)C(O)O | CH$_2$CN | | |
| 250 | OC(O)C(O)O | cyclopropyl | | |
| 251 | OC(O)C(O)O | cyclopropylmethyl | | |
| 252 | OC(O)C(O)O | CH$_2$CO$_2$Me | | |
| 253 | OC(O)C(O)O | CH$_2$CH$_2$NMe$_2$ | | |
| 254 | OC(O)C(O)O | CH$_2$-(N-morpholinyl) | | |
| 255 | OC(O)C(O)O | 2-chloropyridin-5-yl-methyl | | |
| 256 | OC(O)C(O)O | n-Hex | | |
| 257 | OC(O)C(O)O | furanyl | | |
| 258 | OC(O)C(O)O | 2-pyrimidinyl | | |
| 259 | OC(O)C(O)O | 2-oxazolyl | | |
| 260 | OC(O)C(O)O | 5-[1,2,4]-oxadiazolyl | | |
| 261 | OC(O)C(O)O | tetrazolyl | | |
| 262 | S(O)$_2$NR' | H | H | |
| 263 | S(O)$_2$NR' | Me | H | |
| 264 | S(O)$_2$NR' | Et | H | |
| 265 | S(O)$_2$NR' | n-Pr | H | |
| 266 | S(O)$_2$NR' | i-Pr | H | |
| 267 | S(O)$_2$NR' | n-Bu | H | |
| 268 | S(O)$_2$NR' | i-Bu | H | |
| 269 | S(O)$_2$NR' | allyl | H | |
| 270 | S(O)$_2$NR' | CH$_2$C≡CH | H | |
| 271 | S(O)$_2$NR' | CH=CH$_2$ | H | |
| 272 | S(O)$_2$NR' | CH$_2$CH$_2$F | H | |
| 273 | S(O)$_2$NR' | CF$_3$ | H | |
| 274 | S(O)$_2$NR' | CH$_2$CF$_3$ | H | |
| 275 | S(O)$_2$NR' | CH$_2$CN | H | |
| 276 | S(O)$_2$NR' | cyclopropyl | H | |
| 277 | S(O)$_2$NR' | cyclopropylmethyl | H | |
| 278 | S(O)$_2$NR' | CH$_2$CO$_2$Me | H | |
| 279 | S(O)$_2$NR' | CH$_2$CH$_2$NMe$_2$ | H | |
| 280 | S(O)$_2$NR' | CH$_2$-(N-morpholinyl) | H | |
| 281 | S(O)$_2$NR' | 2-chloropyridin-5-yl-methyl | H | |
| 282 | S(O)$_2$NR' | n-Hex | H | |
| 283 | S(O)$_2$NR' | 2-furanyl | H | |
| 284 | S(O)$_2$NR' | 2-pyrimidinyl | H | |
| 285 | S(O)$_2$NR' | 2-oxazolyl | H | |
| 286 | S(O)$_2$NR' | 5-[1,2,4]-oxadiazolyl | H | |
| 287 | S(O)$_2$NR' | tetrazolyl | H | |
| 288 | S(O)$_2$NR' | H | Me | |
| 289 | S(O)$_2$NR' | Me | Me | |
| 290 | S(O)$_2$NR' | Et | Me | |
| 300 | S(O)$_2$NR' | n-Pr | Me | |
| 301 | S(O)$_2$NR' | i-Pr | Me | |
| 302 | S(O)$_2$NR' | n-Bu | Me | |
| 303 | S(O)$_2$NR' | i-Bu | Me | |
| 304 | S(O)$_2$NR' | allyl | Me | |
| 305 | S(O)$_2$NR' | CH$_2$C≡CH | Me | |
| 306 | S(O)$_2$NR' | CH=CH$_2$ | Me | |
| 307 | S(O)$_2$NR' | CH$_2$CH$_2$F | Me | |
| 308 | S(O)$_2$NR' | CF$_3$ | Me | |
| 309 | S(O)$_2$NR' | CH$_2$CF$_3$ | Me | |
| 310 | S(O)$_2$NR' | CH$_2$CN | Me | |
| 311 | S(O)$_2$NR' | cyclopropyl | Me | |
| 312 | S(O)$_2$NR' | cyclopropylmethyl | Me | |
| 313 | S(O)$_2$NR' | CH$_2$CO$_2$Me | Me | |
| 314 | S(O)$_2$NR' | CH$_2$CH$_2$NMe$_2$ | Me | |
| 315 | S(O)$_2$NR' | CH$_2$-(N-morpholinyl) | Me | |
| 316 | S(O)$_2$NR' | 2-chloropyridin-5-yl-methyl | Me | |
| 317 | S(O)$_2$NR' | n-Hex | Me | |
| 318 | S(O)$_2$NR' | 2-furanyl | Me | |
| 319 | S(O)$_2$NR' | 2-pyrimidinyl | Me | |
| 320 | S(O)$_2$NR' | 2-oxazolyl | Me | |
| 321 | S(O)$_2$NR' | 5-[1,2,4]-oxadiazolyl | Me | |
| 322 | S(O)$_2$NR' | tetrazolyl | Me | |
| 323 | S(O)$_2$NR' | H | Et | |
| 324 | S(O)$_2$NR' | Me | Et | |
| 325 | S(O)$_2$NR' | Et | Et | |
| 326 | S(O)$_2$NR' | n-Pr | Et | |
| 327 | S(O)$_2$NR' | i-Pr | Et | |
| 328 | S(O)$_2$NR' | n-Bu | Et | |
| 329 | S(O)$_2$NR' | i-Bu | Et | |
| 330 | S(O)$_2$NR' | allyl | Et | |
| 331 | S(O)$_2$NR' | CH$_2$C≡CH | Et | |
| 332 | S(O)$_2$NR' | CH=CH$_2$ | Et | |
| 333 | S(O)$_2$NR' | CH$_2$CH$_2$F | Et | |
| 334 | S(O)$_2$NR' | CF$_3$ | Et | |
| 335 | S(O)$_2$NR' | CH$_2$CF$_3$ | Et | |
| 336 | S(O)$_2$NR' | CH$_2$CN | Et | |
| 337 | S(O)$_2$NR' | cyclopropyl | Et | |
| 338 | S(O)$_2$NR' | cyclopropylmethyl | Et | |
| 339 | S(O)$_2$NR' | CH$_2$CO$_2$Me | Et | |
| 340 | S(O)$_2$NR' | CH$_2$CH$_2$NMe$_2$ | Et | |
| 341 | S(O)$_2$NR' | CH$_2$-(N-morpholinyl) | Et | |
| 342 | S(O)$_2$NR' | 2-chloropyridin-5-yl-methyl | Et | |
| 344 | S(O)$_2$NR' | n-Hex | Et | |
| 345 | S(O)$_2$NR' | 2-furanyl | Et | |
| 346 | S(O)$_2$NR' | 2-pyrimidinyl | Et | |
| 347 | S(O)$_2$NR' | 2-oxazolyl | Et | |

TABLE 4-continued

Structure: 4-CF3-pyridin-3-yl-[1,2,4]oxadiazole with CH2—CH(CH3)—Y—R substituent

| Ex. No. | Y | R | R' | m.p. [° C.] |
|---|---|---|---|---|
| 348 | S(O)₂NR' | 5-[1,2,4]-oxadiazolyl | Et | |
| 349 | S(O)₂NR' | tetrazolyl | Et | |

TABLE 5

Structure: 4-CF3-pyridin-3-yl-[1,2,4]oxadiazole with CH2—C(CH3)2—Y—R substituent

| Ex. No. | Y | R | R' | m.p. [° C.] |
|---|---|---|---|---|
| 1 | O | H | | |
| 2 | O | Me | | |
| 3 | O | Et | | |
| 4 | O | n-Pr | | |
| 5 | O | i-Pr | | |
| 6 | O | n-Bu | | |
| 7 | O | i-Bu | | |
| 8 | O | allyl | | |
| 9 | O | CH₂C≡CH | | |
| 10 | O | CH=CH₂ | | |
| 11 | O | CH₂CH₂F | | |
| 12 | O | CF₃ | | |
| 13 | O | CH₂CF₃ | | |
| 14 | O | CH₂CN | | |
| 15 | O | cyclopropyl | | |
| 16 | O | cyclopropylmethyl | | |
| 17 | O | CH₂CO₂Me | | |
| 18 | O | CH₂CH₂NMe₂ | | |
| 19 | O | CH₂-(N-morpholinyl) | | |
| 20 | O | 2-chloropyridin-5-yl-methyl | | |
| 21 | O | n-Hex | | |
| 22 | O | 2-furanyl | | |
| 23 | O | 2-pyrimidinyl | | |
| 24 | O | 2-oxazolyl | | |
| 25 | O | 5-[1,2,4]-oxadiazolyl | | |
| 26 | O | tetrazolyl | | |
| 27 | S | H | | |
| 28 | S | Me | | |
| 29 | S | Et | | |
| 30 | S | n-Pr | | |
| 31 | S | i-Pr | | |
| 32 | S | n-Bu | | |
| 33 | S | i-Bu | | |
| 33 | S | allyl | | |
| 34 | S | CH₂C≡CH | | |
| 35 | S | tetrazolyl | | |
| 36 | S | CH=CH₂ | | |
| 37 | S | CH₂CH₂F | | |
| 38 | S | CF₃ | | |
| 39 | S | CH₂CF₃ | | |
| 40 | S | CH₂CN | | |
| 41 | S | cyclopropyl | | |
| 42 | S | cyclopropylmethyl | | |
| 43 | S | CH₂CO₂Me | | |
| 44 | S | CH₂CH₂NMe₂ | | |
| 45 | S | CH₂-(N-morpholinyl) | | |
| 46 | S | 2-chloropyridin-5-yl-methyl | | |
| 47 | S | n-Hex | | |
| 48 | S | 2-furanyl | | |
| 49 | S | 2-pyrimidinyl | | |
| 50 | S | 2-oxazolyl | | |
| 51 | S | 5-[1,2,4]-oxadiazolyl | | |
| 51a | S | tetrazolyl | | |
| 52 | S(O) | cyclobutyl | | |
| 53 | S(O) | Me | | |
| 54 | S(O) | Et | | |
| 55 | S(O) | n-Pr | | |
| 56 | S(O) | i-Pr | | |
| 57 | S(O) | n-Bu | | |
| 58 | S(O) | i-Bu | | |
| 59 | S(O) | allyl | | |
| 60 | S(O) | CH₂C≡CH | | |
| 61 | S(O) | CH=CH₂ | | |
| 62 | S(O) | CH₂CH₂F | | |
| 63 | S(O) | CF₃ | | |
| 64 | S(O) | CH₂CF₃ | | |
| 65 | S(O) | CH₂CN | | |
| 66 | S(O) | cyclopropyl | | |
| 67 | S(O) | cyclopropylmethyl | | |
| 68 | S(O) | CH₂CO₂Me | | |
| 69 | S(O) | CH₂CH₂NMe₂ | | |
| 70 | S(O) | CH₂-(N-morpholinyl) | | |
| 71 | S(O) | 2-chloropyridin-5-yl-methyl | | |
| 72 | S(O) | n-Hex | | |
| 73 | S(O) | 2-furanyl | | |
| 74 | S(O) | 2-pyrimidinyl | | |
| 75 | S(O) | 2-oxazolyl | | |
| 76 | S(O) | 5-[1,2,4]-oxadiazolyl | | |
| 77 | S(O) | tetrazolyl | | |
| 78 | S(O)₂ | cyclobutyl | | |
| 79 | S(O)₂ | Me | | |
| 80 | S(O)₂ | Et | | |
| 81 | S(O)₂ | n-Pr | | |
| 82 | S(O)₂ | i-Pr | | |
| 83 | S(O)₂ | n-Bu | | |
| 84 | S(O)₂ | i-Bu | | |
| 85 | S(O)₂ | allyl | | |
| 86 | S(O)₂ | CH₂C≡CH | | |
| 87 | S(O)₂ | CH=CH₂ | | |
| 88 | S(O)₂ | CH₂CH₂F | | |
| 89 | S(O)₂ | CF₃ | | |
| 90 | S(O)₂ | CH₂CF₃ | | |
| 91 | S(O)₂ | CH₂CN | | |
| 92 | S(O)₂ | cyclopropyl | | |
| 93 | S(O)₂ | cyclopropylmethyl | | |
| 94 | S(O)₂ | CH₂CO₂Me | | |
| 95 | S(O)₂ | CH₂CH₂NMe₂ | | |
| 96 | S(O)₂ | CH₂-(N-morpholinyl) | | |
| 97 | S(O)₂ | 2-chloropyridin-5-yl-methyl | | |
| 98 | S(O)₂ | n-Hex | | |
| 99 | S(O)₂ | 2-furanyl | | |
| 100 | S(O)₂ | 2-pyrimidinyl | | |
| 101 | S(O)₂ | 2-oxazolyl | | |
| 102 | S(O)₂ | 5-[1,2,4]-oxadiazolyl | | |
| 103 | S(O)₂ | tetrazolyl | | |
| 104 | OC(O) | H | | |
| 105 | OC(O) | Me | | |
| 106 | OC(O) | Et | | |
| 107 | OC(O) | n-Pr | | |
| 108 | OC(O) | i-Pr | | |
| 109 | OC(O) | n-Bu | | |
| 110 | OC(O) | i-Bu | | |

TABLE 5-continued

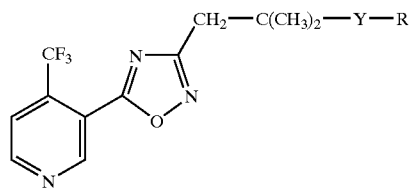

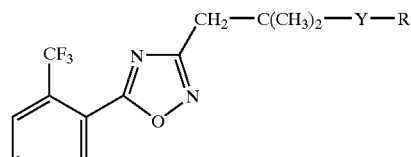

| Ex. No. | Y | R | R' | m.p. [° C.] |
|---|---|---|---|---|
| 111 | OC(O) | allyl | | |
| 112 | OC(O) | CH₂C≡CH | | |
| 113 | OC(O) | CH=CH₂ | | |
| 114 | OC(O) | CH₂CH₂F | | |
| 115 | OC(O) | CF₃ | | |
| 116 | OC(O) | CH₂CF₃ | | |
| 117 | OC(O) | CH₂CN | | |
| 118 | OC(O) | cyclopropyl | | |
| 119 | OC(O) | cyclopropylmethyl | | |
| 120 | OC(O) | CH₂CO₂Me | | |
| 121 | OC(O) | CH₂CH₂NMe₂ | | |
| 122 | OC(O) | CH₂-(N-morpholinyl) | | |
| 123 | OC(O) | 2-chloropyridin-5-yl-methyl | | |
| 124 | OC(O) | n-Hex | | |
| 125 | OC(O) | 2-furanyl | | |
| 126 | OC(O) | 2-pyrimidinyl | | |
| 127 | OC(O) | 2-oxazolyl | | |
| 128 | OC(O) | 5-[1,2,4]-oxadiazolyl | | |
| 129 | OC(O) | tetrazolyl | | |
| 130 | OC(O)O | cyclobutyl | | |
| 131 | OC(O)O | Me | | |
| 132 | OC(O)O | Et | | |
| 133 | OC(O)O | n-Pr | | |
| 134 | OC(O)O | i-Pr | | |
| 135 | OC(O)O | n-Bu | | |
| 136 | OC(O)O | i-Bu | | |
| 137 | OC(O)O | allyl | | |
| 138 | OC(O)O | CH₂C≡CH | | |
| 139 | OC(O)O | CH=CH₂ | | |
| 140 | OC(O)O | CH₂CH₂F | | |
| 141 | OC(O)O | CF₃ | | |
| 142 | OC(O)O | CH₂CF₃ | | |
| 143 | OC(O)O | CH₂CN | | |
| 144 | OC(O)O | cyclopropyl | | |
| 145 | OC(O)O | cyclopropylmethyl | | |
| 146 | OC(O)O | CH₂CO₂Me | | |
| 147 | OC(O)O | CH₂CH₂NMe₂ | | |
| 148 | OC(O)O | CH₂-(N-morpholinyl) | | |
| 149 | OC(O)O | 2-chloropyridin-5-yl-methyl | | |
| 150 | OC(O)O | n-Hex | | |
| 151 | OC(O)O | 2-furanyl | | |
| 152 | OC(O)O | 2-pyrimidinyl | | |
| 153 | OC(O)O | 2-oxazolyl | | |
| 154 | OC(O)O | 5-[1,2,4]-oxadiazolyl | | |
| 155 | OC(O)O | tetrazolyl | | |
| 156 | OC(O)NR' | H | H | |
| 157 | OC(O)NR' | Me | H | |
| 158 | OC(O)NR' | Et | H | |
| 159 | OC(O)NR' | n-Pr | H | |
| 160 | OC(O)NR' | i-Pr | H | |
| 161 | OC(O)NR' | n-Bu | H | |
| 162 | OC(O)NR' | i-Bu | H | |
| 163 | OC(O)NR' | allyl | H | |
| 164 | OC(O)NR' | CH₂C≡CH | H | |
| 165 | OC(O)NR' | CH=CH₂ | H | |
| 166 | OC(O)NR' | CH₂CH₂F | H | |
| 167 | OC(O)NR' | CF₃ | H | |
| 168 | OC(O)NR' | CH₂CF₃ | H | |
| 169 | OC(O)NR' | CH₂CN | H | |
| 170 | OC(O)NR' | cyclopropyl | H | |
| 171 | OC(O)NR' | cyclopropylmethyl | H | |
| 172 | OC(O)NR' | CH₂CO₂Me | H | |
| 173 | OC(O)NR' | CH₂CH₂NMe₂ | H | |
| 174 | OC(O)NR' | CH₂-(N-morpholinyl) | H | |
| 175 | OC(O)NR' | 2-chloropyridin-5-yl-methyl | H | |
| 176 | OC(O)NR' | n-Hex | H | |
| 177 | OC(O)NR' | 2-furanyl | H | |
| 178 | OC(O)NR' | 2-pyrimidinyl | H | |
| 179 | OC(O)NR' | 2-oxazolyl | H | |
| 180 | OC(O)NR' | 5-[1,2,4]-oxadiazolyl | H | |
| 181 | OC(O)NR' | tetrazolyl | H | |
| 182 | OC(O)NR' | H | Me | |
| 183 | OC(O)NR' | Me | Me | |
| 184 | OC(O)NR' | Et | Me | |
| 185 | OC(O)NR' | n-Pr | Me | |
| 186 | OC(O)NR' | i-Pr | Me | |
| 187 | OC(O)NR' | n-Bu | Me | |
| 188 | OC(O)NR' | i-Bu | Me | |
| 189 | OC(O)NR' | allyl | Me | |
| 190 | OC(O)NR' | CH₂C≡CH | Me | |
| 200 | OC(O)NR' | CH=CH₂ | Me | |
| 201 | OC(O)NR' | CH₂CH₂F | Me | |
| 202 | OC(O)NR' | CF₃ | Me | |
| 203 | OC(O)NR' | CH₂CF₃ | Me | |
| 204 | OC(O)NR' | CH₂CN | Me | |
| 205 | OC(O)NR' | cyclopropyl | Me | |
| 206 | OC(O)NR' | cyclopropylmethyl | Me | |
| 207 | OC(O)NR' | CH₂CO₂Me | Me | |
| 208 | OC(O)NR' | CH₂CH₂NMe₂ | Me | |
| 209 | OC(O)NR' | CH₂-(N-morpholinyl) | Me | |
| 210 | OC(O)NR' | 2-chloropyridin-5-yl-methyl | Me | |
| 211 | OC(O)NR' | n-Hex | Me | |
| 212 | OC(O)NR' | 2-furanyl | Me | |
| 213 | OC(O)NR' | 2-pyrimidinyl | Me | |
| 214 | OC(O)NR' | 2-oxazolyl | Me | |
| 215 | OC(O)NR' | 5-[1,2,4]-oxadiazolyl | Me | |
| 216 | OC(O)NR' | tetrazolyl | Me | |
| 217 | OC(O)NR' | H | Et | |
| 218 | OC(O)NR' | Me | Et | |
| 219 | OC(O)NR' | Et | Et | |
| 220 | OC(O)NR' | n-Pr | Et | |
| 221 | OC(O)NR' | i-Pr | Et | |
| 222 | OC(O)NR' | n-Bu | Et | |
| 223 | OC(O)NR' | i-Bu | Et | |
| 224 | OC(O)NR' | allyl | Et | |
| 225 | OC(O)NR' | CH₂C≡CH | Et | |
| 226 | OC(O)NR' | CH=CH₂ | Et | |
| 227 | OC(O)NR' | CH₂CH₂F | Et | |
| 228 | OC(O)NR' | CF₃ | Et | |
| 229 | OC(O)NR' | CH₂CF₃ | Et | |
| 230 | OC(O)NR' | CH₂CN | Et | |
| 231 | OC(O)NR' | cyclopropyl | Et | |
| 232 | OC(O)NR' | cyclopropylmethyl | Et | |
| 233 | OC(O)NR' | CH₂CO₂Me | Et | |
| 234 | OC(O)NR' | CH₂CH₂NMe₂ | Et | |
| 235 | OC(O)NR' | CH₂-(N-morpholinyl) | Et | |
| 236 | OC(O)NR' | 2-chloropyridin-5-yl-methyl | Et | |
| 237 | OC(O)NR' | n-Hex | Et | |
| 238 | OC(O)NR' | 2-furanyl | Et | |
| 239 | OC(O)NR' | 2-pyrimidinyl | Et | |
| 240 | OC(O)NR' | 2-oxazolyl | Et | |
| 241 | OC(O)NR' | 5-[1,2,4]-oxadiazolyl | Et | |
| 242 | OC(O)NR' | tetrazolyl | Et | |
| 243 | OC(O)C(O)O | cyclobutyl | | |
| 244 | OC(O)C(O)O | Me | | |
| 245 | OC(O)C(O)O | Et | | |
| 246 | OC(O)C(O)O | n-Pr | | |
| 247 | OC(O)C(O)O | i-Pr | | |
| 248 | OC(O)C(O)O | n-Bu | | |
| 249 | OC(O)C(O)O | i-Bu | | |
| 250 | OC(O)C(O)O | allyl | | |
| 251 | OC(O)C(O)O | CH₂C≡CH | | |

TABLE 5-continued

Structure: 4-CF3-pyridin-3-yl connected to 1,2,4-oxadiazole with CH2—C(CH3)2—Y—R substituent

| Ex. No. | Y | R | R' | m.p. [° C.] |
|---|---|---|---|---|
| 252 | OC(O)C(O)O | CH=CH2 | | |
| 253 | OC(O)C(O)O | CH2CH2F | | |
| 254 | OC(O)C(O)O | CF3 | | |
| 255 | OC(O)C(O)O | CH2CF3 | | |
| 256 | OC(O)C(O)O | CH2CN | | |
| 257 | OC(O)C(O)O | cyclopropyl | | |
| 258 | OC(O)C(O)O | cyclopropylmethyl | | |
| 259 | OC(O)C(O)O | CH2CO2Me | | |
| 260 | OC(O)C(O)O | CH2CH2NMe2 | | |
| 261 | OC(O)C(O)O | CH2-(N-morpholinyl) | | |
| 262 | OC(O)C(O)O | 2-chloropyridin-5-yl-methyl | | |
| 263 | OC(O)C(O)O | n-Hex | | |
| 264 | OC(O)C(O)O | 2-furanyl | | |
| 265 | OC(O)C(O)O | 2-pyrimidinyl | | |
| 266 | OC(O)C(O)O | 2-oxazolyl | | |
| 267 | OC(O)C(O)O | 5-[1,2,4]-oxadiazolyl | | |
| 268 | OC(O)C(O)O | tetrazolyl | | |
| 269 | S(O)2NR' | H | Me | |
| 270 | S(O)2NR' | Me | Me | |
| 271 | S(O)2NR' | Et | Me | |
| 272 | S(O)2NR' | n-Pr | Me | |
| 273 | S(O)2NR' | i-Pr | Me | |
| 274 | S(O)2NR' | n-Bu | Me | |
| 275 | S(O)2NR' | i-Bu | Me | |
| 276 | S(O)2NR' | allyl | Me | |
| 277 | S(O)2NR' | CH2C≡CH | Me | |
| 278 | S(O)2NR' | CH=CH2 | Me | |
| 279 | S(O)2NR' | CH2CH2F | Me | |
| 280 | S(O)2NR' | CF3 | Me | |
| 281 | S(O)2NR' | CH2CF3 | Me | |
| 282 | S(O)2NR' | CH2CN | Me | |
| 283 | S(O)2NR' | cyclopropyl | Me | |
| 284 | S(O)2NR' | cyclopropylmethyl | Me | |
| 285 | S(O)2NR' | CH2CO2Me | Me | |
| 286 | S(O)2NR' | CH2CH2NMe2 | Me | |
| 287 | S(O)2NR' | CH2-(N-morpholinyl) | Me | |
| 288 | S(O)2NR' | 2-chloropyridin-5-yl-methyl | Me | |
| 289 | S(O)2NR' | n-Hex | Me | |
| 290 | S(O)2NR' | 2-furanyl | Me | |
| 291 | S(O)2NR' | 2-pyrimidinyl | Me | |
| 292 | S(O)2NR' | 2-oxazolyl | Me | |
| 293 | S(O)2NR' | 5-[1,2,4]-oxadiazolyl | Me | |
| 294 | S(O)2NR' | tetrazolyl | Me | |
| 295 | S(O)2NR' | H | Et | |
| 296 | S(O)2NR' | Me | Et | |
| 297 | S(O)2NR' | Et | Et | |
| 298 | S(O)2NR' | n-Pr | Et | |
| 299 | S(O)2NR' | i-Pr | Et | |
| 300 | S(O)2NR' | n-Bu | Et | |
| 301 | S(O)2NR' | i-Bu | Et | |
| 302 | S(O)2NR' | allyl | Et | |
| 303 | S(O)2NR' | CH2C≡CH | Et | |
| 304 | S(O)2NR' | CH=CH2 | Et | |
| 305 | S(O)2NR' | CH2CH2F | Et | |
| 306 | S(O)2NR' | CF3 | Et | |
| 307 | S(O)2NR' | CH2CF3 | Et | |
| 308 | S(O)2NR' | CH2CN | Et | |
| 309 | S(O)2NR' | cyclopropyl | Et | |
| 310 | S(O)2NR' | cyclopropylmethyl | Et | |
| 311 | S(O)2NR' | CH2CO2Me | Et | |
| 312 | S(O)2NR' | CH2CH2NMe2 | Et | |
| 313 | S(O)2NR' | CH2-(N-morpholinyl) | Et | |
| 314 | S(O)2NR' | 2-chloropyridin-5-yl-methyl | Et | |
| 315 | S(O)2NR' | n-Hex | Et | |
| 316 | S(O)2NR' | 2-furanyl | Et | |
| 317 | S(O)2NR' | 2-pyrimidinyl | Et | |
| 318 | S(O)2NR' | 2-oxazolyl | Et | |
| 319 | S(O)2NR' | 5-[1,2,4]-oxadiazolyl | Et | |
| 320 | S(O)2NR' | tetrazolyl | Et | |

TABLE 6

Structure: 4-CF3-pyridin-3-yl connected to 1,2,4-oxadiazole with (CH2)3—Y—R substituent

| Ex. No. | Y | R | R' | m.p. [° C.] |
|---|---|---|---|---|
| 1 | O | H | | |
| 2 | O | Me | | |
| 3 | O | Et | | |
| 4 | O | n-Pr | | |
| 5 | O | i-Pr | | |
| 6 | O | n-Bu | | |
| 7 | O | i-Bu | | |
| 8 | O | allyl | | |
| 9 | O | CH2C≡CH | | |
| 10 | O | CH=CH2 | | |
| 11 | O | CH2CH2F | | |
| 12 | O | CF3 | | |
| 13 | O | CH2CF3 | | |
| 14 | O | CH2CN | | |
| 15 | O | cyclopropyl | | |
| 16 | O | cyclopropylmethyl | | |
| 17 | O | CH2CO2Me | | |
| 18 | O | CH2CH2NMe2 | | |
| 19 | O | CH2-(N-morpholinyl) | | |
| 20 | O | 2-chloropyridin-5-yl-methyl | | |
| 21 | O | 2-furanyl | | |
| 22 | O | 2-pyrimidinyl | | |
| 23 | O | 2-oxazolyl | | |
| 24 | O | 5-[1,2,4]-oxadiazolyl | | |
| 25 | O | tetrazolyl | | |
| 26 | S | H | | |
| 27 | S | Me | | |
| 28 | S | Et | | |
| 29 | S | n-Pr | | |
| 30 | S | i-Pr | | |
| 31 | S | n-Bu | | |
| 32 | S | i-Bu | | |
| 33 | S | allyl | | |
| 34 | S | CH2C≡CH | | |
| 35 | S | CH=CH2 | | |
| 36 | S | CH2CH2F | | |
| 37 | S | CF3 | | |
| 38 | S | CH2CF3 | | |
| 39 | S | CH2CN | | |
| 40 | S | cyclopropyl | | |
| 41 | S | cyclopropylmethyl | | |
| 42 | S | CH2CO2Me | | |
| 43 | S | CH2CH2NMe2 | | |
| 44 | S | CH2-(N-morpholinyl) | | |
| 45 | S | 2-chloropyridin-5-yl-methyl | | |

TABLE 6-continued

Structure: CF₃-pyridine connected to 1,2,4-oxadiazole with (CH₂)₃—Y—R substituent

| Ex. No. | Y | R | R' | m.p. [° C.] |
|---|---|---|---|---|
| 46 | S | 2-furanyl | | |
| 47 | S | 2-pyrimidinyl | | |
| 48 | S | 2-oxazolyl | | |
| 49 | S | 5-[1,2,4]-oxadiazolyl | | |
| 50 | S | tetrazolyl | | |
| 51 | S(O) | n-Hex | | |
| 52 | S(O) | Me | | |
| 53 | S(O) | Et | | |
| 54 | S(O) | n-Pr | | |
| 55 | S(O) | i-Pr | | |
| 56 | S(O) | n-Bu | | |
| 57 | S(O) | i-Bu | | |
| 58 | S(O) | allyl | | |
| 59 | S(O) | CH₂C≡CH | | |
| 60 | S(O) | CH=CH₂ | | |
| 61 | S(O) | CH₂CH₂F | | |
| 62 | S(O) | CF₃ | | |
| 63 | S(O) | CH₂CF₃ | | |
| 64 | S(O) | CH₂CN | | |
| 65 | S(O) | cyclopropyl | | |
| 66 | S(O) | cyclopropylmethyl | | |
| 67 | S(O) | CH₂CO₂Me | | |
| 68 | S(O) | CH₂CH₂NMe₂ | | |
| 69 | S(O) | CH₂—(N-morpholinyl) | | |
| 70 | S(O) | 2-chloropyridin-5-yl-methyl | | |
| 71 | S(O) | 2-furanyl | | |
| 72 | S(O) | 2-pyrimidinyl | | |
| 73 | S(O) | 2-oxazolyl | | |
| 74 | S(O) | 5-[1,2,4]-oxadiazolyl | | |
| 75 | S(O) | tetrazolyl | | |
| 76 | S(O)₂ | n-Hex | | |
| 77 | S(O)₂ | Me | | |
| 78 | S(O)₂ | Et | | |
| 79 | S(O)₂ | n-Pr | | |
| 80 | S(O)₂ | i-Pr | | |
| 81 | S(O)₂ | n-Bu | | |
| 82 | S(O)₂ | i-Bu | | |
| 83 | S(O)₂ | allyl | | |
| 84 | S(O)₂ | CH₂C≡CH | | |
| 85 | S(O)₂ | CH=CH₂ | | |
| 86 | S(O)₂ | CH₂CH₂F | | |
| 87 | S(O)₂ | CF₃ | | |
| 88 | S(O)₂ | CH₂CF₃ | | |
| 89 | S(O)₂ | CH₂CN | | |
| 90 | S(O)₂ | cyclopropyl | | |
| 91 | S(O)₂ | cyclopropylmethyl | | |
| 92 | S(O)₂ | CH₂CO₂Me | | |
| 93 | S(O)₂ | CH₂CH₂NMe₂ | | |
| 94 | S(O)₂ | CH₂—(N-morpholinyl) | | |
| 95 | S(O)₂ | 2-chloropyridin-5-yl-methyl | | |
| 96 | S(O)₂ | 2-furanyl | | |
| 97 | S(O)₂ | 2-pyrimidinyl | | |
| 98 | S(O)₂ | 2-oxazolyl | | |
| 99 | S(O)₂ | 5-[1,2,4]-oxadiazolyl | | |
| 100 | S(O)₂ | tetrazolyl | | |
| 101 | OC(O) | H | | |
| 102 | OC(O) | Me | | |
| 103 | OC(O) | Et | | |
| 104 | OC(O) | n-Pr | | |
| 105 | OC(O) | i-Pr | | |
| 106 | OC(O) | n-Bu | | |
| 107 | OC(O) | i-Bu | | |
| 108 | OC(O) | allyl | | |
| 109 | OC(O) | CH₂C≡CH | | |
| 110 | OC(O) | CH=CH₂ | | |
| 111 | OC(O) | CH₂CH₂F | | |
| 112 | OC(O) | CF₃ | | |
| 113 | OC(O) | CH₂CF₃ | | |
| 114 | OC(O) | CH₂CN | | |
| 115 | OC(O) | cyclopropyl | | |
| 116 | OC(O) | cyclopropylmethyl | | |
| 117 | OC(O) | CH₂CO₂Me | | |
| 118 | OC(O) | CH₂CH₂NMe₂ | | |
| 119 | OC(O) | CH₂—(N-morpholinyl) | | |
| 120 | OC(O) | 2-chloropyridin-5-yl-methyl | | |
| 121 | OC(O) | 2-furanyl | | |
| 122 | OC(O) | 2-pyrimidinyl | | |
| 123 | OC(O) | 2-oxazolyl | | |
| 124 | OC(O) | 5-[1,2,4]-oxadiazolyl | | |
| 125 | OC(O) | tetrazolyl | | |
| 126 | OC(O)O | n-Hex | | |
| 127 | OC(O)O | Me | | |
| 128 | OC(O)O | Et | | |
| 129 | OC(O)O | n-Pr | | |
| 130 | OC(O)O | i-Pr | | |
| 131 | OC(O)O | n-Bu | | |
| 132 | OC(O)O | i-Bu | | |
| 133 | OC(O)O | allyl | | |
| 134 | OC(O)O | CH₂C≡CH | | |
| 135 | OC(O)O | CH=CH₂ | | |
| 136 | OC(O)O | CH₂CH₂F | | |
| 137 | OC(O)O | CF₃ | | |
| 138 | OC(O)O | CH₂CF₃ | | |
| 139 | OC(O)O | CH₂CN | | |
| 140 | OC(O)O | cyclopropyl | | |
| 141 | OC(O)O | cyclopropylmethyl | | |
| 142 | OC(O)O | CH₂CO₂Me | | |
| 143 | OC(O)O | CH₂CH₂NMe₂ | | |
| 144 | OC(O)O | CH₂—(N-morpholinyl) | | |
| 145 | OC(O)O | 2-chloropyridin-5-yl-methyl | | |
| 146 | OC(O)O | 2-furanyl | | |
| 147 | OC(O)O | 2-pyrimidinyl | | |
| 148 | OC(O)O | 2-oxazolyl | | |
| 149 | OC(O)O | 5-[1,2,4]-oxadiazolyl | | |
| 150 | OC(O)O | tetrazolyl | | |
| 151 | OC(O)NR' | H | H | |
| 152 | OC(O)NR' | Me | H | |
| 153 | OC(O)NR' | Et | H | |
| 154 | OC(O)NR' | n-Pr | H | |
| 155 | OC(O)NR' | i-Pr | H | |
| 156 | OC(O)NR' | n-Bu | H | |
| 157 | OC(O)NR' | i-Bu | H | |
| 158 | OC(O)NR' | allyl | H | |
| 159 | OC(O)NR' | CH₂C≡CH | H | |
| 160 | OC(O)NR' | CH=CH₂ | H | |
| 161 | OC(O)NR' | CH₂CH₂F | H | |
| 162 | OC(O)NR' | CF₃ | H | |
| 163 | OC(O)NR' | CH₂CF₃ | H | |
| 164 | OC(O)NR' | CH₂CN | H | |
| 165 | OC(O)NR' | cyclopropyl | H | |
| 166 | OC(O)NR' | cyclopropylmethyl | H | |
| 167 | OC(O)NR' | CH₂CO₂Me | H | |
| 168 | OC(O)NR' | CH₂CH₂NMe₂ | H | |
| 169 | OC(O)NR' | CH₂—(N-morpholinyl) | H | |
| 170 | OC(O)NR' | 2-chloropyridin-5-yl-methyl | H | |
| 171 | OC(O)NR' | 2-furanyl | H | |
| 172 | OC(O)NR' | 2-pyrimidinyl | H | |
| 173 | OC(O)NR' | 2-oxazolyl | H | |
| 174 | OC(O)NR' | 5-[1,2,4]-oxadiazolyl | H | |
| 175 | OC(O)NR' | tetrazolyl | H | |
| 176 | OC(O)NR' | H | Me | |
| 177 | OC(O)NR' | Me | Me | |

TABLE 6-continued

| Ex. No. | Y | R | R' | m.p. [° C.] |
|---|---|---|---|---|
| 178 | OC(O)NR' | Et | Me | |
| 179 | OC(O)NR' | n-Pr | Me | |
| 180 | OC(O)NR' | i-Pr | Me | |
| 181 | OC(O)NR' | n-Bu | Me | |
| 182 | OC(O)NR' | i-Bu | Me | |
| 183 | OC(O)NR' | allyl | Me | |
| 184 | OC(O)NR' | CH$_2$C≡CH | Me | |
| 185 | OC(O)NR' | CH=CH$_2$ | Me | |
| 186 | OC(O)NR' | CH$_2$CH$_2$F | Me | |
| 187 | OC(O)NR' | CF$_3$ | Me | |
| 188 | OC(O)NR' | CH$_2$CF$_3$ | Me | |
| 189 | OC(O)NR' | CH$_2$CN | Me | |
| 190 | OC(O)NR' | cyclopropyl | Me | |
| 191 | OC(O)NR' | cyclopropylmethyl | Me | |
| 192 | OC(O)NR' | CH$_2$CO$_2$Me | Me | |
| 193 | OC(O)NR' | CH$_2$CH$_2$NMe$_2$ | Me | |
| 194 | OC(O)NR' | CH$_2$—(N-morpholinyl) | Me | |
| 195 | OC(O)NR' | 2-chloropyridin-5-yl-methyl | Me | |
| 196 | OC(O)NR' | furanyl | Me | |
| 197 | OC(O)NR' | 2-pyrimidinyl | Me | |
| 198 | OC(O)NR' | 2-oxazolyl | Me | |
| 199 | OC(O)NR' | 5-[1,2,4]-oxadiazolyl | Me | |
| 200 | OC(O)NR' | tetrazolyl | Me | |
| 201 | OC(O)NR' | H | Et | |
| 202 | OC(O)NR' | Me | Et | |
| 203 | OC(O)NR' | Et | Et | |
| 204 | OC(O)NR' | n-Pr | Et | |
| 205 | OC(O)NR' | i-Pr | Et | |
| 206 | OC(O)NR' | n-Bu | Et | |
| 207 | OC(O)NR' | i-Bu | Et | |
| 208 | OC(O)NR' | allyl | Et | |
| 209 | OC(O)NR' | CH$_2$C≡CH | Et | |
| 210 | OC(O)NR' | CH=CH$_2$ | Et | |
| 211 | OC(O)NR' | CH$_2$CH$_2$F | Et | |
| 212 | OC(O)NR' | CF$_3$ | Et | |
| 213 | OC(O)NR' | CH$_2$CF$_3$ | Et | |
| 214 | OC(O)NR' | CH$_2$CN | Et | |
| 215 | OC(O)NR' | cyclopropyl | Et | |
| 216 | OC(O)NR' | cyclopropylmethyl | Et | |
| 217 | OC(O)NR' | CH$_2$CO$_2$Me | Et | |
| 218 | OC(O)NR' | CH$_2$CH$_2$NMe$_2$ | Et | |
| 219 | OC(O)NR' | CH$_2$—(N-morpholinyl) | Et | |
| 220 | OC(O)NR' | 2-chloropyridin-5-yl-methyl | Et | |
| 221 | OC(O)NR' | 2-furanyl | Et | |
| 222 | OC(O)NR' | 2-pyrimidinyl | Et | |
| 223 | OC(O)NR' | 2-oxazolyl | Et | |
| 224 | OC(O)NR' | 5-[1,2,4]-oxadiazolyl | Et | |
| 225 | OC(O)NR' | tetrazolyl | Et | |
| 226 | OC(O)C(O)O | n-Hex | | |
| 227 | OC(O)C(O)O | Me | | |
| 228 | OC(O)C(O)O | Et | | |
| 229 | OC(O)C(O)O | n-Pr | | |
| 230 | OC(O)C(O)O | i-Pr | | |
| 231 | OC(O)C(O)O | n-Bu | | |
| 232 | OC(O)C(O)O | i-Bu | | |
| 233 | OC(O)C(O)O | allyl | | |
| 234 | OC(O)C(O)O | CH$_2$C≡CH | | |
| 235 | OC(O)C(O)O | CH=CH$_2$ | | |
| 236 | OC(O)C(O)O | CH$_2$CH$_2$F | | |
| 237 | OC(O)C(O)O | CF$_3$ | | |
| 238 | OC(O)C(O)O | CH$_2$CF$_3$ | | |
| 239 | OC(O)C(O)O | CH$_2$CN | | |
| 240 | OC(O)C(O)O | cyclopropyl | | |
| 241 | OC(O)C(O)O | cyclopropylmethyl | | |
| 242 | OC(O)C(O)O | CH$_2$CO$_2$Me | | |
| 243 | OC(O)C(O)O | CH$_2$CH$_2$NMe$_2$ | | |
| 244 | OC(O)C(O)O | CH$_2$—(N-morpholinyl) | | |
| 245 | OC(O)C(O)O | 2-chloropyridin-5-yl-methyl | | |
| 246 | OC(O)C(O)O | 2-furanyl | | |
| 247 | OC(O)C(O)O | 2-pyrimidinyl | | |
| 248 | OC(O)C(O)O | 2-oxazolyl | | |
| 249 | OC(O)C(O)O | 5-[1,2,4]-oxadiazolyl | | |
| 250 | OC(O)C(O)O | tetrazolyl | | |
| 251 | S(O)$_2$NR' | H | H | |
| 252 | S(O)$_2$NR' | Me | H | |
| 253 | S(O)$_2$NR' | Et | H | |
| 254 | S(O)$_2$NR' | n-Pr | H | |
| 255 | S(O)$_2$NR' | i-Pr | H | |
| 256 | S(O)$_2$NR' | n-Bu | H | |
| 257 | S(O)$_2$NR' | i-Bu | H | |
| 258 | S(O)$_2$NR' | allyl | H | |
| 259 | S(O)$_2$NR' | CH$_2$C≡CH | H | |
| 260 | S(O)$_2$NR' | CH=CH$_2$ | H | |
| 261 | S(O)$_2$NR' | CH$_2$CH$_2$F | H | |
| 262 | S(O)$_2$NR' | CF$_3$ | H | |
| 263 | S(O)$_2$NR' | CH$_2$CF$_3$ | H | |
| 264 | S(O)$_2$NR' | CH$_2$CN | H | |
| 265 | S(O)$_2$NR' | cyclopropyl | H | |
| 266 | S(O)$_2$NR' | cyclopropylmethyl | H | |
| 267 | S(O)$_2$NR' | CH$_2$CO$_2$Me | H | |
| 268 | S(O)$_2$NR' | CH$_2$CH$_2$NMe$_2$ | H | |
| 269 | S(O)$_2$NR' | CH$_2$—(N-morpholinyl) | H | |
| 270 | S(O)$_2$NR' | 2-chloropyridin-5-yl-methyl | H | |
| 271 | S(O)$_2$NR' | 2-furanyl | H | |
| 272 | S(O)$_2$NR' | 2-pyrimidinyl | H | |
| 273 | S(O)$_2$NR' | 2-oxazolyl | H | |
| 274 | S(O)$_2$NR' | 5-[1,2,4]-oxadiazolyl | H | |
| 275 | S(O)$_2$NR' | tetrazolyl | H | |
| 276 | S(O)$_2$NR' | H | Me | |
| 277 | S(O)$_2$NR' | Me | Me | |
| 278 | S(O)$_2$NR' | Et | Me | |
| 279 | S(O)$_2$NR' | n-Pr | Me | |
| 280 | S(O)$_2$NR' | i-Pr | Me | |
| 281 | S(O)$_2$NR' | n-Bu | Me | |
| 282 | S(O)$_2$NR' | i-Bu | Me | |
| 283 | S(O)$_2$NR' | allyl | Me | |
| 284 | S(O)$_2$NR' | CH$_2$C≡CH | Me | |
| 285 | S(O)$_2$NR' | CH=CH$_2$ | Me | |
| 286 | S(O)$_2$NR' | CH$_2$CH$_2$F | Me | |
| 287 | S(O)$_2$NR' | CF$_3$ | Me | |
| 288 | S(O)$_2$NR' | CH$_2$CF$_3$ | Me | |
| 289 | S(O)$_2$NR' | CH$_2$CN | Me | |
| 290 | S(O)$_2$NR' | cyclopropyl | Me | |
| 291 | S(O)$_2$NR' | cyclopropylmethyl | Me | |
| 292 | S(O)$_2$NR' | CH$_2$CO$_2$Me | Me | |
| 293 | S(O)$_2$NR' | CH$_2$CH$_2$NMe$_2$ | Me | |
| 294 | S(O)$_2$NR' | CH$_2$—(N-morpholinyl) | Me | |
| 295 | S(O)$_2$NR' | 2-chloropyridin-5-yl-methyl | Me | |
| 296 | S(O)$_2$NR' | 2-furanyl | Me | |
| 297 | S(O)$_2$NR' | 2-pyrimidinyl | Me | |
| 298 | S(O)$_2$NR' | 2-oxazolyl | Me | |
| 299 | S(O)$_2$NR' | 5-[1,2,4]-oxadiazolyl | Me | |
| 300 | S(O)$_2$NR' | tetrazolyl | Me | |
| 301 | S(O)$_2$NR' | H | Et | |
| 302 | S(O)$_2$NR' | Me | Et | |
| 303 | S(O)$_2$NR' | Et | Et | |
| 304 | S(O)$_2$NR' | n-Pr | Et | |
| 305 | S(O)$_2$NR' | i-Pr | Et | |
| 306 | S(O)$_2$NR' | n-Bu | Et | |
| 307 | S(O)$_2$NR' | i-Bu | Et | |
| 308 | S(O)$_2$NR' | allyl | Et | |
| 309 | S(O)$_2$NR' | CH$_2$C≡CH | Et | |

TABLE 6-continued

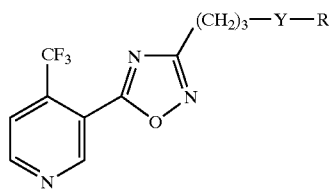

| Ex. No. | Y | R | R' | m.p. [° C.] |
|---|---|---|---|---|
| 310 | S(O)$_2$NR' | CH=CH$_2$ | Et | |
| 311 | S(O)$_2$NR' | CH$_2$CH$_2$F | Et | |
| 312 | S(O)$_2$NR' | CF$_3$ | Et | |
| 313 | S(O)$_2$NR' | CH$_2$CF$_3$ | Et | |
| 314 | S(O)$_2$NR' | CH$_2$CN | Et | |
| 315 | S(O)$_2$NR' | cyclopropyl | Et | |
| 316 | S(O)$_2$NR' | cyclopropylmethyl | Et | |
| 317 | S(O)$_2$NR' | CH$_2$CO$_2$Me | Et | |
| 318 | S(O)$_2$NR' | CH$_2$CH$_2$NMe$_2$ | Et | |
| 319 | S(O)$_2$NR' | CH$_2$—(N-morpholinyl) | Et | |
| 320 | S(O)$_2$NR' | 2-chloropyridin-5-yl-methyl | Et | |
| 321 | S(O)$_2$NR' | 2-furanyl | Et | |
| 322 | S(O)$_2$NR' | 2-pyrimidinyl | Et | |
| 323 | S(O)$_2$NR' | 2-oxazolyl | Et | |
| 324 | S(O)$_2$NR' | 5-[1,2,4]-oxadiazolyl | Et | |
| 325 | S(O)$_2$NR' | tetrazolyl | Et | |

B. Formulation Examples a) A dusting powder is obtained by mixing 10 parts by weight of active compound and 90 parts by weight of talc, as inert substance, and comminuting the mixture in an impact mill.

b) A wettable powder which is readily dispersible in water is obtained by mixing 25 parts by weight of active compound, 65 parts by weight of kaolin-containing quartz, as the inert substance, 10 parts by weight of potassium ligninsulfonate and 1 part by weight of sodium oleoylmethyltaurinate, as wetting and dispersing agent, and grinding the mixture in a pinned disk mill.

c) A dispersion concentrate which is readily dispersible in water is prepared by mixing 40 parts by weight of active compound with 7 parts by weight of a sulfosuccinic monoester, 2 parts by weight of a sodium ligninsulfonate and 51 parts by weight of water and grinding the mixture to a fineness of below 5 microns in a grinding bead mill.

d) An emulsifiable concentrate can be prepared from 15 parts by weight of active compound, 75 parts by weight of cyclohexane, as the solvent, and 10 parts by weight of ethoxylated nonylphenol (10 EO), as the emulsifier.

e) Granules can be prepared from 2 to 15 parts by weight of active compound and an inert granule carrier material, such as attapulgite, pumice granules and/or quartz sand. A suspension of the wettable powder from Example b) having a solids content of 30% is expediently used, and this is sprayed onto the surface of attapulgite granules and the components are dried and mixed intimately. The weight content of the wettable powder is approximately 5% and that of the inert carrier material is approximately 95% of the finished granules.

C. Biological Examples

Example 1

Germinated broad bean seeds (*Vicia faba*) with radicles were transferred into brown glass bottles filled with tap water and subsequently populated with approximately 100 black bean aphids (*Aphis fabae*). Plants and aphids were then dipped for 5 seconds into an aqueous solution of the formulated preparation to be examined. After the solution had dripped off, plants and animals were kept in a climatized chamber (16 hours of light/day, 25° C., 40–60% relative atmospheric humidity). After 3 and 6 days storage, the effect of the preparation on the aphids was determined. At a concentration of 300 ppm (based on the content of active compound), the preparations of Example Nos. 2/29, 2/43, 2/67, 2/6, 3/6, 3/50, 3/75 and 3/49 effected a mortality of 90–100% among the aphids.

The compounds are numbered with the Table/No. in the table.

Example 2

The leaves of 12 rice plants having a stem length of 8 cm were dipped for 5 seconds into an aqueous solution of the formulated preparation to be examined. After the solution had dripped off, the rice plants treated in this manner were placed in a Petri dish and populated with approximately 20 larvae (L3 stage) of the rice leafhopper species *Nilaparvata lugens*. The Petri dish was closed and stored in a climatized chamber (16 hours of light/day, 25° C., 40–60% relative atmospheric humidity). After 6 days storage, the mortality among the leafhopper larvae was determined. At a concentration of 300 ppm (based on the content of active compound), the preparations of Example Nos. 2/97, 2/127, 2/153, 2/255, 3/50 and 3/75 effected a mortality of 90–100%.

Example 3

Germinated broad bean seeds (*Vicia faba*) with radicles were transferred into brown glass bottles filled with tap water. Four milliliters of an aqueous solution of the formulated preparation to be examined were pipetted into the brown glass bottle. The broad bean was subsequently heavily populated with approximately 100 black bean aphids (*Aphis fabae*). Plants and animals were then stored in a climatized chamber (16 hours of light/day, 25° C., 40–60% relative atmospheric humidity). After 3 and 6 days storage, the root-systemic activity of the preparation on the aphids was determined. At a concentration of 30 ppm (based on the content of active compound), the preparations of Example Nos. 2/29, 2/43, 2/55, 2/67, 2/97, 2/6, 2/167, 2/153, 3/6, 3/50, 3/75 and 3/49 effected a mortality of 90–100% among the aphids by root-systemic action.

Although preferred embodiments of the present invention and modifications thereof have been described in detail herein, it is to be understood that this invention is not limited to those precise embodiments and modifications, and that other modifications and variations may be affected by one skilled in the art without departing from the spirit and scope of the invention as defined by the appended claims.

What is claimed is:

1. A 4-trifluoromethyl-3-oxadiazolylpyridine of the formula (I'), or a salt thereof,

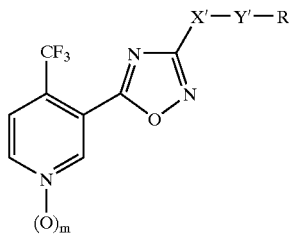

wherein
m is 0 or 1;
X' is a single bond, a straight-chain alkylene group having 1, 2 or 3 carbon atoms or a branched alkylene group having 3 to 9 carbon atoms, where one or more H atoms may be replaced by F;
Y' is —O—, —S—, —SO$_2$—, —O—CO—, —O—CO—O—, —SO$_2$—O—, —O—SO$_2$—, —NR$^1$—, —NR$^2$—CO—, —NR$^3$—CO—O—, —NR$^4$—CO—NR$^5$—, —O—CO—CO—O—, —O—CO—NR$^6$—, —SO$_2$—NR$^7$— or —NR$^8$—SO$_2$—;
R,R$^1$,R$^2$,R$^3$,R$^4$,R$^5$,R$^6$,R$^7$,R$^8$ are identical or different and are independently of one another H, (C$_1$-C$_{10}$)-alkyl, (C$_2$-C$_{10}$)-alkenyl, (C$_2$-Cl$_{10}$)-alkynyl, (C$_3$-C$_8$)-cycloalkyl, (C$_4$-C$_8$)-cycloalkenyl, (C$_6$-C$_8$)-cycloalkynyl, heterocyclyl or —(CH$_2$)$_{1-4}$-heterocyclyl, where each of the eight last-mentioned groups is unsubstituted or mono- or polysubstituted, and where, optionally R and R$^1$, R and R$^2$, R and R$^5$, R and R$^6$, R and R$^7$, R and R$^8$ or X' and R, together form a ring system,
with the proviso, that the compounds in which
X'=-, Y'=O, R=H
X'=-, Y'=O, R=Me
X'=-, Y'=O, R=Et
X'=-, Y'=O, R=CHF$_2$
X'=-, Y'=O, R=CH$_2$Ph
X'=CH$_2$, Y'=O, R=2-furanyl
X'=CH$_2$, Y'=O, R=Me
X'=CH$_2$, Y'=O, R=5-isoxazolyl
X'=CH$_2$, Y'=O, R=5-nitrofuran-2-yl
X'=CH$_2$CH$_2$, Y'=O, R=H
X'=CH$_2$CH$_2$; Y'=O, R=Me
X'=CH$_2$CH$_2$, Y'=O,

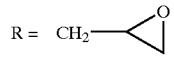

X'=CH$_2$CH$_2$, Y'=O, R=Et
X'=CH$_2$CH$_2$, Y'=O,
X'=CH$_2$CH$_2$; Y'=OC(O), R=4-F-phenyl
X'=CH$_2$CH$_2$, Y'=OC(O), R=2,6-difluorophenyl
X'=CH$_2$CH$_2$, Y'=OC(O), R=4-nitrophenyl
X'=CH$_2$CH$_2$, Y'=OC(O), R=t-Bu
X'=CH$_2$CH$_2$, Y'=OC(O), R=cyclopropyl
X'=CH$_2$CH$_2$, Y'=OC(O), R=Me
X'=CH$_2$CH$_2$CH$_2$, Y'=O, R=H
X'=-, Y'=S(O), R=4-bromobenzyl
X'=CH$_2$, Y'=S, R=Me
X'=CH$_2$, Y'=S(O), R=Me
X'=CH$_2$, Y'=S(O)$_2$, R=t-Bu
X'=CH$_2$, Y'=S, R=2-thienyl
X'=CH$_2$CH$_2$, Y'=S, R=Me
X'=CH$_2$CH$_2$, Y'=S, R=n-Pr
X'=CH$_2$CH$_2$, Y'=S, R=benzyl
X'=CH$_2$CH$_2$, Y'=S, R=2-thienylmethyl
X'=CH$_2$CH$_2$CH$_2$, Y'=S, R=Me
X'=CH$_2$CH$_2$CH$_2$, Y'=SO, R=Me
X'=CH$_2$CH$_2$CH$_2$CH$_2$, Y'=S, R=CH$_2$CH$_2$CH$_2$CH$_2$OMe
are not included.

2. The 4-trifluoromethyl-3-oxadiazolylpyridine as claimed in claim 1, wherein m in the formula (I') is 0.

3. The 4-trifluoromethyl-3-oxadiazolylpyridine as claimed in claim 1, wherein X' in the formula (I') is a single bond, —CH$_2$—, —CH$_2$—CH$_2$—, —CH$_2$—CH(CH$_3$)— or —CH$_2$—C(CH$_3$)$_2$—.

4. The 4-trifluoromethyl-3-oxadiazolylpyridine as claimed in claim 1, wherein Y' in the formula (I') is —O—, —S—, —SO—, —SO$_2$—, —O—CO—, —O—CO—O—, —O—CO—NR$^6$—, —SO$_2$—NR$^7$—, —O—SO$_2$— or —SO$_2$—O—.

5. A process for preparing a compound of the formula (I') as claimed in claim 1, comprising reacting an activated derivative of an acid of the formula (II),

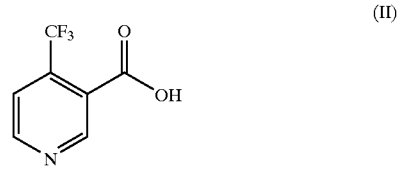

in the presence of a base with a compound of the formula (III),

in which the radical —X'—Y'—R is as defined in formula (I'), or is a precursor of a radical defined therein.

6. A composition having insecticidal, acaricidal and/or nematicidal action, which comprises at least one compound as claimed in claim 1.

7. The composition as claimed in claim 6, further comprising a carrier substance and/or a surface-active substance.

8. The composition as claimed in claim 6, further comprising an active compound from the group of acaricides, fungicides, herbicides, insecticides, nematicides or growth-regulating substances.

9. A veterinary composition for treatment of a patient in need thereof, comprising the compound of claim 1 or the composition of claim 6.

10. A method for controlling harmful insects, acarids and nematodes, which comprises applying an effective amount of the compound as claimed in claim 1 or the composition as claimed in claim 6 to the site of the desired action.

11. A method for protecting useful plants against the undesirable action of harmful insects, acarids and nematodes, which comprises treating the seed of the useful plant with at least one compound as claimed in claim 1 or at least one composition as claimed in claim 6.

12. A method of controlling harmful insects, acarids and nematodes in useful plants, comprising applying an effective amount of the compound of claim 1 or the composition of claim 6 to said useful plant.

* * * * *